US012312410B2

(12) United States Patent
Qiu et al.

(10) Patent No.: US 12,312,410 B2
(45) Date of Patent: May 27, 2025

(54) ANTI-CD39 ANTIBODIES

(71) Applicants: ELPISCIENCE (SUZHOU) BIOPHARMA, LTD., Jiangsu (CN); ELPISCIENCE BIOPHARMA, LTD., Shanghai (CN)

(72) Inventors: Yangsheng Qiu, Shanghai (CN); Meiling Sun, Shanghai (CN); Roumei Xing, Shanghai (CN); Dan Xu, Shanghai (CN); Yufei Shi, Shanghai (CN); Jinfeng Zhao, Shanghai (CN); Qinglin Du, Shanghai (CN); Zhihao Wu, Shanghai (CN); Rui Gao, Shanghai (CN); Robert H. Arch, Shanghai (CN); Hongtao Lu, Shanghai (CN)

(73) Assignee: ELPISCIENCE (SUZHOU) BIOPHARMA, LTD (CN)

( * ) Notice: Subject to any disclaimer, the term of this patent is extended or adjusted under 35 U.S.C. 154(b) by 1020 days.

(21) Appl. No.: 17/283,553

(22) PCT Filed: Aug. 26, 2020

(86) PCT No.: PCT/CN2020/111219
§ 371 (c)(1),
(2) Date: Apr. 8, 2021

(87) PCT Pub. No.: WO2021/037037
PCT Pub. Date: Mar. 4, 2021

(65) Prior Publication Data
US 2021/0388105 A1 Dec. 16, 2021

(30) Foreign Application Priority Data
Aug. 27, 2019 (WO) ............... PCT/CN2019/102778
Aug. 20, 2020 (CN) .......................... 202010842863.9

(51) Int. Cl.
*C07K 16/28* (2006.01)
*A61K 39/00* (2006.01)
*A61K 39/395* (2006.01)
*A61P 35/00* (2006.01)

(52) U.S. Cl.
CPC ...... *C07K 16/2896* (2013.01); *A61K 39/3955* (2013.01); *A61P 35/00* (2018.01); *A61K 2039/505* (2013.01); *C07K 2317/24* (2013.01); *C07K 2317/565* (2013.01); *C07K 2317/567* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 9,334,331 B2 * | 5/2016 | Igawa | ..................... | C07K 16/36 |
| 10,421,807 B2 * | 9/2019 | Gonzales | ................. | A61P 17/08 |
| 2010/0303828 A1 * | 12/2010 | Levy | .................. | C07K 16/2896 |
| | | | | 530/387.3 |
| 2019/0071514 A1 | 3/2019 | Gauthier et al. | | |

FOREIGN PATENT DOCUMENTS

| | | |
|---|---|---|
| JP | 2019-509014 A | 4/2019 |
| WO | 2009095478 A1 | 8/2009 |
| WO | 2016073845 A1 | 5/2016 |
| WO | 2017089334 A1 | 6/2017 |
| WO | 2017/157948 A1 | 9/2017 |
| WO | 2018167267 A1 | 9/2018 |
| WO | 2019027935 A1 | 2/2019 |

OTHER PUBLICATIONS

Al Qaraghuli et al. (2020, Nature Scientific Reports 10:13969).*
Edwards et al. (2003, JMB 334:103-118).*
Lloyd et al. (2009, Protein Engineering, Eng. Design & Selection 22(3): 159-168).*
Goel et al. (2004, J. Immunol. 173: 7358-7367).*
Khan et al. (2014, J. Immunol. 192: 5398-5405).*
Poosarla et al. (2017, Biotechn. Bioeng. 114(6): 1331-1342).*
Rabia, et al. (2018, Biochemical Engineering Journal 137:365-374).*
Gura (Science, v278, 1997, pp. 1041-1042).*
Freshney (Culture of Animal Cells, A Manual of Basic Technique, Alan R. Liss, Inc., 1983, New York, p. 4).*
Dermer (Bio/Technology, 1994, 12:320).*
Zips et al. (2005, In Vivo 19:1-8).*
Editorial, (2013, Nature Biotechnology 31:85).*
First Office Action of the corresponding Chinese application 2020800035998, mailed on Jun. 10, 2023.
Zhulai GA1 et al., "Activation of CD4+CD39+ T Cells in Colorectal Cancer", Bulletin of Rsmu, 2018, pp. 47-53.
Office Action and Search Report for the counterpart Russian Patent application 2022104683, mailed on Nov. 10, 2023.
Antonioli L et al., "CD39 and CD73 in immunity and inflammation", Trends in molecular medicine, Jun. 1, 2014 (Jun. 1, 2014), No. 6, vol. 19, ISSN: 1471-499X, pp. 355-367, see the whole document.
International Search Report of PCT Application No. PCT/CN2020/111219, mailed on Dec. 2, 2020.
J. Bastid, A et al.,"Inhibition of CD39 Enzymatic Function at the Surface of Tumor Cells Alleviates Their Immunosuppressive Activity", Cancer Immunology Research, vol. 3, No. 3, Nov. 17, 2014 (Nov. 17, 2014), pp. 254-265, XP055340441, US ISSN: 2326-6066, DOI: 10.1158/2326-6066.CIR-14-0018 *abstract, p. 259, Fig. 5C, discussion*.

(Continued)

*Primary Examiner* — Elizabeth C. Kemmerer
(74) *Attorney, Agent, or Firm* — Jun He Law Offices P.C; Zhaohui Wang

(57) ABSTRACT

Provided are anti-CD39 antibodies or antigen-binding fragments thereof, isolated polynucleotides encoding the same, pharmaceutical compositions comprising the same and the uses thereof.

24 Claims, 32 Drawing Sheets

Specification includes a Sequence Listing.

(56) References Cited

OTHER PUBLICATIONS

Extended European Search Report for the corresponding EP Application No. 20824060.6, mailed on Apr. 5, 2022.
Office Action for the counterpart Japanese Patent application 2020-572398, mailed on Jul. 23, 2024.

* cited by examiner

A

B

A

B

A

B

A

B

A

B

C

D

A

B

C

D

A

B

A

B

C

B.

SEQUENCE LISTING

```
<160> NUMBER OF SEQ ID NOS: 162

<210> SEQ ID NO 1
<211> LENGTH: 5
<212> TYPE: PRT
<213> ORGANISM: Mus musculus

<400> SEQUENCE: 1

Asn Tyr Gly Met Asn
1               5

<210> SEQ ID NO 2
<211> LENGTH: 5
<212> TYPE: PRT
<213> ORGANISM: Mus musculus

<400> SEQUENCE: 2

Lys Tyr Trp Met Asn
1               5

<210> SEQ ID NO 3
<211> LENGTH: 5
<212> TYPE: PRT
<213> ORGANISM: Mus musculus

<400> SEQUENCE: 3

Asn Tyr Trp Met Asn
1               5

<210> SEQ ID NO 4
<211> LENGTH: 5
<212> TYPE: PRT
<213> ORGANISM: Mus musculus

<400> SEQUENCE: 4

Asp Thr Phe Leu His
1               5

<210> SEQ ID NO 5
<211> LENGTH: 5
<212> TYPE: PRT
<213> ORGANISM: Mus musculus

<400> SEQUENCE: 5

Asp Tyr Asn Met Tyr
1               5

<210> SEQ ID NO 6
<211> LENGTH: 5
<212> TYPE: PRT
<213> ORGANISM: Mus musculus

<400> SEQUENCE: 6
```

Asp Thr Tyr Val His
1               5

<210> SEQ ID NO 7
<211> LENGTH: 17
<212> TYPE: PRT
<213> ORGANISM: Mus musculus

<400> SEQUENCE: 7

Leu Ile Asn Thr Tyr Thr Gly Glu Pro Thr Tyr Ala Asp Asp Phe Lys
1               5                   10                  15

Asp

<210> SEQ ID NO 8
<211> LENGTH: 19
<212> TYPE: PRT
<213> ORGANISM: Mus musculus

<400> SEQUENCE: 8

Glu Ile Arg Leu Lys Ser Asn Lys Tyr Gly Thr His Tyr Ala Glu Ser
1               5                   10                  15

Val Lys Gly

<210> SEQ ID NO 9
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (13)..(13)
<223> OTHER INFORMATION: Xaa can be Tyr or Phe.

<400> SEQUENCE: 9

Gln Ile Arg Leu Asn Pro Asp Asn Tyr Ala Thr His Xaa Ala Glu Ser
1               5                   10                  15

Val Lys Gly

<210> SEQ ID NO 10
<211> LENGTH: 17
<212> TYPE: PRT
<213> ORGANISM: Mus musculus

<400> SEQUENCE: 10

Arg Ile Asp Pro Ala Asn Gly Asn Ile Lys Tyr Asp Pro Lys Phe Gln
1               5                   10                  15

Gly

<210> SEQ ID NO 11
<211> LENGTH: 17
<212> TYPE: PRT
<213> ORGANISM: Mus musculus

<400> SEQUENCE: 11

Phe Ile Asp Pro Tyr Asn Gly Tyr Thr Ser Tyr Asn Gln Lys Phe Lys
1               5                   10                  15

Gly

<210> SEQ ID NO 12
<211> LENGTH: 17
<212> TYPE: PRT
<213> ORGANISM: Mus musculus

<400> SEQUENCE: 12

Arg Ile Asp Pro Ala Ile Asp Asn Ser Lys Tyr Asp Pro Lys Phe Gln
1               5                   10                  15

Gly

<210> SEQ ID NO 13
<211> LENGTH: 13
<212> TYPE: PRT
<213> ORGANISM: Mus musculus

<400> SEQUENCE: 13

Lys Gly Ile Tyr Tyr Asp Tyr Val Trp Phe Phe Asp Val
1               5                   10

<210> SEQ ID NO 14
<211> LENGTH: 10
<212> TYPE: PRT
<213> ORGANISM: Mus musculus

<400> SEQUENCE: 14

Gln Leu Asp Leu Tyr Trp Phe Phe Asp Val
1               5                   10

<210> SEQ ID NO 15
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be Ser or Thr.

<400> SEQUENCE: 15

His Gly Xaa Arg Gly Phe Ala Tyr
1               5

<210> SEQ ID NO 16
<211> LENGTH: 14
<212> TYPE: PRT
<213> ORGANISM: Mus musculus

<400> SEQUENCE: 16

Ser Pro Tyr Tyr Tyr Gly Ser Gly Tyr Arg Ile Phe Asp Val
1               5                   10

<210> SEQ ID NO 17
<211> LENGTH: 12
<212> TYPE: PRT
<213> ORGANISM: Mus musculus

<400> SEQUENCE: 17

Ile Tyr Gly Tyr Asp Asp Ala Tyr Tyr Phe Asp Tyr
1               5                   10

<210> SEQ ID NO 18
<211> LENGTH: 16
<212> TYPE: PRT
<213> ORGANISM: Mus musculus

<400> SEQUENCE: 18

Tyr Tyr Cys Ala Leu Tyr Asp Gly Tyr Asn Val Tyr Ala Met Asp Tyr
1               5                   10                  15

```
<210> SEQ ID NO 19
<211> LENGTH: 11
<212> TYPE: PRT
<213> ORGANISM: Mus musculus

<400> SEQUENCE: 19

Lys Ala Ser Gln Asp Ile Asn Arg Tyr Ile Ala
1               5                   10

<210> SEQ ID NO 20
<211> LENGTH: 11
<212> TYPE: PRT
<213> ORGANISM: Mus musculus

<400> SEQUENCE: 20

Arg Ala Ser Gln Ser Ile Ser Asp Tyr Leu His
1               5                   10

<210> SEQ ID NO 21
<211> LENGTH: 16
<212> TYPE: PRT
<213> ORGANISM: Mus musculus

<400> SEQUENCE: 21

Lys Ser Ser Gln Ser Leu Leu Asp Ser Asp Gly Arg Thr His Leu Asn
1               5                   10                  15

<210> SEQ ID NO 22
<211> LENGTH: 10
<212> TYPE: PRT
<213> ORGANISM: Mus musculus

<400> SEQUENCE: 22

Ser Ala Phe Ser Ser Val Asn Tyr Met His
1               5                   10

<210> SEQ ID NO 23
<211> LENGTH: 10
<212> TYPE: PRT
<213> ORGANISM: Mus musculus

<400> SEQUENCE: 23

Ser Ala Thr Ser Ser Val Ser Tyr Met His
1               5                   10

<210> SEQ ID NO 24
<211> LENGTH: 16
<212> TYPE: PRT
<213> ORGANISM: Mus musculus

<400> SEQUENCE: 24

Arg Ser Ser Lys Asn Leu Leu His Ser Asn Gly Ile Thr Tyr Leu Tyr
1               5                   10                  15

<210> SEQ ID NO 25
<211> LENGTH: 7
<212> TYPE: PRT
<213> ORGANISM: Mus musculus

<400> SEQUENCE: 25

Tyr Thr Ser Thr Leu Leu Pro
1               5
```

-continued

```
<210> SEQ ID NO 26
<211> LENGTH: 7
<212> TYPE: PRT
<213> ORGANISM: Mus musculus

<400> SEQUENCE: 26

Tyr Ala Ser Gln Ser Ile Ser
1               5

<210> SEQ ID NO 27
<211> LENGTH: 7
<212> TYPE: PRT
<213> ORGANISM: Mus musculus

<400> SEQUENCE: 27

Leu Val Ser Lys Leu Asp Ser
1               5

<210> SEQ ID NO 28
<211> LENGTH: 7
<212> TYPE: PRT
<213> ORGANISM: Mus musculus

<400> SEQUENCE: 28

Thr Thr Ser Asn Leu Ala Ser
1               5

<210> SEQ ID NO 29
<211> LENGTH: 7
<212> TYPE: PRT
<213> ORGANISM: Mus musculus

<400> SEQUENCE: 29

Ser Thr Ser Asn Leu Ala Ser
1               5

<210> SEQ ID NO 30
<211> LENGTH: 7
<212> TYPE: PRT
<213> ORGANISM: Mus musculus

<400> SEQUENCE: 30

Arg Ala Ser Thr Leu Ala Ser
1               5

<210> SEQ ID NO 31
<211> LENGTH: 8
<212> TYPE: PRT
<213> ORGANISM: Mus musculus

<400> SEQUENCE: 31

Leu Gln Tyr Ser Asn Leu Leu Thr
1               5

<210> SEQ ID NO 32
<211> LENGTH: 9
<212> TYPE: PRT
<213> ORGANISM: Mus musculus

<400> SEQUENCE: 32

Gln Asn Gly His Ser Leu Pro Leu Thr
1               5

<210> SEQ ID NO 33
<211> LENGTH: 9
```

```
<212> TYPE: PRT
<213> ORGANISM: Mus musculus

<400> SEQUENCE: 33

Trp Gln Gly Thr Leu Phe Pro Trp Thr
1               5

<210> SEQ ID NO 34
<211> LENGTH: 9
<212> TYPE: PRT
<213> ORGANISM: Mus musculus

<400> SEQUENCE: 34

Gln Gln Arg Ser Thr Tyr Pro Phe Thr
1               5

<210> SEQ ID NO 35
<211> LENGTH: 9
<212> TYPE: PRT
<213> ORGANISM: Mus musculus

<400> SEQUENCE: 35

Gln Gln Arg Ile Thr Tyr Pro Phe Thr
1               5

<210> SEQ ID NO 36
<211> LENGTH: 9
<212> TYPE: PRT
<213> ORGANISM: Mus musculus

<400> SEQUENCE: 36

Ala Gln Leu Leu Glu Leu Pro His Thr
1               5

<210> SEQ ID NO 37
<211> LENGTH: 19
<212> TYPE: PRT
<213> ORGANISM: Mus musculus

<400> SEQUENCE: 37

Gln Ile Arg Leu Asn Pro Asp Asn Tyr Ala Thr His Tyr Ala Glu Ser
1               5                   10                  15

Val Lys Gly

<210> SEQ ID NO 38
<211> LENGTH: 19
<212> TYPE: PRT
<213> ORGANISM: Mus musculus

<400> SEQUENCE: 38

Gln Ile Arg Leu Asn Pro Asp Asn Tyr Ala Thr His Phe Ala Glu Ser
1               5                   10                  15

Val Lys Gly

<210> SEQ ID NO 39
<211> LENGTH: 123
<212> TYPE: PRT
<213> ORGANISM: Artificial Sequence
<220> FEATURE:
<223> OTHER INFORMATION: Synthetic

<400> SEQUENCE: 39

Glu Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Leu Lys Asp Thr
            20                  25                  30

Phe Leu His Trp Val Arg Gln Ala Pro Gly Gln Arg Leu Glu Trp Met
        35                  40                  45

Gly Arg Ile Asp Pro Ala Asn Gly Asn Ile Lys Tyr Asp Pro Lys Phe
    50                  55                  60

Gln Gly Arg Val Thr Ile Thr Ala Asp Thr Ser Asn Thr Ala Tyr
65                  70                  75                  80

Met Glu Leu Ser Ser Leu Arg Ser Glu Asp Thr Ala Val Tyr Tyr Cys
                85                  90                  95

Ala Asn Ser Pro Tyr Tyr Gly Ser Gly Tyr Arg Ile Phe Asp Val
                100                 105                 110

Trp Gly Gln Gly Thr Leu Val Thr Val Ser Ser
            115                 120

<210> SEQ ID NO 40
<211> LENGTH: 8
<212> TYPE: PRT
<213> ORGANISM: Mus musculus

<400> SEQUENCE: 40

His Gly Ser Arg Gly Phe Ala Tyr
1               5

<210> SEQ ID NO 41
<211> LENGTH: 8
<212> TYPE: PRT
<213> ORGANISM: Mus musculus

<400> SEQUENCE: 41

His Gly Thr Arg Gly Phe Ala Tyr
1               5

<210> SEQ ID NO 42
<211> LENGTH: 122
<212> TYPE: PRT
<213> ORGANISM: Mus musculus

<400> SEQUENCE: 42

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Arg Trp Met
        35                  40                  45

Gly Leu Ile Asn Thr Tyr Thr Gly Glu Pro Thr Tyr Ala Asp Asp Phe
    50                  55                  60

Lys Asp Arg Phe Ala Phe Ser Leu Glu Thr Ser Ala Ser Thr Ala Phe
65                  70                  75                  80

Leu Gln Ile Asn Asn Leu Lys Asp Glu Asp Met Ala Thr Tyr Phe Cys
                85                  90                  95

Ala Arg Lys Gly Ile Tyr Tyr Asp Tyr Val Trp Phe Phe Asp Val Trp
                100                 105                 110

Gly Ala Gly Thr Thr Val Thr Val Ser Ser
            115                 120

<210> SEQ ID NO 43
<211> LENGTH: 121
```

-continued

```
<212> TYPE: PRT
<213> ORGANISM: Mus musculus

<400> SEQUENCE: 43

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Lys Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Lys Tyr Gly Thr His Tyr Ala Glu
    50                  55                  60

Ser Val Lys Gly Arg Phe Thr Ile Ser Arg Asp Asp Ser Lys Asn Asn
65                  70                  75                  80

Val Tyr Leu Gln Met Asn Asn Leu Arg Pro Glu Asp Thr Gly Ile Tyr
                85                  90                  95

Tyr Cys Thr Thr Gln Leu Asp Leu Tyr Trp Phe Phe Asp Val Trp Gly
            100                 105                 110

Ala Gly Thr Thr Val Thr Val Ser Ser
        115                 120

<210> SEQ ID NO 44
<211> LENGTH: 118
<212> TYPE: PRT
<213> ORGANISM: Mus musculus

<400> SEQUENCE: 44

Glu Val Lys Leu Glu Lys Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Gln Ile Arg Leu Asn Pro Asp Asn Tyr Ala Thr His Tyr Ala Glu
    50                  55                  60

Ser Val Lys Gly Arg Phe Thr Ile Ser Arg Asp Asp Tyr Lys Asn Ser
65                  70                  75                  80

Val Tyr Leu Gln Met Ser Ser Leu Arg Ala Glu Asp Ser Gly Ile Tyr
                85                  90                  95

Tyr Cys Thr Gln His Gly Ser Arg Gly Phe Ala Tyr Trp Gly Gln Gly
            100                 105                 110

Thr Leu Val Thr Val Ser
        115

<210> SEQ ID NO 45
<211> LENGTH: 119
<212> TYPE: PRT
<213> ORGANISM: Mus musculus

<400> SEQUENCE: 45

Glu Val Lys Leu Glu Lys Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Gln Ile Arg Leu Asn Pro Asp Asn Tyr Ala Thr His Phe Ala Glu
```

```
                    50                  55                  60
Ser Val Lys Gly Arg Phe Thr Ile Ser Arg Asp Asp Ser Lys Asn Ser
 65                  70                  75                  80

Val Tyr Leu Gln Met Asn Ser Leu Arg Ala Glu Asp Thr Gly Ile Tyr
                     85                  90                  95

Tyr Cys Thr Glu His Gly Thr Arg Gly Phe Ala Tyr Trp Gly Gln Gly
                100                 105                 110

Thr Leu Val Thr Val Ser Glu
            115
```

<210> SEQ ID NO 46
<211> LENGTH: 121
<212> TYPE: PRT
<213> ORGANISM: Mus musculus

<400> SEQUENCE: 46

```
Gln Ile Gln Leu Val Gln Ser Gly Pro Glu Leu Lys Lys Pro Gly Glu
  1               5                  10                  15

Thr Val Lys Ile Ser Cys Lys Ala Ser Gly Tyr Thr Phe Thr His Tyr
                 20                  25                  30

Gly Met Asn Trp Val Lys Gln Ala Pro Gly Lys Gly Leu Lys Trp Met
                 35                  40                  45

Gly Trp Ile Asn Thr Tyr Thr Gly Glu Leu Thr Tyr Ala Asp Asp Phe
             50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                     85                  90                  95

Ala Arg Arg Ala Tyr Tyr Arg Tyr Asp Tyr Val Met Asp Tyr Trp Gly
                100                 105                 110

Gln Gly Thr Ser Val Thr Val Ser Ser
            115                 120
```

<210> SEQ ID NO 47
<211> LENGTH: 123
<212> TYPE: PRT
<213> ORGANISM: Mus musculus

<400> SEQUENCE: 47

```
Glu Val Gln Leu Gln Gln Ser Gly Ala Glu Leu Leu Arg Pro Gly Ala
  1               5                  10                  15

Ser Val Lys Leu Ser Cys Thr Ala Ser Gly Tyr Asn Leu Lys Asp Thr
                 20                  25                  30

Phe Leu His Trp Val Lys Gln Arg Pro Glu Gln Gly Leu Glu Trp Ile
                 35                  40                  45

Gly Arg Ile Asp Pro Ala Asn Gly Asn Ile Lys Tyr Asp Pro Lys Phe
             50                  55                  60

Gln Gly Lys Ala Thr Leu Thr Ala Asp Thr Ser Ser Asn Thr Ala Tyr
 65                  70                  75                  80

Leu Gln Leu Ile Ser Leu Thr Ser Glu Asp Thr Ala Val Tyr Tyr Cys
                     85                  90                  95

Ala Asn Ser Pro Tyr Tyr Gly Ser Gly Tyr Arg Ile Phe Asp Val
                100                 105                 110

Trp Gly Ala Gly Thr Thr Val Thr Val Ser Ser
            115                 120
```

<210> SEQ ID NO 48
<211> LENGTH: 107
<212> TYPE: PRT
<213> ORGANISM: Mus musculus

<400> SEQUENCE: 48

Asp Ile Val Met Thr Gln Ser Gln Lys Phe Met Ser Thr Ser Val Gly
1               5                   10                  15

Asp Arg Val Ser Val Thr Cys Lys Ala Ser His Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Gly Arg Phe Thr Gly
50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys His Gln Tyr Asn Asn Tyr Pro Tyr
                85                  90                  95

Thr Phe Gly Gly Gly Thr Lys Leu Glu Ile Lys
            100                 105

<210> SEQ ID NO 49
<211> LENGTH: 120
<212> TYPE: PRT
<213> ORGANISM: Mus musculus

<400> SEQUENCE: 49

Glu Ile Gln Val Gln Gln Ser Gly Pro Glu Leu Val Lys Pro Gly Ala
1               5                   10                  15

Ser Val Lys Val Ser Cys Lys Ala Ser Gly Tyr Ser Phe Thr Asp Tyr
            20                  25                  30

Asn Met Tyr Trp Val Lys Gln Ser His Gly Lys Ser Leu Glu Trp Ile
        35                  40                  45

Gly Phe Ile Asp Pro Tyr Asn Gly Tyr Thr Ser Tyr Asn Gln Lys Phe
50                  55                  60

Lys Gly Lys Ala Thr Leu Thr Ile Asp Lys Ser Ser Ser Thr Ala Phe
65                  70                  75                  80

Met His Leu Asn Ser Leu Thr Ser Glu Asp Ser Ala Val Tyr Tyr Cys
                85                  90                  95

Ala Ile Tyr Gly Tyr Asp Asp Ala Tyr Tyr Phe Asp Tyr Trp Gly Gln
            100                 105                 110

Gly Thr Thr Leu Thr Val Ser Ser
        115                 120

<210> SEQ ID NO 50
<211> LENGTH: 120
<212> TYPE: PRT
<213> ORGANISM: Mus musculus

<400> SEQUENCE: 50

Glu Val Arg Leu Gln Gln Ser Gly Ala Glu Leu Val Lys Pro Gly Ala
1               5                   10                  15

Ser Val Lys Leu Ser Cys Thr Ala Ser Gly Phe Asn Ile Glu Asp Thr
            20                  25                  30

Tyr Val His Trp Met Lys Gln Arg Pro Glu Gln Gly Leu Glu Trp Ile
        35                  40                  45

Gly Arg Ile Asp Pro Ala Ile Asp Asn Ser Lys Tyr Asp Pro Lys Phe
50                  55                  60

```
Gln Gly Lys Ala Thr Ile Thr Ala Val Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Ala Leu Tyr Asp Gly Tyr Asn Val Tyr Ala Met Asp Tyr Trp Gly Gln
            100                 105                 110

Gly Thr Ser Val Thr Val Ser Ser
        115                 120

<210> SEQ ID NO 51
<211> LENGTH: 106
<212> TYPE: PRT
<213> ORGANISM: Mus musculus

<400> SEQUENCE: 51

Asp Ile Gln Met Thr Gln Ser Pro Ser Ser Leu Ser Thr Ser Leu Gly
 1               5                  10                  15

Gly Lys Val Ser Ile Thr Cys Lys Ala Ser Gln Asp Ile Asn Arg Tyr
            20                  25                  30

Ile Ala Trp Tyr Gln His Lys Pro Gly Lys Gly Pro Arg Leu Leu Ile
        35                  40                  45

His Tyr Thr Ser Thr Leu Leu Pro Gly Ile Pro Ser Arg Phe Ser Gly
    50                  55                  60

Ser Gly Ser Gly Arg Asp Tyr Ser Phe Ser Ile Ser Asn Leu Glu Pro
 65                  70                  75                  80

Glu Asp Ile Ala Thr Tyr Phe Cys Leu Gln Tyr Ser Asn Leu Leu Thr
                 85                  90                  95

Phe Gly Gly Gly Thr Lys Leu Glu Ile Lys
            100                 105

<210> SEQ ID NO 52
<211> LENGTH: 107
<212> TYPE: PRT
<213> ORGANISM: Mus musculus

<400> SEQUENCE: 52

Asp Ile Val Met Thr Gln Ser Pro Ala Ile Leu Ser Val Thr Pro Gly
 1               5                  10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asn Phe Thr Leu Ser Ile Asn Ser Val Glu Pro
 65                  70                  75                  80

Glu Asp Val Gly Val Tyr Phe Cys Gln Asn Gly His Ser Leu Pro Leu
                 85                  90                  95

Thr Phe Gly Ala Gly Thr Lys Leu Glu Leu Arg
            100                 105

<210> SEQ ID NO 53
<211> LENGTH: 112
<212> TYPE: PRT
<213> ORGANISM: Mus musculus

<400> SEQUENCE: 53
```

```
Asp Val Val Met Thr Gln Thr Pro His Thr Met Ser Ile Thr Ile Gly
1               5                   10                  15

Gln Pro Ala Ser Ile Ser Cys Lys Ser Gln Ser Leu Leu Asp Ser
            20                  25                  30

Asp Gly Arg Thr His Leu Asn Trp Leu Phe Gln Arg Pro Gly Gln Ser
            35                  40                  45

Pro Lys Arg Leu Ile Tyr Leu Val Ser Lys Leu Asp Ser Gly Val Pro
50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr Leu Phe Pro Trp Thr Phe Gly Gly Gly Thr Lys Leu Glu Ile Lys
            100                 105                 110
```

<210> SEQ ID NO 54
<211> LENGTH: 112
<212> TYPE: PRT
<213> ORGANISM: Mus musculus

<400> SEQUENCE: 54

```
Asp Val Val Met Thr Gln Thr Pro Leu Thr Leu Ser Ile Thr Ile Gly
1               5                   10                  15

Gln Pro Ala Ser Ile Ser Cys Lys Ser Gln Ser Leu Leu Asp Ser
            20                  25                  30

Asp Gly Arg Thr His Leu Asn Trp Phe Phe Gln Arg Pro Gly Gln Ser
            35                  40                  45

Pro Lys Arg Leu Ile Tyr Leu Val Ser Lys Leu Asp Ser Gly Val Pro
50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr Leu Phe Pro Trp Thr Phe Gly Gly Gly Thr Lys Leu Glu Ile Lys
            100                 105                 110
```

<210> SEQ ID NO 55
<211> LENGTH: 116
<212> TYPE: PRT
<213> ORGANISM: Mus musculus

<400> SEQUENCE: 55

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Ser His Gly Arg Thr Leu Glu Trp Ile
            35                  40                  45

Gly Tyr Ile Val Pro Leu Asn Gly Gly Ser Thr Phe Asn Gln Lys Phe
50                  55                  60

Lys Gly Arg Ala Thr Leu Thr Val Asn Thr Ser Ser Arg Thr Ala Tyr
65                  70                  75                  80

Met Glu Leu Arg Ser Leu Thr Ser Glu Asp Ser Ala Ala Tyr Tyr Cys
                85                  90                  95

Ala Arg Gly Gly Thr Arg Phe Ala Tyr Trp Gly Gln Gly Thr Leu Val
            100                 105                 110
```

```
Thr Val Ser Ala
        115

<210> SEQ ID NO 56
<211> LENGTH: 106
<212> TYPE: PRT
<213> ORGANISM: Mus musculus

<400> SEQUENCE: 56

Gln Ile Val Leu Thr Gln Ser Pro Ala Ile Met Ser Ala Ser Pro Gly
1               5                   10                  15

Glu Lys Val Thr Ile Thr Cys Ser Ala Phe Ser Ser Val Asn Tyr Met
            20                  25                  30

His Trp Tyr Gln Gln Lys Pro Gly Thr Ser Pro Lys Leu Leu Ile Tyr
        35                  40                  45

Thr Thr Ser Asn Leu Ala Ser Gly Val Pro Thr Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Thr Tyr Pro Phe Thr
                85                  90                  95

Phe Gly Ser Gly Thr Lys Leu Glu Ile Gln
            100                 105

<210> SEQ ID NO 57
<211> LENGTH: 111
<212> TYPE: PRT
<213> ORGANISM: Mus musculus

<400> SEQUENCE: 57

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Phe
            20                  25                  30

Gly Val Ser Phe Met Tyr Trp Phe Gln Gln Lys Pro Gly Gln Pro Pro
        35                  40                  45

Asn Leu Leu Ile Tyr Gly Ala Ser Asn Gln Gly Ser Gly Val Pro Ala
    50                  55                  60

Arg Phe Arg Gly Ser Gly Ser Gly Thr Asp Phe Ser Leu Asn Ile His
65                  70                  75                  80

Pro Met Glu Ala Asp Asp Thr Ala Met Tyr Phe Cys Gln Gln Thr Lys
                85                  90                  95

Glu Val Pro Tyr Thr Phe Gly Gly Gly Thr Lys Leu Glu Ile Lys
            100                 105                 110

<210> SEQ ID NO 58
<211> LENGTH: 106
<212> TYPE: PRT
<213> ORGANISM: Mus musculus

<400> SEQUENCE: 58

Gln Ile Val Leu Thr Gln Ser Pro Ala Ile Met Ser Ala Ser Pro Gly
1               5                   10                  15

Glu Lys Val Thr Ile Thr Cys Ser Ala Thr Ser Ser Val Ser Tyr Met
            20                  25                  30

His Trp Phe Arg Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
```

Gly Ser Gly Thr Ser Tyr Ser Leu Thr Ile Ser Arg Met Ala Ala Glu
65                  70                  75                  80

Asp Ala Ala Thr Tyr Tyr Cys Gln Gln Arg Ile Thr Tyr Pro Phe Thr
                85                  90                  95

Phe Gly Ser Gly Thr Lys Leu Glu Ile Thr
                100                 105

<210> SEQ ID NO 59
<211> LENGTH: 112
<212> TYPE: PRT
<213> ORGANISM: Mus musculus

<400> SEQUENCE: 59

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Asn Leu Leu His Ser
                20                  25                  30

Asn Gly Ile Thr Tyr Leu Tyr Trp Tyr Leu Gln Arg Pro Gly Gln Ser
            35                  40                  45

Pro Gln Leu Leu Ile Tyr Arg Ala Ser Thr Leu Ala Ser Gly Val Pro
    50                  55                  60

Asn Arg Phe Ser Gly Ser Glu Ser Gly Thr Asp Phe Thr Leu Arg Ile
65                  70                  75                  80

Ser Arg Val Glu Ala Glu Asp Val Gly Val Tyr Tyr Cys Ala Gln Leu
                85                  90                  95

Leu Glu Leu Pro His Thr Phe Gly Gly Gly Thr Lys Leu Glu Ile Lys
                100                 105                 110

<210> SEQ ID NO 60
<211> LENGTH: 123
<212> TYPE: PRT
<213> ORGANISM: Artificial Sequence
<220> FEATURE:
<223> OTHER INFORMATION: Synthetic

<400> SEQUENCE: 60

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Leu Lys Asp Thr
                20                  25                  30

Phe Leu His Trp Val Arg Gln Ala Pro Gly Gln Arg Leu Glu Trp Met
            35                  40                  45

Gly Arg Ile Asp Pro Ala Asn Gly Asn Ile Lys Tyr Asp Pro Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Pro Tyr Tyr Tyr Gly Ser Gly Tyr Arg Ile Phe Asp Val
                100                 105                 110

Trp Gly Gln Gly Thr Thr Val Thr Val Ser Ser
            115                 120

<210> SEQ ID NO 61
<211> LENGTH: 106
<212> TYPE: PRT
<213> ORGANISM: Artificial Sequence
<220> FEATURE:
<223> OTHER INFORMATION: Synthetic

<400> SEQUENCE: 61

Glu Ile Val Leu Thr Gln Ser Pro Ala Thr Leu Ser Leu Ser Pro Gly
1               5                   10                  15

Glu Arg Ala Thr Leu Ser Cys Ser Ala Phe Ser Ser Val Asn Tyr Met
            20                  25                  30

His Trp Tyr Gln Gln Lys Pro Gly Gln Ala Pro Arg Leu Leu Ile Tyr
        35                  40                  45

Thr Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Thr Tyr Pro Phe Thr
                85                  90                  95

Phe Gly Gln Gly Thr Lys Leu Glu Ile Lys
            100                 105

<210> SEQ ID NO 62
<211> LENGTH: 123
<212> TYPE: PRT
<213> ORGANISM: Artificial Sequence
<220> FEATURE:
<223> OTHER INFORMATION: Synthetic

<400> SEQUENCE: 62

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Leu Lys Asp Thr
            20                  25                  30

Phe Leu His Trp Val Arg Gln Ala Pro Gly Gln Gly Leu Glu Trp Met
        35                  40                  45

Gly Arg Ile Asp Pro Ala Asn Gly Asn Ile Lys Tyr Asp Pro Lys Phe
    50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Ser Pro Tyr Tyr Gly Ser Gly Tyr Arg Ile Phe Asp Val
            100                 105                 110

Trp Gly Gln Gly Thr Thr Val Thr Val Ser Ser
        115                 120

<210> SEQ ID NO 63
<211> LENGTH: 106
<212> TYPE: PRT
<213> ORGANISM: Artificial Sequence
<220> FEATURE:
<223> OTHER INFORMATION: Synthetic

<400> SEQUENCE: 63

Glu Ile Val Leu Thr Gln Ser Pro Ala Thr Leu Ser Leu Ser Pro Gly
1               5                   10                  15

Glu Arg Ala Thr Leu Ser Cys Ser Ala Phe Ser Ser Val Asn Tyr Met
            20                  25                  30

His Trp Tyr Gln Gln Lys Pro Gly Gln Ala Pro Arg Leu Leu Ile Tyr
        35                  40                  45

-continued

```
Thr Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Arg Ser Thr Tyr Pro Phe Thr
                85                  90                  95

Phe Gly Gln Gly Thr Lys Leu Glu Ile Lys
                100                 105

<210> SEQ ID NO 64
<211> LENGTH: 123
<212> TYPE: PRT
<213> ORGANISM: Artificial Sequence
<220> FEATURE:
<223> OTHER INFORMATION: Synthetic

<400> SEQUENCE: 64

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Asn Leu Lys Asp Thr
                20                  25                  30

Phe Leu His Trp Val Arg Gln Ala Pro Gly Gln Gly Leu Glu Trp Ile
            35                  40                  45

Gly Arg Ile Asp Pro Ala Asn Gly Asn Ile Lys Tyr Asp Pro Lys Phe
    50                  55                  60

Gln Gly Arg Ala Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Ser Pro Tyr Tyr Tyr Gly Ser Gly Tyr Arg Ile Phe Asp Val
                100                 105                 110

Trp Gly Gln Gly Thr Thr Val Thr Val Ser Ser
            115                 120

<210> SEQ ID NO 65
<211> LENGTH: 106
<212> TYPE: PRT
<213> ORGANISM: Artificial Sequence
<220> FEATURE:
<223> OTHER INFORMATION: Synthetic

<400> SEQUENCE: 65

Glu Ile Val Leu Thr Gln Ser Pro Ala Thr Leu Ser Ala Ser Pro Gly
1               5                   10                  15

Glu Arg Ala Thr Leu Ser Cys Ser Ala Phe Ser Ser Val Asn Tyr Met
                20                  25                  30

His Trp Tyr Gln Gln Lys Pro Gly Gln Ala Pro Arg Leu Leu Ile Tyr
            35                  40                  45

Thr Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Ser Met Glu Pro Glu
65                  70                  75                  80

Asp Phe Ala Val Tyr Tyr Cys Gln Gln Arg Ser Thr Tyr Pro Phe Thr
                85                  90                  95

Phe Gly Gln Gly Thr Lys Leu Glu Ile Lys
                100                 105

<210> SEQ ID NO 66
```

<211> LENGTH: 123
<212> TYPE: PRT
<213> ORGANISM: Artificial Sequence
<220> FEATURE:
<223> OTHER INFORMATION: Synthetic

<400> SEQUENCE: 66

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Asn Leu Lys Asp Thr
            20                  25                  30

Phe Leu His Trp Val Lys Gln Ala Pro Gly Gln Gly Leu Glu Trp Ile
        35                  40                  45

Gly Arg Ile Asp Pro Ala Asn Gly Asn Ile Lys Tyr Asp Pro Lys Phe
    50                  55                  60

Gln Gly Arg Ala Thr Leu Thr Ala Asp Thr Ser Ala Ser Thr Ala Tyr
65                  70                  75                  80

Leu Glu Leu Ser Ser Leu Arg Ser Glu Asp Thr Ala Val Tyr Tyr Cys
                85                  90                  95

Ala Asn Ser Pro Tyr Tyr Tyr Gly Ser Gly Tyr Arg Ile Phe Asp Val
            100                 105                 110

Trp Gly Gln Gly Thr Thr Val Thr Val Ser Ser
        115                 120

<210> SEQ ID NO 67
<211> LENGTH: 106
<212> TYPE: PRT
<213> ORGANISM: Artificial Sequence
<220> FEATURE:
<223> OTHER INFORMATION: Synthetic

<400> SEQUENCE: 67

Glu Ile Val Leu Thr Gln Ser Pro Ala Thr Leu Ser Ala Ser Pro Gly
1               5                   10                  15

Glu Arg Val Thr Ile Ser Cys Ser Ala Phe Ser Ser Val Asn Tyr Met
            20                  25                  30

His Trp Tyr Gln Gln Lys Pro Gly Gln Ala Pro Arg Leu Leu Ile Tyr
        35                  40                  45

Thr Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Ser Met Glu Pro Glu
65                  70                  75                  80

Asp Phe Ala Val Tyr Tyr Cys Gln Gln Arg Ser Thr Tyr Pro Phe Thr
                85                  90                  95

Phe Gly Gln Gly Thr Lys Leu Glu Ile Lys
            100                 105

<210> SEQ ID NO 68
<211> LENGTH: 121
<212> TYPE: PRT
<213> ORGANISM: Artificial Sequence
<220> FEATURE:
<223> OTHER INFORMATION: Synthetic

<400> SEQUENCE: 68

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Lys Tyr
            20                  25                  30

-continued

Trp Met Asn Trp Val Arg Gln Ala Pro Gly Lys Gly Leu Glu Trp Val
            35                  40                  45

Gly Glu Ile Arg Leu Lys Ser Asn Lys Tyr Gly Thr His Tyr Ala Glu
 50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                85                  90                  95

Tyr Cys Thr Thr Gln Leu Asp Leu Tyr Trp Phe Phe Asp Val Trp Gly
                100                 105                 110

Gln Gly Thr Thr Val Thr Val Ser Ser
            115                 120

<210> SEQ ID NO 69
<211> LENGTH: 107
<212> TYPE: PRT
<213> ORGANISM: Artificial Sequence
<220> FEATURE:
<223> OTHER INFORMATION: Synthetic

<400> SEQUENCE: 69

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asp Tyr
            20                  25                  30

Leu His Trp Tyr Gln Gln Lys Pro Gly Gln Ala Pro Arg Leu Leu Ile
        35                  40                  45

Tyr Tyr Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Leu Pro Leu
                85                  90                  95

Thr Phe Gly Gly Gly Thr Lys Leu Glu Ile Lys
            100                 105

<210> SEQ ID NO 70
<211> LENGTH: 121
<212> TYPE: PRT
<213> ORGANISM: Artificial Sequence
<220> FEATURE:
<223> OTHER INFORMATION: Synthetic

<400> SEQUENCE: 70

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Lys Tyr
            20                  25                  30

Trp Met Asn Trp Val Arg Gln Ser Pro Gly Lys Gly Leu Glu Trp Val
            35                  40                  45

Gly Glu Ile Arg Leu Lys Ser Asn Lys Tyr Gly Thr His Tyr Ala Glu
 50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                85                  90                  95

Tyr Cys Thr Thr Gln Leu Asp Leu Tyr Trp Phe Phe Asp Val Trp Gly
                100                 105                 110

Gln Gly Thr Thr Val Thr Val Ser Ser
        115                 120

<210> SEQ ID NO 71
<211> LENGTH: 107
<212> TYPE: PRT
<213> ORGANISM: Artificial Sequence
<220> FEATURE:
<223> OTHER INFORMATION: Synthetic

<400> SEQUENCE: 71

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asp Tyr
            20                  25                  30

Leu His Trp Tyr Gln Gln Lys Pro Gly Gln Ser Pro Arg Leu Leu Ile
        35                  40                  45

Tyr Tyr Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Phe Cys Gln Asn Gly His Ser Leu Pro Leu
                85                  90                  95

Thr Phe Gly Gly Gly Thr Lys Leu Glu Ile Lys
            100                 105

<210> SEQ ID NO 72
<211> LENGTH: 121
<212> TYPE: PRT
<213> ORGANISM: Artificial Sequence
<220> FEATURE:
<223> OTHER INFORMATION: Synthetic

<400> SEQUENCE: 72

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Lys Tyr
            20                  25                  30

Trp Met Asn Trp Val Arg Gln Ser Pro Gly Lys Gly Leu Glu Trp Val
        35                  40                  45

Ala Glu Ile Arg Leu Lys Ser Asn Lys Tyr Gly Thr His Tyr Ala Glu
    50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Lys Thr Glu Asp Thr Ala Val Tyr
                85                  90                  95

Tyr Cys Thr Thr Gln Leu Asp Leu Tyr Trp Phe Phe Asp Val Trp Gly
            100                 105                 110

Gln Gly Thr Thr Val Thr Val Ser Ser
        115                 120

<210> SEQ ID NO 73
<211> LENGTH: 107
<212> TYPE: PRT
<213> ORGANISM: Artificial Sequence
<220> FEATURE:
<223> OTHER INFORMATION: Synthetic

<400> SEQUENCE: 73

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asp Tyr
                20                  25                  30

Leu His Trp Tyr Gln Gln Lys Pro Gly Gln Ser Pro Arg Leu Leu Ile
            35                  40                  45

Tyr Tyr Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Val Glu Pro
65                  70                  75                  80

Glu Asp Phe Ala Val Tyr Phe Cys Gln Asn Gly His Ser Leu Pro Leu
                85                  90                  95

Thr Phe Gly Gly Gly Thr Lys Leu Glu Ile Lys
            100                 105

<210> SEQ ID NO 74
<211> LENGTH: 121
<212> TYPE: PRT
<213> ORGANISM: Artificial Sequence
<220> FEATURE:
<223> OTHER INFORMATION: Synthetic

<400> SEQUENCE: 74

Glu Val Gln Leu Val Glu Ser Gly Gly Leu Val Lys Pro Gly Gly
1               5                   10                  15

Ser Met Arg Leu Ser Cys Ala Ala Ser Gly Phe Thr Phe Ser Lys Tyr
                20                  25                  30

Trp Met Asn Trp Val Arg Gln Ser Pro Gly Lys Gly Leu Glu Trp Val
            35                  40                  45

Ala Glu Ile Arg Leu Lys Ser Asn Lys Tyr Gly Thr His Tyr Ala Glu
    50                  55                  60

Ser Val Lys Gly Arg Phe Thr Ile Ser Arg Asp Asp Ser Lys Asn Thr
65                  70                  75                  80

Val Tyr Leu Gln Met Asn Ser Leu Lys Thr Glu Asp Thr Ala Val Tyr
                85                  90                  95

Tyr Cys Thr Thr Gln Leu Asp Leu Tyr Trp Phe Phe Asp Val Trp Gly
            100                 105                 110

Gln Gly Thr Thr Val Thr Val Ser Ser
        115                 120

<210> SEQ ID NO 75
<211> LENGTH: 107
<212> TYPE: PRT
<213> ORGANISM: Artificial Sequence
<220> FEATURE:
<223> OTHER INFORMATION: Synthetic

<400> SEQUENCE: 75

Glu Ile Val Met Thr Gln Ser Pro Ala Thr Leu Ser Val Ser Pro Gly
1               5                   10                  15

Glu Arg Val Thr Leu Ser Cys Arg Ala Ser Gln Ser Ile Ser Asp Tyr
                20                  25                  30

Leu His Trp Tyr Gln Gln Lys Pro Gly Gln Ser Pro Arg Leu Leu Ile
            35                  40                  45

Tyr Tyr Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Val Glu Pro
65                  70                  75                  80

Glu Asp Phe Ala Val Tyr Phe Cys Gln Asn Gly His Ser Leu Pro Leu
                85                  90                  95

Thr Phe Gly Gly Gly Thr Lys Leu Glu Ile Lys
            100                 105

<210> SEQ ID NO 76
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be Gln or Glu.
<220> FEATURE:
<221> NAME/KEY: misc_feature
<222> LOCATION: (6)..(6)
<223> OTHER INFORMATION: Xaa can be Glu or Gln.
<220> FEATURE:
<221> NAME/KEY: misc_feature
<222> LOCATION: (9)..(12)
<223> OTHER INFORMATION: Xaa in location 9 can be Gly or Ala, Xaa in
      location 10 can be Gly or Glu, Xaa in location 11 can be Leu or
      Val, Xaa in location 12 can be Val or Lys.
<220> FEATURE:
<221> NAME/KEY: misc_feature
<222> LOCATION: (16)..(16)
<223> OTHER INFORMATION: Xaa can be Gly or Ala.
<220> FEATURE:
<221> NAME/KEY: misc_feature
<222> LOCATION: (18)..(20)
<223> OTHER INFORMATION: Xaa in location 18 can be Leu, Met or Val, Xaa
      in location 19 can be Arg or Lys, Xaa in location 20 can be Val
      or Leu.
<220> FEATURE:
<221> NAME/KEY: misc_feature
<222> LOCATION: (23)..(23)
<223> OTHER INFORMATION: Xaa can be Ala or Lys.
<220> FEATURE:
<221> NAME/KEY: misc_feature
<222> LOCATION: (27)..(30)
<223> OTHER INFORMATION: Xaa in location 27 can be Phe or Tyr, Xaa in
      location 28 can be Asn or Thr, Xaa in location 29 can be Phe or
      Leu, Xaa in location 30 can be Ser or Lys.

<400> SEQUENCE: 76

Xaa Val Gln Leu Val Xaa Ser Gly Xaa Xaa Xaa Xaa Lys Pro Gly Xaa
1               5                   10                  15

Ser Xaa Xaa Xaa Ser Cys Xaa Ala Ser Gly Xaa Xaa Xaa Xaa
            20                  25                  30

<210> SEQ ID NO 77
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be Arg or Lys.
<220> FEATURE:
<221> NAME/KEY: misc_feature
<222> LOCATION: (5)..(5)
<223> OTHER INFORMATION: Xaa can be Ala or Ser.
<220> FEATURE:
<221> NAME/KEY: misc_feature
<222> LOCATION: (8)..(9)
<223> OTHER INFORMATION: Xaa in location 8 can be Lys or Gln, Xaa in
      location 9 can be Arg or Gly.
<220> FEATURE:
<221> NAME/KEY: misc_feature

```
<222> LOCATION: (13)..(14)
<223> OTHER INFORMATION: Xaa in location 13 can be Met, Ile or Val, Xaa
      in location 14 can be Gly or Ala.

<400> SEQUENCE: 77

Trp Val Xaa Gln Xaa Pro Gly Xaa Xaa Leu Glu Trp Xaa Xaa
1               5                   10

<210> SEQ ID NO 78
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa in location 1 can be Arg or Lys, Xaa in
      location 2 can be Val, Ala or Phe.
<220> FEATURE:
<221> NAME/KEY: misc_feature
<222> LOCATION: (4)..(6)
<223> OTHER INFORMATION: Xaa in location 4 can be Ile or Leu, Xaa in
      location 5 can be Ser or Thr, Xaa in location 6 can be Arg or Ala.
<220> FEATURE:
<221> NAME/KEY: misc_feature
<222> LOCATION: (8)..(8)
<223> OTHER INFORMATION: Xaa can be Asp or Thr.
<220> FEATURE:
<221> NAME/KEY: misc_feature
<222> LOCATION: (10)..(11)
<223> OTHER INFORMATION: Xaa in location 10 can be Lys, Ala or Ser, Xaa
      in location 11 can be Ser or Asn.
<220> FEATURE:
<221> NAME/KEY: misc_feature
<222> LOCATION: (13)..(13)
<223> OTHER INFORMATION: Xaa can be Leu, Val or Ala.
<220> FEATURE:
<221> NAME/KEY: misc_feature
<222> LOCATION: (15)..(18)
<223> OTHER INFORMATION: Xaa in location 15 can be Met or Leu, Xaa in
      location 16 can be Gln or Glu, Xaa in location 17 can be Met or
      Leu, Xaa in location 18 can be Ser, Ile or Asn.
<220> FEATURE:
<221> NAME/KEY: misc_feature
<222> LOCATION: (21)..(22)
<223> OTHER INFORMATION: Xaa in location 21 can be Arg or Lys, Xaa in
      location 22 can be Ser or Thr.
<220> FEATURE:
<221> NAME/KEY: misc_feature
<222> LOCATION: (31)..(32)
<223> OTHER INFORMATION: Xaa in location 31 can be Ala or Thr, Xaa in
      location 32 can be Arg, Asn or Thr.

<400> SEQUENCE: 78

Xaa Xaa Thr Xaa Xaa Xaa Asp Xaa Ser Xaa Xaa Thr Xaa Tyr Xaa Xaa
1               5                   10                  15

Xaa Xaa Ser Leu Xaa Xaa Glu Asp Thr Ala Val Tyr Tyr Cys Xaa Xaa
                20                  25                  30

<210> SEQ ID NO 79
<211> LENGTH: 11
<212> TYPE: PRT
<213> ORGANISM: Artificial Sequence
<220> FEATURE:
<223> OTHER INFORMATION: Synthetic

<400> SEQUENCE: 79

Trp Gly Gln Gly Thr Thr Val Thr Val Ser Ser
1               5                   10

<210> SEQ ID NO 80
```

```
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be Glu or Gln.
<220> FEATURE:
<221> NAME/KEY: misc_feature
<222> LOCATION: (4)..(4)
<223> OTHER INFORMATION: Xaa can be Leu or Met.
<220> FEATURE:
<221> NAME/KEY: misc_feature
<222> LOCATION: (12)..(13)
<223> OTHER INFORMATION: Xaa in location 12 can be Ser or Thr, Xaa in
      location 13 can be leu, Val or Ala.
<220> FEATURE:
<221> NAME/KEY: misc_feature
<222> LOCATION: (19)..(19)
<223> OTHER INFORMATION: Xaa can be Ala or Val.
<220> FEATURE:
<221> NAME/KEY: misc_feature
<222> LOCATION: (21)..(22)
<223> OTHER INFORMATION: Xaa in location 21 can be Leu or Ile, Xaa in
      location 22 can be Ser or Thr.

<400> SEQUENCE: 80

Xaa Ile Val Xaa Thr Gln Ser Pro Ala Thr Leu Xaa Xaa Ser Pro Gly
1               5                   10                  15

Glu Arg Xaa Thr Xaa Xaa Cys
            20

<210> SEQ ID NO 81
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: Xaa can be Ala or Ser.
<220> FEATURE:
<221> NAME/KEY: misc_feature
<222> LOCATION: (11)..(11)
<223> OTHER INFORMATION: Xaa can be Arg or Lys.

<400> SEQUENCE: 81

Trp Tyr Gln Gln Lys Pro Gly Gln Xaa Pro Xaa Leu Leu Ile Tyr
1               5                   10                  15

<210> SEQ ID NO 82
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be Ile or Val.
<220> FEATURE:
<221> NAME/KEY: misc_feature
<222> LOCATION: (4)..(4)
<223> OTHER INFORMATION: Xaa can be Ala or Thr.
<220> FEATURE:
<221> NAME/KEY: misc_feature
<222> LOCATION: (14)..(15)
<223> OTHER INFORMATION: Xaa in location 14 can be Asp or Ser, Xaa in
      location 15 can be Phe or Tyr.
<220> FEATURE:
<221> NAME/KEY: misc_feature
```

```
<222> LOCATION: (22)..(22)
<223> OTHER INFORMATION: Xaa can be Leu, Met or Val.
<220> FEATURE:
<221> NAME/KEY: misc_feature
<222> LOCATION: (31)..(31)
<223> OTHER INFORMATION: Xaa can be Tyr or Phe.

<400> SEQUENCE: 82

Gly Xaa Pro Xaa Arg Phe Ser Gly Ser Gly Ser Gly Thr Xaa Xaa Thr
1               5                   10                  15

Leu Thr Ile Ser Ser Xaa Glu Pro Glu Asp Phe Ala Val Tyr Xaa Cys
            20                  25                  30

<210> SEQ ID NO 83
<211> LENGTH: 10
<212> TYPE: PRT
<213> ORGANISM: Artificial Sequence
<220> FEATURE:
<223> OTHER INFORMATION: Synthetic

<400> SEQUENCE: 83

Phe Gly Gln Gly Thr Lys Leu Glu Ile Lys
1               5                   10

<210> SEQ ID NO 84
<211> LENGTH: 30
<212> TYPE: PRT
<213> ORGANISM: Artificial Sequence
<220> FEATURE:
<223> OTHER INFORMATION: Synthetic

<400> SEQUENCE: 84

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Leu Lys
            20                  25                  30

<210> SEQ ID NO 85
<211> LENGTH: 30
<212> TYPE: PRT
<213> ORGANISM: Artificial Sequence
<220> FEATURE:
<223> OTHER INFORMATION: Synthetic

<400> SEQUENCE: 85

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Asn Leu Lys
            20                  25                  30

<210> SEQ ID NO 86
<211> LENGTH: 30
<212> TYPE: PRT
<213> ORGANISM: Artificial Sequence
<220> FEATURE:
<223> OTHER INFORMATION: Synthetic

<400> SEQUENCE: 86

Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Asn Leu Lys
            20                  25                  30

<210> SEQ ID NO 87
<211> LENGTH: 14
```

```
<212> TYPE: PRT
<213> ORGANISM: Artificial Sequence
<220> FEATURE:
<223> OTHER INFORMATION: Synthetic

<400> SEQUENCE: 87

Trp Val Arg Gln Ala Pro Gly Gln Arg Leu Glu Trp Met Gly
1               5                   10

<210> SEQ ID NO 88
<211> LENGTH: 14
<212> TYPE: PRT
<213> ORGANISM: Artificial Sequence
<220> FEATURE:
<223> OTHER INFORMATION: Synthetic

<400> SEQUENCE: 88

Trp Val Arg Gln Ala Pro Gly Gln Gly Leu Glu Trp Met Gly
1               5                   10

<210> SEQ ID NO 89
<211> LENGTH: 14
<212> TYPE: PRT
<213> ORGANISM: Artificial Sequence
<220> FEATURE:
<223> OTHER INFORMATION: Synthetic

<400> SEQUENCE: 89

Trp Val Arg Gln Ala Pro Gly Gln Gly Leu Glu Trp Ile Gly
1               5                   10

<210> SEQ ID NO 90
<211> LENGTH: 14
<212> TYPE: PRT
<213> ORGANISM: Artificial Sequence
<220> FEATURE:
<223> OTHER INFORMATION: Synthetic

<400> SEQUENCE: 90

Trp Val Lys Gln Ala Pro Gly Gln Gly Leu Glu Trp Ile Gly
1               5                   10

<210> SEQ ID NO 91
<211> LENGTH: 32
<212> TYPE: PRT
<213> ORGANISM: Artificial Sequence
<220> FEATURE:
<223> OTHER INFORMATION: Synthetic

<400> SEQUENCE: 91

Arg Val Thr Ile Thr Arg Asp Thr Ser Ala Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 92
<211> LENGTH: 32
<212> TYPE: PRT
<213> ORGANISM: Artificial Sequence
<220> FEATURE:
<223> OTHER INFORMATION: Synthetic

<400> SEQUENCE: 92

Arg Val Thr Ile Thr Ala Asp Thr Ser Ala Ser Thr Ala Tyr Met Glu
1               5                   10                  15

Leu Ser Ser Leu Arg Ser Glu Asp Thr Ala Val Tyr Tyr Cys Ala Asn
```

<210> SEQ ID NO 93
<211> LENGTH: 32
<212> TYPE: PRT
<213> ORGANISM: Artificial Sequence
<220> FEATURE:
<223> OTHER INFORMATION: Synthetic

<400> SEQUENCE: 93

Arg Ala Thr Ile Thr Ala Asp Thr Ser Ala Ser Thr Ala Tyr Met Glu
1               5                   10                  15

Leu Ser Ser Leu Arg Ser Glu Asp Thr Ala Val Tyr Tyr Cys Ala Asn
            20                  25                  30

<210> SEQ ID NO 94
<211> LENGTH: 32
<212> TYPE: PRT
<213> ORGANISM: Artificial Sequence
<220> FEATURE:
<223> OTHER INFORMATION: Synthetic

<400> SEQUENCE: 94

Arg Ala Thr Leu Thr Ala Asp Thr Ser Ala Ser Thr Ala Tyr Leu Glu
1               5                   10                  15

Leu Ser Ser Leu Arg Ser Glu Asp Thr Ala Val Tyr Tyr Cys Ala Asn
            20                  25                  30

<210> SEQ ID NO 95
<211> LENGTH: 32
<212> TYPE: PRT
<213> ORGANISM: Artificial Sequence
<220> FEATURE:
<223> OTHER INFORMATION: Synthetic

<400> SEQUENCE: 95

Arg Val Thr Ile Thr Ala Asp Thr Ser Ala Asn Thr Ala Tyr Met Glu
1               5                   10                  15

Leu Ile Ser Leu Arg Ser Glu Asp Thr Ala Val Tyr Tyr Cys Ala Asn
            20                  25                  30

<210> SEQ ID NO 96
<211> LENGTH: 32
<212> TYPE: PRT
<213> ORGANISM: Artificial Sequence
<220> FEATURE:
<223> OTHER INFORMATION: Synthetic

<400> SEQUENCE: 96

Arg Ala Thr Ile Thr Ala Asp Thr Ser Ala Asn Thr Ala Tyr Met Glu
1               5                   10                  15

Leu Ile Ser Leu Arg Ser Glu Asp Thr Ala Val Tyr Tyr Cys Ala Asn
            20                  25                  30

<210> SEQ ID NO 97
<211> LENGTH: 32
<212> TYPE: PRT
<213> ORGANISM: Artificial Sequence
<220> FEATURE:
<223> OTHER INFORMATION: Synthetic

<400> SEQUENCE: 97

Lys Ala Thr Leu Thr Ala Asp Thr Ser Ala Asn Thr Ala Tyr Leu Glu
1               5                   10                  15

Leu Ile Ser Leu Arg Ser Glu Asp Thr Ala Val Tyr Tyr Cys Ala Asn
            20                  25                  30

<210> SEQ ID NO 98
<211> LENGTH: 23
<212> TYPE: PRT
<213> ORGANISM: Artificial Sequence
<220> FEATURE:
<223> OTHER INFORMATION: Synthetic

<400> SEQUENCE: 98

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 99
<211> LENGTH: 23
<212> TYPE: PRT
<213> ORGANISM: Artificial Sequence
<220> FEATURE:
<223> OTHER INFORMATION: Synthetic

<400> SEQUENCE: 99

Glu Ile Val Leu Thr Gln Ser Pro Ala Thr Leu Ser Ala Ser Pro Gly
1               5                   10                  15

Glu Arg Ala Thr Leu Ser Cys
            20

<210> SEQ ID NO 100
<211> LENGTH: 23
<212> TYPE: PRT
<213> ORGANISM: Artificial Sequence
<220> FEATURE:
<223> OTHER INFORMATION: Synthetic

<400> SEQUENCE: 100

Glu Ile Val Leu Thr Gln Ser Pro Ala Thr Leu Ser Ala Ser Pro Gly
1               5                   10                  15

Glu Arg Val Thr Ile Ser Cys
            20

<210> SEQ ID NO 101
<211> LENGTH: 23
<212> TYPE: PRT
<213> ORGANISM: Artificial Sequence
<220> FEATURE:
<223> OTHER INFORMATION: Synthetic

<400> SEQUENCE: 101

Gln Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 102
<211> LENGTH: 23
<212> TYPE: PRT
<213> ORGANISM: Artificial Sequence
<220> FEATURE:
<223> OTHER INFORMATION: Synthetic

<400> SEQUENCE: 102

Gln Ile Val Leu Thr Gln Ser Pro Ala Thr Leu Ser Ala Ser Pro Gly
1               5                   10                  15

```
Glu Arg Ala Thr Leu Ser Cys
            20

<210> SEQ ID NO 103
<211> LENGTH: 23
<212> TYPE: PRT
<213> ORGANISM: Artificial Sequence
<220> FEATURE:
<223> OTHER INFORMATION: Synthetic

<400> SEQUENCE: 103

Gln Ile Val Leu Thr Gln Ser Pro Ala Thr Leu Ser Ala Ser Pro Gly
1               5                   10                  15

Glu Arg Val Thr Ile Thr Cys
            20

<210> SEQ ID NO 104
<211> LENGTH: 15
<212> TYPE: PRT
<213> ORGANISM: Artificial Sequence
<220> FEATURE:
<223> OTHER INFORMATION: Synthetic

<400> SEQUENCE: 104

Trp Tyr Gln Gln Lys Pro Gly Gln Ala Pro Arg Leu Leu Ile Tyr
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Synthetic

<400> SEQUENCE: 105

Trp Tyr Gln Gln Lys Pro Gly Gln Ala Pro Lys Leu Leu Ile Tyr
1               5                   10                  15

<210> SEQ ID NO 106
<211> LENGTH: 32
<212> TYPE: PRT
<213> ORGANISM: Artificial Sequence
<220> FEATURE:
<223> OTHER INFORMATION: Synthetic

<400> SEQUENCE: 106

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 107
<211> LENGTH: 32
<212> TYPE: PRT
<213> ORGANISM: Artificial Sequence
<220> FEATURE:
<223> OTHER INFORMATION: Synthetic

<400> SEQUENCE: 107

Gly Ile Pro Ala Arg Phe Ser Gly Ser Gly Ser Gly Thr Asp Tyr Thr
1               5                   10                  15

Leu Thr Ile Ser Ser Leu Glu Pro Glu Asp Phe Ala Val Tyr Tyr Cys
            20                  25                  30
```

<210> SEQ ID NO 108
<211> LENGTH: 32
<212> TYPE: PRT
<213> ORGANISM: Artificial Sequence
<220> FEATURE:
<223> OTHER INFORMATION: Synthetic

<400> SEQUENCE: 108

```
Gly Ile Pro Ala Arg Phe Ser Gly Ser Gly Thr Asp Tyr Thr
1               5                   10                  15

Leu Thr Ile Ser Ser Met Glu Pro Glu Asp Phe Ala Val Tyr Tyr Cys
            20                  25                  30
```

<210> SEQ ID NO 109
<211> LENGTH: 32
<212> TYPE: PRT
<213> ORGANISM: Artificial Sequence
<220> FEATURE:
<223> OTHER INFORMATION: Synthetic

<400> SEQUENCE: 109

```
Gly Ile Pro Thr Arg Phe Ser Gly Ser Gly Thr Ser Tyr Thr
1               5                   10                  15

Leu Thr Ile Ser Ser Leu Glu Pro Glu Asp Phe Ala Val Tyr Tyr Cys
            20                  25                  30
```

<210> SEQ ID NO 110
<211> LENGTH: 32
<212> TYPE: PRT
<213> ORGANISM: Artificial Sequence
<220> FEATURE:
<223> OTHER INFORMATION: Synthetic

<400> SEQUENCE: 110

```
Gly Val Pro Thr Arg Phe Ser Gly Ser Gly Thr Ser Tyr Thr
1               5                   10                  15

Leu Thr Ile Ser Ser Met Glu Pro Glu Asp Phe Ala Val Tyr Tyr Cys
            20                  25                  30
```

<210> SEQ ID NO 111
<211> LENGTH: 106
<212> TYPE: PRT
<213> ORGANISM: Artificial Sequence
<220> FEATURE:
<223> OTHER INFORMATION: Synthetic

<400> SEQUENCE: 111

```
Glu Ile Val Leu Thr Gln Ser Pro Ala Thr Leu Ser Leu Ser Pro Gly
1               5                   10                  15

Glu Arg Ala Thr Leu Ser Cys Ser Ala Phe Ser Ser Val Asn Tyr Met
            20                  25                  30

His Trp Tyr Gln Gln Lys Pro Gly Gln Ser Pro Arg Leu Leu Ile Tyr
        35                  40                  45

Thr Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Arg Ser Thr Tyr Pro Phe Thr
                85                  90                  95

Phe Gly Gln Gly Thr Lys Leu Glu Ile Lys
            100                 105
```

-continued

<210> SEQ ID NO 112
<211> LENGTH: 106
<212> TYPE: PRT
<213> ORGANISM: Artificial Sequence
<220> FEATURE:
<223> OTHER INFORMATION: Synthetic

<400> SEQUENCE: 112

Glu Ile Val Leu Thr Gln Ser Pro Ala Thr Leu Ser Leu Ser Pro Gly
1               5                   10                  15

Glu Arg Ala Thr Leu Ser Cys Ser Ala Phe Ser Ser Val Asn Tyr Met
            20                  25                  30

His Trp Tyr Gln Gln Lys Pro Gly Gln Ala Pro Arg Leu Leu Ile Tyr
        35                  40                  45

Thr Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Arg Ser Thr Tyr Pro Phe Thr
                85                  90                  95

Phe Gly Gln Gly Thr Lys Leu Glu Ile Lys
            100                 105

<210> SEQ ID NO 113
<211> LENGTH: 121
<212> TYPE: PRT
<213> ORGANISM: Homo sapiens

<400> SEQUENCE: 113

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Lys Ser Tyr
            20                  25                  30

Glu Met His Trp Val Arg Gln Ala Pro Gly Gln Gly Leu Glu Trp Met
        35                  40                  45

Gly Arg Ile Asn Pro Ser Val Gly Ser Thr Trp Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Arg Glu Gly Gly Thr Glu Tyr Leu Arg Lys Trp Gly
            100                 105                 110

Gln Gly Thr Leu Val Thr Val Ser Ser
        115                 120

<210> SEQ ID NO 114
<211> LENGTH: 107
<212> TYPE: PRT
<213> ORGANISM: Homo sapiens

<400> SEQUENCE: 114

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ala Ser Ser
            20                  25                  30

Tyr Leu Ala Trp Tyr Gln Gln Lys Pro Gly Gln Ala Pro Arg Leu Leu
        35                  40                  45

```
Ile Tyr Gly Ala Ser Asn Arg His Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr His Asn Ala Ile
                 85                  90                  95

Thr Phe Gly Gly Gly Thr Lys Val Glu Ile Lys
                100                 105

<210> SEQ ID NO 115
<211> LENGTH: 30
<212> TYPE: PRT
<213> ORGANISM: Artificial Sequence
<220> FEATURE:
<223> OTHER INFORMATION: Synthetic

<400> SEQUENCE: 115

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Leu Lys
                 20                  25                  30

<210> SEQ ID NO 116
<211> LENGTH: 32
<212> TYPE: PRT
<213> ORGANISM: Artificial Sequence
<220> FEATURE:
<223> OTHER INFORMATION: Synthetic

<400> SEQUENCE: 116

Arg Val Thr Leu Thr Ala Asp Thr Ser Ser Asn Thr Ala Tyr Met Glu
 1               5                  10                  15

Leu Ser Ser Leu Arg Ser Glu Asp Thr Ala Val Tyr Tyr Cys Ala Asn
                 20                  25                  30

<210> SEQ ID NO 117
<211> LENGTH: 32
<212> TYPE: PRT
<213> ORGANISM: Artificial Sequence
<220> FEATURE:
<223> OTHER INFORMATION: Synthetic

<400> SEQUENCE: 117

Arg Val Thr Ile Thr Ala Asp Thr Ser Ser Asn Thr Ala Tyr Met Glu
 1               5                  10                  15

Leu Ser Ser Leu Arg Ser Glu Asp Thr Ala Val Tyr Tyr Cys Ala Asn
                 20                  25                  30

<210> SEQ ID NO 118
<211> LENGTH: 11
<212> TYPE: PRT
<213> ORGANISM: Artificial Sequence
<220> FEATURE:
<223> OTHER INFORMATION: Synthetic

<400> SEQUENCE: 118

Trp Gly Gln Gly Thr Leu Val Thr Val Ser Ser
 1               5                  10

<210> SEQ ID NO 119
<211> LENGTH: 30
<212> TYPE: PRT
<213> ORGANISM: Artificial Sequence
<220> FEATURE:
```

<223> OTHER INFORMATION: Synthetic

<400> SEQUENCE: 119

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 120
<211> LENGTH: 30
<212> TYPE: PRT
<213> ORGANISM: Artificial Sequence
<220> FEATURE:
<223> OTHER INFORMATION: Synthetic

<400> SEQUENCE: 120

Glu Val Gln Leu Val Glu Ser Gly Gly Gly Leu Val Lys Pro Gly Gly
1               5                   10                  15

Ser Met Arg Leu Ser Cys Ala Ala Ser Gly Phe Thr Phe Ser
            20                  25                  30

<210> SEQ ID NO 121
<211> LENGTH: 14
<212> TYPE: PRT
<213> ORGANISM: Artificial Sequence
<220> FEATURE:
<223> OTHER INFORMATION: Synthetic

<400> SEQUENCE: 121

Trp Val Arg Gln Ala Pro Gly Lys Gly Leu Glu Trp Val Gly
1               5                   10

<210> SEQ ID NO 122
<211> LENGTH: 14
<212> TYPE: PRT
<213> ORGANISM: Artificial Sequence
<220> FEATURE:
<223> OTHER INFORMATION: Synthetic

<400> SEQUENCE: 122

Trp Val Arg Gln Ser Pro Gly Lys Gly Leu Glu Trp Val Gly
1               5                   10

<210> SEQ ID NO 123
<211> LENGTH: 14
<212> TYPE: PRT
<213> ORGANISM: Artificial Sequence
<220> FEATURE:
<223> OTHER INFORMATION: Synthetic

<400> SEQUENCE: 123

Trp Val Arg Gln Ser Pro Gly Lys Gly Leu Glu Trp Val Ala
1               5                   10

<210> SEQ ID NO 124
<211> LENGTH: 32
<212> TYPE: PRT
<213> ORGANISM: Artificial Sequence
<220> FEATURE:
<223> OTHER INFORMATION: Synthetic

<400> SEQUENCE: 124

Arg Phe Thr Ile Ser Arg Asp Asp Ser Lys Asn Thr Leu Tyr Leu Gln
1               5                   10                  15

Met Asn Ser Leu Lys Thr Glu Asp Thr Ala Val Tyr Tyr Cys Thr Thr

```
                    20                  25                  30

<210> SEQ ID NO 125
<211> LENGTH: 32
<212> TYPE: PRT
<213> ORGANISM: Artificial Sequence
<220> FEATURE:
<223> OTHER INFORMATION: Synthetic

<400> SEQUENCE: 125

Arg Phe Thr Ile Ser Arg Asp Asp Ser Lys Asn Thr Val Tyr Leu Gln
1               5                   10                  15

Met Asn Ser Leu Lys Thr Glu Asp Thr Ala Val Tyr Tyr Cys Thr Thr
                20                  25                  30

<210> SEQ ID NO 126
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be Thr or Leu.

<400> SEQUENCE: 126

Trp Gly Gln Gly Thr Xaa Val Thr Val Ser Ser
1               5                   10

<210> SEQ ID NO 127
<211> LENGTH: 23
<212> TYPE: PRT
<213> ORGANISM: Artificial Sequence
<220> FEATURE:
<223> OTHER INFORMATION: Synthetic

<400> SEQUENCE: 127

Glu Ile Val Leu Thr Gln Ser Pro Ala Thr Leu Ser Val Ser Pro Gly
1               5                   10                  15

Glu Arg Ala Thr Leu Ser Cys
                20

<210> SEQ ID NO 128
<211> LENGTH: 23
<212> TYPE: PRT
<213> ORGANISM: Artificial Sequence
<220> FEATURE:
<223> OTHER INFORMATION: Synthetic

<400> SEQUENCE: 128

Glu Ile Val Met Thr Gln Ser Pro Ala Thr Leu Ser Val Ser Pro Gly
1               5                   10                  15

Glu Arg Val Thr Leu Ser Cys
                20

<210> SEQ ID NO 129
<211> LENGTH: 23
<212> TYPE: PRT
<213> ORGANISM: Artificial Sequence
<220> FEATURE:
<223> OTHER INFORMATION: Synthetic

<400> SEQUENCE: 129

Glu Ile Val Leu Thr Gln Ser Pro Ala Thr Leu Thr Leu Ser Pro Gly
1               5                   10                  15
```

Glu Arg Ala Thr Leu Ser Cys
            20

<210> SEQ ID NO 130
<211> LENGTH: 15
<212> TYPE: PRT
<213> ORGANISM: Artificial Sequence
<220> FEATURE:
<223> OTHER INFORMATION: Synthetic

<400> SEQUENCE: 130

Trp Tyr Gln Gln Lys Pro Gly Gln Ser Pro Arg Leu Leu Ile Tyr
1               5                   10                  15

<210> SEQ ID NO 131
<211> LENGTH: 30
<212> TYPE: PRT
<213> ORGANISM: Artificial Sequence
<220> FEATURE:
<223> OTHER INFORMATION: Synthetic

<400> SEQUENCE: 131

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Lys
            20                  25                  30

<210> SEQ ID NO 132
<211> LENGTH: 32
<212> TYPE: PRT
<213> ORGANISM: Artificial Sequence
<220> FEATURE:
<223> OTHER INFORMATION: Synthetic

<400> SEQUENCE: 132

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Phe Cys
            20                  25                  30

<210> SEQ ID NO 133
<211> LENGTH: 32
<212> TYPE: PRT
<213> ORGANISM: Artificial Sequence
<220> FEATURE:
<223> OTHER INFORMATION: Synthetic

<400> SEQUENCE: 133

Gly Ile Pro Ala Arg Phe Ser Gly Ser Gly Ser Gly Thr Asp Phe Thr
1               5                   10                  15

Leu Thr Ile Ser Ser Val Glu Pro Glu Asp Phe Ala Val Tyr Phe Cys
            20                  25                  30

<210> SEQ ID NO 134
<211> LENGTH: 17
<212> TYPE: PRT
<213> ORGANISM: Artificial Sequence
<220> FEATURE:
<223> OTHER INFORMATION: Synthetic

<400> SEQUENCE: 134

Arg Ile Asp Pro Ala Gly Gly Asn Ile Lys Tyr Asp Pro Lys Phe Gln
1               5                   10                  15

Gly

<210> SEQ ID NO 135
<211> LENGTH: 17
<212> TYPE: PRT
<213> ORGANISM: Artificial Sequence
<220> FEATURE:
<223> OTHER INFORMATION: Synthetic

<400> SEQUENCE: 135

Arg Ile Asp Pro Ala Ser Gly Asn Ile Lys Tyr Asp Pro Lys Phe Gln
1               5                   10                  15

Gly

<210> SEQ ID NO 136
<211> LENGTH: 17
<212> TYPE: PRT
<213> ORGANISM: Artificial Sequence
<220> FEATURE:
<223> OTHER INFORMATION: Synthetic

<400> SEQUENCE: 136

Arg Ile Asp Pro Ala Gln Gly Asn Ile Lys Tyr Asp Pro Lys Phe Gln
1               5                   10                  15

Gly

<210> SEQ ID NO 137
<211> LENGTH: 17
<212> TYPE: PRT
<213> ORGANISM: Artificial Sequence
<220> FEATURE:
<223> OTHER INFORMATION: Synthetic

<400> SEQUENCE: 137

Arg Ile Asp Pro Ala Asn Ala Asn Ile Lys Tyr Asp Pro Lys Phe Gln
1               5                   10                  15

Gly

<210> SEQ ID NO 138
<211> LENGTH: 17
<212> TYPE: PRT
<213> ORGANISM: Artificial Sequence
<220> FEATURE:
<223> OTHER INFORMATION: Synthetic

<400> SEQUENCE: 138

Arg Ile Asp Pro Ala Asn Asp Asn Ile Lys Tyr Asp Pro Lys Phe Gln
1               5                   10                  15

Gly

<210> SEQ ID NO 139
<211> LENGTH: 17
<212> TYPE: PRT
<213> ORGANISM: Artificial Sequence
<220> FEATURE:
<223> OTHER INFORMATION: Synthetic

<400> SEQUENCE: 139

Lys Ile Asp Pro Ala Asn Gly Asn Ile Lys Tyr Asp Pro Lys Phe Gln
1               5                   10                  15

Gly

<210> SEQ ID NO 140
<211> LENGTH: 123

```
<212> TYPE: PRT
<213> ORGANISM: Artificial Sequence
<220> FEATURE:
<223> OTHER INFORMATION: Synthetic

<400> SEQUENCE: 140

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Leu Lys Asp Thr
            20                  25                  30

Phe Leu His Trp Val Arg Gln Ala Pro Gly Gln Gly Leu Glu Trp Met
        35                  40                  45

Gly Arg Ile Asp Pro Ala Asn Gly Asn Ile Lys Tyr Asp Pro Lys Phe
    50                  55                  60

Gln Gly Arg Val Thr Ile Thr Ala Asp Thr Ser Ala Asn Thr Ala Tyr
65                  70                  75                  80

Met Glu Leu Ile Ser Leu Arg Ser Glu Asp Thr Ala Val Tyr Tyr Cys
                85                  90                  95

Ala Asn Ser Pro Tyr Tyr Tyr Gly Ser Gly Tyr Arg Ile Phe Asp Val
            100                 105                 110

Trp Gly Gln Gly Thr Thr Val Thr Val Ser Ser
        115                 120

<210> SEQ ID NO 141
<211> LENGTH: 123
<212> TYPE: PRT
<213> ORGANISM: Artificial Sequence
<220> FEATURE:
<223> OTHER INFORMATION: Synthetic

<400> SEQUENCE: 141

Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Asn Leu Lys Asp Thr
            20                  25                  30

Phe Leu His Trp Val Arg Gln Ala Pro Gly Gln Gly Leu Glu Trp Ile
        35                  40                  45

Gly Arg Ile Asp Pro Ala Asn Gly Asn Ile Lys Tyr Asp Pro Lys Phe
    50                  55                  60

Gln Gly Arg Ala Thr Ile Thr Ala Asp Thr Ser Ala Asn Thr Ala Tyr
65                  70                  75                  80

Met Glu Leu Ile Ser Leu Arg Ser Glu Asp Thr Ala Val Tyr Tyr Cys
                85                  90                  95

Ala Asn Ser Pro Tyr Tyr Tyr Gly Ser Gly Tyr Arg Ile Phe Asp Val
            100                 105                 110

Trp Gly Gln Gly Thr Thr Val Thr Val Ser Ser
        115                 120

<210> SEQ ID NO 142
<211> LENGTH: 123
<212> TYPE: PRT
<213> ORGANISM: Artificial Sequence
<220> FEATURE:
<223> OTHER INFORMATION: Synthetic

<400> SEQUENCE: 142

Glu Val Gln Leu Val Gln Ser Gly Ala Glu Val Lys Lys Pro Gly Ala
1               5                   10                  15

Ser Val Lys Leu Ser Cys Lys Ala Ser Gly Tyr Asn Leu Lys Asp Thr
```

```
                  20                  25                  30
Phe Leu His Trp Val Lys Gln Ala Pro Gly Gln Gly Leu Glu Trp Ile
        35                  40                  45
Gly Arg Ile Asp Pro Ala Asn Gly Asn Ile Lys Tyr Asp Pro Lys Phe
    50                  55                  60
Gln Gly Lys Ala Thr Leu Thr Ala Asp Thr Ser Ala Asn Thr Ala Tyr
65                  70                  75                  80
Leu Glu Leu Ile Ser Leu Arg Ser Glu Asp Thr Ala Val Tyr Tyr Cys
                85                  90                  95
Ala Asn Ser Pro Tyr Tyr Tyr Gly Ser Gly Tyr Arg Ile Phe Asp Val
            100                 105                 110
Trp Gly Gln Gly Thr Thr Val Thr Val Ser Ser
        115                 120

<210> SEQ ID NO 143
<211> LENGTH: 106
<212> TYPE: PRT
<213> ORGANISM: Artificial Sequence
<220> FEATURE:
<223> OTHER INFORMATION: Synthetic

<400> SEQUENCE: 143

Gln Ile Val Leu Thr Gln Ser Pro Ala Thr Leu Ser Leu Ser Pro Gly
1               5                   10                  15
Glu Arg Ala Thr Leu Ser Cys Ser Ala Phe Ser Ser Val Asn Tyr Met
            20                  25                  30
His Trp Tyr Gln Gln Lys Pro Gly Gln Ala Pro Arg Leu Leu Ile Tyr
        35                  40                  45
Thr Thr Ser Asn Leu Ala Ser Gly Ile Pro Thr Arg Phe Ser Gly Ser
    50                  55                  60
Gly Ser Gly Thr Ser Tyr Thr Leu Thr Ile Ser Ser Leu Glu Pro Glu
65                  70                  75                  80
Asp Phe Ala Val Tyr Tyr Cys Gln Gln Arg Ser Thr Tyr Pro Phe Thr
                85                  90                  95
Phe Gly Gln Gly Thr Lys Leu Glu Ile Lys
            100                 105

<210> SEQ ID NO 144
<211> LENGTH: 106
<212> TYPE: PRT
<213> ORGANISM: Artificial Sequence
<220> FEATURE:
<223> OTHER INFORMATION: Synthetic

<400> SEQUENCE: 144

Gln Ile Val Leu Thr Gln Ser Pro Ala Thr Leu Ser Ala Ser Pro Gly
1               5                   10                  15
Glu Arg Ala Thr Leu Ser Cys Ser Ala Phe Ser Ser Val Asn Tyr Met
            20                  25                  30
His Trp Tyr Gln Gln Lys Pro Gly Gln Ala Pro Lys Leu Leu Ile Tyr
        35                  40                  45
Thr Thr Ser Asn Leu Ala Ser Gly Val Pro Thr Arg Phe Ser Gly Ser
    50                  55                  60
Gly Ser Gly Thr Ser Tyr Thr Leu Thr Ile Ser Ser Met Glu Pro Glu
65                  70                  75                  80
Asp Phe Ala Val Tyr Tyr Cys Gln Gln Arg Ser Thr Tyr Pro Phe Thr
                85                  90                  95
```

```
Phe Gly Gln Gly Thr Lys Leu Glu Ile Lys
            100                 105

<210> SEQ ID NO 145
<211> LENGTH: 106
<212> TYPE: PRT
<213> ORGANISM: Artificial Sequence
<220> FEATURE:
<223> OTHER INFORMATION: Synthetic

<400> SEQUENCE: 145

Gln Ile Val Leu Thr Gln Ser Pro Ala Thr Leu Ser Ala Ser Pro Gly
1               5                   10                  15

Glu Arg Val Thr Ile Thr Cys Ser Ala Phe Ser Ser Val Asn Tyr Met
            20                  25                  30

His Trp Tyr Gln Gln Lys Pro Gly Gln Ala Pro Lys Leu Leu Ile Tyr
        35                  40                  45

Thr Thr Ser Asn Leu Ala Ser Gly Val Pro Thr Arg Phe Ser Gly Ser
    50                  55                  60

Gly Ser Gly Thr Ser Tyr Thr Leu Thr Ile Ser Ser Met Glu Pro Glu
65                  70                  75                  80

Asp Phe Ala Val Tyr Tyr Cys Gln Gln Arg Ser Thr Tyr Pro Phe Thr
                85                  90                  95

Phe Gly Gln Gly Thr Lys Leu Glu Ile Lys
            100                 105

<210> SEQ ID NO 146
<211> LENGTH: 123
<212> TYPE: PRT
<213> ORGANISM: Artificial Sequence
<220> FEATURE:
<223> OTHER INFORMATION: Synthetic

<400> SEQUENCE: 146

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Lys Asp Thr
            20                  25                  30

Phe Leu His Trp Val Arg Gln Ala Pro Gly Gln Arg Leu Glu Trp Met
        35                  40                  45

Gly Arg Ile Asp Pro Ala Asn Gly Asn Ile Lys Tyr Asp Pro Lys Phe
    50                  55                  60

Gln Gly Arg Val Thr Leu Thr Ala Asp Thr Ser Ser Asn Thr Ala Tyr
65                  70                  75                  80

Met Glu Leu Ser Ser Leu Arg Ser Glu Asp Thr Ala Val Tyr Tyr Cys
                85                  90                  95

Ala Asn Ser Pro Tyr Tyr Gly Ser Gly Tyr Arg Ile Phe Asp Val
            100                 105                 110

Trp Gly Gln Gly Thr Leu Val Thr Val Ser Ser
        115                 120

<210> SEQ ID NO 147
<211> LENGTH: 123
<212> TYPE: PRT
<213> ORGANISM: Artificial Sequence
<220> FEATURE:
<223> OTHER INFORMATION: Synthetic

<400> SEQUENCE: 147

Glu Val Gln Leu Val Gln Ser Gly Ala Glu Val Lys Lys Pro Gly Ala
```

```
                1               5                       10                      15
         Ser Val Lys Val Ser Cys Lys Ala Ser Gly Tyr Thr Leu Lys Asp Thr
                        20                      25                      30
         Phe Leu His Trp Val Arg Gln Ala Pro Gly Gln Arg Leu Glu Trp Met
                        35                      40                      45
         Gly Lys Ile Asp Pro Ala Asn Gly Asn Ile Lys Tyr Asp Pro Lys Phe
                        50                      55                      60
         Gln Gly Arg Val Thr Leu Thr Ala Asp Thr Ser Ser Asn Thr Ala Tyr
         65                      70                      75                      80
         Met Glu Leu Ser Ser Leu Arg Ser Glu Asp Thr Ala Val Tyr Tyr Cys
                        85                      90                      95
         Ala Asn Ser Pro Tyr Tyr Tyr Gly Ser Gly Tyr Arg Ile Phe Asp Val
                        100                     105                     110
         Trp Gly Gln Gly Thr Leu Val Thr Val Ser Ser
                        115                     120

<210> SEQ ID NO 148
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be Ile or Val.
<220> FEATURE:
<221> NAME/KEY: misc_feature
<222> LOCATION: (4)..(4)
<223> OTHER INFORMATION: Xaa can be Ala or Thr.
<220> FEATURE:
<221> NAME/KEY: misc_feature
<222> LOCATION: (14)..(15)
<223> OTHER INFORMATION: Xaa in location 14 can be Asp or Ser, Xaa in
      location 15 can be Phe or Tyr.
<220> FEATURE:
<221> NAME/KEY: misc_feature
<222> LOCATION: (22)..(22)
<223> OTHER INFORMATION: Xaa can be Leu or Met.

<400> SEQUENCE: 148

Gly Xaa Pro Xaa Arg Phe Ser Gly Ser Gly Ser Gly Thr Xaa Xaa Thr
1               5                       10                      15

Leu Thr Ile Ser Ser Xaa Glu Pro Glu Asp Phe Ala Val Tyr Tyr Cys
                20                      25                      30

<210> SEQ ID NO 149
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa in location 1 can be Arg or Lys, Xaa in
      location 2 can be Val or Ala.
<220> FEATURE:
<221> NAME/KEY: misc_feature
<222> LOCATION: (4)..(4)
<223> OTHER INFORMATION: Xaa can be Ile or Leu.
<220> FEATURE:
<221> NAME/KEY: misc_feature
<222> LOCATION: (6)..(6)
<223> OTHER INFORMATION: Xaa can be Arg or Ala.
<220> FEATURE:
<221> NAME/KEY: misc_feature
<222> LOCATION: (10)..(11)
```

```
<223> OTHER INFORMATION: Xaa in location 10 can be Ala or Ser, Xaa in
      location 11 can be Ser or Asn.
<220> FEATURE:
<221> NAME/KEY: misc_feature
<222> LOCATION: (15)..(15)
<223> OTHER INFORMATION: Xaa can be Met or Leu.
<220> FEATURE:
<221> NAME/KEY: misc_feature
<222> LOCATION: (18)..(18)
<223> OTHER INFORMATION: Xaa can be Ser or Ile.
<220> FEATURE:
<221> NAME/KEY: misc_feature
<222> LOCATION: (32)..(32)
<223> OTHER INFORMATION: Xaa can be Arg or Asn.

<400> SEQUENCE: 149

Xaa Xaa Thr Xaa Thr Xaa Asp Thr Ser Xaa Xaa Thr Ala Tyr Xaa Glu
1               5                   10                  15

Leu Xaa Ser Leu Arg Ser Glu Asp Thr Ala Val Tyr Tyr Cys Ala Xaa
            20                  25                  30

<210> SEQ ID NO 150
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be Glu or Gln.
<220> FEATURE:
<221> NAME/KEY: misc_feature
<222> LOCATION: (12)..(13)
<223> OTHER INFORMATION: Xaa in location 12 can be Ser or Thr, Xaa in
      location 13 can be Leu or Ala.
<220> FEATURE:
<221> NAME/KEY: misc_feature
<222> LOCATION: (19)..(19)
<223> OTHER INFORMATION: Xaa can be Ala or Val.
<220> FEATURE:
<221> NAME/KEY: misc_feature
<222> LOCATION: (21)..(22)
<223> OTHER INFORMATION: Xaa in location 21 can be Leu or Ile, Xaa in
      location 22 can be Ser or Thr.

<400> SEQUENCE: 150

Xaa Ile Val Leu Thr Gln Ser Pro Ala Thr Leu Xaa Xaa Ser Pro Gly
1               5                   10                  15

Glu Arg Xaa Thr Xaa Xaa Cys
            20

<210> SEQ ID NO 151
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be Arg or Lys.
<220> FEATURE:
<221> NAME/KEY: misc_feature
<222> LOCATION: (6)..(7)
<223> OTHER INFORMATION: Xaa in location 6 can be Asn, Gly, Ser or Gln,
      Xaa in location 7 can be Gly, Ala or Asp.

<400> SEQUENCE: 151

Xaa Ile Asp Pro Ala Xaa Xaa Asn Ile Lys Tyr Asp Pro Lys Phe Gln
1               5                   10                  15
```

Gly

<210> SEQ ID NO 152
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be Gly or Gln.

<400> SEQUENCE: 152

Phe Gly Xaa Gly Thr Lys Leu Glu Ile Lys
1               5                   10

<210> SEQ ID NO 153
<211> LENGTH: 10
<212> TYPE: PRT
<213> ORGANISM: Artificial Sequence
<220> FEATURE:
<223> OTHER INFORMATION: Synthetic

<400> SEQUENCE: 153

Phe Gly Gly Gly Thr Lys Leu Glu Ile Lys
1               5                   10

<210> SEQ ID NO 154
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (18)..(18)
<223> OTHER INFORMATION: Xaa can be Leu or Met.

<400> SEQUENCE: 154

Glu Val Gln Leu Val Glu Ser Gly Gly Gly Leu Val Lys Pro Gly Gly
1               5                   10                  15

Ser Xaa Arg Leu Ser Cys Ala Ala Ser Gly Phe Thr Phe Ser
            20                  25                  30

<210> SEQ ID NO 155
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be Ala or Ser.
<220> FEATURE:
<221> NAME/KEY: misc_feature
<222> LOCATION: (14)..(14)
<223> OTHER INFORMATION: Xaa can be Gly or Ala.

<400> SEQUENCE: 155

Trp Val Arg Gln Xaa Pro Gly Lys Gly Leu Glu Trp Val Xaa
1               5                   10

<210> SEQ ID NO 156
<211> LENGTH: 32
<212> TYPE: PRT
<213> ORGANISM: Artificial Sequence
<220> FEATURE:

```
<223> OTHER INFORMATION: Synthetic
<220> FEATURE:
<221> NAME/KEY: misc_feature
<222> LOCATION: (13)..(13)
<223> OTHER INFORMATION: Xaa can be Leu or Val.

<400> SEQUENCE: 156

Arg Phe Thr Ile Ser Arg Asp Asp Ser Lys Asn Thr Xaa Tyr Leu Gln
1               5                   10                  15

Met Asn Ser Leu Lys Thr Glu Asp Thr Ala Val Tyr Tyr Cys Thr Thr
            20                  25                  30

<210> SEQ ID NO 157
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa can be Leu or Met.
<220> FEATURE:
<221> NAME/KEY: misc_feature
<222> LOCATION: (13)..(13)
<223> OTHER INFORMATION: Xaa can be Leu or Val.
<220> FEATURE:
<221> NAME/KEY: misc_feature
<222> LOCATION: (19)..(19)
<223> OTHER INFORMATION: Xaa can be Ala or Val.

<400> SEQUENCE: 157

Glu Ile Val Xaa Thr Gln Ser Pro Ala Thr Leu Ser Xaa Ser Pro Gly
1               5                   10                  15

Glu Arg Xaa Thr Leu Ser Cys
            20

<210> SEQ ID NO 158
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: Xaa can be Ala or Ser.

<400> SEQUENCE: 158

Trp Tyr Gln Gln Lys Pro Gly Gln Xaa Pro Arg Leu Leu Ile Tyr
1               5                   10                  15

<210> SEQ ID NO 159
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(22)
<223> OTHER INFORMATION: Xaa can be Leu or Val.
<220> FEATURE:
<221> NAME/KEY: misc_feature
<222> LOCATION: (31)..(31)
<223> OTHER INFORMATION: Xaa can be Tyr or Phe.

<400> SEQUENCE: 159

Gly Ile Pro Ala Arg Phe Ser Gly Ser Gly Ser Gly Thr Asp Phe Thr
1               5                   10                  15
```

Leu Thr Ile Ser Ser Xaa Glu Pro Glu Asp Phe Ala Val Tyr Xaa Cys
            20                  25                  30

<210> SEQ ID NO 160
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be Gln or Glu.
<220> FEATURE:
<221> NAME/KEY: misc_feature
<222> LOCATION: (20)..(20)
<223> OTHER INFORMATION: Xaa can be Val or Leu.
<220> FEATURE:
<221> NAME/KEY: misc_feature
<222> LOCATION: (28)..(28)
<223> OTHER INFORMATION: Xaa can be Asn or Thr.

<400> SEQUENCE: 160

Xaa Val Gln Leu Val Gln Ser Gly Ala Glu Val Lys Lys Pro Gly Ala
1               5                   10                  15

Ser Val Lys Xaa Ser Cys Lys Ala Ser Gly Tyr Xaa Leu Lys
            20                  25                  30

<210> SEQ ID NO 161
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be Arg or Lys.
<220> FEATURE:
<221> NAME/KEY: misc_feature
<222> LOCATION: (9)..(9)
<223> OTHER INFORMATION: Xaa can be Arg or Gly.
<220> FEATURE:
<221> NAME/KEY: misc_feature
<222> LOCATION: (13)..(13)
<223> OTHER INFORMATION: Xaa can be Met or Ile.

<400> SEQUENCE: 161

Trp Val Xaa Gln Ala Pro Gly Gln Xaa Leu Glu Trp Xaa Gly
1               5                   10

<210> SEQ ID NO 162
<211> LENGTH: 510
<212> TYPE: PRT
<213> ORGANISM: Homo sapiens

<400> SEQUENCE: 162

Met Glu Asp Thr Lys Glu Ser Asn Val Lys Thr Phe Cys Ser Lys Asn
1               5                   10                  15

Ile Leu Ala Ile Leu Gly Phe Ser Ser Ile Ile Ala Val Ile Ala Leu
            20                  25                  30

Leu Ala Val Gly Leu Thr Gln Asn Lys Ala Leu Pro Glu Asn Val Lys
        35                  40                  45

Tyr Gly Ile Val Leu Asp Ala Gly Ser Ser His Thr Ser Leu Tyr Ile
    50                  55                  60

Tyr Lys Trp Pro Ala Glu Lys Glu Asn Asp Thr Gly Val Val His Gln
65                  70                  75                  80

```
Val Glu Glu Cys Arg Val Lys Gly Pro Gly Ile Ser Lys Phe Val Gln
             85                  90                  95

Lys Val Asn Glu Ile Gly Ile Tyr Leu Thr Asp Cys Met Glu Arg Ala
        100                 105                 110

Arg Glu Val Ile Pro Arg Ser Gln His Gln Glu Thr Pro Val Tyr Leu
        115                 120                 125

Gly Ala Thr Ala Gly Met Arg Leu Leu Arg Met Glu Ser Glu Glu Leu
        130                 135                 140

Ala Asp Arg Val Leu Asp Val Val Glu Arg Ser Leu Ser Asn Tyr Pro
145                 150                 155                 160

Phe Asp Phe Gln Gly Ala Arg Ile Ile Thr Gly Gln Glu Glu Gly Ala
                165                 170                 175

Tyr Gly Trp Ile Thr Ile Asn Tyr Leu Leu Gly Lys Phe Ser Gln Lys
                180                 185                 190

Thr Arg Trp Phe Ser Ile Val Pro Tyr Glu Thr Asn Asn Gln Glu Thr
                195                 200                 205

Phe Gly Ala Leu Asp Leu Gly Gly Ala Ser Thr Gln Val Thr Phe Val
210                 215                 220

Pro Gln Asn Gln Thr Ile Glu Ser Pro Asp Asn Ala Leu Gln Phe Arg
225                 230                 235                 240

Leu Tyr Gly Lys Asp Tyr Asn Val Tyr Thr His Ser Phe Leu Cys Tyr
                245                 250                 255

Gly Lys Asp Gln Ala Leu Trp Gln Lys Leu Ala Lys Asp Ile Gln Val
                260                 265                 270

Ala Ser Asn Glu Ile Leu Arg Asp Pro Cys Phe His Pro Gly Tyr Lys
                275                 280                 285

Lys Val Val Asn Val Ser Asp Leu Tyr Lys Thr Pro Cys Thr Lys Arg
                290                 295                 300

Phe Glu Met Thr Leu Pro Phe Gln Gln Phe Glu Ile Gln Gly Ile Gly
305                 310                 315                 320

Asn Tyr Gln Gln Cys His Gln Ser Ile Leu Glu Leu Phe Asn Thr Ser
                325                 330                 335

Tyr Cys Pro Tyr Ser Gln Cys Ala Phe Asn Gly Ile Phe Leu Pro Pro
                340                 345                 350

Leu Gln Gly Asp Phe Gly Ala Phe Ser Ala Phe Tyr Phe Val Met Lys
                355                 360                 365

Phe Leu Asn Leu Thr Ser Glu Lys Val Ser Gln Glu Lys Val Thr Glu
        370                 375                 380

Met Met Lys Lys Phe Cys Ala Gln Pro Trp Glu Glu Ile Lys Thr Ser
385                 390                 395                 400

Tyr Ala Gly Val Lys Glu Lys Tyr Leu Ser Glu Tyr Cys Phe Ser Gly
                405                 410                 415

Thr Tyr Ile Leu Ser Leu Leu Leu Gln Gly Tyr His Phe Thr Ala Asp
                420                 425                 430

Ser Trp Glu His Ile His Phe Ile Gly Lys Ile Gln Gly Ser Asp Ala
                435                 440                 445

Gly Trp Thr Leu Gly Tyr Met Leu Asn Leu Thr Asn Met Ile Pro Ala
        450                 455                 460

Glu Gln Pro Leu Ser Thr Pro Leu Ser His Ser Thr Tyr Val Phe Leu
465                 470                 475                 480
```

```
Met Val Leu Phe Ser Leu Val Leu Phe Thr Val Ala Ile Ile Gly Leu
                485                 490                 495

Leu Ile Phe His Lys Pro Ser Tyr Phe Trp Lys Asp Met Val
                500                 505                 510
```

ANTI-CD39 ANTIBODIES

CROSS REFERENCE TO RELATED APPLICATIONS

This application is a national stage application under 35 U.S.C. § 371 of PCT International Application No. PCT/CN2020/111219, filed on Aug. 26, 2020, which claims the benefits of PCT International Application No. PCT/CN2019/102778, filed on Aug. 27, 2019, and Chinese Patent Application No. CN202010842863.9, filed on Aug. 20, 2020, which are hereby incorporated by reference in their entireties.

SEQUENCE LISTING

This application contains a sequence listing, which has been submitted electronically as an ASCII text file and is herein incorporated by reference in its entirety. Said ASCII text file, created on Apr. 6, 2021 is named 4_075431-8001WO02-SL and is 91,259 bytes in size.

FIELD OF THE INVENTION

The present disclosure generally relates to novel anti-CD39 antibodies.

BACKGROUND

CD39, also known as ecto-nucleoside triphosphate diphosphohydrolase-1 (ENTPDase1), is an integral membrane protein that converts ATP or ADP into AMP, and then CD73 dephosphorylates AMP into adenosine, which is a potent immunosuppressor and binds to adenosine receptors (for example, A2A receptor) at the surface of CD4, CD8 T cells and natural killer (NK) cells, and inhibits T-cell and NK-cell responses, thereby suppressing the immune system. Adenosine also binds to A2A or A2B receptors on macrophages and dendritic cells, inhibits phagocytosis and antigen presentation and increases secretion of pro-tumorigenic factors, such as VEGF, TGFb and IL-6. The enzymatic activities of CD39 and CD73 play strategic roles in calibrating the duration, magnitude, and chemical nature of purinergic signals delivered to immune cells through the conversion of ADP and ATP to AMP and AMP to adenosine, respectively (Luca Antonioli et al., *Trends Mol Med.* 2013 June; 19(6): 355-367). Increased adenosine levels mediated by CD39 and CD73 generate an immunosuppressive environment which promotes the development and progression of cancer.

Needs remain for novel anti-CD39 antibodies.

SUMMARY OF THE INVENTION

Throughout the present disclosure, the articles "a," "an," and "the" are used herein to refer to one or to more than one (i.e., to at least one) of the grammatical object of the article. By way of example, "an antibody" means one antibody or more than one antibody.

In one respect, the present disclosure provides an antibody or an antigen-binding fragment thereof capable of specifically binding to human CD39, comprising a heavy chain variable region comprising HCDR1, HCDR2 and HCDR3, and/or a light chain variable region comprising LCDR1, LCDR2 and LCDR3, wherein, a) the HCDR1 comprises an amino acid sequence selected from the group consisting of NYGMN (SEQ ID NO: 1), KYWMN (SEQ ID NO: 2), NYWMN (SEQ ID NO: 3), DTFLH (SEQ ID NO: 4), DYNMY (SEQ ID NO: 5), DTYVH (SEQ ID NO: 6); and b) the HCDR2 comprises an amino acid sequence selected from the group consisting of LINTYTGEPTYADDFKD (SEQ ID NO: 7), EIRLKSNKYGTHYAESVKG (SEQ ID NO: 8), QIRLNPDNYATHX$_1$AESVKG (SEQ ID NO: 9), X$_{58}$IDPAX$_{59}$X$_{60}$NIKYDPKFQG (SEQ ID NO: 151), FIDPYNGYTSYNQKFKG (SEQ ID NO: 11), RIDPAIDNSKYDPKFQG (SEQ ID NO: 12); and c) the HCDR3 comprises an amino acid sequence selected from the group consisting of KGIYYDYVWFFDV (SEQ ID NO: 13), QLDLYWFFDV (SEQ ID NO: 14), HGX$_2$RGFAY (SEQ ID NO: 15), SPYYYGSGYRIFDV (SEQ ID NO: 16), IYGYDDAYYFDY (SEQ ID NO: 17), YYCALYDGYNVYAMDY (SEQ ID NO: 18); and d) the LCDR1 comprises an amino acid sequence selected from the group consisting of KASQDINRYIA (SEQ ID NO: 19), RASQSISDYLH (SEQ ID NO: 20), KSSQSLLDSDGRTHLN (SEQ ID NO: 21), SAFSSVNYMH (SEQ ID NO: 22), SATSSVSYMH (SEQ ID NO: 23), RSSKNLLHSNGITYLY (SEQ ID NO: 24); and e) the LCDR2 comprises an amino acid sequence selected from the group consisting of YTSTLLP (SEQ ID NO: 25), YASQSIS (SEQ ID NO: 26), LVSKLDS (SEQ ID NO: 27), TTSNLAS (SEQ ID NO: 28), STSNLAS (SEQ ID NO: 29), RASTLAS (SEQ ID NO: 30); and f) the LCDR3 comprises an amino acid sequence selected from the group consisting of LQYSNLLT (SEQ ID NO: 31), QNGHSLPLT (SEQ ID NO: 32), WQGTLFPWT (SEQ ID NO: 33), QQRSTYPFT (SEQ ID NO: 34), QQRITYPFT (SEQ ID NO: 35), AQLLELPHT (SEQ ID NO: 36); wherein X$_1$ is Y or F, X$_2$ is S or T, X$_{58}$ is R or K, X$_{59}$ is N, G, S or Q, X$_{60}$ is G, A or D.

In some embodiments, the HCDR1 comprises the amino acid sequence of SEQ ID NO: 3, and/or the HCDR2 comprises the amino acid sequence of SEQ ID NO: 9, and/or the HCDR3 comprises the amino acid sequence of SEQ ID NO: 15, and/or the LCDR1 comprises the amino acid sequence of SEQ ID NO: 21, and/or the LCDR2 comprises the amino acid sequence of SEQ ID NO: 27, and/or the LCDR3 comprises the amino acid sequence of SEQ ID NO: 33, wherein X$_1$ and X$_2$ are as defined above.

In some embodiments, the HCDR1 comprises the amino acid sequence of SEQ ID NO: 3, and/or the HCDR2 comprises an amino acid sequence selected from the group consisting of SEQ ID NO: 37 and SEQ ID NO: 38, and/or the HCDR3 comprises an amino acid sequence selected from the group consisting of SEQ ID NO: 40 and SEQ ID NO: 41, and/or the LCDR1 comprises the amino acid sequence of SEQ ID NO: 21, and/or the LCDR2 comprises the amino acid sequence of SEQ ID NO: 27, and/or the LCDR3 comprises the amino acid sequence of SEQ ID NO: 33.

In some embodiments, the HCDR1 comprises the amino acid sequence of SEQ ID NO: 4, and/or the HCDR2 comprises the amino acid sequence of SEQ ID NO: 151, and/or the HCDR3 comprises the amino acid sequence of SEQ ID NO: 16, and/or the LCDR1 comprises the amino acid sequence of SEQ ID NO: 22, and/or the LCDR2 comprises the amino acid sequence of SEQ ID NO: 28, and/or the LCDR3 comprises the amino acid sequence of SEQ ID NO: 34, wherein X$_{58}$, X$_{59}$ and X$_{60}$ are as defined above.

In some embodiments, the heavy chain variable region of the antibody or an antigen-binding fragment thereof provided herein comprises
  a) a HCDR1 comprising the sequence of SEQ ID NO: 1, a HCDR2 comprising the sequence of SEQ ID NO: 7, and a HCDR3 comprising the sequence of SEQ ID NO: 13; or
  b) a HCDR1 comprising the sequence of SEQ ID NO: 2, a HCDR2 comprising the sequence of SEQ ID NO: 8, and a HCDR3 comprising the sequence of SEQ ID NO: 14; or
  c) a HCDR1 comprising the sequence of SEQ ID NO: 3, a HCDR2 comprising the sequence of SEQ ID NO: 37, and a HCDR3 comprising the sequence of SEQ ID NO: 40; or
  d) a HCDR1 comprising the sequence of SEQ ID NO: 3, a HCDR2 comprising the sequence of SEQ ID NO: 38, and a HCDR3 comprising the sequence of SEQ ID NO: 41; or
  e) a HCDR1 comprising the sequence of SEQ ID NO: 4, a HCDR2 comprising the sequence of SEQ ID NO: 10, and a HCDR3 comprising the sequence of SEQ ID NO: 16; or
  f) a HCDR1 comprising the sequence of SEQ ID NO: 4, a HCDR2 comprising a sequence selected from the group consisting of SEQ ID NOs: 134, 135, 136, 137, 138, and 139, and a HCDR3 comprising the sequence of SEQ ID NO: 16; or
  g) a HCDR1 comprising the sequence of SEQ ID NO: 5, a HCDR2 comprising the sequence of SEQ ID NO: 11, and a HCDR3 comprising the sequence of SEQ ID NO: 17; or
  h) a HCDR1 comprising the sequence of SEQ ID NO: 6, a HCDR2 comprising the sequence of SEQ ID NO: 12, and a HCDR3 comprising the sequence of SEQ ID NO: 18.

In some embodiments, the light chain variable region of the antibody or an antigen-binding fragment thereof provided herein comprises
  a) a LCDR1 comprising the sequence of SEQ ID NO: 19, a LCDR2 comprising the sequence of SEQ ID NO: 25, and a LCDR3 comprising the sequence of SEQ ID NO: 31; or
  b) a LCDR1 comprising the sequence of SEQ ID NO: 20, a LCDR2 comprising the sequence of SEQ ID NO: 26, and a LCDR3 comprising the sequence of SEQ ID NO: 32; or
  c) a LCDR1 comprising the sequence of SEQ ID NO: 21, a LCDR2 comprising the sequence of SEQ ID NO: 27, and a LCDR3 comprising the sequence of SEQ ID NO: 33; or
  d) a LCDR1 comprising the sequence of SEQ ID NO: 22, a LCDR2 comprising the sequence of SEQ ID NO: 28, and a LCDR3 comprising the sequence of SEQ ID NO: 34; or
  e) a LCDR1 comprising the sequence of SEQ ID NO: 23, a LCDR2 comprising the sequence of SEQ ID NO: 29, and a LCDR3 comprising the sequence of SEQ ID NO: 35; or
  f) a LCDR1 comprising the sequence of SEQ ID NO: 24, a LCDR2 comprising the sequence of SEQ ID NO: 30, and a LCDR3 comprising the sequence of SEQ ID NO: 36.

In some embodiments, in the antibody or an antigen-binding fragment thereof provided herein,
  (a) the HCDR1 comprises the sequence of SEQ ID NO: 1, the HCDR2 comprises the sequence of SEQ ID NO: 7, the HCDR3 comprises the sequence of SEQ ID NO: 13, the LCDR1 comprises the sequence of SEQ ID NO: 19, the LCDR2 comprises the sequence of SEQ ID NO: 25, and the LCDR3 comprises the sequence of SEQ ID NO: 31; or
  (b) the HCDR1 comprises the sequence of SEQ ID NO: 2, the HCDR2 comprises the sequence of SEQ ID NO: 8, the HCDR3 comprises the sequence of SEQ ID NO: 14, the LCDR1 comprises the sequence of SEQ ID NO: 20, the LCDR2 comprises the sequence of SEQ ID NO: 26, and the LCDR3 comprises the sequence of SEQ ID NO: 32; or
  (c) the HCDR1 comprises the sequence of SEQ ID NO: 3, the HCDR2 comprises the sequence of SEQ ID NO: 37, the HCDR3 comprises the sequence of SEQ ID NO: 40, the LCDR1 comprises the sequence of SEQ ID NO: 21, the LCDR2 comprises the sequence of SEQ ID NO: 27, and the LCDR3 comprises the sequence of SEQ ID NO: 33; or
  (d) the HCDR1 comprises the sequence of SEQ ID NO: 3, the HCDR2 comprises the sequence of SEQ ID NO: 38, the HCDR3 comprises the sequence of SEQ ID NO: 41, the LCDR1 comprises the sequence of SEQ ID NO: 21, the LCDR2 comprises the sequence of SEQ ID NO: 27, and the LCDR3 comprises the sequence of SEQ ID NO: 33; or
  (e) the HCDR1 comprises the sequence of SEQ ID NO: 4, the HCDR2 comprises the sequence of SEQ ID NO: 10, the HCDR3 comprises the sequence of SEQ ID NO: 16, the LCDR1 comprises the sequence of SEQ ID NO: 22, the LCDR2 comprises the sequence of SEQ ID NO: 28, and the LCDR3 comprises the sequence of SEQ ID NO: 34; or
  (f) the HCDR1 comprises the sequence of SEQ ID NO: 4, the HCDR2 comprises a sequence selected from the group consisting of SEQ ID NOs: 134, 135, 136, 137, 138, and 139, the HCDR3 comprises the sequence of SEQ ID NO: 16, the LCDR1 comprises the sequence of SEQ ID NO: 22, the LCDR2 comprises the sequence of SEQ ID NO: 28, and the LCDR3 comprises the sequence of SEQ ID NO: 34; or (g) the HCDR1 comprises the sequence of SEQ ID NO: 5, the HCDR2 comprises the sequence of SEQ ID NO: 11, the HCDR3 comprises the sequence of SEQ ID NO: 17, the LCDR1 comprises the sequence of SEQ ID NO: 23, the LCDR2 comprises the sequence of SEQ ID NO: 29, and the LCDR3 comprises the sequence of SEQ ID NO: 35; or
  (h) the HCDR1 comprises the sequence of SEQ ID NO: 6, the HCDR2 comprises the sequence of SEQ ID NO: 12, the HCDR3 comprises the sequence of SEQ ID NO: 18, the LCDR1 comprises the sequence of SEQ ID NO: 24, the LCDR2 comprises the sequence of SEQ ID NO: 30, and the LCDR3 comprises the sequence of SEQ ID NO: 36.

In some embodiments, the antibody or an antigen-binding fragment thereof provided herein further comprises one or more of heavy chain HFR1, HFR2, HFR3 and HFR4, and/or one or more of light chain LFR1, LFR2, LFR3 and LFR4, wherein
  (a) the HFR1 comprises the sequence of $X_{19}VQLVX_{20}SGX_{21}X_{22}X_{23}X_{24}KPGX_{25}SX_{26}X_{27}X_{28}SCX_{29}ASGX_{30}X_{31}X_{32}X_{33}$ (SEQ ID NO: 76) or a homologous sequence of at least 80% sequence identity thereof, (b) the HFR2 comprises the sequence of WVX$_{34}$QX$_{35}$PGX$_{36}$X$_{37}$LEWX$_{38}$X$_{39}$ (SEQ ID NO: 77) or a homologous sequence of at least 80% sequence identity thereof, (c) the HFR3 sequence comprises the sequence of X$_{40}$X$_{41}$TX$_{42}$X$_{43}$X$_{44}$DX$_{45}$SX$_{46}$X$_{47}$TX$_{48}$YX$_{49}$X$_{50}$X$_{51}$X$_{52}$SLX$_{53}$X$_{54}$EDTAVYYCX$_{55}$X$_{56}$ (SEQ ID NO: 78) or a homologous sequence of at least 80% sequence identity thereof, (d) the HFR4 comprises the sequence of WGQGTX$_{57}$VTVSS (SEQ ID NO: 126) or a homologous sequence of at least 80% sequence identity thereof, (e) the LFR1 comprises the sequence of X$_3$IVX$_4$TQSPATLX$_5$X$_6$SPGERX$_7$TX$_8$X$_9$C (SEQ ID NO: 80) or a homologous sequence of at least 80% sequence identity thereof, (f) the LFR2 comprises the sequence of WYQQKPGQX$_{10}$PX$_{11}$LLIY (SEQ ID NO: 81) or a homologous sequence of at least 80% sequence identity thereof, (g) the LFR3 comprises the sequence of GX$_{12}$PX$_{13}$RFSGSGSGTX$_{14}$X$_{15}$TLTISSX$_{16}$EPEDFAVYX$_{17}$C (SEQ ID NO: 82) or a homologous sequence of at least 80% sequence identity thereof, and (h) the LFR4 comprises the sequence of FGX$_{18}$GTKLEIK (SEQ ID NO: 152) or a homologous sequence of at least 80% sequence identity thereof, wherein X$_3$ is E or Q; X$_4$ is L or M; X$_5$ is S or T; X$_6$ is L, V or A; X$_7$ is A or V; X$_8$ is L or I; X$_9$ is S or T; X$_{10}$ is A or S; X$_1$ is R or K; X$_{12}$ is I or V; X$_{13}$ is A or T; X$_{14}$ is D or S; X$_{15}$ is F or Y; X$_{16}$ is L, M or V; X$_{17}$ is Y or F; X$_{18}$ is G or Q; X$_{19}$ is Q or E; X$_{20}$ is E or Q; X$_{21}$ is G or A; X$_{22}$ is G or E; X$_{23}$ is L or V; X$_{24}$ is V or K; X$_{25}$ is G or A; X$_{26}$ is L, M or V; X$_{27}$ is R or K; X$_{28}$ is V or L; X$_{29}$ is A or K; X$_{30}$ is F or Y; X$_{31}$ is N or T; X$_{32}$ is F or L; X$_{33}$ is S or K; X$_{34}$ is R or K; X$_{35}$ is A or S; X$_{36}$ is K or Q; X$_{37}$ is R or G; X$_{38}$ is M, I or V; X$_{39}$ is G or A; X$_{40}$ is R or K; X$_{41}$ is V, A or F; X$_{42}$ is I or L; X$_{43}$ is S or T; X$_{44}$ is R or A; X$_{45}$ is D or T; X$_{46}$ is K, A or S; X$_{47}$ is S or N; X$_{48}$ is L, V or A; X$_{49}$ is M or L; X$_{50}$ is Q or E; X$_{51}$ is M or L; X$_{52}$ is S, I or N; X$_{53}$ is R or K; X$_{54}$ is S or T; X$_{55}$ is A or T; X$_{56}$ is R, N or T; and X$_{57}$ is T or L.

In some embodiments, the HFR1 comprises the sequence of EVQLVESGGGLVKPGGSX$_{61}$RLSCAASGFTFS (SEQ ID NO: 154), or a homologous sequence of at least 80% sequence identity thereof; the HFR2 comprises the sequence of WVRQX$_{62}$PGKGLEWVX$_{63}$ (SEQ ID NO: 155) or a homologous sequence of at least 80% sequence identity thereof; the HFR3 comprises the sequence of RFTISRDDSKNTX$_{64}$YLQMNSLKTEDTAVYYCTT (SEQ ID NO: 156), or a homologous sequence of at least 80% sequence identity thereof; the HFR4 comprises the sequence of WGQGTTVTVSS (SEQ ID NO: 79), or a homologous sequence of at least 80% sequence identity thereof, the LFR1 comprises the sequence of EIVX$_{65}$TQSPATLSX$_{66}$SPGERX$_{67}$TLSC (SEQ ID NO: 157), or a homologous sequence of at least 80% sequence identity thereof; the LFR2 comprises the sequence of WYQQKPGQX$_{68}$PRLLIY (SEQ ID NO: 158), or a homologous sequence of at least 80% sequence identity thereof, the LFR3 comprises the sequence of GIPARFSGSGSGTDFTLTISSX$_{69}$EPEDFAVYX$_{70}$C (SEQ ID NO: 159), or a homologous sequence of at least 80% sequence identity thereof, and the LFR4 comprises the sequence of FGGGTKLEIK (SEQ ID NO: 153), or a homologous sequence of at least 80% sequence identity thereof, wherein X$_{61}$ is L or M; X$_{62}$ is A or S; X$_{63}$ is G or A; X$_{64}$ is L or V; X$_{65}$ is L or M; X$_{66}$ is L or V; X$_{67}$ is A or V; X$_{68}$ is A or S; X$_{69}$ is L or V; and X$_{70}$ is Y or F.

In some embodiments, the HFR1 comprises the sequence of X$_{71}$VQLVQSGAEVKKPGASVKX$_{72}$SCKASGYX$_{73}$LK (SEQ ID NO: 160), or a homologous sequence of at least 80% sequence identity thereof; the HFR2 comprises the sequence of WVX$_{74}$QAPGQX$_{75}$LEWX$_{76}$G (SEQ ID NO: 161) or a homologous sequence of at least 80% sequence identity thereof; the HFR3 comprises the sequence of X$_{77}$X$_{78}$TX$_{79}$TX$_{80}$DTSX$_{81}$X$_{82}$TAYX$_{83}$ELX$_{84}$SLRSEDTAVYYCAX$_{85}$ (SEQ ID NO: 149), or a homologous sequence of at least 80% sequence identity thereof; the HFR4 comprises the sequence of WGQGTX$_{57}$VTVSS (SEQ ID NO: 126), or a homologous sequence of at least 80% sequence identity thereof; the LFR1 comprises the sequence of X$_{86}$IVLTQSPATLX$_{87}$X$_{88}$SPGERX$_{89}$TX$_{90}$X$_{91}$C (SEQ ID NO: 150), or a homologous sequence of at least 80% sequence identity thereof, the LFR2 comprises the sequence of WYQQKPGQX$_{10}$PX$_{11}$LLIY (SEQ ID NO: 81), or a homologous sequence of at least 80% sequence identity thereof; the LFR3 comprises the sequence of GX$_{92}$PX$_{93}$RFSGSGSGTX$_{94}$X$_{95}$TLTISSX$_{96}$EPEDFAVYYC (SEQ ID NO: 148), or a homologous sequence of at least 80% sequence identity thereof, and the LFR4 comprises the sequence of FGQGTKLEIK (SEQ ID NO: 83), or a homologous sequence of at least 80% sequence identity thereof, wherein X$_{10}$, X$_{11}$ and X$_{57}$ are as defined above, X$_{71}$ is Q or E; X$_{72}$ is V or L; X$_{73}$ is N or T; X$_{74}$ is R or K; X$_{75}$ is R or G; X$_{76}$ is M or I; X$_{77}$ is R or K; X$_{78}$ is V or A; X$_{79}$ is I or L; X$_{80}$ is R or A; X$_{81}$ is A or S; X$_{82}$ is S or N; X$_{83}$ is M or L; X$_{84}$ is S or I; X$_{85}$ is R or N; X$_{86}$ is E or Q; X$_{87}$ is S or T; X$_{88}$ is L or A; X$_{89}$ is A or V; X$_{90}$ is L or I; X$_{91}$ is S or T; X$_{92}$ is I or V; X$_{93}$ is A or T; X$_{94}$ is D or S; X$_{95}$ is F or Y; and X$_{96}$ is L or M.

In some embodiments, the HFR1 comprises a sequence selected from the group consisting of SEQ ID NOs: 84-86, 115, 119-120, and 131; the HFR2 comprises a sequence selected from the group consisting of SEQ ID NOs: 87-90, and 121-123; the HFR3 comprises a sequence selected from the group consisting of SEQ ID NOs: 91-97, 116-117, and 124-125; the HFR4 comprises a sequence selected from the group consisting of SEQ ID NOs: 79 and 118; the LFR1 comprises a sequence selected from the group consisting of SEQ ID NOs: 98-103 and 127-129; the LFR2 comprises a sequence selected from the group consisting of SEQ ID NOs: 104, 105 and 130; the LFR3 comprises a sequence selected from the group consisting of SEQ ID NOs: 106-110 and 132-133, and the LFR4 comprises a sequence selected from the group consisting of SEQ ID NOs: 83 and 153.

In some embodiments, the antibody or an antigen-binding fragment thereof provided herein comprises a heavy chain variable region comprising a sequence selected from the group consisting of SEQ ID NOs: 60, 62, 64, 66, 140, 141, 142, 146, 147, 39, and a homologous sequence thereof having at least 80% sequence identity yet retaining specific binding affinity to human CD39, and a light chain variable region comprising a sequence selected from the group consisting of SEQ ID NOs: 61, 63, 65, 67, 143, 144, 145, 111, 112, 63, and a homologous sequence thereof having at least 80% sequence identity yet retaining specific binding affinity to human CD39.

In some embodiments, the antibody or an antigen-binding fragment thereof provided herein comprises a heavy chain variable region comprising a sequence selected from the group consisting of SEQ ID NOs: 68, 70, 72, 74, and a homologous sequence thereof having at least 80% sequence identity yet retaining specific binding affinity to human CD39, and a light chain variable region comprising the sequence selected from the group consisting of SEQ ID NOs: 69, 71, 73, 75, and a homologous sequence thereof having at least 80% sequence identity yet retaining specific binding affinity to human CD39.

In some embodiments, the antibody or an antigen-binding fragment thereof provided herein comprises:

(1) a heavy chain variable region comprising the sequence of SEQ ID NO: 42 and a light chain variable region comprising the sequence of SEQ ID NO: 51; or
(2) a heavy chain variable region comprising the sequence of SEQ ID NO: 43 and a light chain variable region comprising the sequence of SEQ ID NO: 52; or
(3) a heavy chain variable region comprising the sequence of SEQ ID NO: 44 and a light chain variable region comprising the sequence of SEQ ID NO: 53; or
(4) a heavy chain variable region comprising the sequence of SEQ ID NO: 45 and a light chain variable region comprising the sequence of SEQ ID NO: 54; or
(5) a heavy chain variable region comprising the sequence of SEQ ID NO: 47 and a light chain variable region comprising the sequence of SEQ ID NO: 56; or
(6) a heavy chain variable region comprising the sequence of SEQ ID NO: 49 and a light chain variable region comprising the sequence of SEQ ID NO: 58; or
(7) a heavy chain variable region comprising the sequence of SEQ ID NO: 50 and a light chain variable region comprising the sequence of SEQ ID NO: 59, or
(8) a heavy chain variable region comprising the sequence of SEQ ID NO: 60 and a light chain variable region comprising the sequence of SEQ ID NO: 61, or
(9) a heavy chain variable region comprising the sequence of SEQ ID NO: 62 and a light chain variable region comprising the sequence of SEQ ID NO: 61, or
(10) a heavy chain variable region comprising the sequence of SEQ ID NO: 64 and a light chain variable region comprising the sequence of SEQ ID NO: 61, or
(11) a heavy chain variable region comprising the sequence of SEQ ID NO: 66 and a light chain variable region comprising the sequence of SEQ ID NO: 61, or
(12) a heavy chain variable region comprising the sequence of SEQ ID NO: 60 and a light chain variable region comprising the sequence of SEQ ID NO: 63, or
(13) a heavy chain variable region comprising the sequence of SEQ ID NO: 62 and a light chain variable region comprising the sequence of SEQ ID NO: 63, or
(14) a heavy chain variable region comprising the sequence of SEQ ID NO: 64 and a light chain variable region comprising the sequence of SEQ ID NO: 63, or
(15) a heavy chain variable region comprising the sequence of SEQ ID NO: 66 and a light chain variable region comprising the sequence of SEQ ID NO: 63, or
(16) a heavy chain variable region comprising the sequence of SEQ ID NO: 60 and a light chain variable region comprising the sequence of SEQ ID NO: 65, or
(17) a heavy chain variable region comprising the sequence of SEQ ID NO: 62 and a light chain variable region comprising the sequence of SEQ ID NO: 65, or
(18) a heavy chain variable region comprising the sequence of SEQ ID NO: 64 and a light chain variable region comprising the sequence of SEQ ID NO: 65, or
(19) a heavy chain variable region comprising the sequence of SEQ ID NO: 66 and a light chain variable region comprising the sequence of SEQ ID NO: 65, or
(20) a heavy chain variable region comprising the sequence of SEQ ID NO: 60 and a light chain variable region comprising the sequence of SEQ ID NO: 67, or
(21) a heavy chain variable region comprising the sequence of SEQ ID NO: 62 and a light chain variable region comprising the sequence of SEQ ID NO: 67, or
(22) a heavy chain variable region comprising the sequence of SEQ ID NO: 64 and a light chain variable region comprising the sequence of SEQ ID NO: 67, or
(23) a heavy chain variable region comprising the sequence of SEQ ID NO: 66 and a light chain variable region comprising the sequence of SEQ ID NO: 67, or
(24) a heavy chain variable region comprising the sequence of SEQ ID NO: 140 and a light chain variable region comprising the sequence of SEQ ID NO: 61, or
(25) a heavy chain variable region comprising the sequence of SEQ ID NO: 141 and a light chain variable region comprising the sequence of SEQ ID NO: 61, or
(26) a heavy chain variable region comprising the sequence of SEQ ID NO: 142 and a light chain variable region comprising the sequence of SEQ ID NO: 61, or
(27) a heavy chain variable region comprising the sequence of SEQ ID NO: 60 and a light chain variable region comprising the sequence of SEQ ID NO: 143, or
(28) a heavy chain variable region comprising the sequence of SEQ ID NO: 140 and a light chain variable region comprising the sequence of SEQ ID NO: 143, or
(29) a heavy chain variable region comprising the sequence of SEQ ID NO: 141 and a light chain variable region comprising the sequence of SEQ ID NO: 143, or
(30) a heavy chain variable region comprising the sequence of SEQ ID NO: 142 and a light chain variable region comprising the sequence of SEQ ID NO: 143, or
(31) a heavy chain variable region comprising the sequence of SEQ ID NO: 60 and a light chain variable region comprising the sequence of SEQ ID NO: 144, or
(32) a heavy chain variable region comprising the sequence of SEQ ID NO: 140 and a light chain variable region comprising the sequence of SEQ ID NO: 144, or
(33) a heavy chain variable region comprising the sequence of SEQ ID NO: 141 and a light chain variable region comprising the sequence of SEQ ID NO: 144, or
(34) a heavy chain variable region comprising the sequence of SEQ ID NO: 142 and a light chain variable region comprising the sequence of SEQ ID NO: 144, or
(35) a heavy chain variable region comprising the sequence of SEQ ID NO: 60 and a light chain variable region comprising the sequence of SEQ ID NO: 145, or
(36) a heavy chain variable region comprising the sequence of SEQ ID NO: 140 and a light chain variable region comprising the sequence of SEQ ID NO: 145, or
(37) a heavy chain variable region comprising the sequence of SEQ ID NO: 141 and a light chain variable region comprising the sequence of SEQ ID NO: 145, or
(38) a heavy chain variable region comprising the sequence of SEQ ID NO: 142 and a light chain variable region comprising the sequence of SEQ ID NO: 145, or
(39) a heavy chain variable region comprising the sequence of SEQ ID NO: 146 and a light chain variable region comprising the sequence of SEQ ID NO: 111, or
(40) a heavy chain variable region comprising the sequence of SEQ ID NO: 146 and a light chain variable region comprising the sequence of SEQ ID NO: 112, or
(41) a heavy chain variable region comprising the sequence of SEQ ID NO: 147 and a light chain variable region comprising the sequence of SEQ ID NO: 111, or

(42) a heavy chain variable region comprising the sequence of SEQ ID NO: 39 and a light chain variable region comprising the sequence of SEQ ID NO: 63, or
(43) a heavy chain variable region comprising the sequence of SEQ ID NO: 68 and a light chain variable region comprising the sequence of SEQ ID NO: 69, or
(44) a heavy chain variable region comprising the sequence of SEQ ID NO: 70 and a light chain variable region comprising the sequence of SEQ ID NO: 69, or
(45) a heavy chain variable region comprising the sequence of SEQ ID NO: 72 and a light chain variable region comprising the sequence of SEQ ID NO: 69, or
(46) a heavy chain variable region comprising the sequence of SEQ ID NO: 74 and a light chain variable region comprising the sequence of SEQ ID NO: 69, or
(47) a heavy chain variable region comprising the sequence of SEQ ID NO: 68 and a light chain variable region comprising the sequence of SEQ ID NO: 71, or
(48) a heavy chain variable region comprising the sequence of SEQ ID NO: 70 and a light chain variable region comprising the sequence of SEQ ID NO: 71, or
(49) a heavy chain variable region comprising the sequence of SEQ ID NO: 72 and a light chain variable region comprising the sequence of SEQ ID NO: 71, or
(50) a heavy chain variable region comprising the sequence of SEQ ID NO: 74 and a light chain variable region comprising the sequence of SEQ ID NO: 71, or
(51) a heavy chain variable region comprising the sequence of SEQ ID NO: 68 and a light chain variable region comprising the sequence of SEQ ID NO: 73, or
(52) a heavy chain variable region comprising the sequence of SEQ ID NO: 70 and a light chain variable region comprising the sequence of SEQ ID NO: 73, or
(53) a heavy chain variable region comprising the sequence of SEQ ID NO: 72 and a light chain variable region comprising the sequence of SEQ ID NO: 73, or
(54) a heavy chain variable region comprising the sequence of SEQ ID NO: 74 and a light chain variable region comprising the sequence of SEQ ID NO: 73, or
(55) a heavy chain variable region comprising the sequence of SEQ ID NO: 68 and a light chain variable region comprising the sequence of SEQ ID NO: 75, or
(56) a heavy chain variable region comprising the sequence of SEQ ID NO: 70 and a light chain variable region comprising the sequence of SEQ ID NO: 75, or
(57) a heavy chain variable region comprising the sequence of SEQ ID NO: 72 and a light chain variable region comprising the sequence of SEQ ID NO: 75, or
(58) a heavy chain variable region comprising the sequence of SEQ ID NO: 74 and a light chain variable region comprising the sequence of SEQ ID NO: 75.

In some embodiments, the antibody or an antigen-binding fragment thereof provided herein further comprises one or more amino acid residue substitutions or modifications yet retains specific binding affinity to human CD39. In some embodiments, at least one of the substitutions or modifications is in one or more of the CDR sequences, and/or in one or more of the non-CDR sequences of the heavy chain variable region or light chain variable region. In some embodiments, at least one of the substitutions is a conservative substitution.

In some embodiments, the antibody or an antigen-binding fragment thereof provided herein further comprises an Fc region, optionally an Fc region of human immunoglobulin (Ig), or optionally an Fc region of human IgG. In some embodiments, the Fc region is derived from human IgG1, IgG2, IgG3, IgG4, IgA1, IgA2 or IgM. In some embodiments, the Fc region is derived from human IgG1 or IgG4. In some embodiments, the Fc region derived from human IgG1 or IgG4 with reduced effector functions. In some embodiments, the Fc region derived from human IgG1 comprises a L234A and/or L235A mutation. In some embodiments, the Fc region derived from human IgG4, optionally with reduced effector functions. In some embodiments, the Fc region derived from human IgG4 comprises a S228P mutation and/or a L235E mutation and/or a F234A and L235A mutation.

In some embodiments, the antibody or an antigen-binding fragment thereof provided herein is humanized. In some embodiments, the antibody or an antigen-binding fragment thereof provided herein is a monoclonal antibody, a bispecific antibody, a multi-specific antibody, a recombinant antibody, a chimeric antibody, a labeled antibody, a bivalent antibody, an anti-idiotypic antibody or a fusion protein.

In some embodiments, the antibody or an antigen-binding fragment thereof provided herein is a diabody, a Fab, a Fab', a F(ab')$_2$, a Fd, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a multispecific antibody, a camelized single domain antibody, a nanobody, a domain antibody, or a bivalent domain antibody.

In some embodiments, the antibody or an antigen-binding fragment thereof provided herein is capable of specifically binding to human CD39 at an $EC_{50}$ of no more than $10^{-8}$ M as measured by FACS (Fluorescence Activated Cell Sorting) assay.

In some embodiments, the antibody or an antigen-binding fragment thereof provided herein has one or more properties selected from the group consisting of:
a) specifically binding to human CD39 but not specifically binding to mouse CD39 as measured by FACS assay;
b) specifically binding to cynomolgus CD39 at an $EC_{50}$ of no more than $10^{-8}$ M as measured by FACS assay;
c) specifically binding to human CD39 at a $K_D$ value of no more than $10^{-7}$ M (e.g. no more than $5\times10^{-8}$ M, no more than $3\times10^{-8}$ M, no more than $2\times10^{-8}$ M, no more than $1\times10^{-8}$ M, or no more than $8\times10^{-9}$ M) as measured by Biacore assay;
d) specifically binding to human CD39 at a $K_D$ value of no more than $10^{-8}$ M (e.g. no more than $8\times10^{-9}$ M, no more than $5\times10^{-9}$ M, no more than $4\times10^{-9}$ M, no more than $3\times10^{-9}$ M, no more than $1\times10^{-9}$ M, or no more than $9\times10^{-10}$ M) as measured by Octet assay;
e) inhibiting ATPase activity in a CD39 expressing cell at an $IC_{50}$ of no more than 50 nM (e.g. no more than 1 nM, no more than 5 nM, no more than 10 nM, or no more than 30 nM) as measured by ATPase activity assay;
f) capable of enhancing ATP mediated monocytes activation at a concentration of no more than 50 nM (e.g. no more than 40 nM, no more than 30 nM, no more than 20 nM, no more than 10 nM, no more than 5 nM, no more than 3 nM, no more than 2 nM, no more than 1 nM, no more than 0.5 nM, or no more than 0.2 nM) as measured by analysis of CD80, CD86 and CD40 expression by FACS assay;
g) capable of enhancing ATP mediated T cell activation in peripheral blood mononuclear cell (PBMC) at a concentration of no more than 25 nM as measured by IL-2 secretion, IFN-γ secretion, CD4+ or CD8+ T cells proliferation;
h) capable of enhancing ATP mediated dendritic cell (DC) activation at a concentration of no more than 25 nM (or no more than 10 nM, or no more than 5 nM, or no more than 1 nM, or no more than 0.5 nM, or no more than 0.2 nM) as measured by analysis of CD83 expression by FACS assay, or by the capability of the activated DC to promote T cell proliferation, or by the capability of the activated DC to promote IFN-γ production in the mix-lymphocyte reaction (MLR) assay;

i) capable of blocking the inhibition of CD4+ T cell proliferation induced by adenosine (hydrolyzed from ATP) at a concentration of no more than 1 nM (e.g. no more than 0.1 nM, no more than 0.01 nM) as measured by FACS assay;

j) capable of inhibiting tumor growth in a NK cell or macrophage cell dependent manner;

k) capable of reversing human CD8+ T cell proliferation which was inhibited by eATP as measured by T cell proliferation, CD25+ cells, and living cells population; and l) capable of enhancing human macrophage IL1β release induced by LPS stimulation at a concentration of no more than 50 nM (or no more than 12.5 nM, or no more than 3.13 nM, or no more than 0.78 nM, or no more than 0.2 nM, or no more than 0.049 nM, or no more than 0.012 nM, or no more than 0.003 nM, or no more than 0.0008 nM) as measured by ELISA assay.

In another aspect, the present disclosure provides an anti-CD39 antibody or an antigen-binding fragment thereof that competes for binding to human CD39 with the antibody or an antigen-binding fragment thereof provided herein. In some embodiments, the anti-CD39 antibody or an antigen-binding fragment thereof competes for binding to human CD39 with an antibody comprising a heavy chain variable region comprising the sequence of SEQ ID NO: 43 and a light chain variable region comprising the sequence of SEQ ID NO: 52. In some embodiments, the anti-CD39 antibody or an antigen-binding fragment thereof competes for binding to human CD39 with an antibody comprising a heavy chain variable region comprising the sequence of SEQ ID NO: 44 and a light chain variable region comprising the sequence of SEQ ID NO: 53, or competes with an antibody comprising a heavy chain variable region comprising the sequence of SEQ ID NO: 45 and a light chain variable region comprising the sequence of SEQ ID NO: 54. In some embodiments, the anti-CD39 antibody or an antigen-binding fragment thereof competes for binding to human CD39 with an antibody comprising a heavy chain variable region comprising the sequence of SEQ ID NO: 47 and a light chain variable region comprising the sequence of SEQ ID NO: 56.

In another aspect, the present disclosure provides an anti-CD39 antibody or an antigen-binding fragment thereof which specifically binds to an epitope of CD39, wherein the epitope comprises one or more residues selected from the group consisting of Q96, N99, E143, R147, R138, M139, E142, K5, E100, D107, V81, E82, R111, and V115.

In some embodiments, the epitope comprises one or more residues selected from the group consisting of Q96, N99, E143, and R147. In some embodiments, the epitope comprises one or more residues selected from the group consisting of R138, M139, and E142. In some embodiments, the epitope comprises one or more residues selected from the group consisting of K5, E100, and D107. In some embodiments, the epitope comprises one or more residues selected from the group consisting of V81, E82, R111, and V115. In some embodiments, the CD39 is a human CD39. In some embodiments, the CD39 is a human CD39 comprising an amino acid sequence of SEQ ID NO: 162.

In some embodiments, the anti-CD39 antibody or an antigen-binding fragment thereof is not any of Antibody 9-8B, Antibody T895, and Antibody I394, wherein Antibody 9-8B comprises a heavy chain variable region comprising the sequence of SEQ ID NO: 46, and a light chain variable region comprising the sequence of SEQ ID NO: 48; Antibody T895 comprises a heavy chain variable region comprising the sequence of SEQ ID NO: 55, and a light chain variable region comprising the sequence of SEQ ID NO: 57; and Antibody I394 comprises a heavy chain variable region comprising the sequence of SEQ ID NO: 113, and a light chain variable region comprising the sequence of SEQ ID NO: 114.

In some embodiments, the antibody or an antigen-binding fragment thereof provided herein is bispecific. In some embodiments, the antibody or an antigen-binding fragment thereof provided herein is capable of specifically binding to a second antigen other than CD39, or a second epitope on CD39. In certain embodiments, the second antigen is selected from the group consisting of TGFbeta, CD73, PD1, PDL1, 4-1BB, CTLA4, TIGIT, GITA, VISTA, TIGIT, B7-H3, B7-H4, B7-H5, CD112R, Siglec-15, LAG3, and TIM-3.

In some embodiments, the antibody or an antigen-binding fragment thereof provided herein is linked to one or more conjugate moieties. In some embodiments, the conjugate moiety comprises a clearance-modifying agent, a chemotherapeutic agent, a toxin, a radioactive isotope, a lanthanide, a luminescent label, a fluorescent label, an enzyme-substrate label, a DNA-alkylator, a topoisomerase inhibitor, a tubulin-binder, or other anticancer drugs.

In another aspect, the present disclosure provides a pharmaceutical composition comprising the antibody or an antigen-binding fragment thereof of the present disclosure and one or more pharmaceutically acceptable carriers.

In another aspect, the present disclosure provides an isolated polynucleotide encoding the antibody or an antigen-binding fragment thereof of the present disclosure.

In another aspect, the present disclosure provides a vector comprising the isolated polynucleotide of the present disclosure.

In another aspect, the present disclosure provides a host cell comprising the vector of the present disclosure.

In another aspect, the present disclosure provides a kit comprising the antibody or an antigen-binding fragment thereof and/or the pharmaceutical composition of the present disclosure, and a second therapeutic agent.

In another aspect, the present disclosure provides a method of expressing the antibody or an antigen-binding fragment thereof of the present disclosure, comprising culturing the host cell of the present disclosure under the condition at which the vector of the present disclosure is expressed.

In another aspect, the present disclosure provides a method of treating, preventing or alleviating a CD39 related disease, disorder or condition in a subject, comprising administering to the subject a therapeutically effective amount of the antibody or an antigen-binding fragment thereof of the present disclosure and/or the pharmaceutical composition of the present disclosure.

In another aspect, the present disclosure provides a method of treating, preventing or alleviating a disease treatable by reducing the ATPase activity of CD39 in a subject, comprising administering to the subject a therapeutically effective amount of the antibody or an antigen-binding fragment thereof of the present disclosure and/or the pharmaceutical composition of the present disclosure.

In another aspect, the present disclosure provides a method of treating, preventing or alleviating a disease associated with adenosine-mediated inhibition of T cell, Monocyte, Macrophage, Dendritic cell, Antigen Presenting Cell, NK and/or B cell activity in a subject, comprising administering to the subject a therapeutically effective amount of the antibody or an antigen-binding fragment thereof of the present disclosure and/or the pharmaceutical composition of the present disclosure.

In some embodiments, the disease, disorder or condition is cancer. In some embodiments, the cancer is anal cancer, appendix cancer, astrocytoma, basal cell carcinoma, gallbladder cancer, gastric cancer, lung cancer, bronchial cancer, bone cancer, liver and bile duct cancer, pancreatic cancer, breast cancer, liver cancer, ovarian cancer, testicle cancer, kidney cancer, renal pelvis and ureter cancer, salivary gland cancer, small intestine cancer, urethral cancer, bladder cancer, head and neck cancer, spine cancer, brain cancer, cervix cancer, uterine cancer, endometrial cancer, colon cancer, colorectal cancer, rectal cancer, anal cancer, esophageal cancer, gastrointestinal cancer, skin cancer, prostate cancer, pituitary cancer, vagina cancer, thyroid cancer, throat cancer, glioblastoma, melanoma, myelodysplastic syndrome, sarcoma, teratoma, chronic lymphocytic leukemia (CLL), chronic myeloid leukemia (CML), acute lymphocytic leukemia (ALL), acute myeloid leukemia (AML), Hodgkin lymphoma, non-Hodgkin lymphoma, multiple myeloma, T or B cell lymphoma, GI organ interstitialoma, soft tissue tumor, hepatocellular carcinoma, and adenocarcinoma. In some embodiments, the cancer is a leukemia, lymphoma, bladder cancer, glioma, glioblastoma, ovarian cancer, melanoma, prostate cancer, thyroid cancer, esophageal cancer or breast cancer. In some embodiments, the subject has been identified as having cancer cells or tumor infiltrating immune cells or immune suppression cells expressing CD39, optionally at a level significantly higher from the level normally found on non-cancer cells or non-immune suppression cells. Examples of immune suppression cells expressing CD39 include myeloid-derived suppressor cells (MDSCs) or regulatory T cells (Tregs).

In some embodiments, the disease, disorder or condition is an autoimmune disease or infection. In some embodiments, the autoimmune disease is immune thrombocytopenia, systemic scleroderma, sclerosis, adult respiratory distress syndrome, eczema, asthma, Sjogren's syndrome, Addison's disease, giant cell arteritis, immune complex nephritis, immune thrombocytopenic purpura, autoimmune thrombocytopenia, Celiac disease, psoriasis, dermatitis, colitis or systemic lupus erythematosus. In some embodiments, the infection is a viral infection or a bacterial infection. In some embodiments, the infection is HIV infection, HBV infection, HCV infection, inflammatory bowel disease, or Crohn's disease.

In some embodiments, the subject is human. In some embodiments, the administration is via oral, nasal, intravenous, subcutaneous, sublingual, or intramuscular administration. In some embodiments, the method further comprises administering a therapeutically effective amount of a second therapeutic agent. In some embodiments, the second therapeutic agent is selected from the group consisting of a chemotherapeutic agent, an anti-cancer drug, a radiation therapy agent, an immunotherapy agent, an anti-angiogenesis agent, a targeted therapy agent, a cellular therapy agent, a gene therapy agent, a hormonal therapy agent, an antiviral agent, an antibiotic, an analgesics, an antioxidant, a metal chelator, and cytokines.

In another aspect, the present disclosure provides a method of modulating CD39 activity in a CD39-positive cell, comprising exposing the CD39-positive cell to the antibody or antigen-binding fragment thereof of the present disclosure and/or the pharmaceutical composition of the present disclosure. In some embodiments, the cell is an immune cell.

In another aspect, the present disclosure provides a method of detecting the presence or amount of CD39 in a sample, comprising contacting the sample with the antibody or an antigen-binding fragment thereof of the present disclosure and/or the pharmaceutical composition of the present disclosure, and determining the presence or the amount of CD39 in the sample.

In another aspect, the present disclosure provides a method of diagnosing a CD39 related disease, disorder or condition in a subject, comprising: a) contacting a sample obtained from the subject with the antibody or an antigen-binding fragment thereof of the present disclosure and/or the pharmaceutical composition of the present disclosure; b) determining the presence or amount of CD39 in the sample; and c) correlating the presence or the amount of CD39 to existence or status of the CD39 related disease, disorder or condition in the subject.

In another aspect, the present disclosure provides use of the antibody or an antigen-binding fragment thereof of the present disclosure and/or the pharmaceutical composition of the present disclosure in the manufacture of a medicament for treating, preventing or alleviating a CD39 related disease, disorder or condition in a subject.

In another aspect, the present disclosure provides use of the antibody or an antigen-binding fragment thereof of the present disclosure and/or the pharmaceutical composition of the present disclosure in the manufacture of a diagnostic reagent for diagnosing a CD39 related disease, disorder or condition in a subject.

In another aspect, the present disclosure provides a kit comprising the antibody or an antigen-binding fragment thereof of the present disclosure and/or the pharmaceutical composition of the present disclosure, useful in detecting CD39.

CD39L3), ENTPD5 (i.e. CD39L4) and ENTPD6 (i.e. CD39L2) proteins, respectively.

Figure 7:
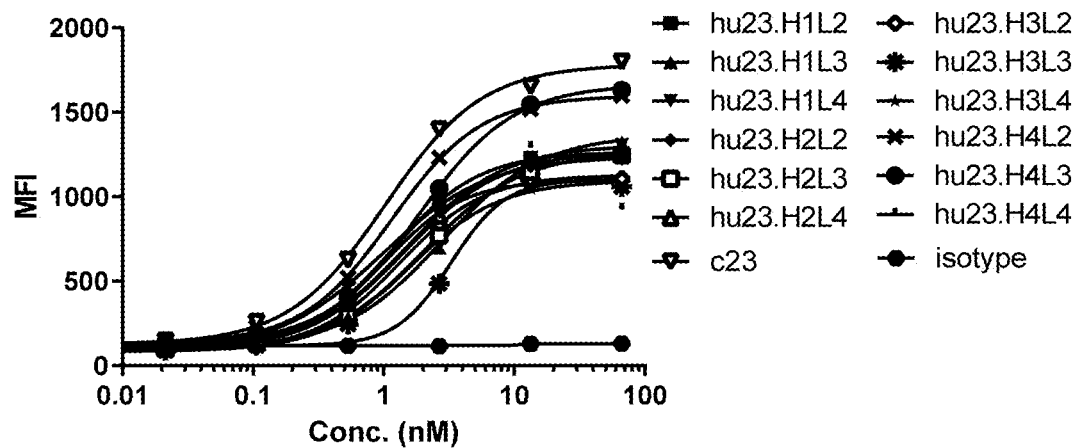
Figure 7:
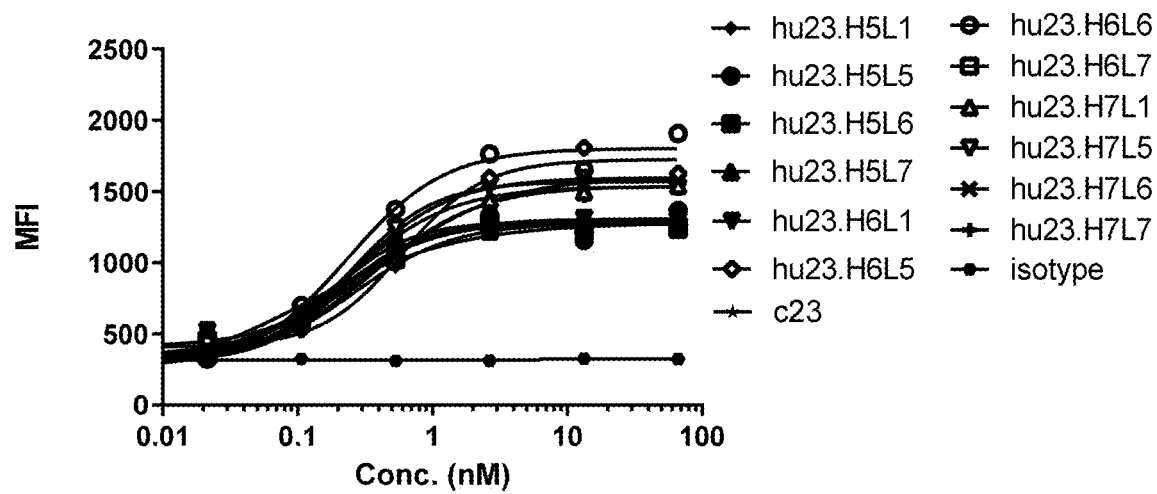

FIGS. 7A and 7B show binding activity of c23 humanized antibodies with MOLP-8 cells by FACS.

Figure 8:
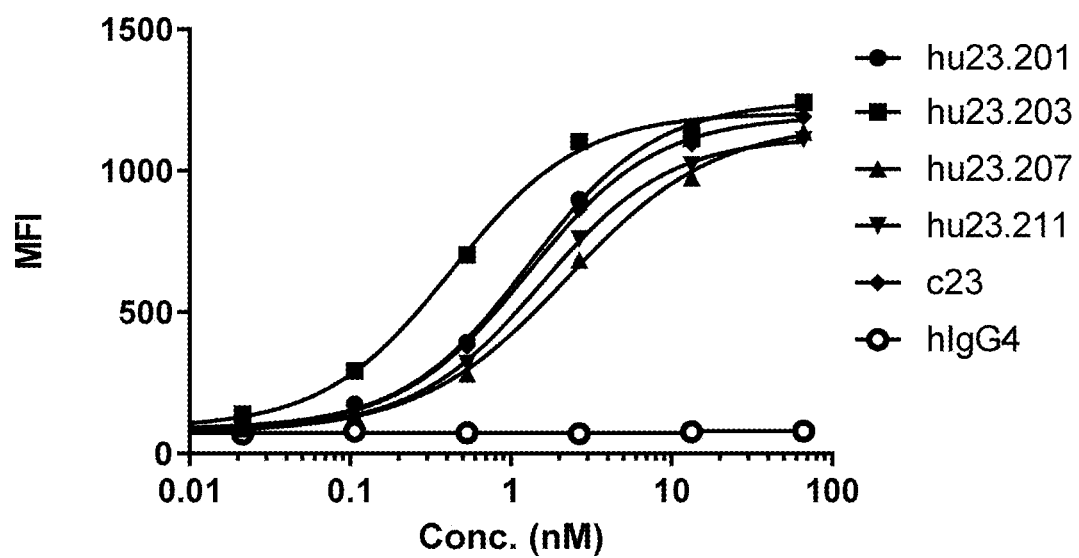

FIG. 8 shows binding activity of c23 humanized antibodies (obtained by yeast display) with MOLP-8 cells.

Figure 9:
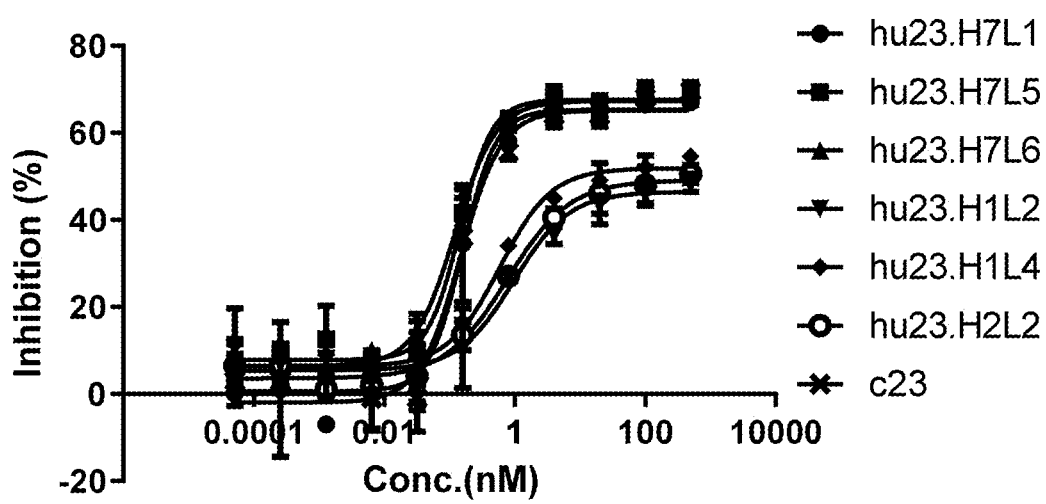
Figure 9:
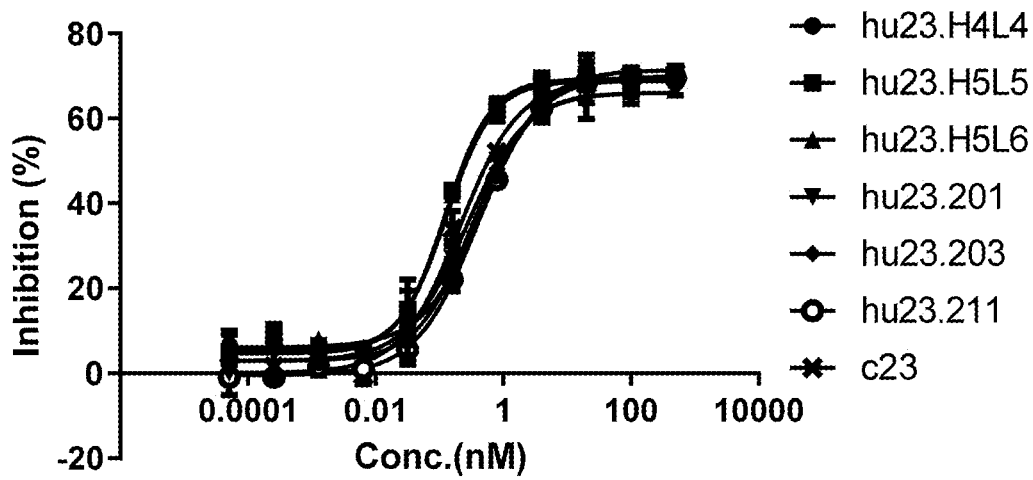

FIGS. 9A and 9B show ATPase inhibition of c23 humanized antibodies on SK-MEL-28 cells by FACS.

Figure 10:
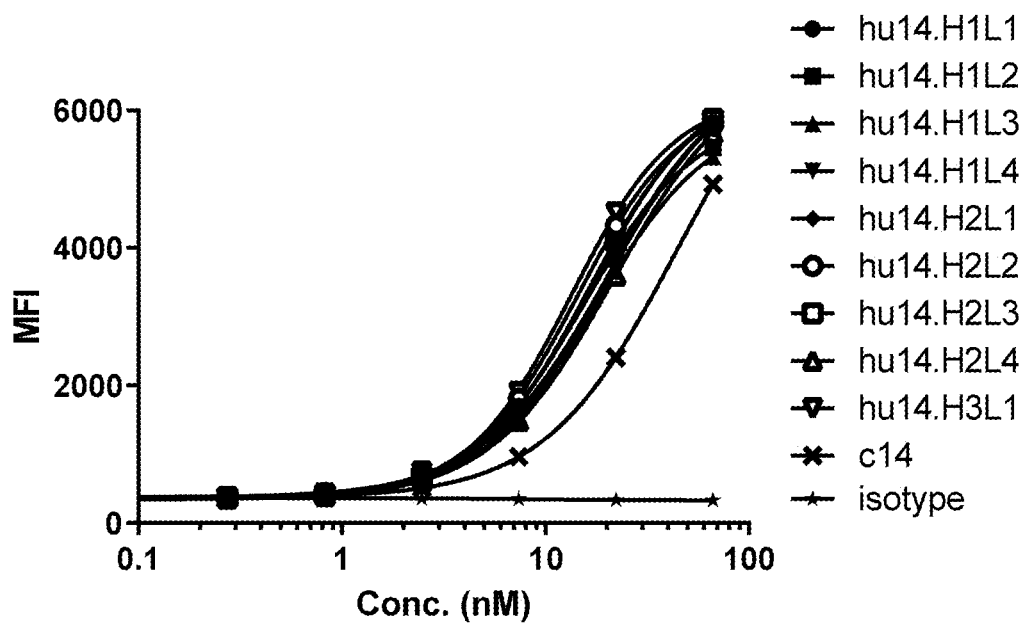
Figure 10:
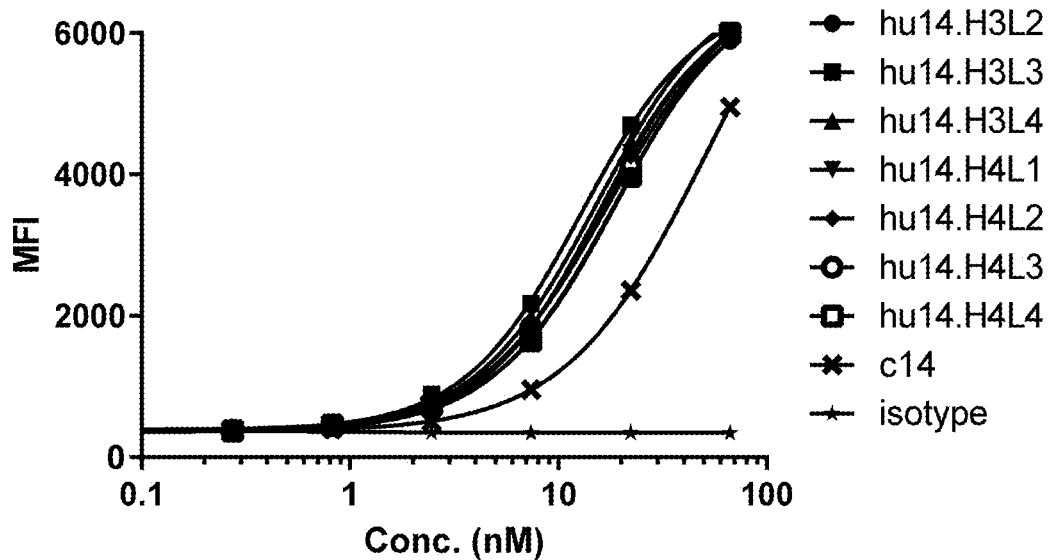
Figure 10:
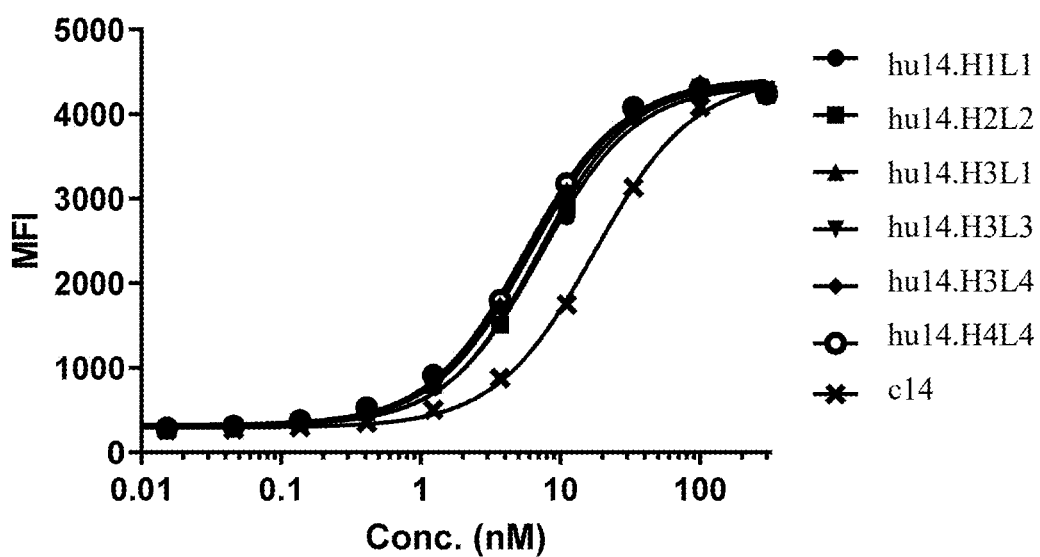

FIGS. 10A to 10C show binding activity of c14 humanized antibodies with MOLP-8 cells by FACS.

Figure 11:
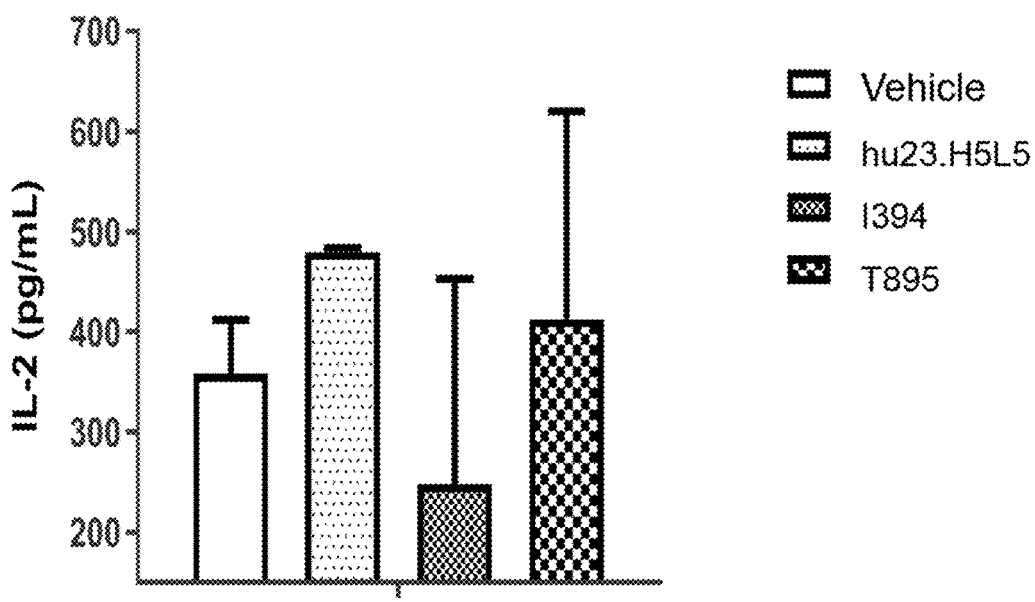
Figure 11:
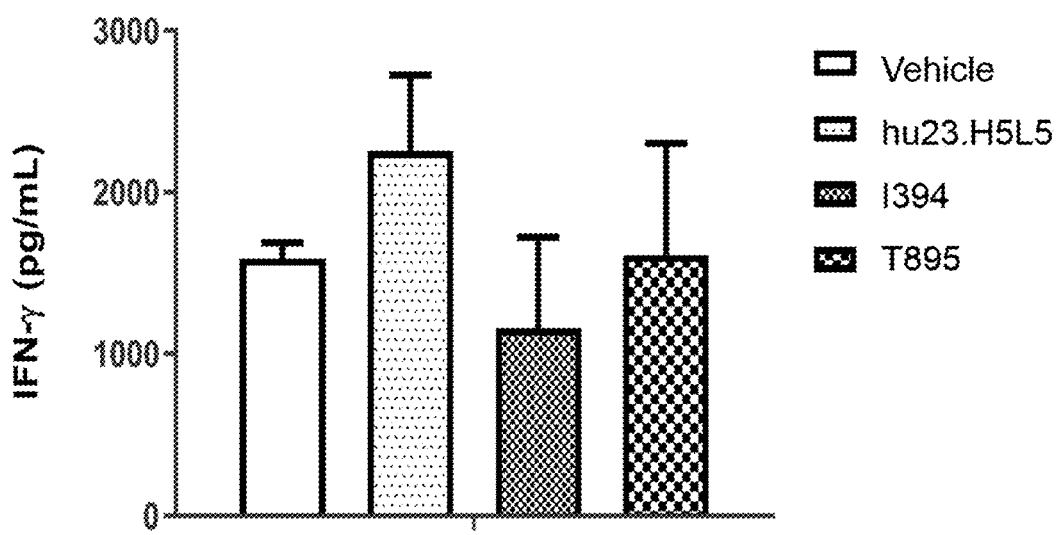
Figure 11:
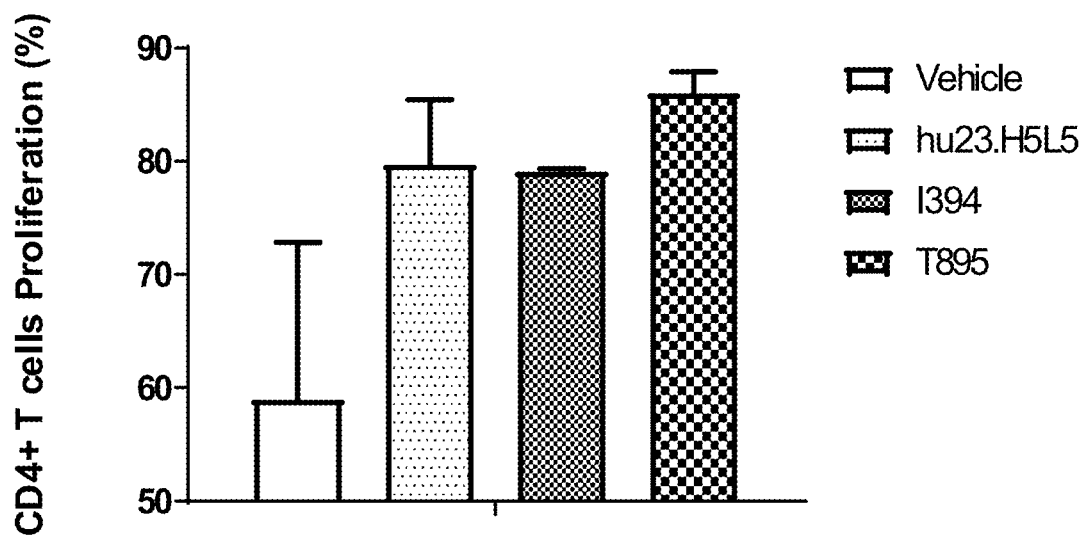
Figure 11:
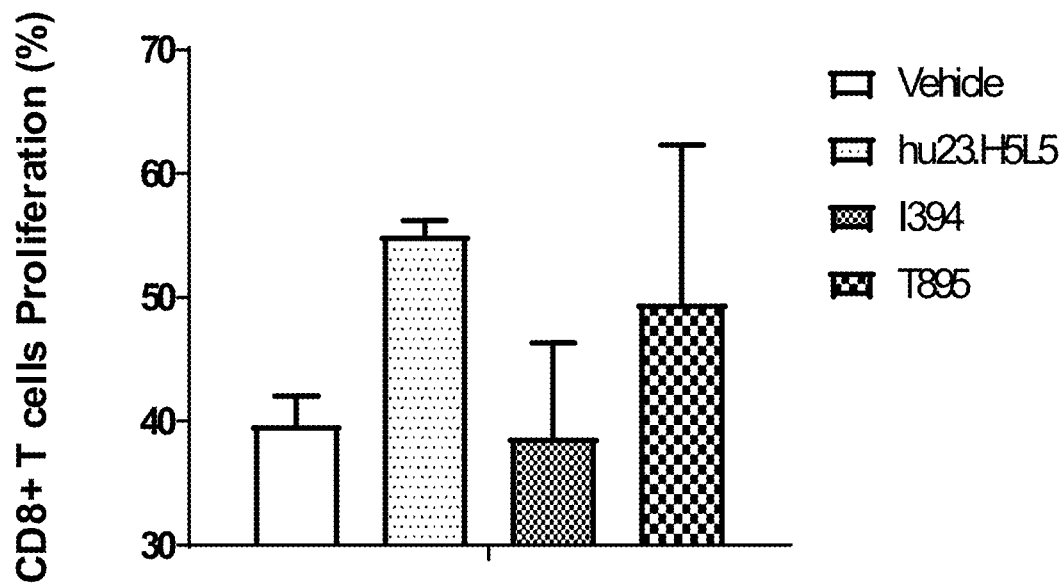
Figure 12:
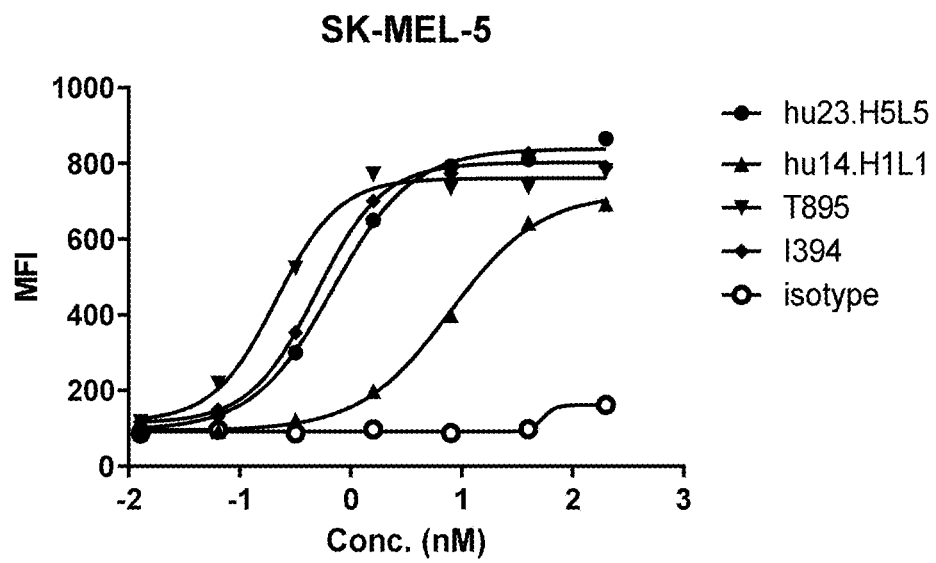
Figure 12:
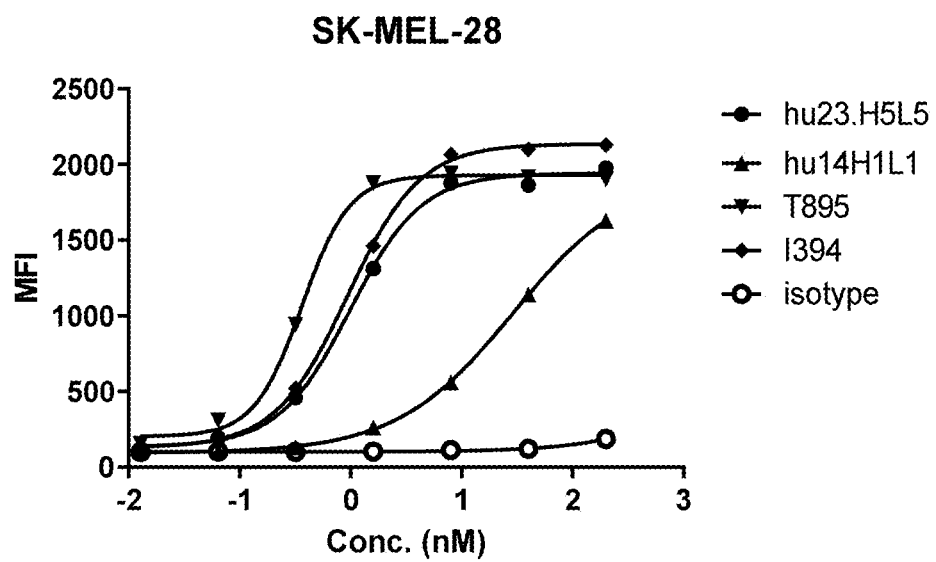
Figure 12:
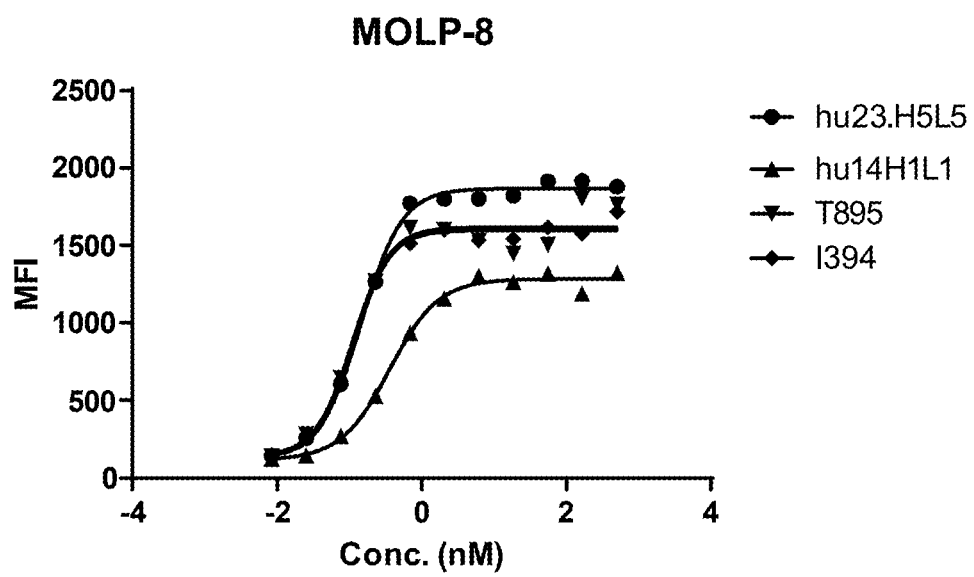
Figure 12:
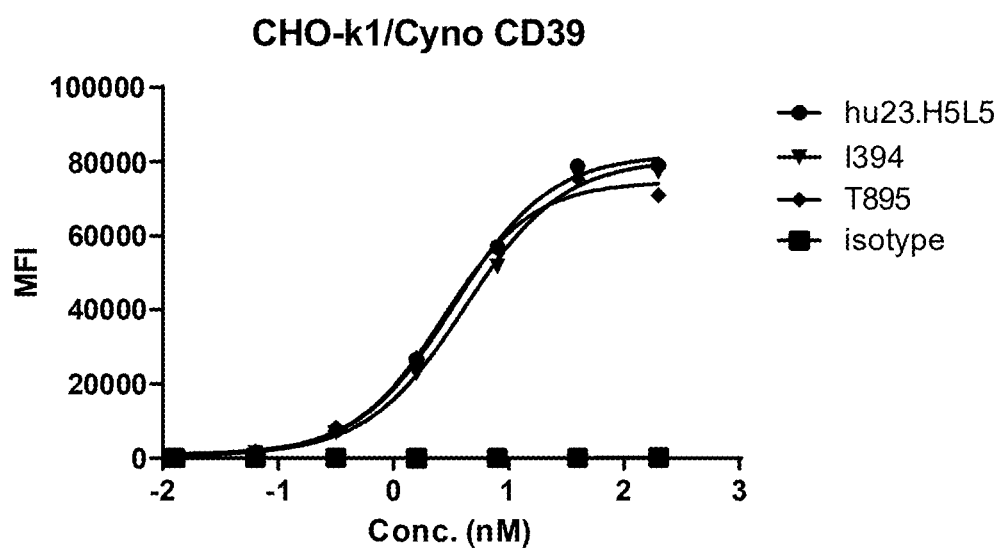
Figure 12:
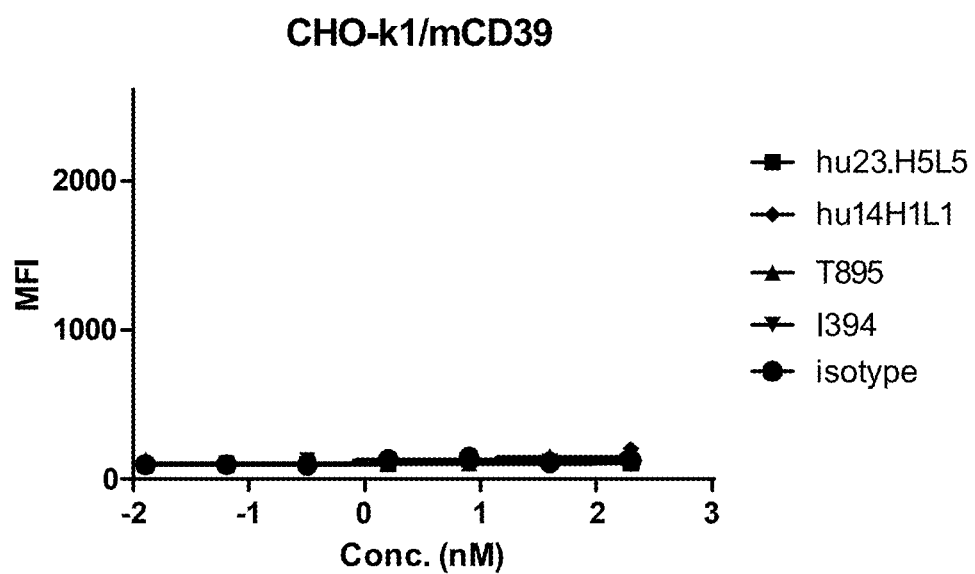

FIGS. 11A to 11D show ATP-mediated T cell activation in PBMC by humanized antibody hu23.H5L5, as measured by IL-2 (FIG. 11A), IFN-γ (FIG. 11B), CD4+ T cell proliferation (FIG. 11C) and CD8+ T cell proliferation (FIG. 11D).

FIGS. 12A to 12E show binding activity of humanized antibodies hu23.H5L5 and hu14.H1L1 with SK-MEL-5 (FIG. 12A), SK-MEL-28 (FIG. 12B), MOLP-8 (FIG. 12C), CHOK1-cynoCD39 (FIG. 12D) and CHOK1-mCD39 (FIG. 12E) cells by FACS.

FIGS. 13A to 13B show ATPase inhibition activity by humanized antibodies hu23.H5L5 and hu14.H1L1 on SK-MEL-5 (FIG. 13A) and MOLP-8 (FIG. 13B).

FIGS. 14A to 14C show ATP-mediated monocyte activation by anti-CD39 humanized antibody hu23.H5L5, as measured by CD80 (FIG. 14A), CD86 (FIG. 14B) and CD40 (FIG. 14C) expression.

Figure 15:
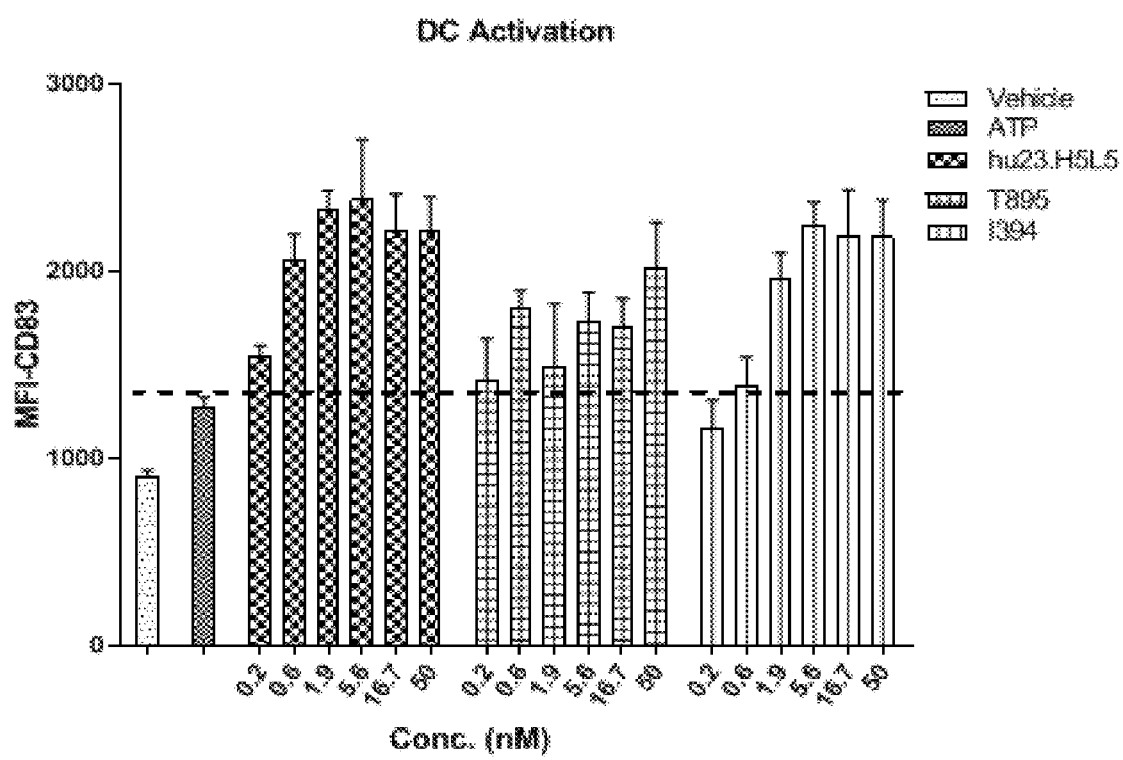
Figure 15:
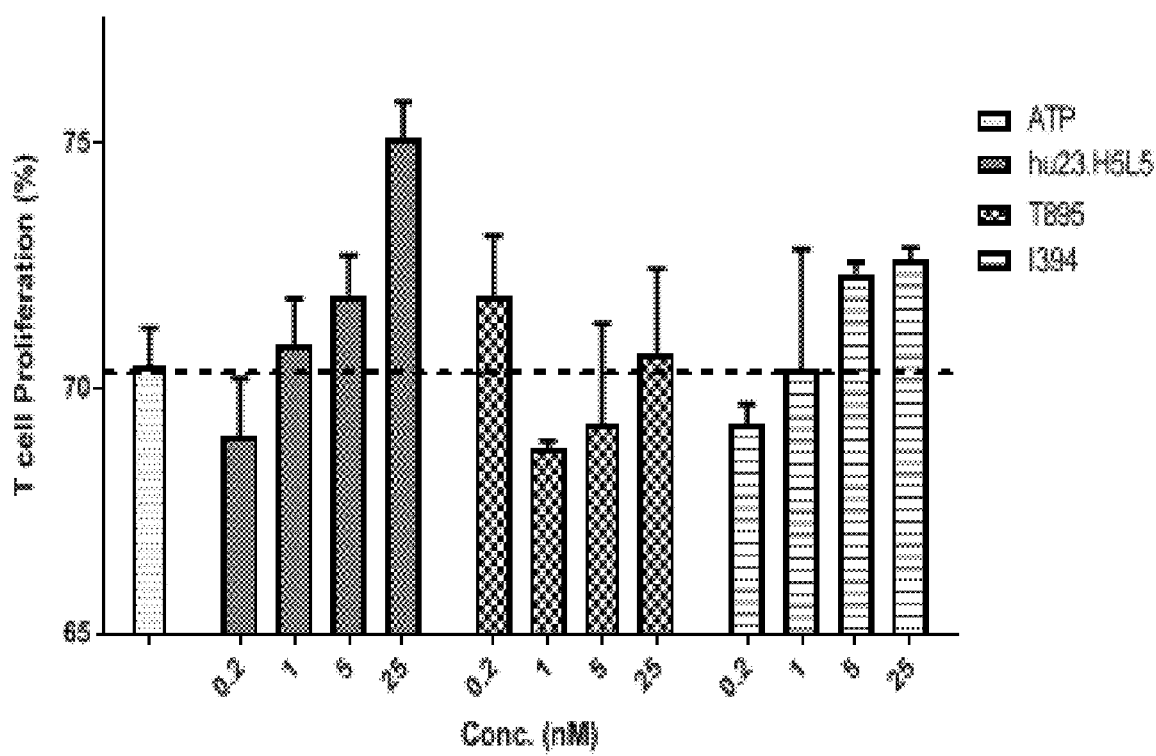
Figure 15:
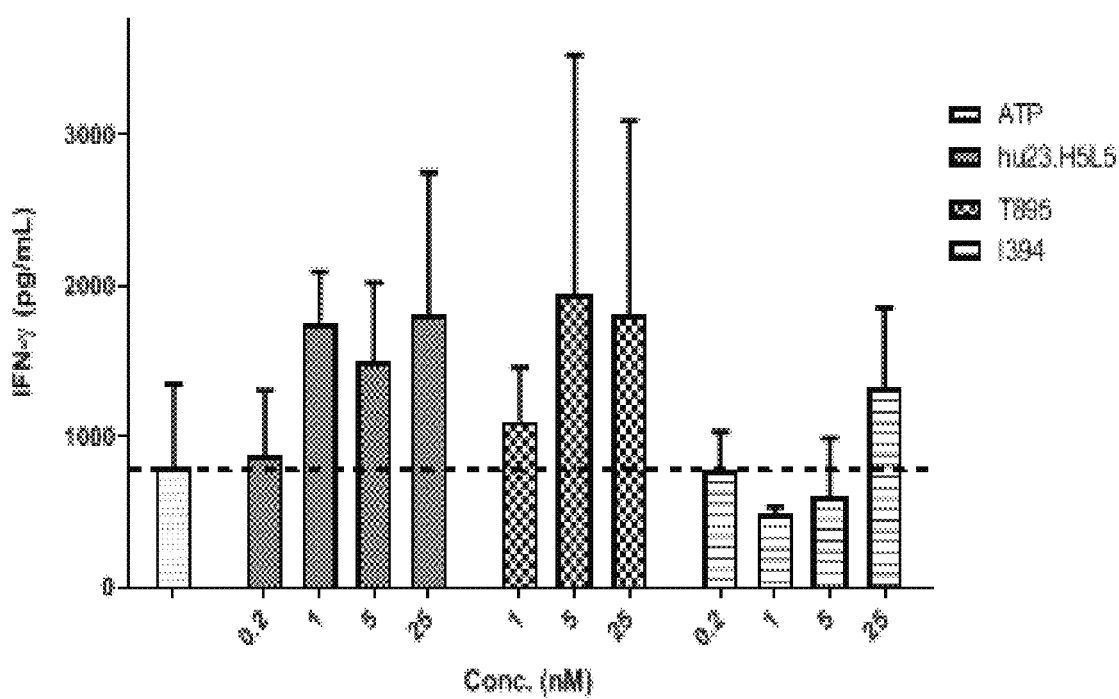

FIG. 15 shows that humanized antibody hu23.H5L5 increased ATP-mediated DC activation as measured by CD83 expression (FIG. 15A), and enhanced T cell proliferation (FIG. 15B) and T cell activation (FIG. 15C).

Figure 16:
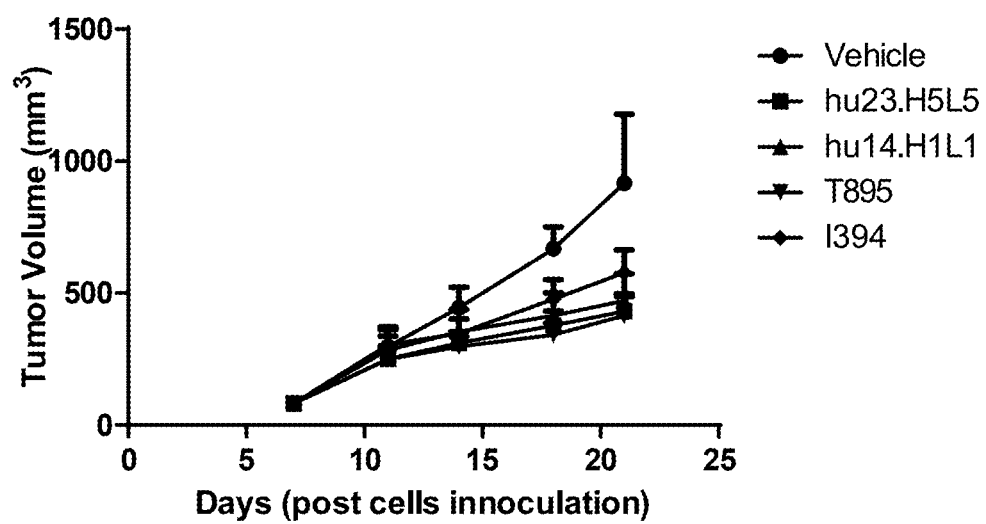

FIG. 16 shows the tumor growth inhibition by humanized antibodies hu23.H5L5 and hu14.H1L1 in MOLP-8 xenograft mice.

Figure 17:
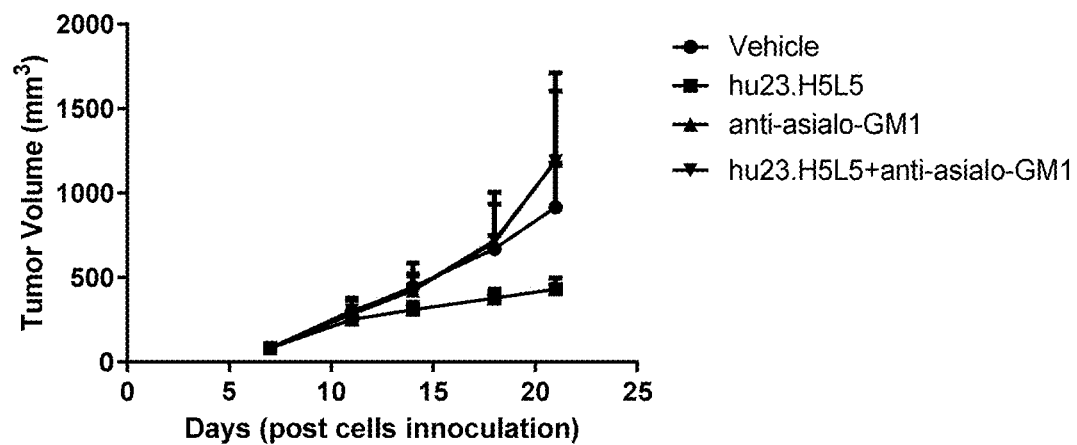

FIG. 17 shows the tumor growth inhibition of anti-CD39 humanized antibody hu23.H5L5 in NK depleted MOLP-8 xenograft mice.

Figure 18:
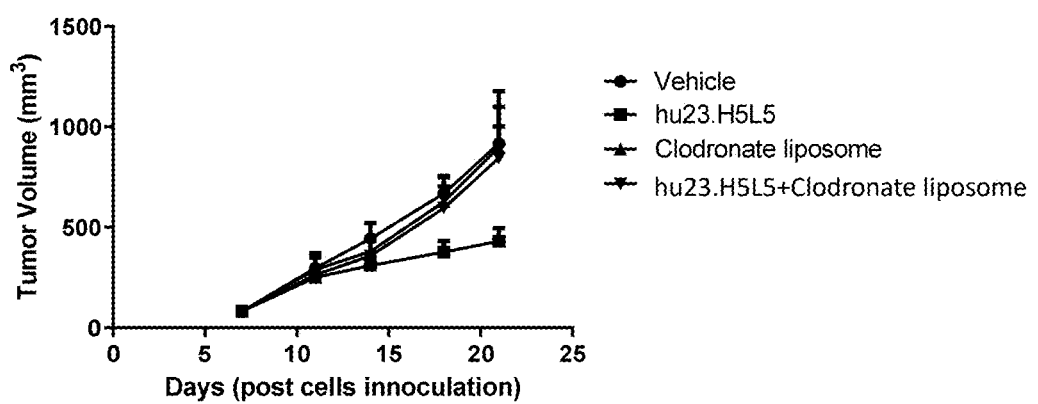

FIG. 18 shows the tumor growth inhibition of anti-CD39 humanized antibody hu23.H5L5 in macrophage depleted MOLP-8 xenograft mice.

Figure 19:
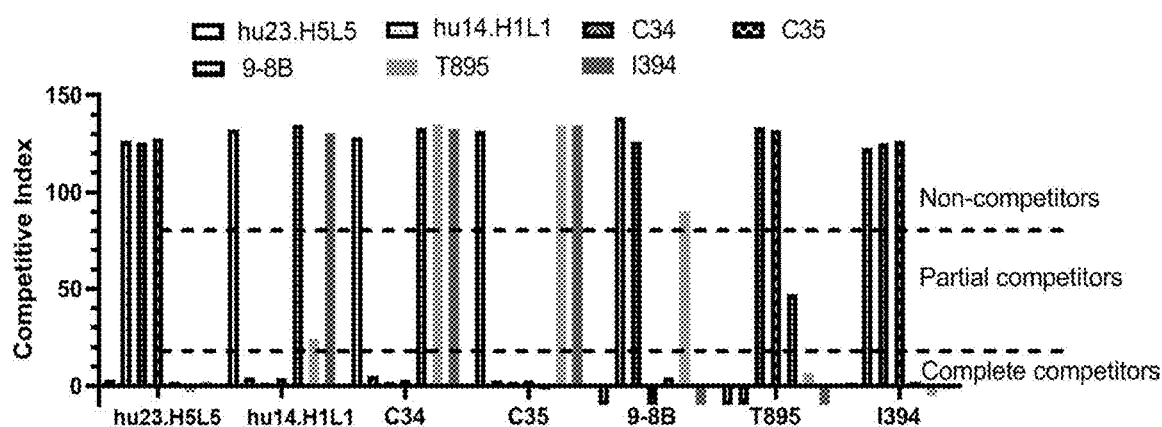
Figure 19:
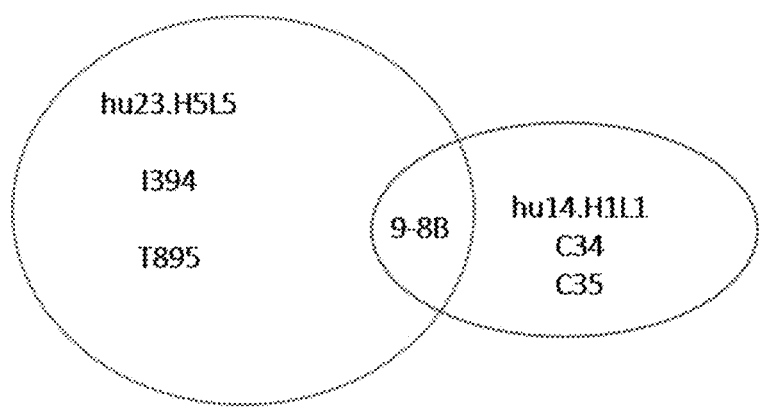

FIG. 19A shows epitope binning results of humanized antibodies hu23.H5L5 and hu14.H1L1 with references antibodies. FIG. 19B shows the epitope grouping of the tested antibodies.

Figure 20:
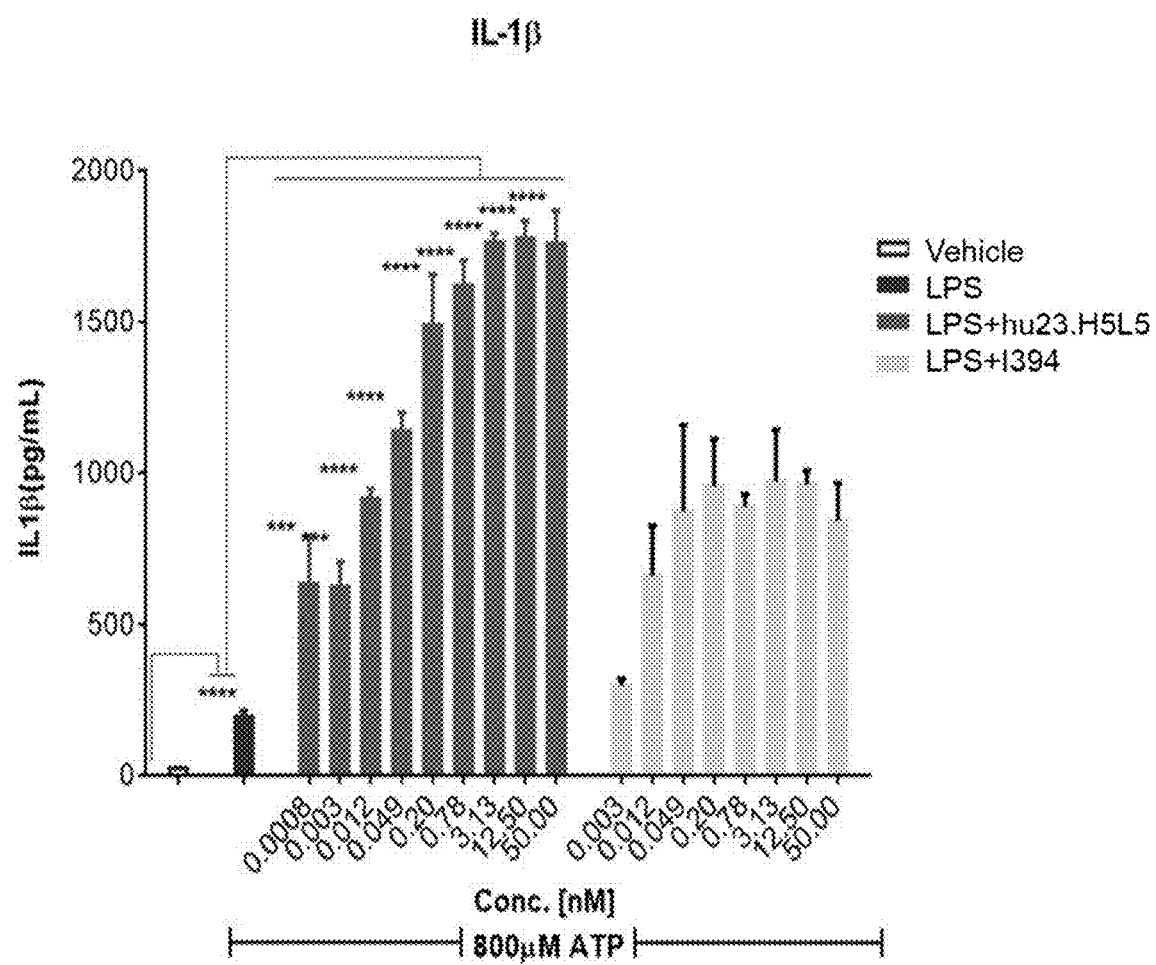

FIG. 20 shows the effect of anti-CD39 humanized antibody hu23.H5L5 on human macrophage IL1β release induced by LPS stimulation.

Figure 21:
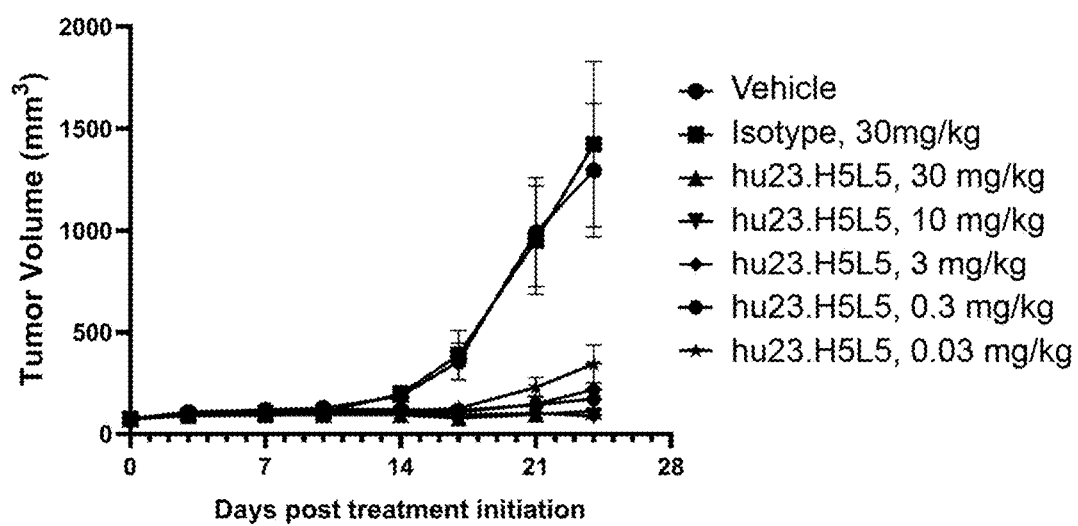

FIG. 21 shows the tumor growth inhibition of humanized antibody hu23.H5L5 at different dosages (0.03 mg/kg, 0.3 mg/kg, 3 mg/kg, 10 mg/kg, 30 mg/kg) in PBMC adoption mice.

Figure 22:
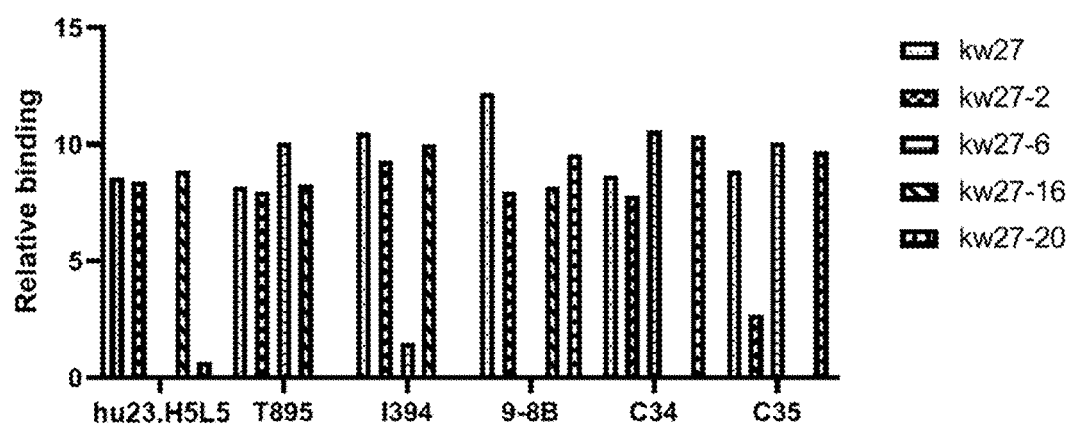

FIG. 22 shows the epitope mapping results of humanized antibody hu23. H5L5, chimeric antibodies c34 and c35, as well as reference antibodies T895, I394 and 9-8B.

Figure 23:
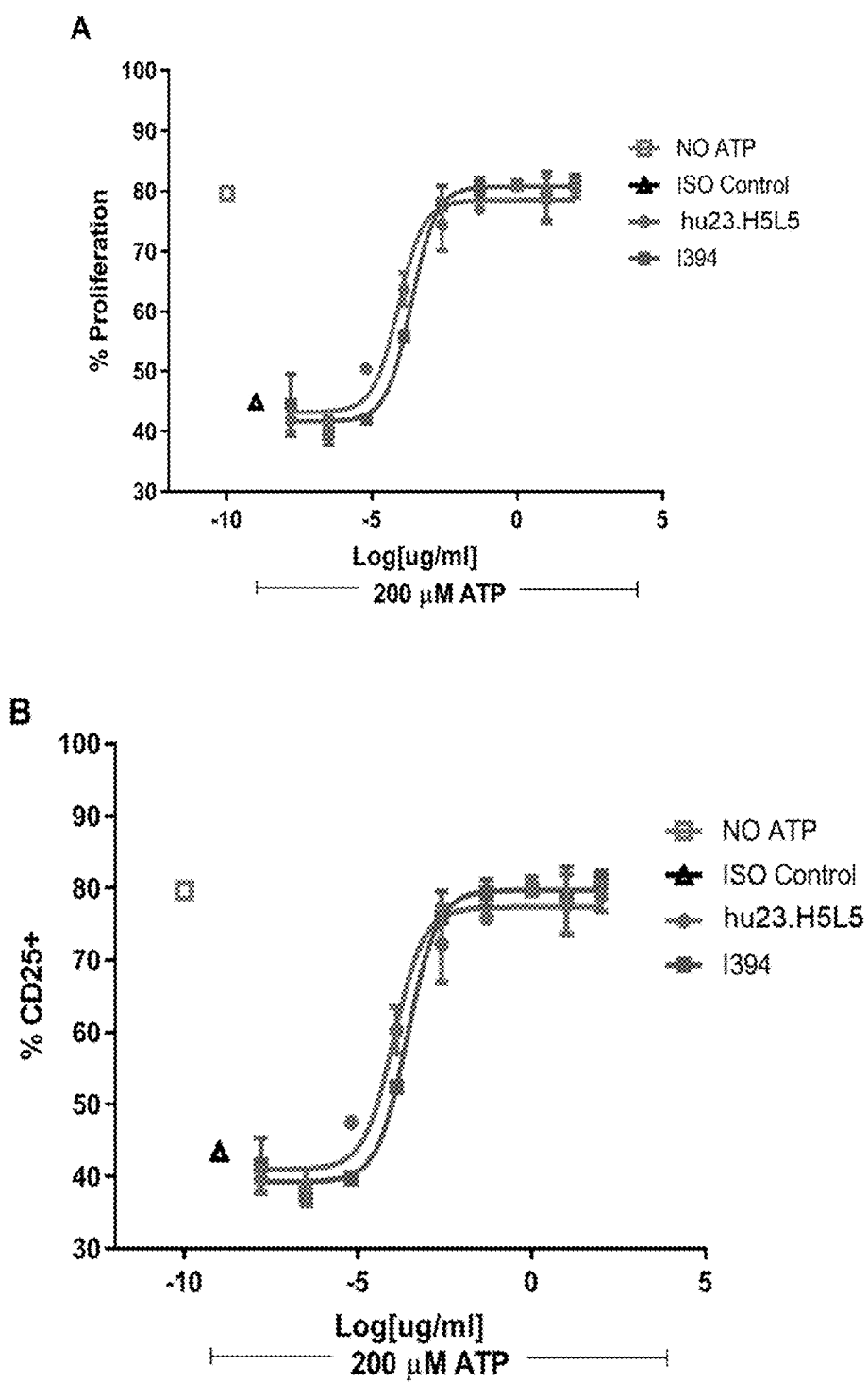
Figure 23:
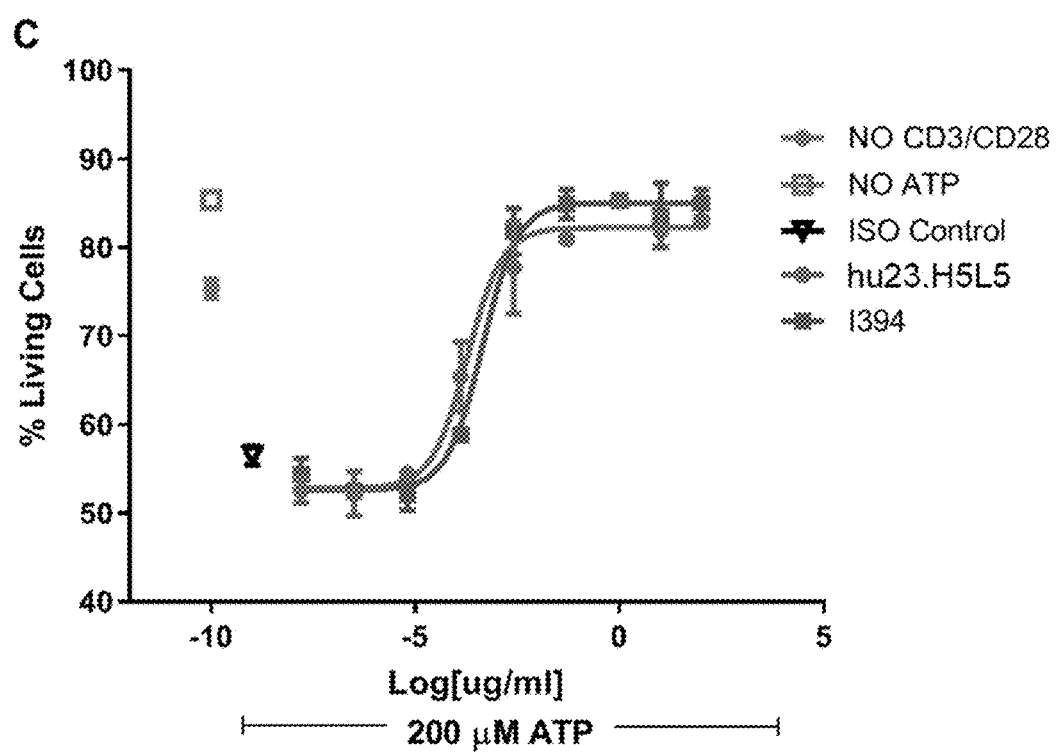

FIGS. 23A to 23C show extracellular ATP inhibited CD8+ T cell proliferation reversed by humanized antibody hu23.H5L5, as measured by T cell proliferation (FIG. 23A), CD25+ Cells (FIG. 23B), and living cells population (FIG. 23C).

DETAILED DESCRIPTION OF THE INVENTION

The following description of the disclosure is merely intended to illustrate various embodiments of the disclosure. As such, the specific modifications discussed are not to be construed as limitations on the scope of the disclosure. It will be apparent to a person skilled in the art that various equivalents, changes, and modifications may be made without departing from the scope of the disclosure, and it is understood that such equivalent embodiments are to be included herein. All references cited herein, including publications, patents and patent applications are incorporated herein by reference in their entirety.

Definitions

The term "antibody" as used herein includes any immunoglobulin, monoclonal antibody, polyclonal antibody, multivalent antibody, bivalent antibody, monovalent antibody, multispecific antibody, or bispecific antibody that binds to a specific antigen. A native intact antibody comprises two heavy (H) chains and two light (L) chains. Mammalian heavy chains are classified as alpha, delta, epsilon, gamma, and mu, each heavy chain consists of a variable region (VH) and a first, second, third, and optionally fourth constant region (CH1, CH2, CH3, CH4 respectively); mammalian light chains are classified as λ or κ, while each light chain consists of a variable region (VL) and a constant region. The antibody has a "Y" shape, with the stem of the Y consisting of the second and third constant regions of two heavy chains bound together via disulfide bonding. Each arm of the Y includes the variable region and first constant region of a single heavy chain bound to the variable and constant regions of a single light chain. The variable regions of the light and heavy chains are responsible for antigen binding. The variable regions in both chains generally contain three highly variable loops called the complementarity determining regions (CDRs) (light chain CDRs including LCDR1, LCDR2, and LCDR3, heavy chain CDRs including HCDR1, HCDR2, HCDR3). CDR boundaries for the antibodies and antigen-binding fragments disclosed herein may be defined or identified by the conventions of Kabat, IMGT, Chothia, or Al-Lazikani (Al-Lazikani, B., Chothia, C., Lesk, A. M., *J. Mol. Biol.*, 273(4), 927 (1997); Chothia, C. et al., *J Mol Biol.* December 5; 186(3):651-63 (1985); Chothia, C. and Lesk, A. M., *J. Mol. Biol.*, 196,901 (1987); Chothia, C. et al., *Nature*. December 21-28; 342(6252):877-83 (1989); Kabat E. A. et al., Sequences of Proteins of immunological Interest, 5th Ed. Public Health Service, National Institutes of Health, Bethesda, Md. (1991); Marie-Paule Lefranc et al., *Developmental and Comparative Immunology*, 27: 55-77 (2003); Marie-Paule Lefranc et al., *Immunome Research*, 1(3), (2005); Marie-Paule Lefranc, Molecular Biology of B cells (second edition), chapter 26, 481-514, (2015)). The three CDRs are interposed between flanking stretches known as framework regions (FRs) (light chain FRs including LFR1, LFR2, LFR3, and LFR4, heavy chain FRs including HFR1, HFR2, HFR3, and HFR4), which are more highly conserved than the CDRs and form a scaffold to support the highly variable loops. The constant regions of the heavy and light chains are not involved in antigen-binding, but exhibit various effector functions. Antibodies are assigned to classes based on the amino acid sequences of the constant regions of their heavy chains. The five major classes or isotypes of antibodies are IgA, IgD, IgE, IgG, and IgM, which are characterized by the presence of alpha, delta, epsilon, gamma, and mu heavy chains, respectively. Several of the major antibody classes are divided into subclasses such as IgG1 (gamma1 heavy chain), IgG2 (gamma2 heavy chain), IgG3 (gamma3 heavy chain), IgG4 (gamma4 heavy chain), IgA1 (alpha1 heavy chain), or IgA2 (alpha2 heavy chain).

In certain embodiments, the antibody provided herein encompasses any antigen-binding fragments thereof. The term "antigen-binding fragment" as used herein refers to an antibody fragment formed from a portion of an antibody comprising one or more CDRs, or any other antibody fragment that binds to an antigen but does not comprise an intact native antibody structure. Examples of antigen-binding fragments include, without limitation, a diabody, a Fab, a Fab', a F(ab')$_2$, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a bispecific antibody, a multispecific antibody, a camelized single domain antibody, a nanobody, a domain antibody, and a bivalent domain antibody. An antigen-binding fragment is capable of binding to the same antigen to which the parent antibody binds.

"Fab" with regard to an antibody refers to that portion of the antibody consisting of a single light chain (both variable and constant regions) bound to the variable region and first constant region of a single heavy chain by a disulfide bond.

"Fab'" refers to a Fab fragment that includes a portion of the hinge region.

"F(ab')$_2$" refers to a dimer of Fab'.

"Fc" with regard to an antibody (e.g. of IgG, IgA, or IgD isotype) refers to that portion of the antibody consisting of the second and third constant domains of a first heavy chain bound to the second and third constant domains of a second heavy chain via disulfide bonding. Fc with regard to antibody of IgM and IgE isotype further comprises a fourth constant domain. The Fc portion of the antibody is responsible for various effector functions such as antibody-dependent cell-mediated cytotoxicity (ADCC), and complement dependent cytotoxicity (CDC), but does not function in antigen binding.

"Fv" with regard to an antibody refers to the smallest fragment of the antibody to bear the complete antigen binding site. An Fv fragment consists of the variable region of a single light chain bound to the variable region of a single heavy chain.

"Single-chain Fv antibody" or "scFv" refers to an engineered antibody consisting of a light chain variable region and a heavy chain variable region connected to one another directly or via a peptide linker sequence (Huston J S et al. *Proc Natl Acad Sci USA*, 85:5879(1988)).

"Single-chain Fv-Fc antibody" or "scFv-Fc" refers to an engineered antibody consisting of a scFv connected to the Fc region of an antibody.

"Camelized single domain antibody," "heavy chain antibody," or "HCAb" refers to an antibody that contains two $V_H$ domains and no light chains (Riechmann L. and Muyldermans S., *J Immunol Methods*. December 10; 231(1-2): 25-38 (1999); Muyldermans S., *J Biotechnol*. June; 74(4): 277-302 (2001); WO94/04678; WO94/25591; U.S. Pat. No. 6,005,079). Heavy chain antibodies were originally derived from Camelidae (camels, dromedaries, and llamas). Although devoid of light chains, camelized antibodies have an authentic antigen-binding repertoire (Hamers-Casterman C. et al., *Nature*. June 3; 363(6428):446-8 (1993); Nguyen V K. et al. *Immunogenetics*. April; 54(1):39-47 (2002); Nguyen V K. et al. *Immunology*. May; 109(1):93-101 (2003)). The variable domain of a heavy chain antibody (VHH domain) represents the smallest known antigen-binding unit generated by adaptive immune responses (Koch-Nolte F. et al., *FASEB J*. November; 21(13):3490-8. Epub 2007 Jun. 15 (2007)).

A "nanobody" refers to an antibody fragment that consists of a VHH domain from a heavy chain antibody and two constant domains, CH2 and CH3.

A "diabody" or "dAb" includes small antibody fragments with two antigen-binding sites, wherein the fragments comprise a $V_H$ domain connected to a $V_L$ domain in the same polypeptide chain ($V_H$-$V_L$ or $V_L$-$V_H$) (see, e.g. Holliger P. et al., *Proc Natl Acad Sci USA*. July 15; 90(14):6444-8 (1993); EP404097; WO93/11161). By using a linker that is too short to allow pairing between the two domains on the same chain, the domains are forced to pair with the complementary domains of another chain, thereby creating two antigen-binding sites. The antigen-binding sites may target the same or different antigens (or epitopes). In certain embodiments, a "bispecific ds diabody" is a diabody target two different antigens (or epitopes).

A "domain antibody" refers to an antibody fragment containing only the variable region of a heavy chain or the variable region of a light chain. In certain instances, two or more $V_H$ domains are covalently joined with a peptide linker to create a bivalent or multivalent domain antibody. The two $V_H$ domains of a bivalent domain antibody may target the same or different antigens.

The term "valent" as used herein refers to the presence of a specified number of antigen binding sites in a given molecule. The term "monovalent" refers to an antibody or an antigen-binding fragment having only one single antigen-binding site; and the term "multivalent" refers to an antibody or antigen-binding fragment having multiple antigen-binding sites. As such, the terms "bivalent", "tetravalent", and "hexavalent" denote the presence of two binding sites, four binding sites, and six binding sites, respectively, in an antigen-binding molecule. In some embodiments, the antibody or antigen-binding fragment thereof is bivalent.

As used herein, a "bispecific" antibody refers to an artificial antibody which has fragments derived from two different monoclonal antibodies and is capable of binding to two different epitopes. The two epitopes may present on the same antigen, or they may present on two different antigens.

In certain embodiments, an "scFv dimer" is a bivalent diabody or bispecific scFv (BsFv) comprising $V_H$-$V_L$ (linked by a peptide linker) dimerized with another VH-VL moiety such that VH'S of one moiety coordinate with the $V_L$'s of the other moiety and form two binding sites which can target the same antigens (or epitopes) or different antigens (or epitopes). In other embodiments, an "scFv dimer" is a bispecific diabody comprising $V_{H1}$-$V_{L2}$ (linked by a peptide linker) associated with $V_{L1}$-$V_{H2}$ (also linked by a peptide linker) such that $V_{H1}$ and $V_{L1}$ coordinate and $V_{H2}$ and $V_{L2}$ coordinate and each coordinated pair has a different antigen specificity.

A "dsFv" refers to a disulfide-stabilized Fv fragment that the linkage between the variable region of a single light chain and the variable region of a single heavy chain is a disulfide bond. In some embodiments, a "(dsFv)$_2$" or "(dsFv-dsFv')" comprises three peptide chains: two VH moieties linked by a peptide linker (e.g. a long flexible linker) and bound to two $V_L$ moieties, respectively, via disulfide bridges. In some embodiments, dsFv-dsFv' is bispecific in which each disulfide paired heavy and light chain has a different antigen specificity.

The term "chimeric" as used herein, means an antibody or antigen-binding fragment, having a portion of heavy and/or light chain derived from one species, and the rest of the heavy and/or light chain derived from a different species. In an illustrative example, a chimeric antibody may comprise a constant region derived from human and a variable region from a non-human animal, such as from mouse. In some embodiments, the non-human animal is a mammal, for example, a mouse, a rat, a rabbit, a goat, a sheep, a guinea pig, or a hamster.

The term "humanized" as used herein means that the antibody or antigen-binding fragment comprises CDRs derived from non-human animals, FR regions derived from human, and when applicable, the constant regions derived from human.

The term "affinity" as used herein refers to the strength of non-covalent interaction between an immunoglobulin molecule (i.e. antibody) or fragment thereof and an antigen.

The term "specific binding" or "specifically binds" as used herein refers to a non-random binding reaction between two molecules, such as for example between an antibody and an antigen. Specific binding can be characterized in binding affinity, for example, represented by $K_D$ value, i.e., the ratio of dissociation rate to association rate ($k_{off}/k_{on}$) when the binding between the antigen and antigen-binding molecule reaches equilibrium. $K_D$ may be determined by using any conventional method known in the art, including but are not limited to surface plasmon resonance method, Octet method, microscale thermophoresis method, HPLC-MS method and FACS assay method. A $K_D$ value of $\leq 10^{-6}$ M (e.g. $\leq 5 \times 10^{-7}$ M, $\leq 2 \times 10^{-7}$ M, $10^{-7}$ M, $\leq 5 \times 10^{-8}$ M, $\leq 2 \times 10^{-8}$ M, $\leq 10^{-8}$ M, $\leq 5 \times 10^{-9}$ M, $\leq 4 \times 10^{-9}$ M, $\leq 3 \times 10^{-9}$ M, $\leq 2 \times 10^{-9}$ M, or $10^{-9}$ M) can indicate specific binding between an antibody or antigen binding fragments thereof and CD39 (e.g. human CD39).

The ability to "compete for binding to human CD39" as used herein refers to the ability of a first antibody or antigen-binding fragment to inhibit the binding interaction between human CD39 and a second anti-CD39 antibody to any detectable degree. In certain embodiments, an antibody or antigen-binding fragment that compete for binding to human CD39 inhibits the binding interaction between human CD39 and a second anti-CD39 antibody by at least 85%, or at least 90%. In certain embodiments, this inhibition may be greater than 95%, or greater than 99%.

The term "epitope" as used herein refers to the specific group of atoms or amino acids on an antigen to which an antibody binds. Two antibodies may bind the same or a closely related epitope within an antigen if they exhibit competitive binding for the antigen. An epitope can be linear or conformational (i.e. including amino acid residues spaced apart). For example, if an antibody or antigen-binding fragment blocks binding of a reference antibody to the antigen by at least 85%, or at least 90%, or at least 95%, then the antibody or antigen-binding fragment may be considered to bind the same/closely related epitope as the reference antibody.

The term "amino acid" as used herein refers to an organic compound containing amine (—NH$_2$) and carboxyl (—COOH) functional groups, along with a side chain specific to each amino acid. The names of amino acids are also represented as standard single letter or three-letter codes in the present disclosure, which are summarized as follows.

| Names | Three-letter Code | Single-letter Code |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A "conservative substitution" with reference to amino acid sequence refers to replacing an amino acid residue with a different amino acid residue having a side chain with similar physiochemical properties. For example, conservative substitutions can be made among amino acid residues with hydrophobic side chains (e.g. Met, Ala, Val, Leu, and Ile), among amino acid residues with neutral hydrophilic side chains (e.g. Cys, Ser, Thr, Asn and Gln), among amino acid residues with acidic side chains (e.g. Asp, Glu), among amino acid residues with basic side chains (e.g. His, Lys, and Arg), or among amino acid residues with aromatic side chains (e.g. Trp, Tyr, and Phe). As known in the art, conservative substitution usually does not cause significant change in the protein conformational structure, and therefore could retain the biological activity of a protein.

The term "homologous" as used herein refers to nucleic acid sequences (or its complementary strand) or amino acid sequences that have sequence identity of at least 60% (e.g. at least 65%, 70%, 75%, 80%, 85%, 88%, 90%, 91%, 92%, 93%, 94%, 95%, 96%, 97%, 98%, 99%) to another sequences when optimally aligned.

"Percent (%) sequence identity" with respect to amino acid sequence (or nucleic acid sequence) is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum number of identical amino acids (or nucleic acids). In other words, percent (%) sequence identity of an amino acid sequence (or nucleic acid sequence) can be calculated by dividing the number of amino acid residues (or bases) that are identical relative to the reference sequence to which it is being compared by the total number of the amino acid residues (or bases) in the candidate sequence or in the reference sequence, whichever is shorter. Conservative substitution of the amino acid residues may or may not be considered as identical residues. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al., *J. Mol. Biol.*, 215:403-410 (1990); Stephen F. et al., *Nucleic Acids Res.*, 25:3389-3402 (1997)), ClustalW2 (available on the website of European Bioinformatics Institute, see also, Higgins D. G. et al., *Methods in Enzymology*, 266:383-402 (1996); Larkin M. A. et al., *Bioinformatics* (Oxford, England), 23(21): 2947-8 (2007)), and ALIGN or Megalign (DNASTAR) software. A person skilled in the art may use the default parameters provided by the tool, or may customize the parameters as appropriate for the alignment, such as for example, by selecting a suitable algorithm.

"Effector functions" as used herein refer to biological activities attributable to the binding of Fc region of an antibody to its effectors such as C1 complex and Fc receptor. Exemplary effector functions include: complement dependent cytotoxicity (CDC) mediated by interaction of antibodies and C1q on the C1 complex; antibody-dependent cell-mediated cytotoxicity (ADCC) mediated by binding of Fc region of an antibody to Fc receptor on an effector cell; and phagocytosis. Effector functions can be evaluated using various assays such as Fc receptor binding assay, C1q binding assay, and cell lysis assay.

An "isolated" substance has been altered by the hand of man from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide is "isolated" if it has been sufficiently separated from the coexisting materials of its natural state so as to exist in a substantially pure state. An "isolated nucleic acid sequence" refers to the sequence of an isolated nucleic acid molecule. In certain embodiments, an "isolated antibody or an antigen-binding fragment thereof" refers to the antibody or antigen-binding fragments thereof having a purity of at least 60%, 70%, 75%, 80%, 81%, 82%, 83%, 84%, 85%, 86%, 87%, 88%, 89%, 90%, 91%, 92%, 93%, 94%, 95%, 96%, 97%, 98%, 99% as determined by electrophoretic methods (such as SDS-PAGE, isoelectric focusing, capillary electrophoresis), or chromatographic methods (such as ion exchange chromatography or reverse phase HPLC).

The term "vector" as used herein refers to a vehicle into which a genetic element may be operably inserted so as to bring about the expression of that genetic element, such as to produce the protein, RNA or DNA encoded by the genetic element, or to replicate the genetic element. A vector may be used to transform, transduce, or transfect a host cell so as to bring about expression of the genetic element it carries within the host cell. Examples of vectors include plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating. A vector can be an expression vector or a cloning vector. The present disclosure provides vectors (e.g. expression vectors) containing the nucleic acid sequence provided herein encoding the antibody or an antigen-binding fragment thereof, at least one promoter (e.g. SV40, CMV, EF-1α) operably linked to the nucleic acid sequence, and at least one selection marker.

The phrase "host cell" as used herein refers to a cell into which an exogenous polynucleotide and/or a vector can be or has been introduced.

The term "subject" includes human and non-human animals. Non-human animals include all vertebrates, e.g., mammals and non-mammals, such as non-human primates, mice, rats, cats, rabbits, sheep, dogs, cows, chickens, amphibians, and reptiles. Except when noted, the terms "patient" or "subject" are used herein interchangeably.

The term "anti-tumor activity" means a reduction in tumor cell proliferation, viability, or metastatic activity. For example, anti-tumor activity can be shown by a decline in growth rate of abnormal cells that arises during therapy or tumor size stability or reduction, or longer survival due to therapy as compared to control without therapy. Such activity can be assessed using accepted in vitro or in vivo tumor models, including but not limited to xenograft models, allograft models, mouse mammary tumor virus (MMTV) models, and other known models known in the art to investigate anti-tumor activity.

"Treating" or "treatment" of a disease, disorder or condition as used herein includes preventing or alleviating a disease, disorder or condition, slowing the onset or rate of development of a disease, disorder or condition, reducing the risk of developing a disease, disorder or condition, preventing or delaying the development of symptoms associated with a disease, disorder or condition, reducing or ending symptoms associated with a disease, disorder or condition, generating a complete or partial regression of a disease, disorder or condition, curing a disease, disorder or condition, or some combination thereof.

The term "diagnosis", "diagnose" or "diagnosing" refers to the identification of a pathological state, disease or condition, such as identification of a CD39 related disease, or refer to identification of a subject with a CD39 related disease who may benefit from a particular treatment regimen. In some embodiments, diagnosis contains the identification of abnormal amount or activity of CD39. In some embodiments, diagnosis refers to the identification of a cancer or an autoimmune disease in a subject.

As used herein, the term "biological sample" or "sample" refers to a biological composition that is obtained or derived from a subject of interest that contains a cellular and/or other molecular entity that is to be characterized and/or identified, for example based on physical, biochemical, chemical and/or physiological characteristics. A biological sample includes, but is not limited to, cells, tissues, organs and/or biological fluids of a subject, obtained by any method known by those of skill in the art. In some embodiments, the biological sample is a fluid sample. In some embodiments, the fluid sample is whole blood, plasma, blood serum, mucus (including nasal drainage and phlegm), peritoneal fluid, pleural fluid, chest fluid, saliva, urine, synovial fluid, cerebrospinal fluid (CSF), thoracentesis fluid, abdominal fluid, ascites or pericardial fluid. In some embodiments, the biological sample is a tissue or cell obtained from heart, liver, spleen, lung, kidney, skin or blood vessels of the subject.

"CD39" as used herein, also known as ENTPD1 or ENTPDase1, refers to an integral membrane protein that coverts ATP to AMP. Structurally, it is characterized by two transmembrane domains, a small cytoplasmic domain, and a large extracellular hydrophobic domain. In certain embodiments, the CD39 is human CD39. CD39 as used herein may be from other animal species, such as from mouse, and cynomolgus, among others. Exemplary sequence of human CD39 protein is disclosed in NCBI Ref Seq No. NP_001767.3. Exemplary sequence of Mus musculus (mouse) CD39 protein is disclosed in NCBI Ref Seq No. NP_033978.1. Exemplary sequence of Cynomolgus (monkey) CD39 protein is disclosed in NCBI Ref Seq No. XP_015311945.1.

In addition to CD39, the ENTPDase family also comprise several other members, including, ENTPDases 2, 3, 4, 5, 6, 7, and 8 (also known as ENTPD 2, 3, 4, 5, 6, 7, and 8, and are used interchangeably in the present disclosure). Four of the ENTPDases are typical cell surface-located enzymes with an extracellularly facing catalytic site (ENTPDase1, 2, 3, 8). ENTPDases 5 and 6 exhibit intracellular localization and undergo secretion after heterologous expression. ENTPDases 4 and 7 are entirely intracellularly located, facing the lumen of cytoplasmic organelles. In some embodiments, the antibody or an antigen-binding fragment thereof provided herein specifically bind to CD39 (i.e. ENTPDase 1), but does not bind to the other family members, for example, ENTPDases 2, 3, 5, or 6.

The term "anti-CD39 antibody" refers to an antibody that is capable of specific binding to CD39 (e.g. human or monkey CD39). The term "anti-human CD39 antibody" refers to an antibody that is capable of specific binding to human CD39.

A "CD39 related" disease, disorder or condition as used herein refers to any disease or condition caused by, exacerbated by, or otherwise linked to increased or decreased expression or activities of CD39. In some embodiments, the CD39 related disease, disorder or condition is an immune-related disorder, such as, for example, an autoimmune disease. In some embodiments, the CD39 related disease, disorder or condition is a disorder related to excessive cell proliferation, such as, for example, cancer. In certain embodiments, the CD39 related disease or condition is characterized in expressing or over-expressing of CD39 and/or CD39 related genes such as ENTPD1, 2, 3, 4, 5, 6, 7, or 8 genes.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

The term "CD39-positive cell" as used herein refer to a cell (e.g. a phagocytic cell) that expresses CD39 on the surface of the cell.

Anti-CD39 Antibodies

The present disclosure provides anti-CD39 antibodies and antigen-binding fragments thereof. The anti-CD39 antibodies and antigen-binding fragments provided herein are capable of specific binding to CD39.

In certain embodiments, the antibodies and the antigen-binding fragments thereof provided herein specifically bind to human CD39 at an $K_D$ value of no more than $10^{-7}$ M, no more than $8 \times 10^{-8}$ M, no more than $5 \times 10^{-8}$ M, no more than $2 \times 10^{-8}$ M, no more than $8 \times 10^{-9}$ M, no more than $5 \times 10^{-9}$ M, no more than $2 \times 10^{-9}$ M, no more than $10^{-9}$ M, no more than $8 \times 10^{-10}$ M, no more than $7 \times 10^{-10}$ M, or no more than $6 \times 10^{-10}$ M by Biacore assay. Biacore assay is based on surface plasmon resonance technology, see, for example, Murphy, M. et al., *Current protocols in protein science*, Chapter 19, unit 19.14, 2006. In certain embodiments, the $K_D$ value is measured by the method as described in Example 5.1 of the present disclosure. In certain embodiments, the $K_D$ value is measured at about 25° C., or at about 37° C. In certain embodiments, the antibodies and the antigen-binding fragments thereof provided herein have a $K_D$ value measured at 25° C. comparable to that measured at 37° C., for example of about 80% to about 150%, of about 90% to about 130%, or of about 90% to about 120%, of about 90% to about 110% of that measured at 37° C.

In certain embodiments, the antibodies and the antigen-binding fragments thereof provided herein specifically bind to human CD39 at an $K_D$ value of no more than $10^{-8}$ M, no more than $8 \times 10^{-9}$ M, no more than $5 \times 10^{-9}$ M, no more than $4 \times 10^{-9}$ M, no more than $3 \times 10^{-9}$ M, no more than $2 \times 10^{-9}$ M, no more than $1 \times 10^{-9}$ M, no more than $9 \times 10^{-10}$ M, no more than $8 \times 10^{-10}$ M, no more than $7 \times 10^{-10}$ M, or no more than $6 \times 10^{-10}$ M by Octet assay. Octet assay is based on bio-layer interferometry technology, see, for example, Abdiche, Yasmina N., et al. *Analytical biochemistry* 386.2 (2009): 172-180, and Sun Y S., Instrumentation Science & Technology, 2014, 42(2): 109-127. In certain embodiments, the $K_D$ value is measured by the method as described in Example 5.1 of the present disclosure.

Binding of the antibodies or the antigen-binding fragments thereof provided herein to human CD39 can also be represented by "half maximal effective concentration" ($EC_{50}$) value, which refers to the concentration of an antibody where 50% of its maximal binding is observed. The $EC_{50}$ value can be measured by binding assays known in the art, for example, direct or indirect binding assay such as enzyme-linked immunosorbent assay (ELISA), FACS assay, and other binding assay. In certain embodiments, the antibodies and antigen-binding fragments thereof provided herein specifically bind to human CD39 at an $EC_{50}$ (i.e. 50% binding concentration) of no more than $10^{-7}$ M, no more than $8 \times 10^{-8}$ M, no more than $5 \times 10^{-8}$ M, no more than $2 \times 10^{-8}$ M, no more than $10^{-8}$ M, no more than $8 \times 10^{-9}$ M, no more than $5 \times 10^{-9}$ M, no more than $2 \times 10^{-9}$ M, no more than $10^{-9}$ M, no more than $8 \times 10^{-10}$ M, no more than $7 \times 10^{-10}$ M, or no more than $6 \times 10^{-10}$ M as measured by FACS (Fluorescence Activated Cell Sorting) assay. In certain embodiments, the binding is measured by ELISA or FACS assay.

In some embodiments, the antibody or an antigen-binding fragment thereof provided herein specifically binds to human CD39 (i.e. ENTPDase 1). In some embodiments, the antibody or an antigen-binding fragment thereof provided herein does not bind to other members of ENTPDase family. In some embodiments, the antibody or an antigen-binding fragment thereof provided herein specifically binds to human CD39, but does not specifically bind to ENTPDases 2, 3, 5, 6, for example, as measured by ELISA assay.

In certain embodiments, the antibodies and antigen-binding fragments thereof provided herein specifically bind to human CD39 but not specifically bind to mouse CD39, for example, as measured by FACS assay.

In certain embodiments, the antibodies and antigen-binding fragments thereof provided herein specifically bind to cynomolgus CD39 at an $EC_{50}$ of no more than $10^{-7}$ M, no more than $8 \times 10^{-8}$ M, no more than $5 \times 10^{-8}$ M, no more than $2 \times 10^{-8}$ M, no more than $10^{-8}$ M, no more than $8 \times 10^{-9}$ M, no more than $5 \times 10^{-9}$ M, no more than $2 \times 10^{-9}$ M, no more than $10^{-9}$ M, no more than $8 \times 10^{-10}$ M, no more than $7 \times 10^{-10}$ M, or no more than $6 \times 10^{-10}$ M by FACS assay.

In certain embodiments, the antibodies and antigen-binding fragments thereof provided herein inhibit ATPase activity in a CD39 expressing cell at an $IC_{50}$ of no more than 50 nM, no more than 40 nM, no more than 30 nM, no more than 20 nM, no more than 10 nM, no more than 8 nM, no more than 5 nM, no more than 3 nM, no more than 1 nM, no more than 0.9 nM, no more than 0.8 nM, no more than 0.7 nM, no more than 0.6 nM, no more than 0.5 nM, no more than 0.4 nM, no more than 0.3 nM, no more than 0.2 nM, no more than 0.1 nM, no more than 0.09 nM, no more than 0.08 nM, no more than 0.07 nM, no more than 0.06 nM, or no more than 0.05 nM as measured by ATPase activity assay. ATPase activity assay can be determined using any methods known in the art, for example by colorimetric detection of the phosphate released as a result of the ATPase activity. In certain embodiments, the ATPase activity is determined by the method as described in Example 3.3 of the present disclosure.

In certain embodiments, the antibodies and antigen-binding fragments thereof provided herein are capable of enhancing ATP mediated monocytes activation at a concentration of no more than 50 nM (e.g., no more than 40 nM, no more than 30 nM, no more than 20 nM, no more than 10 nM, no more than 5 nM, no more than 3 nM, no more than 2 nM, no more than 1 nM, no more than 0.5 nM, or no more than 0.2 nM), as measured by analysis of CD80, CD86 and/or CD40 expression by FACS assay, where upregulation of CD80, CD86 and/or CD40 indicates monocytes activation. The activity of ATP mediated monocytes can be determined using methods known in the art, for example, by the method as described in Example 5.5 of the present disclosure.

In certain embodiments, the antibodies and antigen-binding fragments thereof provided herein are capable of enhancing ATP mediated T cell activation in PBMC at a concentration of no more than 25 nM, no more than 20 nM, no more than 15 nM, no more than 10 nM, no more than 9 nM, no more than 8 nM, no more than 7 nM, no more than 6 nM, no more than 5 nM, no more than 4 nM, no more than 3 nM, no more than 2 nM, or no more than 1 nM, as measured by IL-2 secretion, or IFN-γ secretion, or CD4$^+$ or CD8$^+$ T cells proliferation, for example, by the method as described in Example 5.5 of the present disclosure.

In certain embodiments, the antibodies and antigen-binding fragments thereof provided herein are capable of enhancing ATP mediated dendritic cell (DC) activation at a concentration of no more than 25 nM (or no more than 10 nM, or no more than 5 nM, or no more than 1 nM, or no more than 0.5 nM) as measured by analysis of CD83 expression by FACS assay.

In certain embodiments, the antibodies and antigen-binding fragments thereof provided herein are capable of enhancing ATP mediated DC activation at a concentration of no more than 25 nM (or no more than 10 nM, or no more than 5 nM, or no more than 1 nM, or no more than 0.5 nM) as measured by the capability of the activated DC to promote T cell proliferation.

In certain embodiments, the antibodies and antigen-binding fragments thereof provided herein are capable of enhancing ATP mediated DC activation at a concentration of no more than 25 nM (or no more than 10 nM, or no more than 5 nM, or no more than 1 nM, or no more than 0.5 nM) as measured by the capability of the activated DC to promote IFN-γ production in the mix-lymphocyte reaction (MLR) assay.

The activity of ATP mediated DC maturation can be determined using methods known in the art, for example the method as described in Example 5.5 of the present disclosure.

In certain embodiments, the antibodies and antigen-binding fragments thereof provided herein are capable of blocking the inhibition of CD4$^+$ T cell proliferation induced by adenosine (hydrolyzed from ATP) at a concentration of no more than 1 nM (e.g. no more than 0.1 nM, no more than 0.01 nM) as measured by FACS assay. T cell proliferation can be determined using methods known in the art, for example the method as described in Example 3.4 of the present disclosure.

In certain embodiments, the antibodies and antigen-binding fragments thereof provided herein are capable of inhibiting tumor growth in a mammal in a NK cell or macrophage cell dependent manner.

In certain embodiments, the antibodies and antigen-binding fragments thereof provided herein are capable of reversing human CD8$^+$ T cell proliferation which was inhibited by eATP as measured by T cell proliferation, CD25$^+$ cells, and living cells population. % T cell proliferation, % CD25$^+$ cells, and % living cells can be determined using methods known in the art, for example the method as described in Example 3.4 of the present disclosure.

In certain embodiments, the antibodies and antigen-binding fragments thereof provided herein are capable of enhancing human macrophage IL1β release induced by LPS stimulation at a concentration of no more than 50 nM (or no more than 12.5 nM, or no more than 3.13 nM, or no more than 0.78 nM, or no more than 0.2 nM, or no more than 0.049 nM, or no more than 0.012 nM, or no more than 0.003 nM, or no more than 0.0008 nM) as measured by ELISA assay. Macrophage IL-1β release can be determined using methods known in the art, for example the method as described in Example 5.5.4 of the present disclosure.

Illustrative Anti-CD39 Antibodies

In certain embodiments, the present disclosure provides anti-CD39 antibodies (e.g. anti-human CD39 antibodies) and antigen-binding fragments thereof comprising one or more (e.g. 1, 2, 3, 4, 5, or 6) CDRs comprising the sequences selected from the group consisting of NYGMN (SEQ ID NO: 1), KYWMN (SEQ ID NO: 2), NYWMN (SEQ ID NO: 3), DTFLH (SEQ ID NO: 4), DYNMY (SEQ ID NO: 5), DTYVH (SEQ ID NO: 6), LINTYTGEPTYADDFKD (SEQ ID NO: 7), EIRLKSNKYGTHYAESVKG (SEQ ID NO: 8), QIRLNPDNYATHX$_1$AESVKG (SEQ ID NO: 9), X$_{58}$IDPAX$_{59}$X$_{60}$NIKYDPKFQG (SEQ ID NO: 151), FIDPYNGYTSYNQKFKG (SEQ ID NO: 11), RIDPAID-NSKYDPKFQG (SEQ ID NO: 12), KGIYYDYVWFFDV (SEQ ID NO: 13), QLDLYWFFDV (SEQ ID NO: 14), HGX$_2$RGFAY (SEQ ID NO: 15), SPYYYGSGYRIFDV (SEQ ID NO: 16), IYGYDDAYYFDY (SEQ ID NO: 17), YYCALYDGYNVYAMDY (SEQ ID NO: 18), KASQDIN-RYIA (SEQ ID NO: 19), RASQSISDYLH (SEQ ID NO: 20), KSSQSLLDSDGRTHLN (SEQ ID NO: 21), SAFSSVNYMH (SEQ ID NO: 22), SATSSVSYMH (SEQ ID NO: 23), RSSKNLLHSNGITYLY (SEQ ID NO: 24), YTSTLLP (SEQ ID NO: 25), YASQSIS (SEQ ID NO: 26), LVSKLDS (SEQ ID NO: 27), TTSNLAS (SEQ ID NO: 28), STSNLAS (SEQ ID NO: 29), RASTLAS (SEQ ID NO: 30), LQYSNLLT (SEQ ID NO: 31), QNGHSLPLT (SEQ ID NO: 32), WQGTLFPWT (SEQ ID NO: 33), QQRSTYPFT (SEQ ID NO: 34), QQRITYPFT (SEQ ID NO: 35), and AQL-LELPHT (SEQ ID NO: 36), wherein X$_1$ is Y or F, X$_2$ is S or T, X$_{58}$ is R or K, X$_{59}$ is N, G, S or Q, X$_{60}$ is G, A or D. In certain embodiments, the present disclosure further encompass antibodies and antigen binding fragments thereof having no more than one, two or three amino acid residue substitutions to any of SEQ ID NOs: 1-9, 11-36, and 151.

Antibody "mAb13" as used herein refers to a monoclonal antibody comprising a heavy chain variable region having the sequence of SEQ ID NO: 42, and a light chain variable region having the sequence of SEQ ID NO: 51.

Antibody "mAb14" as used herein refers to a monoclonal antibody comprising a heavy chain variable region having the sequence of SEQ ID NO: 43, and a light chain variable region having the sequence of SEQ ID NO: 52.

Antibody "mAb19" as used herein refers to a monoclonal antibody comprising a heavy chain variable region having the sequence of SEQ ID NO: 44, and a light chain variable region having the sequence of SEQ ID NO: 53.

Antibody "mAb21" as used herein refers to a monoclonal antibody comprising a heavy chain variable region having the sequence of SEQ ID NO: 45, and a light chain variable region having the sequence of SEQ ID NO: 54.

Antibody "mAb23" as used herein refers to a monoclonal antibody comprising a heavy chain variable region having the sequence of SEQ ID NO: 47, and a light chain variable region having the sequence of SEQ ID NO: 56.

Antibody "mAb34" as used herein refers to a monoclonal antibody comprising a heavy chain variable region having the sequence of SEQ ID NO: 49, and a light chain variable region having the sequence of SEQ ID NO: 58.

Antibody "mAb35" as used herein refers to a monoclonal antibody comprising a heavy chain variable region having the sequence of SEQ ID NO: 50, and a light chain variable region having the sequence of SEQ ID NO: 59.

In certain embodiments, the present disclosure provides anti-CD39 antibodies and antigen-binding fragments thereof comprising one or more (e.g. 1, 2, 3, 4, 5, or 6) CDR sequences of Antibody mAb13, mAb14, mAb19, mAb21, mAb23, mAb34, or mAb35.

In certain embodiments, the present disclosure provides anti-CD39 antibodies and antigen-binding fragments thereof comprising HCDR1 comprising an amino acid sequence selected from the group consisting of SEQ ID NOs: 1-6, HCDR2 comprising an amino acid sequence selected from the group consisting of SEQ ID NOs: 7-9, 11-12, and 151, and HCDR3 comprising an amino acid sequence selected from the group consisting of SEQ ID NOs: 13-18, and/or LCDR1 comprising an amino acid sequence selected from the group consisting of SEQ ID NOs: 19-24, LCDR2 comprising an amino acid sequence selected from the group consisting of SEQ ID NOs: 25-30, and LCDR3 comprising an amino acid sequence selected from the group consisting of SEQ ID NOs: 31-36.

In certain embodiments, the present disclosure provides anti-CD39 antibodies and antigen-binding fragments thereof comprising a HCDR1 comprising the sequence of SEQ ID NO: 1, a HCDR2 comprising the sequence of SEQ ID NO: 7, a HCDR3 comprising the sequence of SEQ ID NO: 13, and/or a LCDR1 comprising the sequence of SEQ ID NO: 19, a LCDR2 comprising the sequence of SEQ ID NO: 25, and a LCDR3 comprising the sequence of SEQ ID NO: 31.

In certain embodiments, the present disclosure provides anti-CD39 antibodies and antigen-binding fragments thereof comprising a HCDR1 comprising the sequence of SEQ ID NO: 2, a HCDR2 comprising the sequence of SEQ ID NO: 8, a HCDR3 comprising the sequence of SEQ ID NO: 14, and/or a LCDR1 comprising the sequence of SEQ ID NO: 20, a LCDR2 comprising the sequence of SEQ ID NO: 26, and a LCDR3 comprising the sequence of SEQ ID NO: 32.

In certain embodiments, the present disclosure provides anti-CD39 antibodies and antigen-binding fragments thereof comprising a HCDR1 comprising the sequence of SEQ ID NO: 3, a HCDR2 comprising the sequence of SEQ ID NO: 37, a HCDR3 comprising the sequence of SEQ ID NO: 40, and/or a LCDR1 comprising the sequence of SEQ ID NO: 21, a LCDR2 comprising the sequence of SEQ ID NO: 27, and a LCDR3 comprising the sequence of SEQ ID NO: 33.

In certain embodiments, the present disclosure provides anti-CD39 antibodies and antigen-binding fragments thereof comprising a HCDR1 comprising the sequence of SEQ ID NO: 3, a HCDR2 comprising the sequence of SEQ ID NO: 38, a HCDR3 comprising the sequence of SEQ ID NO: 41, and/or a LCDR1 comprising the sequence of SEQ ID NO: 21, a LCDR2 comprising the sequence of SEQ ID NO: 27, and a LCDR3 comprising the sequence of SEQ ID NO: 33.

In certain embodiments, the present disclosure provides anti-CD39 antibodies and antigen-binding fragments thereof comprising a HCDR1 comprising the sequence of SEQ ID NO: 4, a HCDR2 comprising the sequence of SEQ ID NO: 10, a HCDR3 comprising the sequence of SEQ ID NO: 16, and/or a LCDR1 comprising the sequence of SEQ ID NO: 22, a LCDR2 comprising the sequence of SEQ ID NO: 28, and a LCDR3 comprising the sequence of SEQ ID NO: 34.

In certain embodiments, the present disclosure provides anti-CD39 antibodies and antigen-binding fragments thereof comprising a HCDR1 comprising the sequence of SEQ ID NO: 5, a HCDR2 comprising the sequence of SEQ ID NO: 11, a HCDR3 comprising the sequence of SEQ ID NO: 17, and/or a LCDR1 comprising the sequence of SEQ ID NO: 23, a LCDR2 comprising the sequence of SEQ ID NO: 29, and a LCDR3 comprising the sequence of SEQ ID NO: 35.

In certain embodiments, the present disclosure provides anti-CD39 antibodies and antigen-binding fragments thereof comprising a HCDR1 comprising the sequence of SEQ ID NO: 6, a HCDR2 comprising the sequence of SEQ ID NO: 12, a HCDR3 comprising the sequence of SEQ ID NO: 18, and/or a LCDR1 comprising the sequence of SEQ ID NO: 24, a LCDR2 comprising the sequence of SEQ ID NO: 30, and a LCDR3 comprising the sequence of SEQ ID NO: 36.

Table 1 below shows the CDR amino acid sequences of antibodies mAb 13, mAb 14, mAb 19, mAb21, mAb23, mAb34, and mAb35. The CDR boundaries were defined or identified by the convention of Kabat. Table 2 below shows the heavy chain and light chain variable region amino acid sequences of antibodies mAb 13, mAb 14, mAb 19, mAb21, mAb23, mAb34, and mAb35.

TABLE 1

CDR amino acid sequences of 7 monoclonal antibodies.

| Antibody | | CDR1 | CDR2 | CDR3 |
|---|---|---|---|---|
| mAb13 | HCDR | SEQ ID NO: 1<br>NYGMN | SEQ ID NO: 7<br>LINTYTGEPTYADD<br>FKD | SEQ ID NO: 13<br>KGIYYDYVWFF<br>DV |
| | LCDR | SEQ ID NO: 19<br>KASQDINRYIA | SEQ ID NO: 25<br>YTSTLLP | SEQ ID NO: 31<br>LQYSNLLT |
| mAb14 | HCDR | SEQ ID NO: 2<br>KYWMN | SEQ ID NO: 8<br>EIRLKSNKYGTHYA<br>ESVKG | SEQ ID NO: 14<br>QLDLYWFFDV |
| | LCDR | SEQ ID NO: 20<br>RASQSISDYLH | SEQ ID NO: 26<br>YASQSIS | SEQ ID NO: 32<br>QNGHSLPLT |
| mAb19 | HCDR | SEQ ID NO: 3<br>NYWMN | SEQ ID NO: 37<br>QIRLNPDNYATHY<br>AESVKG | SEQ ID NO: 40<br>HGSRGFAY |
| | LCDR | SEQ ID NO: 21<br>KSSQSLLDSDG<br>RTHLN | SEQ ID NO: 27<br>LVSKLDS | SEQ ID NO: 33<br>WQGTLFPWT |

TABLE 1-continued

CDR amino acid sequences of 7 monoclonal antibodies.

| Antibody | | CDR1 | CDR2 | CDR3 |
|---|---|---|---|---|
| mAb21 | HCDR | SEQ ID NO: 3<br>NYWMN | SEQ ID NO: 38<br>QIRLNPDNYATHFA<br>ESVKG | SEQ ID NO: 41<br>HGTRGFAY |
|  | LCDR | SEQ ID NO: 21<br>KSSQSLLDSDG<br>RTHLN | SEQ ID NO: 27<br>LVSKLDS | SEQ ID NO: 33<br>WQGTLFPWT |
| mAb23 | HCDR | SEQ ID NO: 4<br>DTFLH | SEQ ID NO: 10<br>RIDPANGNIKYDPK<br>FQG | SEQ ID NO: 16<br>SPYYYGSGYRIF<br>DV |
|  | LCDR | SEQ ID NO: 22<br>SAFSSVNYMH | SEQ ID NO: 28<br>TTSNLAS | SEQ ID NO: 34<br>QQRSTYPFT |
| mAb34 | HCDR | SEQ ID NO: 5<br>DYNMY | SEQ ID NO: 11<br>FIDPYNGYTSYNQK<br>FKG | SEQ ID NO: 17<br>IYGYDDAYYFD<br>Y |
|  | LCDR | SEQ ID NO: 23<br>SATSSVSYMH | SEQ ID NO: 29<br>STSNLAS | SEQ ID NO: 35<br>QQRITYPFT |
| mAb35 | HCDR | SEQ ID NO: 6<br>DTYVH | SEQ ID NO: 12<br>RIDPAIDNSKYDPK<br>FQG | SEQ ID NO: 18<br>YYCALYDGYNV<br>YAMDY |
|  | LCDR | SEQ ID NO: 24<br>RSSKNLLHSNG<br>ITYLY | SEQ ID NO: 30<br>RASTLAS | SEQ ID NO: 36<br>AQLLELPHT |

TABLE 2

Variable region amino acid sequences of 7 monoclonal antibodies.

| Antibody | VH | VL |
|---|---|---|
| mAb13 | SEQ ID NO: 42<br>QIQLVQSGPELKKPGETVKISC<br>KASGYTFTNYGMNWVKQAPG<br>KGLRWMGLINTYTGEPTYADD<br>FKDRFAFSLETSASTAFLQINNL<br>KDEDMATYFCARKGIYYDYV<br>WFFDVWGAGTTVTVSS | SEQ ID NO: 51<br>DIQMTQSPSSLSTSLGGKVSI<br>TCKASQDINRYIAWYQHKPG<br>KGPRLLIHYTSTLLPGIPSRFS<br>GSGSGRDYSFSISNLEPEDIA<br>TYFCLQYSNLLTFGGGTKLEI<br>K |
| mAb14 | SEQ ID NO: 43<br>EVKLEESGGGLVQPGGSMKLS<br>CVASGFTFSKYWMNWVRQSPE<br>KGLEWVAEIRLKSNKYGTHYA<br>ESVKGRFTISRDDSKNNVYLQ<br>MNNLRPEDTGIYYCTTQLDLY<br>WFFDVWGAGTTVTVSS | SEQ ID NO: 52<br>DIVMTQSPAILSVTPGDRVSL<br>SCRASQSISDYLHWYQQKSH<br>ESPRLLIKYASQSISGIPSRFS<br>GSGSGSNFTLSINSVEPEDVG<br>VYFCQNGHSLPLTFGAGTKL<br>ELR |
| mAb19 | SEQ ID NO: 44<br>EVKLEKSGGGLVQPGGSMKLS<br>CVASGFTFSNYWMNWVRQSPE<br>KGLEWVAQIRLNPDNYATHYA<br>ESVKGRFTISRDDYKNSVYLQ<br>MSSLRAEDSGIYYCTQHGSRGF<br>AYWGQGTLVTVS | SEQ ID NO: 53<br>DVVMTQTPHTMSITIGQPASI<br>SCKSSQSLLDSDGRTHLNWL<br>FQRPGQSPKRLIYLVSKLDSG<br>VPDRFTGSGSGTDFTLKISRV<br>EAEDLGVYYCWQGTLFPWT<br>FGGGTKLEIK |
| mAb21 | SEQ ID NO: 45<br>EVKLEKSGGGLVQPGGSMKLS<br>CVASGFTFSNYWMNWVRQSPE<br>KGLEWVAQIRLNPDNYATHFAE<br>SVKGRFTISRDDSKNSVYLQM<br>NSLRAEDTGIYYCTEHGTRGFA<br>YWGQGTLVTVSE | SEQ ID NO: 54<br>DVVMTQTPLTLSITIGQPASIS<br>CKSSQSLLDSDGRTHLNWFF<br>QRPGQSPKRLIYLVSKLDSG<br>VPDRFTGSGSGTDFTLKISRV<br>EAEDLGVYYCWQGTLFPWT<br>FGGGTKLEIK |
| mAb23 | SEQ ID NO: 47<br>EVQLQQSGAELLRPGASVKLSC<br>TASGYNLKDTFLHWVKQRPEQ<br>GLEWIGRIDPANGNIKYDPKFQ<br>GKATLTADTSSNTAYLQLISLTS<br>EDTAVYYCANSPYYYGSGYRIF<br>DVWGAGTTVTVSS | SEQ ID NO: 56<br>QIVLTQSPAIMSASPGEKVTI<br>TCSAFSSVNYMHWYQQKPG<br>TSPKLLIYTTSNLASGVPTRF<br>SGSGSGTSYSLTISRMEADA<br>ATYYCQQRSTYPFTFGSGTK<br>LEIQ |

TABLE 2-continued

Variable region amino acid sequences
of 7 monoclonal antibodies.

| Antibody | VH | VL |
| --- | --- | --- |
| mAb34 | SEQ ID NO: 49<br>EIQVQQSGPELVKPGASVKVSC<br>KASGYSFTDYNMYWVKQSHG<br>KSLEWIGFIDPYNGYTSYNQKF<br>KGKATLTIDKSSSTAFMHLNSLT<br>SEDSAVYYCAIYGYDDAYYFD<br>YWGQGTTLTVSS | SEQ ID NO: 58<br>QIVLTQSPAIMSASPGEKVTI<br>TCSATSSVSYMHWFRQKPGT<br>SPKLWIYSTSNLASGVPARFS<br>GSGSGTSYSLTISRMAAEDA<br>ATYYCQQRITYPFTFGSGTK<br>LEIT |
| mAb35 | SEQ ID NO: 50<br>EVRLQQSGAELVKPGASVKLS<br>CTASGFNIEDTYVHWMKQRPE<br>QGLEWIGRIDPAIDNSKYDPKF<br>QGKATITAVSSSNTAYLQLSSLT<br>SEDTAVYYCALYDGYNVYAMD<br>YWGQGTSVTVSS | SEQ ID NO: 59<br>DIVMTQAAFSNPVTLGTSASI<br>SCRSSKNLLHSNGITYLYWY<br>LQRPGQSPQLLIYRASTLASG<br>VPNRFSGSESGTDFTLRISRV<br>EAEDVGVYYCAQLLELPHTF<br>GGGTKLEIK |

Given that each of antibodies mAb13, mAb14, mAb19, mAb21, mAb23, mAb34, and mAb35 can bind to CD39 and that antigen-binding specificity is provided primarily by the CDR1, CDR2 and CDR3 regions, the HCDR1, HCDR2 and HCDR3 sequences and LCDR1, LCDR2 and LCDR3 sequences of antibodies mAb13, mAb14, mAb19, mAb21, mAb23, mAb34, and mAb35 can be "mixed and matched" (i.e., CDRs from different antibodies can be mixed and matched, but each antibody must contain a HCDR1, HCDR2 and HCDR3 and a LCDR1, LCDR2 and LCDR3) to create anti-CD39 binding molecules of the present disclosure. CD39 binding of such "mixed and matched" antibodies can be tested using the binding assays described above and in the Examples. Preferably, when VH CDR sequences are mixed and matched, the HCDR1, HCDR2 and/or HCDR3 sequence from a particular VH sequence is replaced with a structurally similar CDR sequence (s). Likewise, when VL CDR sequences are mixed and matched, the LCDR1, LCDR2 and/or LCDR3 sequence from a particular VL sequence preferably is replaced with a structurally similar CDR sequence (s). For example, the HCDR1s of antibodies mAb13 and mAb19 share some structural similarity and therefore are amenable to mixing and matching. It will be readily apparent to a person skilled in the art that novel VH and VL sequences can be created by substituting one or more VH and/or VL CDR sequences with structurally similar sequences from the CDR sequences disclosed herein for monoclonal antibodies mAb13, mAb14, mAb19, mAb21, mAb23, mAb34, and mAb35.

CDRs are known to be responsible for antigen binding. However, it has been found that not all of the 6 CDRs are indispensable or unchangeable. In other words, it is possible to replace or change or modify one or more CDRs in anti-CD39 antibodies mAb13, mAb14, mAb19, mAb21, mAb23, mAb34, and mAb35, yet substantially retain the specific binding affinity to CD39.

In certain embodiments, the antibodies and antigen-binding fragments thereof provided herein comprise suitable framework region (FR) sequences, as long as the antibodies and antigen-binding fragments thereof can specifically bind to CD39. The CDR sequences provided in Table 1 above are obtained from mouse antibodies, but they can be grafted to any suitable FR sequences of any suitable species such as mouse, human, rat, rabbit, among others, using suitable methods known in the art such as recombinant techniques.

In certain embodiments, the antibodies and antigen-binding fragments thereof provided herein are humanized. A humanized antibody or antigen-binding fragment thereof is desirable in its reduced immunogenicity in human. A humanized antibody is chimeric in its variable regions, as non-human CDR sequences are grafted to human or substantially human FR sequences. Humanization of an antibody or antigen-binding fragment can be essentially performed by substituting the non-human (such as murine) CDR genes for the corresponding human CDR genes in a human immunoglobulin gene (see, for example, Jones et al. (1986) *Nature* 321:522-525; Riechmann et al. (1988) *Nature* 332:323-327; Verhoeyen et al. (1988) *Science* 239:1534-1536).

Suitable human heavy chain and light chain variable domains can be selected to achieve this purpose using methods known in the art. In an illustrative example, "best-fit" approach can be used, where a non-human (e.g. rodent) antibody variable domain sequence is screened or BLASTed against a database of known human variable domain sequences, and the human sequence closest to the non-human query sequence is identified and used as the human scaffold for grafting the non-human CDR sequences (see, for example, Sims et al., (1993) *J. Immunol.* 151:2296; Chothia et al. (1987) *J. Mot. Biol.* 196:901). Alternatively, a framework derived from the consensus sequence of all human antibodies may be used for the grafting of the non-human CDRs (see, for example, Carter et al. (1992) *Proc. Natl. Acad. Sci. USA,* 89:4285; Presta et al. (1993) *J. Immunol.,* 151:2623).

In some embodiments, the present disclosure provides 16 humanized antibodies of c14, which are designated as hu14.H1L1, hu14.H2L1, hu14.H3L1, hu14.H4L1, hu14.H1L2, hu14.H2L2, hu14.H3L2, hu14.H4L2, hu14.H1L3, hu14.H2L3, hu14.H3L3, hu14.H4L3, hu14.H1L4, hu14.H2L4, hu14.H3L4, and hu14.H4L4, respectively. The SEQ ID NOs of the heavy and light chain variable regions of each humanized antibody of c14 are shown in Table 16 of Example 5.1. Each of the 16 humanized antibodies of c14 comprises a HCDR1 comprising the sequence of SEQ ID NO: 2, a HCDR2 comprising the sequence of SEQ ID NO: 8, a HCDR3 comprising the sequence of SEQ ID NO: 14, a LCDR1 comprising the sequence of SEQ ID NO: 20, a LCDR2 comprising the sequence of SEQ ID NO: 26, and a LCDR3 comprising the sequence of SEQ ID NO: 32. The CDR boundaries were defined or identified by the convention of Kabat.

In some embodiments, the present disclosure provides 31 humanized antibodies of c23, which are designated as hu23.H1L1, hu23.H2L1, hu23.H3L1, hu23.H4L1, hu23.H1L2, hu23.H2L2, hu23.H3L2, hu23.H4L2, hu23.H1L3, hu23.H2L3, hu23.H3L3, hu23.H4L3, hu23.H1L4, hu23.H2L4, hu23.H3L4, hu23.H4L4, hu23.H5L1, hu23.H6L1, hu23.H7L1, hu23.H1L5, hu23.H5L5, hu23.H6L5, hu23.H7L5, hu23.H1L6, hu23.H5L6, hu23.H6L6, hu23.H7L6, hu23.H1L7, hu23.H5L7, hu23.H6L7, and hu23.H7L7, respectively. The SEQ ID NOs of the heavy and light chain variable regions of each humanized antibody of c23 are shown in Table 13 and Table 14 of Example 5.1. Each of the 31 humanized antibodies for antibody c23 above comprises a HCDR1 comprising the sequence of SEQ ID NO: 4, a HCDR2 comprising the sequence of SEQ ID NO: 10, a HCDR3 comprising the sequence of SEQ ID NO: 16; a LCDR1 comprising the sequence of SEQ ID NO: 22, a LCDR2 comprising the sequence of SEQ ID NO: 28, and a LCDR3 comprising the sequence of SEQ ID NO: 34. The CDR boundaries were defined or identified by the convention of Kabat.

In some embodiments, the present disclosure also provides 6 humanized antibodies which have the same CDRs as c23 except that the amino acid sequences of HCDR2 are different. In some embodiments, the amino acid sequence of HCDR2 of the humanized antibodies of these c23 variants (c23') comprises the amino acid sequence of $X_{58}$IDPA$X_{59}$$X_{60}$NIKYDPKFQG (SEQ ID NO: 151), wherein $X_{58}$ is R or K, $X_{59}$ is N, G, S or Q, $X_{60}$ is G, A or D. In some embodiments, the amino acid sequence of HCDR2 of the humanized antibodies of these c23 variants (c23') comprises a sequence selected from the group consisting of RIDPAGGNIKYDPKFQG (SEQ ID NO: 134), RIDPASGNIKYDPKFQG (SEQ ID NO: 135), RID-PAQGNIKYDPKFQG (SEQ ID NO: 136), RIDPANANI-KYDPKFQG (SEQ ID NO: 137), RIDPANDNI-KYDPKFQG (SEQ ID NO: 138), and KIDPANGNIKYDPKFQG (SEQ ID NO: 139). The CDR boundaries were defined or identified by the convention of Kabat.

In some embodiments, the present disclosure also provided 4 humanized antibodies for c23 variants by yeast display, which are designated as hu23.201, hu23.203, hu23.207, and hu23.211. The heavy chain variable regions and light chain variable regions of humanized antibodies hu23.201, hu23.203, hu23.207, and hu23.211 are shown in Table 15 of Example 5.1. Each of the 4 humanized antibodies hu23.201, hu23.203, hu23.207, and hu23.211 comprises a HCDR1 comprising the sequence of SEQ ID NO: 4, a HCDR2 comprising the sequence of SEQ ID NO: 10, a HCDR3 comprising the sequence of SEQ ID NO: 16; a LCDR1 comprising the sequence of SEQ ID NO: 22, a LCDR2 comprising the sequence of SEQ ID NO: 28, and a LCDR3 comprising the sequence of SEQ ID NO: 34. The CDR boundaries were defined or identified by the convention of Kabat.

Table 3 below shows the 4 variants of humanized c14 heavy chain variable regions (i.e. hu14.VH_1, hu14.VH_2, hu14.VH_3, and hu14.VH_4) and 4 variants of humanized c14 light chain variable regions (i.e. hu14.VL_1, hu14.VL_2, hu14.VL_3, and hu14.VL_4). Table 4 below shows the amino acid sequences of the FR for the humanized c14 heavy chain and light chain variable regions. Table 5 below shows the FR amino acid sequences for each heavy and light chains of 16 humanized antibodies for chimeric antibody c14, which are designated as hu14.H1L1, hu14.H2L1, hu14.H3L1, hu14.H4L1, hu14.H1L2, hu14.H2L2, hu14.H3L2, hu14.H4L2, hu14.H1L3, hu14.H2L3, hu14.H3L3, hu14.H4L3, hu14.H1L4, hu14.H2L4, hu14.H3L4, hu14.H4L4, respectively. The heavy chain variable regions and light chain variable regions of these 16 humanized antibodies are shown in Table 16 of Example 5.1.

TABLE 3

Amino acid sequences of the humanized variable regions for humanized antibody of c14.

| Antibody | VH | VL |
|---|---|---|
| hu14.H1L1 | hu14.VH_1; SEQ ID NO: 68<br>EVQLVESGGGLVKPGGSLRLS<br>CAASGFTFSKYWMNWVRQA<br>PGKGLEWVGEIRLKSNKYGT<br>HYAESVKGRFTISRDDSKNTL<br>YLQMNSLKTEDTAVYYCTTQ<br>LDLYWFFDVWGQGTTVTVSS | hu14.VL_1; SEQ ID NO: 69<br>EIVLTQSPATLSLSPGERATLS<br>CRASQSISDYLHWYQQKPG<br>QAPRLLIYYASQSISGIPARFS<br>GSGSGTDFTLTISSLEPEDFAV<br>YYCQNGHSLPLTFGGGTKLE<br>IK |
| hu14.H2L2 | hu14.VH_2; SEQ ID NO: 70<br>EVQLVESGGGLVKPGGSLRLS<br>CAASGFTFSKYWMNWVRQSP<br>GKGLEWVGEIRLKSNKYGTH<br>YAESVKGRFTISRDDSKNTLY<br>LQMNSLKTEDTAVYYCTTQL<br>DLYWFFDVWGQGTTVTVSS | hu14.VL_2; SEQ ID NO: 71<br>EIVLTQSPATLSLSPGERATLS<br>CRASQSISDYLHWYQQKPG<br>QSPRLLIYYASQSISGIPARFS<br>GSGSGTDFTLTISSLEPEDFAV<br>YFCQNGHSLPLTFGGGTKLEI<br>K |

TABLE 3-continued

Amino acid sequences of the humanized variable regions for humanized antibody of c14.

| Antibody | VH | VL |
|---|---|---|
| hu14.H3L3 | hu14.VH_3; SEQ ID NO: 72<br>EVQLVESGGGLVKPGGSLRLS<br>CAASGFTFSKYWMNWVRQSP<br>GKGLEWVAEIRLKSNKYGTH<br>YAESVKGRFTISRDDSKNTVY<br>LQMNSLKTEDTAVYYCTTQL<br>DLYWFFDVWGQGTTVTVSS | hu14.VL_3; SEQ ID NO: 73<br>EIVLTQSPATLSVSPGERATLS<br>CRASQSISDYLHWYQQKPG<br>QSPRLLIYYASQSISGIPARFS<br>GSGSGTDFTLTISSVEPEDFA<br>VYFCQNGHSLPLTFGGGTKL<br>EIK |
| hu14.H4L4 | hu14.VH_4; SEQ ID NO: 74<br>EVQLVESGGGLVKPGGSMRL<br>SCAASGFTFSKYWMNWVRQS<br>PGKGLEWVAEIRLKSNKYGT<br>HYAESVKGRFTISRDDSKNTV<br>YLQMNSLKTEDTAVYYCTTQ<br>LDLYWFFDVWGQGTTVTVSS | hu14.VL_4; SEQ ID NO: 75<br>EIVMTQSPATLSVSPGERVTL<br>SCRASQSISDYLHWYQQKPG<br>QSPRLLIYYASQSISGIPARFS<br>GSGSGTDFTLTISSVEPEDFA<br>VYFCQNGHSLPLTFGGGTKL<br>EIK |

TABLE 4

Amino acid sequences of the humanized FR for humanized antibody of c14.

| SEQ ID NO. | Sequence |
|---|---|
| 79 | WGQGTTVTVSS |
| 98 | EIVLTQSPATLSLSPGERATLSC |
| 104 | WYQQKPGQAPRLLIY |
| 106 | GIPARFSGSGSGTDFTLTISSLEPEDFAVYYC |
| 119 | EVQLVESGGGLVKPGGSLRLSCAASGFTFS |
| 120 | EVQLVESGGGLVKPGGSMRLSCAASGFTFS |
| 121 | WVRQAPGKGLEWVG |
| 122 | WVRQSPGKGLEWVG |
| 123 | WVRQSPGKGLEWVA |
| 124 | RFTISRDDSKNTLYLQMNSLKTEDTAVYYCTT |
| 125 | RFTISRDDSKNTVYLQMNSLKTEDTAVYYCTT |
| 127 | EIVLTQSPATLSVSPGERATLSC |
| 128 | EIVMTQSPATLSVSPGERVTLSC |
| 130 | WYQQKPGQSPRLLIY |
| 132 | GIPARFSGSGSGTDFTLTISSLEPEDFAVYFC |
| 133 | GIPARFSGSGSGTDFTLTISSVEPEDFAVYFC |
| 153 | FGGGTKLEIK |

TABLE 5

The FR amino acid sequences for each humanized heavy and light chain variable regions for humanized antibody of c14.

| VH or VL Name | FR1 (SEQ ID NO.) | FR2 (SEQ ID NO.) | FR3 (SEQ ID NO.) | FR4 (SEQ ID NO.) |
|---|---|---|---|---|
| hu14.VH_1 | 119 | 121 | 124 | 79 |
| hu14.VH_2 | 119 | 122 | 124 | 79 |
| hu14.VH_3 | 119 | 123 | 125 | 79 |
| hu14.VH_4 | 120 | 123 | 125 | 79 |
| hu14.VL_1 | 98 | 104 | 106 | 153 |
| hu14.VL_2 | 98 | 130 | 132 | 153 |
| hu14.VL_3 | 127 | 130 | 133 | 153 |
| hu14.VL_4 | 128 | 130 | 133 | 153 |

Table 6 below shows the 7 variants of humanized c23 heavy chain variable regions (i.e. hu23.VH_1, hu23.VH_2, hu23.VH_3, hu23.VH_4, hu23.VH_5, hu23.VH_6, and hu23.VH_7) and 7 variants of humanized c23 light chain variable regions (i.e. hu23.VL_1 hu23.VL_2, hu23.VL_3, hu23.VL_4, hu23.VL_5 hu23.VL_6, and hu23.VL_7). Table 7 below shows the heavy and light chain variable region amino acid sequences of 4 humanized antibodies for chimeric antibody c23 obtained by yeast display. Table 8 below shows the FR amino acid sequences of 35 humanized antibodies of c23. Table 9 below shows the FR amino acid sequences for each heavy and light chains of 35 humanized antibodies of c23.

TABLE 6

Amino acid sequences of the variable regions for humanized antibody of c23.

| Antibody | VH | VL |
|---|---|---|
| hu23.H1L1 | hu23.VH_1, SEQ ID NO: 60<br>QVQLVQSGAEVKKPGASVKV<br>SCKASGYNLKDTFLHWVRQA<br>PGQRLEWMGRIDPANGNIKY<br>DPKFQGRVTITRDTSASTAYM<br>ELSSLRSEDTAVYYCARSPYY<br>YGSGYRIFDVWGQGTTVTVS<br>S | hu23.VL_1, SEQ ID NO: 61<br>EIVLTQSPATLSLSPGERATLS<br>CSAFSSVNYMHWYQQKPGQ<br>APRLLIYTTSNLASGIPARFS<br>GSGSGTDFTLTISSLEPEDFAV<br>YYCQQRSTYPFTFGQGTKLE<br>IK |
| hu23.H2L2 | hu23.VH_2, SEQ ID NO: 62<br>QVQLVQSGAEVKKPGASVKV<br>SCKASGYNLKDTFLHWVRQA<br>PGQGLEWMGRIDPANGNIKY<br>DPKFQGRVTITADTSASTAYM<br>ELSSLRSEDTAVYYCANSPYY<br>YGSGYRIFDVWGQGTTVTVS<br>S | hu23.VL_2, SEQ ID NO: 63<br>EIVLTQSPATLSLSPGERATLS<br>CSAFSSVNYMHWYQQKPGQ<br>APRLLIYTTSNLASGIPARFS<br>GSGSGTDYTLTISSLEPEDFA<br>VYYCQQRSTYPFTFGQGTKL<br>EIK |
| hu23.H3L3 | hu23.VH_3, SEQ ID NO: 64<br>QVQLVQSGAEVKKPGASVKL<br>SCKASGYNLKDTFLHWVRQA<br>PGQGLEWIGRIDPANGNIKYD<br>PKFQGRATITADTSASTAYME<br>LSSLRSEDTAVYYCANSPYYY<br>GSGYRIFDVWGQGTTVTVSS | hu23.VL_3, SEQ ID NO: 65<br>EIVLTQSPATLSASPGERATLS<br>CSAFSSVNYMHWYQQKPGQ<br>APRLLIYTTSNLASGIPARFS<br>GSGSGTDYTLTISSMEPEDFA<br>VYYCQQRSTYPFTFGQGTKL<br>EIK |
| hu23.H4L4 | hu23.VH_4, SEQ ID NO: 66<br>QVQLVQSGAEVKKPGASVKL<br>SCKASGYNLKDTFLHWVKQA<br>PGQGLEWIGRIDPANGNIKYD<br>PKFQGRATLTADTSASTAYLEL<br>SSLRSEDTAVYYCANSPYYYG<br>SGYRIFDVWGQGTTVTVSS | hu23.VL_4, SEQ ID NO: 67<br>EIVLTQSPATLSASPGERVTIS<br>CSAFSSVNYMHWYQQKPGQ<br>APRLLIYTTSNLASGIPARFS<br>GSGSGTDYTLTISSMEPEDFA<br>VYYCQQRSTYPFTFGQGTKL<br>EIK |
| hu23.H5L5 | hu23.VH_5, SEQ ID NO: 140<br>QVQLVQSGAEVKKPGASVKV<br>SCKASGYNLKDTFLHWVRQA<br>PGQGLEWMGRIDPANGNIKY<br>DPKFQGRVTITADTSANTAYM<br>ELISLRSEDTAVYYCANSPYY<br>YGSGYRIFDVWGQGTTVTVS<br>S | hu23.VL_5, SEQ ID NO: 143<br>QIVLTQSPATLSLSPGERATLS<br>CSAFSSVNYMHWYQQKPGQ<br>APRLLIYTTSNLASGIPTRFS<br>GSGSGTSYTLTISSLEPEDFAV<br>YYCQQRSTYPFTFGQGTKLE<br>IK |
| hu23.H6L6 | hu23.VH_6, SEQ ID NO: 141<br>EVQLVQSGAEVKKPGASVKL<br>SCKASGYNLKDTFLHWVRQA<br>PGQGLEWIGRIDPANGNIKYD<br>PKFQGRATITADTSANTAYME<br>LISLRSEDTAVYYCANSPYYY<br>GSGYRIFDVWGQGTTVTVSS | hu23.VL_6, SEQ ID NO: 144<br>QIVLTQSPATLSASPGERATLS<br>CSAFSSVNYMHWYQQKPGQ<br>APKLLIYTTSNLASGVPTRFS<br>GSGSGTSYTLTISSMEPEDFA<br>VYYCQQRSTYPFTFGQGTKL<br>EIK |
| hu23.H7L7 | hu23.VH_7, SEQ ID NO: 142<br>EVQLVQSGAEVKKPGASVKL<br>SCKASGYNLKDTFLHWVKQA<br>PGQGLEWIGRIDPANGNIKYD<br>PKFQGKATLTADTSANTAYLE<br>LISLRSEDTAVYYCANSPYYY<br>GSGYRIFDVWGQGTTVTVSS | hu23.VL_7, SEQ ID NO: 145<br>QIVLTQSPATLSASPGERVTIT<br>CSAFSSVNYMHWYQQKPGQ<br>APKLLIYTTSNLASGVPTRFS<br>GSGSGTSYTLTISSMEPEDFA<br>VYYCQQRSTYPFTFGQGTKL<br>EIK |

TABLE 7

Amino acid sequences of the humanized variable regions for humanized antibody of c23 obtained by yeast display.

| Antibody | VH | VL |
|---|---|---|
| hu23.201 | SEQ ID NO: 146<br>QVQLVQSGAEVKKPGASVKV<br>SCKASGYTLKDTFLHWVRQA<br>PGQRLEWMGRIDPANGNIKY<br>DPKFQGRVTLTADTSSNTAYM<br>ELSSLRSEDTAVYYCANSPYY<br>YGSGYRIFDVWGQGTLVTSS | SEQ ID NO: 111<br>EIVLTQSPATLSLSPGERATLS<br>CSAFSSVNYMHWYQQKPGQ<br>SPRLLIYTTSNLASGIPARFSG<br>SGSGTDYTLTISSLEPEDFAV<br>YYCQQRSTYPFTFGQGTKLE<br>IK |
| hu23.203 | SEQ ID NO: 146<br>QVQLVQSGAEVKKPGASVKV<br>SCKASGYTLKDTFLHWVRQA<br>PGQRLEWMGRIDPANGNIKY<br>DPKFQGRVTLTADTSSNTAYM<br>ELSSLRSEDTAVYYCANSPYY<br>YGSGYRIFDVWGQGTLVTSS | SEQ ID NO: 112<br>EIVLTQSPATLTLSPGERATLS<br>CSAFSSVNYMHWYQQKPGQ<br>APRLLIYTTSNLASGIPARFS<br>GSGSGTDYTLTISSLEPEDFA<br>VYYCQQRSTYPFTFGQGTKL<br>EIK |
| hu23.207 | SEQ ID NO: 147<br>EVQLVQSGAEVKKPGASVKV<br>SCKASGYTLKDTFLHWVRQA<br>PGQRLEWMGKIDPANGNIKY<br>DPKFQGRVTLTADTSSNTAYM<br>ELSSLRSEDTAVYYCANSPYY<br>YGSGYRIFDVWGQGTLVTSS | SEQ ID NO: 111<br>EIVLTQSPATLSLSPGERATLS<br>CSAFSSVNYMHWYQQKPGQ<br>SPRLLIYTTSNLASGIPARFSG<br>SGSGTDYTLTISSLEPEDFAV<br>YYCQQRSTYPFTFGQGTKLE<br>IK |
| hu23.211 | SEQ ID NO: 39<br>EVQLVQSGAEVKKPGASVKV<br>SCKASGYTLKDTFLHWVRQA<br>PGQRLEWMGRIDPANGNIKY<br>DPKFQGRVTITADTSSNTAYM<br>ELSSLRSEDTAVYYCANSPYY<br>YGSGYRIFDVWGQGTLVTSS | SEQ ID NO: 63<br>EIVLTQSPATLSLSPGERATLS<br>CSAFSSVNYMHWYQQKPGQ<br>APRLLIYTTSNLASGIPARFS<br>GSGSGTDYTLTISSLEPEDFA<br>VYYCQQRSTYPFTFGQGTKL<br>EIK |

TABLE 8

Amino acid sequences of the humanized FR for humanized antibody of c23.

| SEQ ID NO. | Sequence |
|---|---|
| 79 | WGQGTTVTVSS |
| 83 | FGQGTKLEIK |
| 84 | QVQLVQSGAEVKKPGASVKVSCKASGYNLK |
| 85 | QVQLVQSGAEVKKPGASVKLSCKASGYNLK |
| 86 | EVQLVQSGAEVKKPGASVKLSCKASGYNLK |
| 87 | WVRQAPGQRLEWMG |
| 88 | WVRQAPGQGLEWMG |
| 89 | WVRQAPGQGLEWIG |
| 90 | WVKQAPGQGLEWIG |
| 91 | RVTITRDTSASTAYMELSSLRSEDTAVYYCAR |
| 92 | RVTITADTSASTAYMELSSLRSEDTAVYYCAN |
| 93 | RATITADTSASTAYMELSSLRSEDTAVYYCAN |
| 94 | RATLTADTSASTAYLELSSLRSEDTAVYYCAN |
| 95 | RVTITADTSANTAYMELISLRSEDTAVYYCAN |
| 96 | RATITADTSANTAYMELISLRSEDTAVYYCAN |
| 97 | KATLTADTSANTAYLELISLRSEDTAVYYCAN |
| 98 | EIVLTQSPATLSLSPGERATLSC |
| 99 | EIVLTQSPATLSASPGERATLSC |
| 100 | EIVLTQSPATLSASPGERVTISC |
| 101 | QIVLTQSPATLSLSPGERATLSC |
| 102 | QIVLTQSPATLSASPGERATLSC |
| 103 | QIVLTQSPATLSASPGERVTITC |
| 104 | WYQQKPGQAPRLLIY |
| 105 | WYQQKPGQAPKLLIY |
| 106 | GIPARFSGSGSGTDFTLTISSLEPEDFAVYYC |
| 107 | GIPARFSGSGSGTDYTLTISSLEPEDFAVYYC |
| 108 | GIPARFSGSGSGTDYTLTISSMEPEDFAVYYC |
| 109 | GIPTRFSGSGSGTSYTLTISSLEPEDFAVYYC |
| 110 | GVPTRFSGSGSGTSYTLTISSMEPEDFAVYYC |
| 115 | EVQLVQSGAEVKKPGASVKVSCKASGYTLK |
| 116 | RVTLTADTSSNTAYMELSSLRSEDTAVYYCAN |
| 117 | RVTITADTSSNTAYMELSSLRSEDTAVYYCAN |
| 118 | WGQGTLVTVSS |

TABLE 8-continued

Amino acid sequences of the humanized FR for humanized antibody of c23.

| SEQ ID NO. | Sequence |
|---|---|
| 129 | EIVLTQSPATLTLSPGERATLSC |
| 130 | WYQQKPGQSPRLLIY |
| 131 | QVQLVQSGAEVKKPGASVKVSCKASGYTLK |

TABLE 9

The FR amino acid sequences for each humanized heavy and light chain variable regions for humanized antibody of c23.

| VH or VL Name | FR1 (SEQ ID NO.) | FR2 (SEQ ID NO.) | FR3 (SEQ ID NO.) | FR4 (SEQ ID NO.) |
|---|---|---|---|---|
| hu23.VH_1 | 84 | 87 | 91 | 79 |
| hu23.VH_2 | 84 | 88 | 92 | 79 |
| hu23.VH_3 | 85 | 89 | 93 | 79 |
| hu23.VH_4 | 85 | 90 | 94 | 79 |
| hu23.VH_5 | 84 | 88 | 95 | 79 |
| hu23.VH_6 | 86 | 89 | 96 | 79 |
| hu23.VH_7 | 86 | 90 | 97 | 79 |
| hu23.VH_201 | 131 | 87 | 116 | 118 |
| hu23.VH_207 | 115 | 87 | 116 | 118 |
| hu23.VH_211 | 115 | 87 | 117 | 118 |
| hu23.VL_1 | 98 | 104 | 106 | 83 |
| hu23.VL_2 | 98 | 104 | 107 | 83 |
| hu23.VL_3 | 99 | 104 | 108 | 83 |
| hu23.VL_4 | 100 | 104 | 108 | 83 |
| hu23.VL_5 | 101 | 104 | 109 | 83 |
| hu23.VL_6 | 102 | 105 | 110 | 83 |
| hu23.VL_7 | 103 | 105 | 110 | 83 |
| hu23.VL_201 | 98 | 130 | 107 | 83 |
| hu23.VL_203 | 129 | 104 | 107 | 83 |
| hu23.VL_211 | 98 | 104 | 107 | 83 |

In certain embodiments, the humanized antibodies or antigen-binding fragments thereof provided herein are composed of substantially all human sequences except for the CDR sequences which are non-human. In some embodiments, the variable region FRs, and constant regions if present, are entirely or substantially from human immunoglobulin sequences. The human FR sequences and human constant region sequences may be derived from different human immunoglobulin genes, for example, FR sequences derived from one human antibody and constant region from another human antibody. In some embodiments, the humanized antibody or antigen-binding fragment thereof comprises human heavy chain HFR1-4, and/or light chain LFR1-4.

In some embodiments, the FR regions derived from human may comprise the same amino acid sequence as the human immunoglobulin from which it is derived. In some embodiments, one or more amino acid residues of the human FR are substituted with the corresponding residues from the parent non-human antibody. This may be desirable in certain embodiments to make the humanized antibody or its fragment closely approximate the non-human parent antibody structure, so as to optimize binding characteristics (for example, increase binding affinity). In certain embodiments, the humanized antibody or antigen-binding fragment thereof provided herein comprises no more than 10, 9, 8, 7, 6, 5, 4, 3, 2, or 1 amino acid residue substitutions in each of the human FR sequences, or no more than 10, 9, 8, 7, 6, 5, 4, 3, 2, or 1 amino acid residue substitutions in all the FR sequences of a heavy or a light chain variable domain. In some embodiments, such change in amino acid residue could be present in heavy chain FR regions only, in light chain FR regions only, or in both chains. In certain embodiments, one or more amino acids of the human FR sequences are randomly mutated to increase binding affinity. In certain embodiments, one or more amino acids of the human FR sequences are back mutated to the corresponding amino acid(s) of the parent non-human antibody so as to increase binding affinity.

In certain embodiments, the present disclosure also provides humanized anti-CD39 antibodies and antigen-binding fragments thereof comprising a heavy chain HFR1 comprising the sequence of $X_{19}VQLVX_{20}SGX_{21}X_{22}X_{23}X_{24}KPGX_{25}SX_{26}X_{27}X_{28}SCX_{29}ASGX_{30}X_{31}X_{32}X_{33}$ (SEQ ID NO: 76) or a homologous sequence of at least 80% sequence identity thereof, a heavy chain HFR2 comprising the sequence of $WVX_{34}QX_{35}PGX_{36}X_{37}LEWX_{38}X_{39}$ (SEQ ID NO: 77) or a homologous sequence of at least 80% sequence identity thereof, a heavy chain HFR3 comprising the sequence of $X_{40}X_{41}TX_{42}X_{43}X_{44}DX_{45}SX_{46}X_{47}TX_{48}YX_{49}X_{50}X_{51}X_{52}SLX_{53}X_{54}EDTAVYYCX_{55}X_{56}$ (SEQ ID NO: 78) or a homologous sequence of at least 80% sequence identity thereof, and a heavy chain HFR4 comprising the sequence of $WGQGTX_{57}VTVSS$ (SEQ ID NO: 126) or a homologous sequence of at least 80% sequence identity thereof, wherein $X_{19}$ is Q or E; $X_{20}$ is E or Q; $X_{21}$ is G or A; $X_{22}$ is G or E; $X_{23}$ is L or V; $X_{24}$ is V or K; $X_{25}$ is G or A; $X_{26}$ is L, M or V; $X_{27}$ is R or K; $X_{28}$ is V or L; $X_{29}$ is A or K; $X_{30}$ is F or Y; $X_{31}$ is N or T; $X_{32}$ is F or L; $X_{33}$ is S or K; $X_{34}$ is R or K; $X_{35}$ is A or S; $X_{36}$ is K or Q; $X_{37}$ is R or G; $X_{38}$ is M, I or V; $X_{39}$ is G or A; $X_{40}$ is R or K; $X_{41}$ is V, A or F; $X_{42}$ is I or L; $X_{43}$ is S or T; $X_{44}$ is R or A; $X_{45}$ is D or T; $X_{46}$ is K, A or S; $X_{47}$ is S or N; $X_{48}$ is L, V or A; $X_{49}$ is M or L; $X_{50}$ is Q or E; $X_{51}$ is M or L; $X_{52}$ is S, I or N; $X_{53}$ is R or K; $X_{54}$ is S or T; $X_{55}$ is A or T; $X_{56}$ is R, N or T; and $X_{57}$ is T or L.

In certain embodiments, the present disclosure also provides humanized anti-CD39 antibodies and antigen-binding fragments thereof comprising a light chain LFR1 comprising the sequence of $X_3IVX_4TQSPATLX_5X_6SPGERX_7TX_8X_9C$ (SEQ ID NO: 80) or a homologous sequence of at least 80% sequence identity thereof, a light chain LFR2 comprising the sequence of WYQQKPGQX$_{10}$PX11LLIY (SEQ ID NO: 81) or a homologous sequence of at least 80% sequence identity thereof, a light chain LFR3 comprising the sequence of GX$_{12}$PX$_{13}$RFSGSGSGTX$_{14}$X$_{15}$TLTISSX$_{16}$EPEDFAV YX$_{17}$C (SEQ ID NO: 82) or a homologous sequence of at least 80% sequence identity thereof, and a light chain LFR4 comprising the sequence of FGX$_{18}$GTKLEIK (SEQ ID NO: 152) or a homologous sequence of at least 80% sequence identity thereof, wherein X$_3$ is E or Q; X$_4$ is L or M; X$_5$ is S or T; X$_6$ is L, V or A; X$_7$ is A or V; X$_8$ is L or I; X$_9$ is S or T; X$_{10}$ is A or S; X$_{11}$ is R or K; X$_{12}$ is I or V; X$_{13}$ is A or T; X$_{14}$ is D or S; X$_{15}$ is F or Y; X$_{16}$ is L, M or V; X$_{17}$ is Y or F; X$_{18}$ is G or Q.

In certain embodiments, the present disclosure also provides humanized anti-CD39 antibodies and antigen-binding fragments thereof comprising a heavy chain HFR1 comprising the sequence of EVQLVESGGGLVKPGGSX$_{61}$RLSCAASGFTFS (SEQ ID NO: 154), or a homologous sequence of at least 80% sequence identity thereof; a heavy chain HFR2 comprising the sequence of WVRQX$_{62}$PGKGLEWVX$_{63}$ (SEQ ID NO: 155) or a homologous sequence of at least 80% sequence identity thereof; a heavy chain HFR3 comprising the sequence of RFTISRDDSKNTX$_{64}$YLQMNSLKTEDTAVYYCTT (SEQ ID NO: 156), or a homologous sequence of at least 80% sequence identity thereof, a heavy chain HFR4 comprising the sequence of WGQGTTVTVSS (SEQ ID NO: 79), or a homologous sequence of at least 80% sequence identity thereof, wherein X$_{61}$ is L or M, X$_{62}$ is A or S, X$_{63}$ is G or A, X$_{64}$ is L or V.

In certain embodiments, the present disclosure also provides humanized anti-CD39 antibodies and antigen-binding fragments thereof comprising a light chain LFR1 comprising the sequence of EIVX$_{65}$TQSPATLSX$_{66}$SPGERX$_{67}$TLSC (SEQ ID NO: 157), or a homologous sequence of at least 80% sequence identity thereof, a light chain LFR2 comprising the sequence of WYQQKPGQX$_{68}$PRLLIY (SEQ ID NO: 158), or a homologous sequence of at least 80% sequence identity thereof; a light chain LFR3 comprising the sequence of GIPARFSGSGSGTDFTLTISSX$_{69}$EPED FAVYX$_{70}$C (SEQ ID NO: 159), or a homologous sequence of at least 80% sequence identity thereof, and a light chain LFR4 comprising the sequence of FGGGTKLEIK (SEQ ID NO: 153), or a homologous sequence of at least 80% sequence identity thereof, wherein X$_{65}$ is L or M; X$_{66}$ is L or V; X$_{67}$ is A or V; X$_{68}$ is A or S; X$_{69}$ is L or V; and X$_{70}$ is Y or F.

In certain embodiments, the present disclosure also provides humanized anti-CD39 antibodies and antigen-binding fragments thereof comprising a heavy chain HFR1 comprising the sequence of X$_{71}$VQLVQSGAEVKKPGASVKX$_{72}$SCKASGYX$_{73}$LK (SEQ ID NO: 160), or a homologous sequence of at least 80% sequence identity thereof; a heavy chain HFR2 comprising the sequence of WVX$_{74}$QAPGQX$_{75}$LEWX$_{76}$G (SEQ ID NO: 161) or a homologous sequence of at least 80% sequence identity thereof; a heavy chain HFR3 comprising the sequence of X$_{77}$X$_{78}$TX$_{79}$TX$_{80}$DTSX$_{81}$X$_{82}$TAYX$_{83}$ELX$_{84}$SLRSEDTAV YYCAX$_{85}$ (SEQ ID NO: 149), or a homologous sequence of at least 80% sequence identity thereof; a heavy chain HFR4 comprising the sequence of WGQGTX$_{57}$VTVSS (SEQ ID NO: 126), or a homologous sequence of at least 80% sequence identity thereof, wherein X$_{57}$ is as defined above, X$_{71}$ is Q or E; X$_{72}$ is V or L; X$_{73}$ is N or T; X$_{74}$ is R or K; X$_{75}$ is R or G; X$_{76}$ is M or I; X$_{77}$ is R or K; X$_{78}$ is V or A;

X$_{79}$ is I or L; X$_{80}$ is R or A; X$_{81}$ is A or S; X$_{82}$ is S or N; X$_{83}$ is M or L; X$_{84}$ is S or I; X$_{85}$ is R or N.

In certain embodiments, the present disclosure also provides humanized anti-CD39 antibodies and antigen-binding fragments thereof comprising a light chain LFR1 comprising the sequence of X$_{86}$IVLTQSPATLX$_{87}$X$_{88}$SPGERX$_{89}$TX$_{90}$X$_{91}$C (SEQ ID NO: 150), or a homologous sequence of at least 80% sequence identity thereof, a light chain LFR2 comprising the sequence of WYQQKPGQX$_{10}$PX$_{11}$LLIY (SEQ ID NO: 81), or a homologous sequence of at least 80% sequence identity thereof, a light chain LFR3 comprises the sequence of GX$_{92}$PX$_{93}$RFSGSGSGTX$_{94}$X$_{95}$TLTISSX$_{96}$ EPEDFAVYYC (SEQ ID NO: 148), or a homologous sequence of at least 80% sequence identity thereof, and a light chain LFR4 comprising the sequence of FGQGTKLEIK (SEQ ID NO: 83), or a homologous sequence of at least 80% sequence identity thereof, wherein X$_{10}$ and X$_{11}$ are as defined above, X$_{86}$ is E or Q; X$_{87}$ is S or T; X$_{88}$ is L or A; X$_{89}$ is A or V; X$_{90}$ is L or I; X$_{91}$ is S or T; X$_{92}$ is I or V; X$_{93}$ is A or T; X$_{94}$ is D or S; X$_{95}$ is F or Y; and X$_{96}$ is L or M.

In certain embodiments, the present disclosure also provides humanized anti-CD39 antibodies and antigen-binding fragments thereof comprising a heavy chain HFR1 comprising a sequence selected from the group consisting of SEQ ID NOs: 84-86, 115, 119-120, and 131, a heavy chain HFR2 comprising the sequence of SEQ ID NOs: 87-90, and 121-123, a heavy chain HFR3 comprising a sequence selected from the group consisting of SEQ ID NOs: 91-97, 116-117, and 124-125, and a heavy chain HFR4 comprising a sequence selected from the group consisting of SEQ ID NOs: 79 and 118; and/or a light chain LFR1 comprising a sequence from the group consisting of SEQ ID NOs: 98-103 and 127-129, a light chain LFR2 comprising a sequence selected from the group consisting of SEQ ID NOs: 104, 105 and 130, a light chain LFR3 comprising a sequence selected from the group consisting of SEQ ID NOs: 106-110 and 132-133, and a light chain LFR4 comprising a sequence selected from the group consisting of SEQ ID NOs: 83 and 153.

In certain embodiments, the present disclosure also provides humanized anti-CD39 antibodies and antigen-binding fragments thereof comprising HFR1, HFR2, HFR3, and/or HFR4 sequences contained in a heavy chain variable region selected from a group consisting of: hu14.VH_1 (SEQ ID NO: 68), hu14.VH_2 (SEQ ID NO: 70), hu14.VH_3 (SEQ ID NO: 72), hu14.VH_4 (SEQ ID NO: 74), hu23.VH_1 (SEQ ID NO: 60), hu23.VH_2 (SEQ ID NO: 62), hu23.VH_3 (SEQ ID NO: 64), hu23.VH_4 (SEQ ID NO: 66), hu23.VH_5 (SEQ ID NO: 140), hu23.VH_6 (SEQ ID NO: 141), hu23.VH_7 (SEQ ID NO: 142), hu23.201H (SEQ ID NO: 146), hu23.207H (SEQ ID NO: 147), and hu23.211H (SEQ ID NO: 39).

In certain embodiments, the present disclosure also provides humanized anti-CD39 antibodies and antigen-binding fragments thereof comprising LFR1, LFR2, LFR3, and/or LFR4 sequences contained in a light chain variable region selected from a group consisting of: hu14.VL_1 (SEQ ID NO: 69), hu14.VL_2 (SEQ ID NO: 71), hu14.VL_3 (SEQ ID NO: 73), hu14.VL_4 (SEQ ID NO: 75), hu23.VL_1 (SEQ ID NO: 61), hu23.VL_2 (SEQ ID NO: 63), hu23.VL_3 (SEQ ID NO: 65), hu23.VL_4 (SEQ ID NO: 67), hu23.VL_5 (SEQ ID NO: 143), hu23.VL_6 (SEQ ID NO: 144), hu23.VL_7 (SEQ ID NO: 145), hu23.201L (SEQ ID NO: 111), hu23.203L (SEQ ID NO: 112), and hu23.211L (SEQ ID NO: 63).

In certain embodiments, the humanized anti-CD39 antibodies and antigen-binding fragments thereof provided herein comprise a heavy chain variable domain sequence selected from the group consisting of SEQ ID NOs: 39, 60, 62, 64, 66, 68, 70, 72, 74, 140, 141, 142, 146, 147; and/or a light chain variable domain sequence selected from the group consisting of SEQ ID NOs: 61, 63, 65, 67, 69, 71, 73, 75, 111, 112, 143, 144, and 145.

The present disclosure also provides exemplary humanized antibodies of chimeric antibody c14, including:
1) "hu14.H1L1" comprising the heavy chain variable region of hu14.VH_1 (SEQ ID NO: 68) and the light chain variable region of hu14.VL_1 (SEQ ID NO: 69);
2) "hu14.H2L1" comprising the heavy chain variable region of hu14.VH_2 (SEQ ID NO: 70) and the light chain variable region of hu14.VL_1 (SEQ ID NO: 69);
3) "hu14.H3L1" comprising the heavy chain variable region of hu14.VH_3 (SEQ ID NO: 72) and the light chain variable region of hu14.VL_1 (SEQ ID NO: 69);
4) "hu14.H4L1" comprising the heavy chain variable region of hu14.VH_4 (SEQ ID NO: 74) and the light chain variable region of hu14.VL_1 (SEQ ID NO: 69);
5) "hu14.H1L2" comprising the heavy chain variable region of hu14.VH_1 (SEQ ID NO: 68), and the light chain variable region of hu14.VL_2 (SEQ ID NO: 71);
6) "hu14.H2L2" comprising the heavy chain variable region of hu14.VH_2 (SEQ ID NO: 70), and the light chain variable region of hu14.VL_2 (SEQ ID NO: 71);
7) "hu14.H3L2" comprising the heavy chain variable region of hu14.VH_3 (SEQ ID NO: 72), and the light chain variable region of hu14.VL_2 (SEQ ID NO: 71);
8) "hu14.H4L2" comprising the heavy chain variable region of hu14.VH_4 (SEQ ID NO: 74), and the light chain variable region of hu14.VL_2 (SEQ ID NO: 71);
9) "hu14.H1L3" comprising the heavy chain variable region of hu14.VH_1 (SEQ ID NO: 68), and the light chain variable region of hu14.VL_3 (SEQ ID NO: 73);
10) "hu14.H2L3" comprising the heavy chain variable region of hu14.VH_2 (SEQ ID NO: 70), and the light chain variable region of hu14.VL_3 (SEQ ID NO: 73);
11) "hu14.H3L3" comprising the heavy chain variable region of hu14.VH_3 (SEQ ID NO: 72), and the light chain variable region of hu14.VL_3 (SEQ ID NO: 73);
12) "hu14.H4L3" comprising the heavy chain variable region of hu14.VH_4 (SEQ ID NO: 74), and the light chain variable region of hu14.VL_3 (SEQ ID NO: 73);
13) "hu14.H1L4" comprising the heavy chain variable region of hu14.VH_1 (SEQ ID NO: 68), and the light chain variable region of hu14.VL_4 (SEQ ID NO: 75);
14) "hu14.H2L4" comprising the heavy chain variable region of hu14.VH_2 (SEQ ID NO: 70), and the light chain variable region of hu14.VL_4 (SEQ ID NO: 75);
15) "hu14.H3L4" comprising the heavy chain variable region of hu14.VH_3 (SEQ ID NO: 72), and the light chain variable region of hu14.VL_4 (SEQ ID NO: 75); and
16) "hu14.H4L4" comprising the heavy chain variable region of hu14.VH_4 (SEQ ID NO: 74), and the light chain variable region of hu14.VL_4 (SEQ ID NO: 75).

The present disclosure also provides exemplary humanized antibodies of chimeric antibody c23, including:
1) "hu23.H1L1" comprising the heavy chain variable region of hu23.VH_1 (SEQ ID NO: 60) and the light chain variable region of hu23.VL_1 (SEQ ID NO: 61);
2) "hu23.H2L1" comprising the heavy chain variable region of hu23.VH_2 (SEQ ID NO: 62) and the light chain variable region of hu23.VL_1 (SEQ ID NO: 61);
3) "hu23.H3L1" comprising the heavy chain variable region of hu23.VH_3 (SEQ ID NO: 64) and the light chain variable region of hu23.VL_1 (SEQ ID NO: 61);
4) "hu23.H4L1" comprising the heavy chain variable region of hu23.VH_4 (SEQ ID NO: 66) and the light chain variable region of hu23.VL_1 (SEQ ID NO: 61);
5) "hu23.H1L2" comprising the heavy chain variable region of hu23.VH_1 (SEQ ID NO: 60) and the light chain variable region of hu23.VL_2 (SEQ ID NO: 63);
6) "hu23.H2L2" comprising the heavy chain variable region of hu23.VH_2 (SEQ ID NO: 62) and the light chain variable region of hu23.VL_2 (SEQ ID NO: 63);
7) "hu23.H3L2" comprising the heavy chain variable region of hu23.VH_3 (SEQ ID NO: 64) and the light chain variable region of hu23.VL_2 (SEQ ID NO: 63);
8) "hu23.H4L2" comprising the heavy chain variable region of hu23.VH_4 (SEQ ID NO: 66) and the light chain variable region of hu23.VL_2 (SEQ ID NO: 63);
9) "hu23.H1L3" comprising the heavy chain variable region of hu23.VH_1 (SEQ ID NO: 60) and the light chain variable region of hu23.VL_3 (SEQ ID NO: 65);
10) "hu23.H2L3" comprising the heavy chain variable region of hu23.VH_2 (SEQ ID NO: 62) and the light chain variable region of hu23.VL_3 (SEQ ID NO: 65);
11) "hu23.H3L3" comprising the heavy chain variable region of hu23.VH_3 (SEQ ID NO: 64) and the light chain variable region of hu23.VL_3 (SEQ ID NO: 65);
12) "hu23.H4L3" comprising the heavy chain variable region of hu23.VH_4 (SEQ ID NO: 66) and the light chain variable region of hu23.VL_3 (SEQ ID NO: 65);
13) "hu23.H1L4" comprising the heavy chain variable region of hu23.VH_1 (SEQ ID NO: 60) and the light chain variable region of hu23.VL_4 (SEQ ID NO: 67);
14) "hu23.H2L4" comprising the heavy chain variable region of hu23.VH_2 (SEQ ID NO: 62) and the light chain variable region of hu23.VL_4 (SEQ ID NO: 67);
15) "hu23.H3L4" comprising the heavy chain variable region of hu23.VH_3 (SEQ ID NO: 64) and the light chain variable region of hu23.VL_4 (SEQ ID NO: 67);
16) "hu23.H4L4" comprising the heavy chain variable region of hu23.VH_4 (SEQ ID NO: 66) and the light chain variable region of hu23.VL_4 (SEQ ID NO: 67);
17) "hu23.H5L1" comprising the heavy chain variable region of hu23.VH_5 (SEQ ID NO: 140) and the light chain variable region of hu23.VL_1 (SEQ ID NO: 61);
18) "hu23.H6L1" comprising the heavy chain variable region of hu23.VH_6 (SEQ ID NO: 141) and the light chain variable region of hu23.VL_1 (SEQ ID NO: 61);
19) "hu23.H7L1" comprising the heavy chain variable region of hu23.VH_7 (SEQ ID NO: 142) and the light chain variable region of hu23.VL_1 (SEQ ID NO: 61);
20) "hu23.H1L5" comprising the heavy chain variable region of hu23.VH_1 (SEQ ID NO: 60) and the light chain variable region of hu23.VL_5 (SEQ ID NO: 143);
21) "hu23.H5L5" comprising the heavy chain variable region of hu23.VH_5 (SEQ ID NO: 140) and the light chain variable region of hu23.VL_5 (SEQ ID NO: 143);
22) "hu23.H6L5" comprising the heavy chain variable region of hu23.VH_6 (SEQ ID NO: 141) and the light chain variable region of hu23.VL_5 (SEQ ID NO: 143);

23) "hu23.H7L5" comprising the heavy chain variable region of hu23.VH_7 (SEQ ID NO: 142) and the light chain variable region of hu23.VL_5 (SEQ ID NO: 143);
24) "hu23.H1L6" comprising the heavy chain variable region of hu23.VH_1 (SEQ ID NO: 60) and the light chain variable region of hu23.VL_6 (SEQ ID NO: 144);
25) "hu23.H5L6" comprising the heavy chain variable region of hu23.VH_5 (SEQ ID NO: 140) and the light chain variable region of hu23.VL_6 (SEQ ID NO: 144);
26) "hu23.H6L6" comprising the heavy chain variable region of hu23.VH_6 (SEQ ID NO: 141) and the light chain variable region of hu23.VL_6 (SEQ ID NO: 144);
27) "hu23.H7L6" comprising the heavy chain variable region of hu23.VH_7 (SEQ ID NO: 142) and the light chain variable region of hu23.VL_6 (SEQ ID NO: 144);
28) "hu23.H1L7" comprising the heavy chain variable region of hu23.VH_1 (SEQ ID NO: 60) and the light chain variable region of hu23.VL_7 (SEQ ID NO: 145);
29) "hu23.H5L7" comprising the heavy chain variable region of hu23.VH_5 (SEQ ID NO: 140) and the light chain variable region of hu23.VL_7 (SEQ ID NO: 145);
30) "hu23.H6L7" comprising the heavy chain variable region of hu23.VH_6 (SEQ ID NO: 141) and the light chain variable region of hu23.VL_7 (SEQ ID NO: 145);
31) "hu23.H7L7" comprising the heavy chain variable region of hu23.VH_7 (SEQ ID NO: 142) and the light chain variable region of hu23.VL_7 (SEQ ID NO: 145);
32) "hu23.201" comprising the heavy chain variable region of hu23.201H (SEQ ID NO: 146) and the light chain variable region of hu23.201L (SEQ ID NO: 111);
33) "hu23.203" comprising the heavy chain variable region of hu23.201H (SEQ ID NO: 146) and the light chain variable region of hu23.203L (SEQ ID NO: 112);
34) "hu23.207" comprising the heavy chain variable region of hu23.207H (SEQ ID NO: 147) and the light chain variable region of hu23.201L (SEQ ID NO: 111); and
35) "hu23.211" comprising the heavy chain variable region of hu23.211H (SEQ ID NO: 39) and the light chain variable region of hu23.211L (SEQ ID NO: 63).

These exemplary humanized anti-CD39 antibodies retained the specific binding capacity or affinity to CD39, and are at least comparable to, or even better than, the parent mouse antibody mAb14 or mAb23 in that aspect.

In some embodiments, the anti-CD39 antibodies and antigen-binding fragments provided herein comprise all or a portion of the heavy chain variable domain and/or all or a portion of the light chain variable domain. In one embodiment, the anti-CD39 antibody or an antigen-binding fragment thereof provided herein is a single domain antibody which consists of all or a portion of the heavy chain variable domain provided herein. More information of such a single domain antibody is available in the art (see, e.g. U.S. Pat. No. 6,248,516).

In certain embodiments, the anti-CD39 antibodies or the antigen-binding fragments thereof provided herein further comprise an immunoglobulin (Ig) constant region, which optionally further comprises a heavy chain and/or a light chain constant region. In certain embodiments, the heavy chain constant region comprises CH1, hinge, and/or CH2-CH3 regions (or optionally CH2-CH3-CH4 regions). In certain embodiments, the anti-CD39 antibodies or the antigen-binding fragments thereof provided herein comprises heavy chain constant regions of human IgG1, IgG2, IgG3, IgG4, IgA1, IgA2 or IgM. In certain embodiments, the light chain constant region comprises Cκ or Cλ. The constant region of the anti-CD39 antibodies or the antigen-binding fragments thereof provided herein may be identical to the wild-type constant region sequence or be different in one or more mutations.

In certain embodiments, the heavy chain constant region comprises an Fc region. Fc region is known to mediate effector functions such as antibody-dependent cellular cytotoxicity (ADCC) and complement-dependent cytotoxicity (CDC) of the antibody. Fc regions of different Ig isotypes have different abilities to induce effector functions. For example, Fc regions of IgG1 and IgG3 have been recognized to induce both ADCC and CDC more effectively than those of IgG2 and IgG4. In certain embodiments, the anti-CD39 antibodies and antigen-binding fragments thereof provided herein comprises an Fc region of IgG1, or IgG3 isotype, which could induce ADCC or CDC; or alternatively, a constant region of IgG4 or IgG2 isotype, which has reduced or depleted effector function. In some embodiments, the Fc region derived from human IgG1 with reduced effector functions. In some embodiments, the Fc region derived from human IgG1 comprises a L234A and/or L235A mutation. In certain embodiments, the anti-CD39 antibodies or antigen-binding fragments thereof provided herein comprise a wild type human IgG4 Fc region or other wild type human IgG4 alleles. In certain embodiments, the anti-CD39 antibodies or antigen-binding fragments thereof provided herein comprise a human IgG4 Fc region comprising a S228P mutation and/or a L235E mutation, and/or a F234A and L235A mutation. In some embodiments, the Fc region derived from human IgG4 comprises a S228P mutation and/or a F234A and L235A mutation.

In certain embodiments, the antibodies or the antigen-binding fragments thereof provided herein have a specific binding affinity to human CD39 which is sufficient to provide for diagnostic and/or therapeutic use.

The antibodies or antigen-binding fragments thereof provided herein can be a monoclonal antibody, a polyclonal antibody, a humanized antibody, a chimeric antibody, a recombinant antibody, a bispecific antibody, a multi-specific antibody, a labeled antibody, a bivalent antibody, an anti-idiotypic antibody, or a fusion protein. A recombinant antibody is an antibody prepared in vitro using recombinant methods rather than in animals.

In certain embodiments, the present disclosure provides an anti-CD39 antibody or antigen-binding fragment thereof, which competes for binding to CD39 with the antibody or antigen-binding fragment thereof provided herein. In certain embodiments, the present disclosure provides an anti-CD39 antibody or antigen-binding fragment thereof, which competes for binding to human CD39 with an antibody comprising a heavy chain variable region comprising the sequence of SEQ ID NO: 43, and a light chain variable region comprising the sequence of SEQ ID NO: 52. In certain embodiments, the present disclosure provides an anti-CD39 antibody or antigen-binding fragment thereof, which competes for binding to human CD39 with an antibody comprising a heavy chain variable region comprising the sequence of SEQ ID NO: 44, and a light chain variable region comprising the sequence of SEQ ID NO: 53. In certain embodiments, the present disclosure provides an anti-CD39 antibody or antigen-binding fragment thereof, which competes for binding to human CD39 with an antibody comprising a heavy chain variable region comprising the sequence of SEQ ID NO: 45, and a light chain variable region comprising the sequence of SEQ ID NO: 54, or competes for binding to human CD39 with an antibody comprising a heavy chain variable region comprising the sequence of SEQ ID NO: 47, and a light chain variable region comprising the sequence of SEQ ID NO: 56.

In some embodiments, the present disclosure provides an anti-CD39 antibody or an antigen-binding fragment thereof which specifically binds to an epitope of CD39, wherein the epitope comprises one or more residues selected from the group consisting of Q96, N99, E143, R147, R138, M139, E142, K5, E100, D107, V81, E82, R111, and V115.

In some embodiments, the epitope comprises one or more residues selected from the group consisting of Q96, N99, E143, and R147. In some embodiments, the epitope comprises all of the residues Q96, N99, E143, and R147.

In some embodiments, the epitope comprises one or more residues selected from the group consisting of R138, M139, and E142. In some embodiments, the epitope comprises all of the residues R138, M139, and E142.

In some embodiments, the epitope comprises one or more residues selected from the group consisting of K5, E100, and D107. In some embodiments, the epitope comprises all of the residues K5, E100, and D107.

In some embodiments, the epitope comprises one or more residues selected from the group consisting of V81, E82, R111, and V115. In some embodiments, the epitope comprises all of the residues V81, E82, R111, and V115.

In some embodiments, the CD39 is a human CD39. In some embodiments, the CD39 is a human CD39 comprising an amino acid sequence of SEQ ID NO: 162.

In certain embodiments, the anti-CD39 antibody or antigen-binding fragment thereof provided herein is not any of Antibody 9-8B, Antibody T895, and Antibody I394.

"9-8B" as used herein refers to an antibody or antigen binding fragment thereof comprising a heavy chain variable region having an amino acid sequence of SEQ ID NO: 46, and a light chain variable region having an amino acid sequence of SEQ ID NO: 48.

"T895" as used herein refers to an antibody or antigen binding fragment thereof comprising a heavy chain variable region having an amino acid sequence of SEQ ID NO: 55, and a light chain variable region having an amino acid sequence of SEQ ID NO: 57.

"I394" as used herein refers to an antibody or antigen binding fragment thereof comprising a heavy chain variable region having an amino acid sequence of SEQ ID NO: 113, and a light chain variable region having an amino acid sequence of SEQ ID NO: 114.

Antibody Variants

The antibodies and antigen-binding fragments thereof provided herein also encompass various variants of the antibody sequences provided herein.

In certain embodiments, the antibody variants comprise one or more modifications or substitutions in one or more of the CDR sequences provided in Table 1 above, one or more of the non-CDR sequences of the heavy chain variable region or light chain variable region provided in Tables 4, 5, 8 and 9 above, and/or the constant region (e.g. Fc region). Such variants retain binding specificity to CD39 of their parent antibodies, but have one or more desirable properties conferred by the modification(s) or substitution(s). For example, the antibody variants may have improved antigen-binding affinity, improved glycosylation pattern, reduced risk of glycosylation, reduced deamination, reduced or depleted effector function(s), improved FcRn receptor binding, increased pharmacokinetic half-life, pH sensitivity, and/or compatibility to conjugation (e.g. one or more introduced cysteine residues).

The parent antibody sequence may be screened to identify suitable or preferred residues to be modified or substituted, using methods known in the art, for example, "alanine scanning mutagenesis" (see, for example, Cunningham and Wells (1989) Science, 244:1081-1085). Briefly, target residues (e.g. charged residues such as Arg, Asp, His, Lys, and Glu) can be identified and replaced by a neutral or negatively charged amino acid (e.g. alanine or polyalanine), and the modified antibodies are produced and screened for the interested property. If substitution at a particular amino acid location demonstrates an interested functional change, then the position can be identified as a potential residue for modification or substitution. The potential residues may be further assessed by substituting with a different type of residue (e.g. cysteine residue, positively charged residue, etc.).

Affinity Variants

Affinity variants of antibodies may contain modifications or substitutions in one or more CDR sequences provided in Table 1 above, one or more FR sequences provided in Tables 4, 5, 8, and 9 above, or the heavy or light chain variable region sequences provided in Tables 2, 3, 6 and 7 above. FR sequences can be readily identified by a person skilled in the art based on the CDR sequences in Table 1 above and variable region sequences in Tables 2, 3, 6 and 7 above, as it is well-known in the art that a CDR region is flanked by two FR regions in the variable region. The affinity variants retain specific binding affinity to CD39 of the parent antibody, or even have improved CD39 specific binding affinity over the parent antibody. In certain embodiments, at least one (or all) of the substitution(s) in the CDR sequences, FR sequences, or variable region sequences comprises a conservative substitution.

A person skilled in the art will understand that in the CDR sequences provided in Table 1 above, and variable region sequences provided in Tables 2, 3, 6 and 7 above, one or more amino acid residues may be substituted yet the resulting antibody or antigen-binding fragment still retain the binding affinity or binding capacity to CD39, or even have an improved binding affinity or capacity. Various methods known in the art can be used to achieve this purpose. For example, a library of antibody variants (such as Fab or scFv variants) can be generated and expressed with phage display technology, and then screened for the binding affinity to human CD39. For another example, computer software can be used to virtually simulate the binding of the antibodies to human CD39, and identify the amino acid residues on the antibodies which form the binding interface. Such residues may be either avoided in the substitution so as to prevent reduction in binding affinity, or targeted for substitution to provide for a stronger binding.

In certain embodiments, the humanized antibody or antigen-binding fragment thereof provided herein comprises one or more amino acid residue substitutions in one or more of the CDR sequences, and/or one or more of the FR sequences. In certain embodiments, an affinity variant comprises no more than 20, 15, 10, 9, 8, 7, 6, 5, 4, 3, 2, or 1 substitutions in the CDR sequences and/or FR sequences in total.

In certain embodiments, the anti-CD39 antibodies or antigen-binding fragments thereof comprise 1, 2, or 3 CDR sequences having at least 80% (e.g. at least 85%, 88%, 90%, 91%, 92%, 93%, 94%, 95%, 96%, 97%, 98%, 99%) sequence identity to that (or those) listed in Table 1 above yet retaining the specific binding affinity to CD39 at a level similar to or even higher than its parent antibody.

In certain embodiments, the anti-CD39 antibodies or antigen-binding fragments thereof comprise one or more variable region sequences having at least 80% (e.g. at least 85%, 88%, 90%, 91%, 92%, 93%, 94%, 95%, 96%, 97%, 98%, 99%) sequence identity to that (or those) listed in Tables 2, 3, 6 and 7 above yet retaining the specific binding affinity to CD39 at a level similar to or even higher than its parent antibody. In some embodiments, a total of 1 to 10 amino acids have been substituted, inserted, or deleted in a variable region sequence listed in Tables 2, 3, 6 and 7 above. In some embodiments, the substitutions, insertions, or deletions occur in regions outside the CDRs (e.g. in the FRs).

Glycosylation Variants

The anti-CD39 antibodies or antigen-binding fragments thereof provided herein also encompass glycosylation variants, which can be obtained to either increase or decrease the extent of glycosylation of the antibodies or antigen binding fragments thereof.

The antibodies or antigen binding fragments thereof may comprise one or more modifications that introduce or remove a glycosylation site. A glycosylation site is an amino acid residue with a side chain to which a carbohydrate moiety (e.g. an oligosaccharide structure) can be attached. Glycosylation of antibodies is typically either N-linked or O-linked. N-linked refers to the attachment of the carbohydrate moiety to the side chain of an asparagine residue, for example, an asparagine residue in a tripeptide sequence such as asparagine-X-serine and asparagine-X-threonine, where X is any amino acid except proline. O-linked glycosylation refers to the attachment of one of the sugars N-aceylgalactosamine, galactose, or xylose to a hydroxyamino acid, most commonly to serine or threonine. Removal of a native glycosylation site can be conveniently accomplished, for example, by altering the amino acid sequence such that one of the above-described tripeptide sequences (for N-linked glycosylation sites) or serine or threonine residues (for O-linked glycosylation sites) present in the sequence in the is substituted. A new glycosylation site can be created in a similar way by introducing such a tripeptide sequence or serine or threonine residue.

In certain embodiments, the anti-CD39 antibodies and antigen-binding fragments provided herein comprise one or more mutations at a position selected from the group consisting of N55, G56, and N297, to remove one or more deamidation site. In certain embodiments, the anti-CD39 antibodies and antigen-binding fragments provided herein comprise a mutation at N55 (for example, N55G, N55S or N55Q), and/or a mutation at G56 (for example, G56A, G56D), and/or a mutation at N297 (for example, N297A, N297Q, or N297G). These mutations are tested and are believed not to negatively affect the binding affinity of the antibodies provided herein.

Cysteine-Engineered Variants

The anti-CD39 antibodies or antigen-binding fragments thereof provided herein also encompass cysteine-engineered variants, which comprise one or more introduced free cysteine amino acid residues.

A free cysteine residue is one which is not part of a disulfide bridge. A cysteine-engineered variant is useful for conjugation with for example, a cytotoxic and/or imaging compound, a label, or a radioisoptype among others, at the site of the engineered cysteine, through for example a maleimide or haloacetyl. Methods for engineering antibodies or antigen-binding fragments thereof to introduce free cysteine residues are known in the art, see, for example, WO2006/034488.

Fc Variants

The anti-CD39 antibodies or antigen-binding fragments thereof provided herein also encompass Fc variants, which comprise one or more amino acid residue modifications or substitutions at the Fc region and/or hinge region, for example, to provide for altered effector functions such as ADCC and CDC. Methods of altering ADCC activity by antibody engineering have been described in the art, see for example, Shields R L. et al., *J Biol Chem.* 2001. 276(9): 6591-604; Idusogie E E. et al., *J Immunol.* 2000. 164(8): 4178-84; Steurer W. et al., *J Immunol.* 1995, 155(3): 1165-74; Idusogie E E. et al., *J Immunol.* 2001, 166(4): 2571-5; Lazar G A. et al., *PNAS*, 2006, 103(11): 4005-4010; Ryan M C. et al., *Mol. Cancer Ther.,* 2007, 6: 3009-3018; Richards J O,. et al., *Mol Cancer Ther.* 2008, 7(8): 2517-27; Shields R. L. et al., *J. Biol. Chem,* 2002, 277: 26733-26740; Shinkawa T. et al., *J. Biol. Chem,* 2003, 278: 3466-3473.

CDC activity of the antibodies or antigen-binding fragments provided herein can also be altered, for example, by improving or diminishing C1q binding and/or CDC (see, for example, WO99/51642; Duncan & Winter Nature 322:738-40 (1988); U.S. Pat. Nos. 5,648,260; 5,624,821); and WO94/29351 concerning other examples of Fe region variants. One or more amino acids selected from amino acid residues 329, 331 and 322 of the Fc region can be replaced with a different amino acid residue to alter C1q binding and/or reduced or abolished complement dependent cytotoxicity (CDC) (see, U.S. Pat. No. 6,194,551 by Idusogie et al.). One or more amino acid substitution(s) can also be introduced to alter the ability of the antibody to fix complement (see PCT Publication WO 94/29351 by Bodmer et al.).

In certain embodiments, the anti-CD39 antibodies or antigen-binding fragments thereof provided herein has reduced effector functions, and comprise one or more amino acid substitution(s) in IgG1 at a position selected from the group consisting of: 234, 235, 237, 238, 268, 297, 309, 330, and 331. In certain embodiments, the anti-CD39 antibodies or antigen-binding fragments thereof provided herein is of IgG1 isotype and comprise one or more amino acid substitution(s) selected from the group consisting of: N297A, N297Q, N297G, L235E, L234A, L235A, L234F, L235E, P331S, and any combination thereof. In certain embodiments, the anti-CD39 antibodies or antigen-binding fragments thereof provided herein is of IgG1 isotype and comprise a L234A and L235A mutation. In certain embodiments, the anti-CD39 antibodies or antigen-binding fragments thereof provided herein is of IgG2 isotype, and comprises one or more amino acid substitution(s) selected from the group consisting of: H268Q, V309L, A330S, P331S, V234A, G237A, P238S, H268A, and any combination thereof (e.g. H268Q/V309L/A330S/P331S, V234A/G237A/P238S/H268A/V309L/A330S/P331S). In certain embodiments, the anti-CD39 antibodies or antigen-binding fragments thereof provided herein is of IgG4 isotype, and comprises one or more amino acid substitution(s) selected from the group consisting of: S228P, N297A, N297Q, N297G, L235E, F234A, L235A, and any combination thereof. In certain embodiments, the anti-CD39 antibodies or antigen-binding fragments thereof provided herein is of IgG2/IgG4 cross isotype. Examples of IgG2/IgG4 cross isotype is described in Rother R P et al., *Nat Biotechnol* 25:1256-1264 (2007).

In certain embodiments, the anti-CD39 antibodies and antigen-binding fragments thereof provided herein is of IgG4 isotype and comprises one or more amino acid substitution(s) at one or more points of 228, 234 and 235. In certain embodiments, the anti-CD39 antibodies and antigen-binding fragments provided herein is of IgG4 isotype and comprises a S228P mutation and/or a L235E mutation and/or a F234A and L235A mutation in the Fc region.

In certain embodiments, the anti-CD39 antibodies or antigen-binding fragments thereof comprise one or more amino acid substitution(s) that improves pH-dependent binding to neonatal Fc receptor (FcRn). Such a variant can have an extended pharmacokinetic half-life, as it binds to FcRn at acidic pH which allows it to escape from degradation in the lysosome and then be translocated and released out of the cell. Methods of engineering an antibody or antigen-binding fragment thereof to improve binding affinity with FcRn are well-known in the art, see, for example, Vaughn, D. et al., *Structure*, 6(1): 63-73, 1998; Kontermann, R. et al., *Antibody Engineering*, Volume 1, Chapter 27: Engineering of the Fc region for improved PK, published by Springer, 2010; Yeung, Y. et al., *Cancer Research*, 70: 3269-3277 (2010); and Hinton, P. et al., *J. Immunology*, 176:346-356 (2006).

In certain embodiments, anti-CD39 antibodies or antigen-binding fragments thereof comprise one or more amino acid substitution(s) in the interface of the Fc region to facilitate and/or promote heterodimerization. These modifications comprise introduction of a protuberance into a first Fc polypeptide and a cavity into a second Fc polypeptide, wherein the protuberance can be positioned in the cavity so as to promote interaction of the first and second Fc polypeptides to form a heterodimer or a complex. Methods of generating antibodies with these modifications are known in the art, e.g. as described in U.S. Pat. No. 5,731,168.

Antigen-Binding Fragments

Provided herein are also anti-CD39 antigen-binding fragments. Various types of antigen-binding fragments are known in the art and can be developed based on the anti-CD39 antibodies provided herein, including for example, the exemplary antibodies whose CDRs are shown in Table 1 above, and variable sequences are shown in Tables 2, 3, 6 and 7, and their different variants (such as affinity variants, glycosylation variants, Fc variants, cysteine-engineered variants and so on).

In certain embodiments, an anti-CD39 antigen-binding fragment provided herein is a diabody, a Fab, a Fab', a F(ab')$_2$, a Fd, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a multispecific antibody, a camelized single domain antibody, a nanobody, a domain antibody, and a bivalent domain antibody.

Various techniques can be used for the production of such antigen-binding fragments. Illustrative methods include, enzymatic digestion of intact antibodies (see, e.g. Morimoto et al., *Journal of Biochemical and Biophysical Methods* 24:107-117 (1992); and Brennan et al., *Science*, 229:81 (1985)), recombinant expression by host cells such as *E. Coli* (e.g. for Fab, Fv and ScFv antibody fragments), screening from a phage display library as discussed above (e.g. for ScFv), and chemical coupling of two Fab'-SH fragments to form F(ab')$_2$ fragments (Carter et al., *Bio/Technology* 10:163-167 (1992)). Other techniques for the production of antibody fragments will be apparent to a person skilled in the art.

In certain embodiments, the antigen-binding fragment is a scFv. Generation of scFv is described in, for example, WO 93/16185; U.S. Pat. Nos. 5,571,894; and 5,587,458. ScFv may be fused to an effector protein at either the amino or the carboxyl terminus to provide for a fusion protein (see, for example, Antibody Engineering, ed. Borrebaeck).

In certain embodiments, the anti-CD39 antibodies or antigen-binding fragments thereof provided herein are bivalent, tetravalent, hexavalent, or multivalent. Any molecule being more than bivalent is considered multivalent, encompassing for example, trivalent, tetravalent, hexavalent, and so on.

A bivalent molecule can be monospecific if the two binding sites are both specific for binding to the same antigen or the same epitope. This, in certain embodiments, provides for stronger binding to the antigen or the epitope than a monovalent counterpart. Similar, a multivalent molecule may also be monospecific. In certain embodiments, in a bivalent or multivalent antigen-binding moiety, the first valent of binding site and the second valent of binding site are structurally identical (i.e. having the same sequences), or structurally different (i.e. having different sequences albeit with the same specificity).

A bivalent can also be bispecific, if the two binding sites are specific for different antigens or epitopes. This also applies to a multivalent molecule. For example, a trivalent molecule can be bispecific when two binding sites are monospecific for a first antigen (or epitope) and the third binding site is specific for a second antigen (or epitope).

Bispecific Antibodies

In certain embodiments, the anti-CD39 antibodies or antigen-binding fragments thereof is bispecific. In certain embodiments, the antibody or antigen-binding fragment thereof is further linked to a second functional moiety having a different binding specificity from said CD39 antibody, or antigen binding fragment thereof.

In certain embodiments, the bispecific antibodies or antigen-binding fragments thereof provided herein are capable of specifically binding to a second antigen other than CD39, or a second epitope on CD39. In certain embodiments, the second antigen is selected from the group consisting of TGFbeta, CD73, PD1, PDL1, 4-1BB, CTLA4, TIGIT, GITA, VISTA, TIGIT, B7-H3, B7-H4, B7-H5, CD112R, Siglec-15, LAG3 and TIM-3.

Conjugates

In some embodiments, the anti-CD39 antibodies or antigen-binding fragments thereof further comprise one or more conjugate moieties. The conjugate moiety can be linked to the antibodies or antigen-binding fragments thereof. A conjugate moiety is a moiety that can be attached to the antibody or antigen-binding fragment thereof. It is contemplated that a variety of conjugate moieties may be linked to the antibodies or antigen-binding fragments thereof provided herein (see, for example, "Conjugate Vaccines", Contributions to Microbiology and Immunology, J. M. Cruse and R. E. Lewis, Jr. (eds.), Carger Press, New York, (1989)). These conjugate moieties may be linked to the antibodies or antigen-binding fragments thereof by covalent binding, affinity binding, intercalation, coordinate binding, complexation, association, blending, or addition, among other methods. In some embodiments, the antibodies or antigen-binding fragments thereof can be linked to one or more conjugates via a linker.

In certain embodiments, the antibodies or antigen-binding fragments thereof provided herein may be engineered to contain specific sites outside the epitope binding portion that may be utilized for binding to one or more conjugate moieties. For example, such a site may include one or more reactive amino acid residues, such as for example cysteine or histidine residues, to facilitate covalent linkage to a conjugate moiety.

In certain embodiments, the antibodies or antigen-binding fragments thereof may be linked to a conjugate moiety indirectly, or through another conjugate moiety. For example, the antibodies or antigen-binding fragments thereof provided herein may be conjugated to biotin, then indirectly conjugated to a second conjugate that is conjugated to avidin. In some embodiments, the conjugate moiety comprises a clearance-modifying agent (e.g. a polymer such as PEG which extends half-life), a chemotherapeutic agent, a toxin, a radioactive isotope, a lanthanide, a detectable label (e.g. a luminescent label, a fluorescent label, an enzyme-substrate label), a DNA-alkylator, a topoisomerase inhibitor, a tubulin-binder, a purification moiety or other anticancer drugs.

A "toxin" can be any agent that is detrimental to cells or that can damage or kill cells. Examples of toxin include, without limitation, taxol, cytochalasin B, gramicidin D, ethidium bromide, emetine, mitomycin, etoposide, tenoposide, vincristine, MMAE, MMAF, DM1, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin and analogs thereof, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, and anthramycin (AMC)), anti-mitotic agents (e.g. vincristine and vinblastine), a topoisomerase inhibitor, and a tubulin-binders.

Examples of detectable label may include a fluorescent labels (e.g. fluorescein, rhodamine, dansyl, phycoerythrin, or Texas Red), enzyme-substrate labels (e.g. horseradish peroxidase, alkaline phosphatase, luceriferases, glucoamylase, lysozyme, saccharide oxidases or β-D-galactosidase), radioisotopes (e.g. $^{123}$I, $^{124}$I, $^{125}$I, 131I, $^{35}$S, $^{3}$H, $^{111}$In, $^{112}$In, $^{14}$C, $^{64}$Cu, $^{67}$Cu, $^{86}$Y, $^{88}$Y, $^{90}$Y, $^{177}$Lu, $^{211}$At, $^{186}$Re, $^{188}$Re, $^{153}$Sm, $^{212}$Bi, and $^{32}$P, other lanthanides), luminescent labels, chromophoric moieties, digoxigenin, biotin/avidin, DNA molecules or gold for detection.

In certain embodiments, the conjugate moiety can be a clearance-modifying agent which helps increase half-life of the antibody. Illustrative examples include water-soluble polymers, such as PEG, carboxymethylcellulose, dextran, polyvinyl alcohol, polyvinyl pyrrolidone, copolymers of ethylene glycol/propylene glycol, and the like. The polymer may be of any molecular weight, and may be branched or unbranched. The number of polymers attached to the antibody may vary, and if more than one polymer are attached, they can be the same or different molecules.

In certain embodiments, the conjugate moiety can be a purification moiety such as a magnetic bead.

In certain embodiments, the antibodies or antigen-binding fragments thereof provided herein is used as a base for a conjugate.

Polynucleotides and Recombinant Methods

The present disclosure provides isolated polynucleotides that encode the anti-CD39 antibodies or antigen-binding fragments thereof provided herein. The term "nucleic acid" or "polynucleotide" as used herein refers to deoxyribonucleic acids (DNA) or ribonucleic acids (RNA) and polymers thereof in either single- or double-stranded form. Unless otherwise indicated, a particular polynucleotide sequence also implicitly encompasses conservatively modified variants thereof (e.g. degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (see Batzer et al., *Nucleic Acid Res.* 19:5081 (1991); Ohtsuka et al., *J Biol. Chem.* 260: 2605-2608 (1985); and Rossolini et al., *Mol. Cell. Probes* 8:91-98 (1994)).

DNA encoding the monoclonal antibody is readily isolated and sequenced using conventional procedures (e.g. by using oligonucleotide probes that are capable of binding specifically to genes encoding the heavy and light chains of the antibody). The encoding DNA may also be obtained by synthetic methods.

The isolated polynucleotide that encodes the anti-CD39 antibodies or antigen-binding fragments thereof can be inserted into a vector for further cloning (amplification of the DNA) or for expression, using recombinant techniques known in the art. Many vectors are available. The vector components generally include, but are not limited to, one or more of the following: a signal sequence, an origin of replication, one or more marker genes, an enhancer element, a promoter (e.g. SV40, CMV, EF-1α), and a transcription termination sequence.

The present disclosure provides vectors comprising the isolated polynucleotides provided herein. In certain embodiments, the polynucleotide provided herein encodes the antibodies or antigen-binding fragments thereof, at least one promoter (e.g. SV40, CMV, EF-1α) operably linked to the nucleic acid sequence, and at least one selection marker. Examples of vectors include, but are not limited to, retrovirus (including lentivirus), adenovirus, adeno-associated virus, herpesvirus (e.g. herpes simplex virus), poxvirus, baculovirus, papillomavirus, papovavirus (e.g. SV40), lambda phage, and M13 phage, plasmid pcDNA3.3, pMD18-T, pOptivec, pCMV, pEGFP, pIRES, pQD-Hyg-GSeu, pALTER, pBAD, pcDNA, pCal, pL, pET, pGEMEX, pGEX, pCI, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS10, pLexA, pACT2.2, pCMV-SCRIPT.RTM., pCDM8, pCDNA1.1/amp, pcDNA3.1, pRc/RSV, PCR 2.1, pEF-1, pFB, pSG5, pXT1, pCDEF3, pSVSPORT, pEF-Bos etc.

Vectors comprising the polynucleotide sequence encoding the antibody or antigen-binding fragment thereof can be introduced to a host cell for cloning or gene expression. Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g. *E. coli, Enterobacter, Erwinia, Klebsiella, Proteus, Salmonella*, e.g. *Salmonella typhimurium, Serratia*, e.g. *Serratia marcescans*, and *Shigella*, as well as Bacilli such as *B. subtilis* and *B. licheniformis, Pseudomonas* such as *P. aeruginosa*, and *Streptomyces*.

In addition to prokaryotes, eukaryotic microbes such as filamentous fungi or yeast are suitable cloning or expression hosts for anti-CD39 antibody-encoding vectors. *Saccharo-* myces cerevisiae, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g. *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans,* and *K. marxianus; yarrowia* (EP 402,226); *Pichia pastoris* (EP 183,070); *Candida; Trichoderma* reesia (EP 244,234); *Neurospora crassa; Schwanniomyces* such as *Schwanniomyces occidentalis*; and filamentous fungi such as, e.g. *Neurospora, Penicillium, Tolypocladium,* and *Aspergillus* hosts such as *A. nidulans* and *A. niger.*

Suitable host cells for the expression of glycosylated antibodies or antigen-fragment thereof provided herein are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruifly), and *Bombyx mori* have been identified. A variety of viral strains for transfection are publicly available, e.g. the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, *Mather, Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2). In some embodiments, the host cell is a mammalian cultured cell line, such as CHO, BHK, NS0, 293 and their derivatives.

Host cells are transformed with the above-described expression or cloning vectors for anti-CD39 antibody production and cultured in conventional nutrient media modified as appropriate for inducing promoters, selecting transformants, or amplifying the genes encoding the desired sequences. In another embodiment, the antibody may be produced by homologous recombination known in the art. In certain embodiments, the host cell is capable of producing the antibody or antigen-binding fragment thereof provided herein.

The present disclosure also provides a method of expressing the antibody or an antigen-binding fragment thereof provided herein, comprising culturing the host cell provided herein under the condition at which the vector of the present disclosure is expressed. The host cells used to produce the antibodies or antigen-binding fragments thereof provided herein may be cultured in a variety of media. Commercially available media such as Ham's F10 (Sigma), Minimal Essential Medium (MEM), (Sigma), RPMI-1640 (Sigma), and Dulbecco's Modified Eagle's Medium (DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to a person skilled in the art. The culture conditions, such as temperature, pH, and the like, are those previously used with the host cell selected for expression, and will be apparent to a person skilled in the art.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., *Bio/Technology* 10:163-167 (1992) describe a procedure for isolating antibodies which are secreted to the periplasmic space of *E. coli.* Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The anti-CD39 antibodies or antigen-binding fragments thereof prepared from the cells can be purified using, for example, hydroxylapatite chromatography, gel electrophoresis, dialysis, DEAE-cellulose ion exchange chromatography, ammonium sulfate precipitation, salting out, and affinity chromatography, with affinity chromatography being the preferred purification technique.

In certain embodiments, Protein A immobilized on a solid phase is used for immunoaffinity purification of the antibody and antigen-binding fragment thereof. The suitability of protein A as an affinity ligand depends on the species and isotype of any immunoglobulin Fc domain that is present in the antibody. Protein A can be used to purify antibodies that are based on human gamma1, gamma2, or gamma4 heavy chains (Lindmark et al., *J. Immunol. Meth.* 62:1-13 (1983)). Protein G is recommended for all mouse isotypes and for human gamma3 (Guss et al., *EMBO J.* 5:1567 1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g. from about 0-0.25M salt).

Pharmaceutical Composition

The present disclosure further provides pharmaceutical compositions comprising the anti-CD39 antibodies or antigen-binding fragments thereof and one or more pharmaceutically acceptable carriers.

Pharmaceutical acceptable carriers for use in the pharmaceutical compositions disclosed herein may include, for example, pharmaceutically acceptable liquid, gel, or solid carriers, aqueous vehicles, nonaqueous vehicles, antimicrobial agents, isotonic agents, buffers, antioxidants, anesthetics, suspending/dispensing agents, sequestering or chelating agents, diluents, adjuvants, excipients, or non-toxic auxiliary substances, other components known in the art, or various combinations thereof.

Suitable components may include, for example, antioxidants, fillers, binders, disintegrants, buffers, preservatives, lubricants, flavorings, thickeners, coloring agents, emulsifiers or stabilizers such as sugars and cyclodextrins. Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. As disclosed herein, inclusion of one or more antioxidants such as methionine in a composition comprising an antibody or antigen-binding fragment thereof and conjugates provided herein decreases oxidation of the antibody or antigen-binding fragment thereof. This reduction in oxidation prevents or reduces loss of binding affinity, thereby improving antibody stability and maximizing shelf-life. Therefore, in certain embodiments, pharmaceutical compositions are provided that comprise one or more antibodies or antigen-binding fragments thereof as disclosed herein and one or more antioxidants such as methionine. Further provided are methods for preventing oxidation of, extending the shelf-life of, and/or improving the efficacy of an antibody or antigen-binding fragment provided herein by mixing the antibody or antigen-binding fragment with one or more antioxidants such as methionine.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylceluose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

The pharmaceutical compositions can be a liquid solution, suspension, emulsion, pill, capsule, tablet, sustained release formulation, or powder. Oral formulations can include standard carriers such as pharmaceutical grades of mannitol, lactose, starch, magnesium stearate, polyvinyl pyrollidone, sodium saccharine, cellulose, magnesium carbonate, etc.

In certain embodiments, the pharmaceutical compositions are formulated into an injectable composition. The injectable pharmaceutical compositions may be prepared in any conventional form, such as for example liquid solution, suspension, emulsion, or solid forms suitable for generating liquid solution, suspension, or emulsion. Preparations for injection may include sterile and/or non-pyretic solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile and/or non-pyretic emulsions. The solutions may be either aqueous or nonaqueous.

In certain embodiments, unit-dose parenteral preparations are packaged in an ampoule, a vial or a syringe with a needle. All preparations for parenteral administration should be sterile and not pyretic, as is known and practiced in the art.

In certain embodiments, a sterile, lyophilized powder is prepared by dissolving an antibody or antigen-binding fragment as disclosed herein in a suitable solvent. The solvent may contain an excipient which improves the stability or other pharmacological components of the powder or reconstituted solution, prepared from the powder. Excipients that may be used include, but are not limited to, water, dextrose, sorbital, fructose, corn syrup, xylitol, glycerin, glucose, sucrose or other suitable agent. The solvent may contain a buffer, such as citrate, sodium or potassium phosphate or other such buffer known to a person skilled in the art at, in one embodiment, about neutral pH. Subsequent sterile filtration of the solution followed by lyophilization under standard conditions known to a person skilled in the art provides a desirable formulation. In one embodiment, the resulting solution will be apportioned into vials for lyophilization. Each vial can contain a single dosage or multiple dosages of the anti-CD39 antibody or antigen-binding fragment thereof or composition thereof. Overfilling vials with a small amount above that needed for a dose or set of doses (e.g. about 10%) is acceptable so as to facilitate accurate sample withdrawal and accurate dosing. The lyophilized powder can be stored under appropriate conditions, such as at about 4° C. to room temperature.

Reconstitution of a lyophilized powder with water for injection provides a formulation for use in parenteral administration. In one embodiment, for reconstitution the sterile and/or non-pyretic water or other liquid suitable carrier is added to lyophilized powder. The precise amount depends upon the selected therapy being given, and can be empirically determined.

Kits

In certain embodiments, the present disclosure provides a kit comprising the antibody or an antigen-binding fragment thereof provided herein and/or the pharmaceutical composition provided herein. In certain embodiments, the present disclosure provides a kit comprising the antibody or an antigen-binding fragment thereof provided herein, and a second therapeutic agent. In certain embodiments, the second therapeutic agent is selected from the group consisting of a chemotherapeutic agent, an anti-cancer drug, radiation therapy, an immunotherapy agent, an anti-angiogenesis agent, a targeted therapy, a cellular therapy, a gene therapy, a hormonal therapy, an antiviral agent, an antibiotic, an analgesics, an antioxidant, a metal chelator, and cytokines.

Such kits can further include, if desired, one or more of various conventional pharmaceutical kit components, such as, for example, containers with one or more pharmaceutically acceptable carriers, additional containers etc., as will be readily apparent to a person skilled in the art. Instructions, either as inserts or a labels, indicating quantities of the components to be administered, guidelines for administration, and/or guidelines for mixing the components, can also be included in the kit.

Methods of Use

The present disclosure also provides methods of treating a CD39 related disease, disorder or condition in a subject, comprising administering to the subject a therapeutically effective amount of the antibody or antigen-binding fragment thereof provided herein, and/or the pharmaceutical composition provided herein. In certain embodiments, the subject is human.

In some embodiments, the CD39 related disease, disorder or condition is characterized in expressing or over-expressing of CD39.

In certain embodiments, the CD39 related disease, disorder or condition is cancer. In certain embodiments, the cancer is a CD39-expressing cancer. "CD39-expressing" cancer as used herein refers to a cancer characterized in expressing CD39 protein in a cancer cell, a tumor infiltrating immune cell or an immune suppression cell, or expressing CD39 in a cancer cell, a tumor infiltrating immune cell or an immune suppression cell at a level significantly higher than that would have been expected of a normal cell. Various methods can be used to determine the presence and/or amount of CD39 in a test biological sample from the subject. For example, the test biological sample can be exposed to anti-CD39 antibody or antigen-binding fragment thereof, which binds to and detects the expressed CD39 protein. Alternatively, CD39 can also be detected at nucleic acid expression level, using methods such as qPCR, reverse transcriptase PCR, microarray, SAGE, FISH, and the like. In some embodiments, the test sample is derived from a cancer cell or tissue, or tumor infiltrating immune cells. The reference sample can be a control sample obtained from a healthy or non-diseased individual, or a healthy or non-diseased sample obtained from the same individual from whom the test sample is obtained. For example, the reference sample can be a non-diseased sample adjacent to or in the neighborhood of the test sample (e.g. tumor).

In certain embodiments, the cancer is selected from the group consisting of anal cancer, appendix cancer, astrocytoma, basal cell carcinoma, gallbladder cancer, gastric cancer, lung cancer, bronchial cancer, bone cancer, liver and bile duct cancer, pancreatic cancer, breast cancer, liver cancer, ovarian cancer, testicle cancer, kidney cancer, renal pelvis and ureter cancer, salivary gland cancer, small intestine cancer, urethral cancer, bladder cancer, head and neck cancer, spine cancer, brain cancer, cervix cancer, uterine cancer, endometrial cancer, colon cancer, colorectal cancer, rectal cancer, anal cancer, esophageal cancer, gastrointestinal cancer, skin cancer, prostate cancer, pituitary cancer, vagina cancer, thyroid cancer, throat cancer, glioblastoma, melanoma, myelodysplastic syndrome, sarcoma, teratoma, chronic lymphocytic leukemia (CLL), chronic myeloid leukemia (CML), acute lymphocytic leukemia (ALL), acute myeloid leukemia (AML), Hodgkin lymphoma, non-Hodgkin lymphoma, multiple myeloma, T or B cell lymphoma, GI organ interstitialoma, soft tissue tumor, hepatocellular carcinoma, and adenocarcinoma. In certain embodiments, the cancer is a leukemia, lymphoma, bladder cancer, glioma, glioblastoma, ovarian cancer, melanoma, prostate cancer, thyroid cancer, esophageal cancer or breast cancer.

In some embodiments, the subject has been identified as having a cancer cell or tumor infiltrating immune cells or immune suppression cells expressing CD39, optionally at a level significantly higher from the level normally found on non-cancer cells or non-immune suppression cells.

In some embodiments, the disease, disorder or condition is an autoimmune disease or infection. In some embodiments, the autoimmune disease is immune thrombocytopenia, systemic scleroderma, sclerosis, adult respiratory distress syndrome, eczema, asthma, Sjogren's syndrome, Addison's disease, giant cell arteritis, immune complex nephritis, immune thrombocytopenic purpura, autoimmune thrombocytopenia, Celiac disease, psoriasis, dermatitis, colitis or systemic lupus erythematosus. In some embodiments, the infection is a viral infection or a bacterial infection. In some embodiments, the infection is HIV infection, HBV infection, HCV infection, inflammatory bowel disease, or Crohn's disease.

In another aspect, methods are provided to treat a disease, disorder or condition in a subject that would benefit from modulation of CD39 activity, comprising administering a therapeutically effective amount of the antibody or antigen-binding fragment thereof provided herein and/or the pharmaceutical composition provided herein to a subject in need thereof. In certain embodiments, the disease, disorder or condition is a CD39 related disease, disorder or condition, which is defined above.

The therapeutically effective amount of an antibody or antigen-binding fragment provided herein will depend on various factors known in the art, such as for example body weight, age, past medical history, present medications, state of health of the subject and potential for cross-reaction, allergies, sensitivities and adverse side-effects, as well as the administration route and extent of disease development. Dosages may be proportionally reduced or increased by a person skilled in the art (e.g. physician or veterinarian) as indicated by these and other circumstances or requirements.

In certain embodiments, the antibody or antigen-binding fragment provided herein may be administered at a therapeutically effective dosage of about 0.01 mg/kg to about 100 mg/kg. In certain embodiments, the administration dosage may change over the course of treatment. For example, in certain embodiments the initial administration dosage may be higher than subsequent administration dosages. In certain embodiments, the administration dosage may vary over the course of treatment depending on the reaction of the subject.

Dosage regimens may be adjusted to provide the optimum desired response (e.g. a therapeutic response). For example, a single dose may be administered, or several divided doses may be administered overtime.

The antibodies or antigen-binding fragments thereof provided herein may be administered by any route known in the art, such as for example parenteral (e.g. subcutaneous, intraperitoneal, intravenous, including intravenous infusion, intramuscular, or intradermal injection) or non-parenteral (e.g. oral, intranasal, intraocular, sublingual, rectal, or topical) routes.

In some embodiments, the antibodies or antigen-binding fragments thereof provided herein may be administered alone or in combination with a therapeutically effective amount of a second therapeutic agent. For example, the antibodies or antigen-binding fragments thereof disclosed herein may be administered in combination with a second therapeutic agent, for example, a chemotherapeutic agent, an anti-cancer drug, radiation therapy, an immunotherapy agent, an anti-angiogenesis agent, a targeted therapy, a cellular therapy, a gene therapy, a hormonal therapy, an antiviral agent, an antibiotic, an analgesics, an antioxidant, a metal chelator, or cytokines.

The term "immunotherapy" as used herein, refers to a type of therapy that stimulates immune system to fight against disease such as cancer or that boosts immune system in a general way. Examples of immunotherapy include, without limitation, checkpoint modulators, adoptive cell transfer, cytokines, oncolytic virus and therapeutic vaccines.

"Targeted therapy" is a type of therapy that acts on specific molecules associated with cancer, such as specific proteins that are present in cancer cells but not normal cells or that are more abundant in cancer cells, or the target molecules in the cancer microenvironment that contributes to cancer growth and survival. Targeted therapy targets a therapeutic agent to a tumor, thereby sparing of normal tissue from the effects of the therapeutic agent.

In certain of these embodiments, an antibody or antigen-binding fragment thereof provided herein that is administered in combination with one or more additional therapeutic agents may be administered simultaneously with the one or more additional therapeutic agents, and in certain of these embodiments the antibody or antigen-binding fragment thereof and the additional therapeutic agent(s) may be administered as part of the same pharmaceutical composition. However, an antibody or antigen-binding fragment thereof administered "in combination" with another therapeutic agent does not have to be administered simultaneously with or in the same composition as the agent. An antibody or antigen-binding fragment thereof administered prior to or after another agent is considered to be administered "in combination" with that agent as the phrase is used herein, even if the antibody or antigen-binding fragment and the second agent are administered via different routes. Where possible, additional therapeutic agents administered in combination with the antibodies or antigen-binding fragments thereof disclosed herein are administered according to the schedule listed in the product information sheet of the additional therapeutic agent, or according to the Physicians' Desk Reference 2003 (Physicians' Desk Reference, 57th Ed; Medical Economics Company; ISBN: 1563634457; 57th edition (November 2002)) or protocols well known in the art.

The present disclosure further provides methods of modulating CD39 activity in CD39-positive cells, comprising exposing the CD39-positive cells to the antibodies or antigen-binding fragments thereof provided herein. In some embodiments, the CD39-positive cell is an immune cell.

In another aspect, the present disclosure provides methods of detecting the presence or amount of CD39 in a sample, comprising contacting the sample with the antibody or antigen-binding fragment thereof provided herein and/or the pharmaceutical composition provided herein, and determining the presence or the amount of CD39 in the sample.

In another aspect, the present disclosure provides a method of diagnosing a CD39 related disease, disorder or condition in a subject, comprising: a) contacting a sample obtained from the subject with the antibody or an antigen-binding fragment thereof provided herein and/or the pharmaceutical composition provided herein; b) determining the presence or amount of CD39 in the sample; and c) correlating the presence or the amount of CD39 to existence or status of the CD39 related disease, disorder or condition in the subject.

In another aspect, the present disclosure provides kits comprising the antibody or antigen-binding fragment thereof provided herein and/or the pharmaceutical composition provided herein, optionally conjugated with a detectable moiety, which is useful in detecting a CD39 related disease, disorder or condition. The kits may further comprise instructions for use.

In another aspect, the present disclosure also provides use of the antibody or antigen-binding fragment thereof provided herein and/or the pharmaceutical composition provided herein in the manufacture of a medicament for treating, preventing or alleviating a CD39 related disease, disorder or condition in a subject, in the manufacture of a diagnostic reagent for diagnosing a CD39 related disease, disorder or condition.

In another aspect, the present disclosure provides a method of treating, preventing or alleviating a disease treatable by reducing the ATPase activity of CD39 in a subject, comprising administering to the subject a therapeutically effective amount of the antibody or an antigen-binding fragment thereof provided herein and/or the pharmaceutical composition provided herein. For example, the antibody or an antigen-binding fragment thereof provided herein may be administered to reduce the ATPase activity of cancer cells, tumor infiltrating immune cells, immune suppression cells that express CD39. In some embodiments, the subject is human. In some embodiments, the subject has a disease, disorder or condition selected from the group consisting of cancer, an autoimmune disease, and an infection.

In another aspect, the present disclosure provides a method of treating, preventing or alleviating a disease associated with adenosine-mediated inhibition of T cell, Monocyte, Macrophage, DC, APC, NK and/or B cell activity in a subject, comprising administering to the subject a therapeutically effective amount of the antibody or an antigen-binding fragment thereof provided herein and/or the pharmaceutical composition provided herein.

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. A person skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1. Materials Generation 1.1. Reference Antibody Generation

Anti-CD39 reference antibodies were generated based on the published sequences. Antibody 9-8B was disclosed in patent application WO 2016/073845A1, and its heavy and light chain variable region sequences are included herein as SEQ ID NOs: 46 and 48, respectively. Antibody T895 was disclosed as antibody 31895 in patent application WO 2019/027935A1, and its heavy and light chain variable region sequences are included herein as SEQ ID NOs: 55 and 57, respectively. Antibody I394 was disclosed in the patent application WO 2018/167267A1, and its heavy and light chain variable region sequences are included herein as SEQ ID NOs: 113 and 114, respectively. The heavy chain and light chain variable regions of Antibodies 9-8B, T895, and I394 are shown in Table 10 below. The DNA sequences encoding the reference antibodies were cloned and expressed in Expi293 cells (Invitrogen). The cell culture medium was collected and centrifuged to remove cell pellets. The harvested supernatant was purified using Protein A affinity chromatography column (Mabselect Sure, GE Healthcare) to obtain the reference antibody preparations.

isolated by limiting dilution. The cells were subsequently screened by FACS using anti-human CD39 antibody (BD, Cat #555464), anti-cyno CD39 (9-8B), anti-mouse CD39 (Biolegend, Cat #143810).

In a similar way, CHOK1 cells (Invitrogen) transfected with human CD39, cyno CD39 or mouse CD39 expression plasmid were cultured in a selective medium. Single cell clones stably expressing human CD39, cyno CD39 or mouse CD39 were isolated by limiting dilution, and subsequently screened by FACS using the anti-human CD39 antibody, the anti-cyno CD39 antibody or the anti-mouse CD39 antibody.

The stable cell lines were designated as HEK293-hCD39, HEK293-cynoCD39, HEK293-mCD39, CHOK1-hCD39, CHOK1-cynoCD39, and CHOK1-mCD39, respectively, all of which showed high expression and ATPase activity.

1.3. Recombinant Proteins Generation

The DNA sequence encoding extracellular domain (ECD) of human CD39 was cloned into the expression vector, and was transfected into HEK293 cells to allow expression of the recombinant ECD protein.

Example 2. Antibody Generation 2.1 Immunization and Hybridoma Generation and Screening To generate antibodies to CD39, Balb/c and SJL/J mice (SLAC) were immunized with recombinantly expressed human CD39 antigen or its fragments, or DNA encoding full length human CD39 and/or cells expressing human CD39. The immune response was monitored over the course of the immunization protocol with plasma and serum samples were obtained by tail vein or retroorbital bleeds. Mice with

TABLE 10

Variable region amino acid sequences of 3 reference antibodies.

| Antibody | VH | VL |
|---|---|---|
| 9-8B | SEQ ID NO: 46<br>QIQLVQSGPELKKPGETVKISC<br>KASGYTFTHYGMNWVKQAPG<br>KGLKWMGW1NTYTGELTYAD<br>DFKGRFAFSLETSASTAYLQIN<br>NLKNEDTATYFCARRAYYRYD<br>YVMDYWGQGTSVTVSS | SEQ ID NO: 48<br>DIVMTQSQKFMSTSVGDRVSV<br>TCKASHNVGTNVAWYQQKPG<br>QSPKALIYSASYRYSGVPGRFT<br>GSGSGTDFTLTISNVQSEDLAE<br>YFCHQYNNYPYTFGGGTKLEI<br>K |
| T895 | SEQ ID NO: 55<br>EVQLQQSGPELVKPGASVKMS<br>CKASGYTFTDYNMHWVKQSH<br>GRTLEWIGYIVPLNGGSTFNQK<br>FKGRATLTVNTSSRTAYMELRS<br>LTSEDSAAYYCARGGTRFAYW<br>GQGTLVTVSA | SEQ ID NO: 57<br>DIVLTQSPASLAVSLGQRATIS<br>CRASESVDNFGVSFMYWFQQ<br>KPGQPPNLLIYGASNQGSGVP<br>ARFRGSGSGTDFSLNIHPMEA<br>DDTAMYFCQQTKEVPYTFGG<br>GTKLEIK |
| I394 | SEQ ID NO: 113<br>QVQLVQSGAEVKKPGASVKVS<br>CKASGYTFKSYEMHWVRQAP<br>GQGLEWMGRINPSVGSTWYA<br>QKFQGRVTMTRDTSTSTVYME<br>LSSLRSEDTAVYYCARGKREG<br>GTEYLRKWGQGTLVTVSS | SEQ ID NO: 114<br>EIVLTQSPGTLSLSPGERATLSC<br>RASQSVASSYLAWYQQKPGQ<br>APRLLIYGASNRHTGIPDRFSG<br>SGSGTDFTLTISRLEPEDFAVY<br>YCQQYHNAITFGGGTKVEIK |

1.2. Generation of Human, Cynomolgus Monkey, and Mouse CD39 Stable Expression Cell Lines The DNA sequences encoding full length human CD39 (NP_001767.3), cyno CD39 (XP_015311944.1) and mouse CD39 (NP_033978.1) respectively were cloned into an expression vector, followed by transfection and expression in HEK293 cells. The transfected cells expressing human CD39, cyno CD39 and mouse CD39 respectively were cultured in a selective medium. Single cell clones stably expressing human CD39, cyno CD39 or mouse CD39 were sufficient titers of anti-CD39 antibodies were used for fusions. Splenocytes and/or lymph node cells from immunized mice were isolated and fused to mouse myeloma cell line (SP2/0). The resulting hybridomas were screened for the production of CD39-specific antibodies, by ELISA assay with human CD39 ECD recombinant protein, or by Acumen assay (TTP Labtech) with CHOK1-hCD39 cells stably expressing human CD39. Hybridoma clones specific to hCD39 were confirmed by FACS and enzyme activity blocking assay, and were subcloned to get stable hybridoma clones. After 1-2 rounds of subcloning, hybridoma monoclones were expanded for antibody production and frozen as stock.

The antibody secreting hybridomas were subcloned by limiting dilution. The stable subclones were cultured in vitro to generate antibody in tissue culture medium for characterization. After 1-2 rounds of subcloning, hybridoma monoclones were expanded for antibody production.

After about 14 days of culturing, the hybridoma cell culture medium were collected and purified by Protein A affinity chromatography column (GE). The hybridoma antibody clones were designated as mAb13, mAb14, mAb19, mAb21, mAb23, mAb34 and mAb35, respectively.

Example 3. Antibody Characterization 3.1. Antibodies

The hybridoma antibody clones mAb13, mAb14, mAb19, mAb21, mAb23, mAb34 and mAb35 were characterized in a series of binding and functional assays as described below.

3.2. Binding Affinity to Human CD39, Cynomolgus CD39 and Mouse CD39

FACS were used to determine binding of the antibodies to cell lines expressing CD39 naturally (SK-MEL-28) or recombinantly (CHOK1-hCD39, CHOK1-cynoCD39, and CHOK1-mCD39), or with cells lacking CD39 expression (CHOK1-blank) as a negative control.

CHOK1-hCD39, CHOK1-cCD39, CHOK1-mCD39 and CHOK1-blank cells were maintained in culture medium according to ATCC procedure. Cells were collected and re-suspended in blocking buffer at a density of $3\times10^6$ cells/ml. Cells were transferred to 96 well FACS plates at 100 μl/well ($3\times10^5$ cells/well), the plates were centrifuged and washed twice with FACS buffer (PBS, 1% FBS, 0.05% Tween-20). 4-folds serial dilution of anti-CD39 antibodies were prepared in FACS buffer starting from 30 μg/ml. Reference antibody 9-8B and mouse/human control IgG were used as positive and negative controls, respectively. Cells were re-suspended in 100 μL/well diluted antibodies, and the plates were incubated at 4° C. for 60 min. The plates were washed with FACS buffer, Alexa Fluor® 488-labeled secondary antibody (1:1000 in FACS buffer) were added to each well and incubated at 4° C. for 30 min. The plates were washed with FACS buffer, and cells were re-suspended in 100 μL/well of PBS. Cells were then analyzed with FACS-Verse™ and mean fluorescence intensity were determined. Full binding curves were generated on the CD39 expressing cells by testing a range of antibody concentrations. Apparent affinity was determined for each antibody using Prism software.

Similarly, human CD39 expressing cells SK-MEL-5, SK-MEL-28 or MOLP-8, were incubated with a gradient concentration of anti-CD39 antibodies for 30 minutes at 4° C. Cells were washed 3 times using FACS buffer and next incubated with fluorescence labelled secondary antibody (goat-anti-mouse IgG or goat anti-human IgG) for 30 minutes at 4° C. Cells were washed 3 times and then re-suspended in FACS buffer and analyzed by flow cytometry analysis on BD Celesta. Data plotted and analyzed using GraphPad Prism 8.02.

The binding affinity of the 7 purified hybridoma antibodies is summarized in Table 11, in comparison with known anti-CD39 antibody 9-8B. All the hybridoma antibodies bound to human and cynomolgus CD39 in a dose-dependent manner, however none recognized mouse CD39 in the FACS study.

TABLE 11

Anti-CD39 hybridoma antibodies characterization summary.

| ES-Number | Binding affinity $EC_{50}$ (M) | | | SK-MEL-28 cell based ATPase inhibition % | | T Cell Proliferation Suppression Assay | | Octet Binding Affinity | | |
|---|---|---|---|---|---|---|---|---|---|---|
| | human | cynomolgus | mouse | SK-MEL-28 | 10 nM | $EC_{50}$ | 100 nM | $EC_{50}$ | KD | K-off | epitope |
| mAb13 | 3.0E−08 | 2.1E−08 | − | 1.1E−08 | 43% | 3.5E−10 | n.d. | n.d. | n.d. | n.d. | n.d. |
| mAb14 | 2.5E−09 | 3.4E−09 | − | 2.8E−08 | 57% | 4.5E−09 | ++ | n.d. | 2.4E−10 | 2.2E−04 | IV |
| mAb19 | 4.5E−09 | 5.8E−09 | − | 4.6E−08 | 65% | 4.0E−09 | ++ | n.d. | 2.6E−10 | 1.5E−04 | I |
| mAb21 | 6.7E−09 | 1.1E−08 | − | 9.0E−08 | 70% | 1.5E−09 | ++ | 1.4E−10 | 4.4E−10 | 2.2E−04 | I |
| mAb23 | 1.7E−09 | 2.3E−09 | − | 1.6E−09 | 75% | 6.0E−11 | ++ | ~1.0E−10 | 8.2E−10 | 3.6E−04 | II |
| mAb34 | 4.4E−09 | 3.1E−09 | − | 4.7E−09 | 72% | 1.3E−10 | n.d. | n.d. | n.d. | n.d. | n.d. |
| mAb35 | 5.2E−09 | 5.3E−09 | − | 1.8E−09 | 56% | 1.6E−09 | n.d. | n.d. | n.d. | n.d. | n.d. |
| 9-8B | 1.7E−09 | 1.6E−09 | − | 8.0E−10 | 21% | 5.0E−11 | n.d. | n.d. | n.d. | n.d. | III |

−: negative
++: p < 0.01
n.d.: not determined yet 3.3. ATPase Inhibition Detection CD39 expressing cells, SK-MEL-5 and MOLP-8 were washed with PBS buffer and incubated with a gradient of antibodies for 30 minutes at 37° C. 50 mM ATP was added to each well and incubated with cells for 16 hours. The supernatants were collected and the orthophosphate product from ATP degradation was measured by a Malachite Green Phosphate Detection Kit (R&D systems, Catalog #DY996) according to manufacturer's manual. Isotype and/or 9-8B was used as control. Data plotted and analyzed using GraphPad Prism 8.02. $EC_{50}$ is the concentration of the indicated antibody to reach 50% of the signal in this assay.

As summarized in Table 11, all 7 purified hybridoma antibodies had good ATPase inhibition activity compared with reference antibody 9-8B.

3.4. ATP-Mediated T Cell Proliferation Suppression Assay

Human T cells labeled with CSFE and stimulated with anti-CD3 and anti-CD28 were incubated with anti-CD39 antibodies or isotype control in the presence of ATP. Proliferation of T cells was analyzed in FACS by CSFE dilution. mIgG2a was used as an isotype control.

Figure 1:
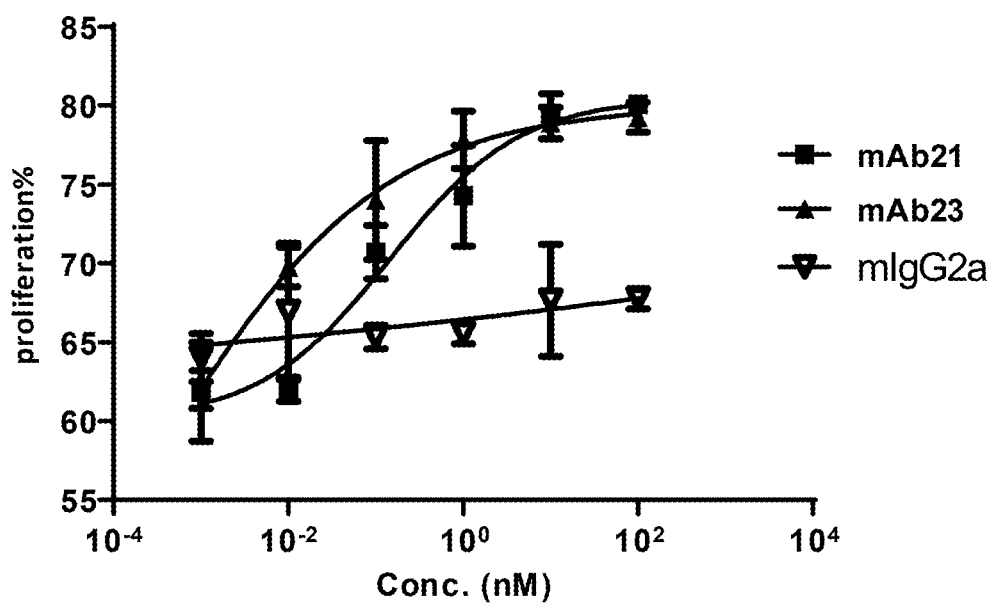
FIG. 1 shows ATP-mediated enhanced T cell proliferation by anti-CD39 monoclonal antibodies mAb21 and mAb23.

The T cell proliferation activity of selected anti-CD39 antibodies mAb21 and mAb23 were shown in FIG. 1 and summarized in Table 11. $EC_{50}$ is the concentration of the indicated antibody to reach 50% of the signal in this assay. Both antibodies enhanced the T cell proliferation in a dose-dependent manner, that is, both antibodies blocked the ATP-mediated inhibition on T cell proliferation.

3.5. Epitope Binning

Anti-CD39 antibodies were labeled using Alex488 labeling kit and were diluted in a series of concentrations, before mixing with CHOK1-hCD39 cells to test binding $EC_{50}$ using FACS. The non-labeled antibodies were tested for their blocking efficacy to the labelled ones. Briefly, mononuclear CHOK1-hCD39 cells were prepared to $2\times10^6$/ml and plated into 96 well at 50 µl/well, then mixed with antibodies gradients to final volume at 100 µl, and then equal volume of Alex488 label antibodies were added at two folds $EC_{50}$ concentration. 96 well plates were incubated at 4° C. for 1 hour, and spun down and washed 3 times with 200 µl FACS buffer. The FACS analysis was performed on FACScelesta machine and data was analyzed by Flowjo software. The blocking percentages were calculated and those having above 80% competition rate were allocated into one epitope group, compared with the non-competing well (Alex488 labeled antibody only).

The competition results are shown in Table 12. Based on the competition results, the 4 anti-CD39 hybridoma antibodies (mAb14, mAb19, mAb21, mAb23) can be grouped into 4 different epitope groups, as shown in Table 11. Specifically, anti-CD39 antibodies mAb19 and mAb21 compete for highly similar epitopes, and are grouped into epitope group I, as shown in Table 11. mAb14 did not compete with any other antibody as tested, and was grouped into epitope group IV, as shown in Table 11. mAb23 showed cross-competition with mAb19 and mAb21, and was grouped into epitope group II in Table 11.

TABLE 12

Anti-CD39 hybridoma antibodies epitope binning summary.

| | mAb19-Alexa488 | mAb21-Alexa488 | mAb23-Alexa488 | 9-8B-Alexa488 | mAb14-Alexa488 |
|---|---|---|---|---|---|
| mAb19 | 96% | 83% | 91% | 6% | 23% |
| mAb21 | 98% | 90% | 97% | 20% | 24% |
| mAb23 | 98% | 93% | 100% | 98% | 86% |
| 9-8B | 19% | 16% | 100% | 98% | 55% |
| mAb14 | 6% | 10% | −26% | −11% | 98% |

3.6. Hybridoma Sequencing

RNAs were isolated from monoclonal hybridoma cells and reverse transcribed into cDNA using a commercial kit. Then the cDNA was used as templates to amplify heavy chain and light chain variable regions with the primers of Mouse Ig-Primer Set (Novagen). PCR products with correct size were collected and purified followed by ligation with a suitable plasmid vector. The ligation products were transformed into DH5a competent cells. Clones were selected and the inserted fragments were analyzed by DNA sequencing.

The variable region sequences of the hybridoma antibodies are provided herein in Table 2.

Example 4. Chimeric Antibody Generation and Characterization 4.1. Chimeric Antibody Generation and Production DNA encoding variable regions of 4 selected hybridoma antibodies (mAb14, mAb19, mAb21 and mAb23) was synthesized and subcloned into an expression vector where human IgG constant gene was included in advance. The vectors were transfected into mammalian cells for recombinant protein expression and the expressed antibody was purified using protein A affinity chromatography column. The resulting chimeric antibodies are referred to herein as c14, c19, c21 and c23, where the prefix "c" indicates "chimeric", and the number indicates the hybridoma antibody clone, for example number "14" indicates that it is from the hybridoma antibody mAb14.

4.2. Chimeric Antibody Characterization

Figure 2:
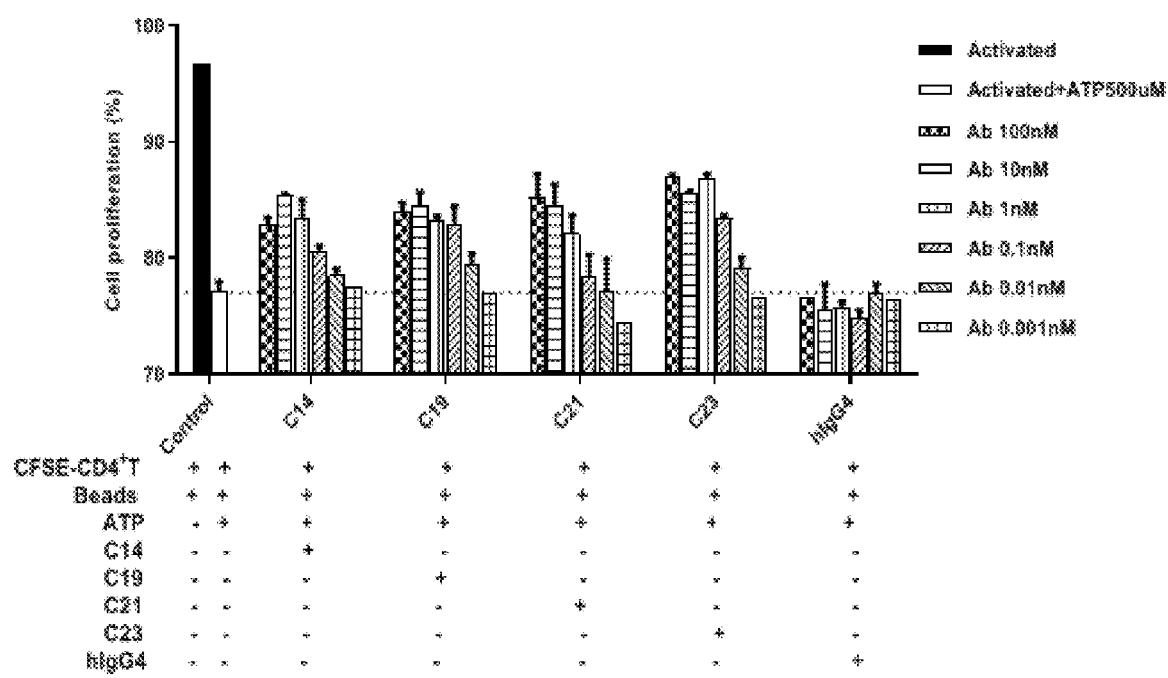
FIG. 2 shows blockade of ATP-mediated suppression of T cell proliferation by anti-CD39 chimeric antibodies c14, c19, c21 and c23. hIgG4 refers the human IgG4 isotype control antibody.

The purified 4 chimeric antibodies were tested for activity to block ATP-mediated suppression on T cell proliferation (similar as the methods described in Example 3.4). As shown in FIG. 2, anti-CD39 chimeric antibodies c14, c19, c21 and c23 blocked suppression on $CD4^+$ T cell proliferation in a dose-dependent manner (at a concentration ranging from 100 nM, 10 nM, 1 nM, 0.1 nM, 0.01 nM, and 0.001 nM). CFSE-$CD4^+$ T and hIgG4 were used as positive and negative controls respectively for ATP-mediated T cell proliferation.

The purified 4 chimeric antibodies were further tested for the ability to enhance ATP induced dendritic cell (DC) activation and maturation in the presence of ATP. ATP induces DC maturation through stimulation of the P2Y11 receptor on monocyte-derived dendritic cells.

Briefly, human monocytes were isolated from human healthy blood and differentiated into MoDC in presence of GM-CSF and IL-4 for 6 days. Then the differentiated MoDCs were treated with the 4 anti-CD39 chimeric antibodies with different doses and in presence of ATP for additional 24 h. DC maturation were then evaluated by analyzing CD86, CD83 and HLA-DR expression by FACS assay.

Figure 3:
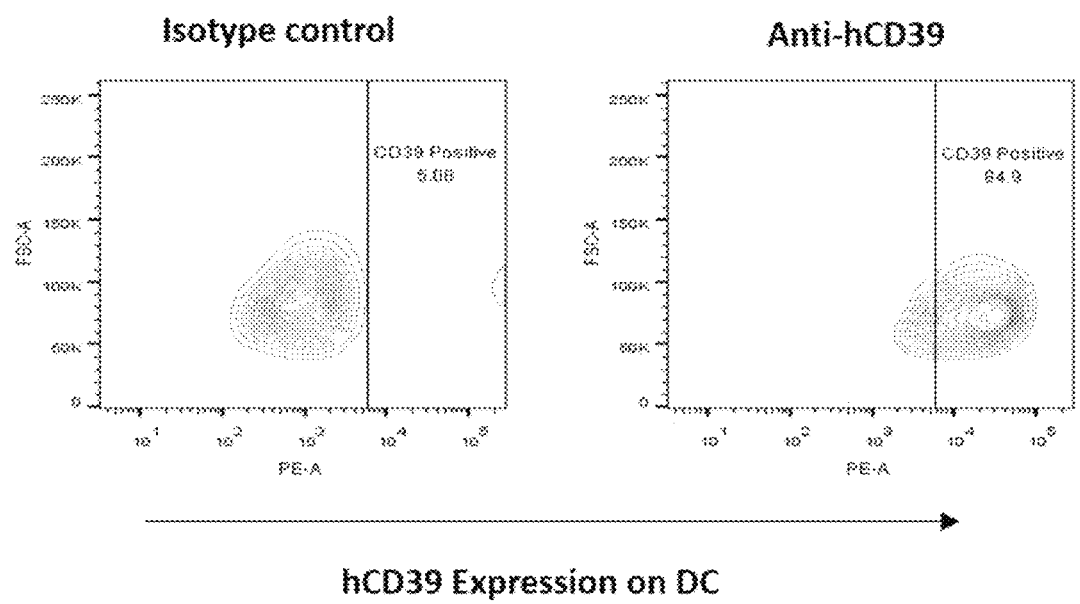
FIG. 3 shows the CD39 expression level on dendritic cells (DC).
Figure 4:
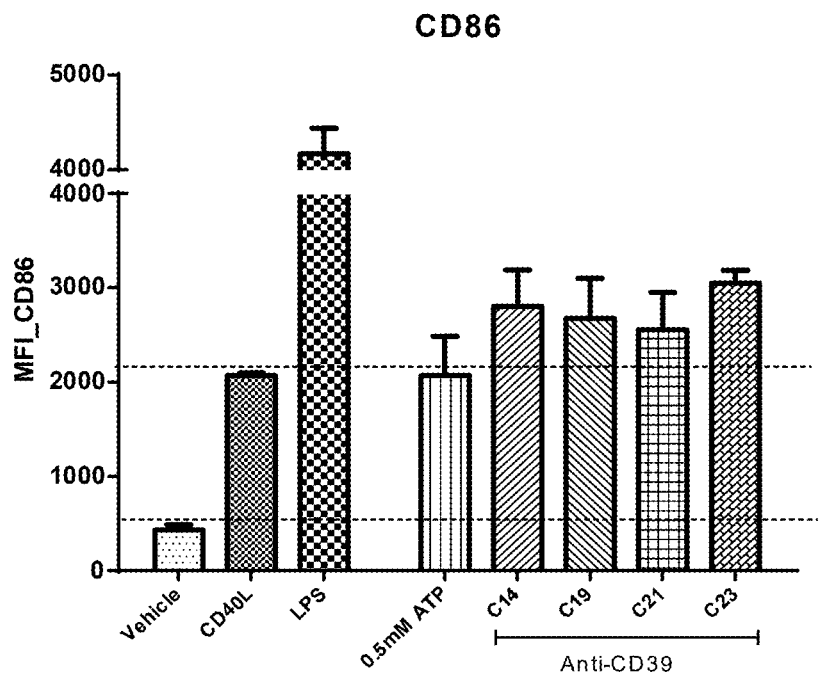
FIGS. 4A to 4C show ATP-mediated DC activation by anti-CD39 chimeric antibodies c14, c19, c21 and c23, as measured by CD86 (FIG. 4A), CD83 (FIG. 4B) and HLA-DR (FIG. 4C) expression using FACS.
Figure 4:
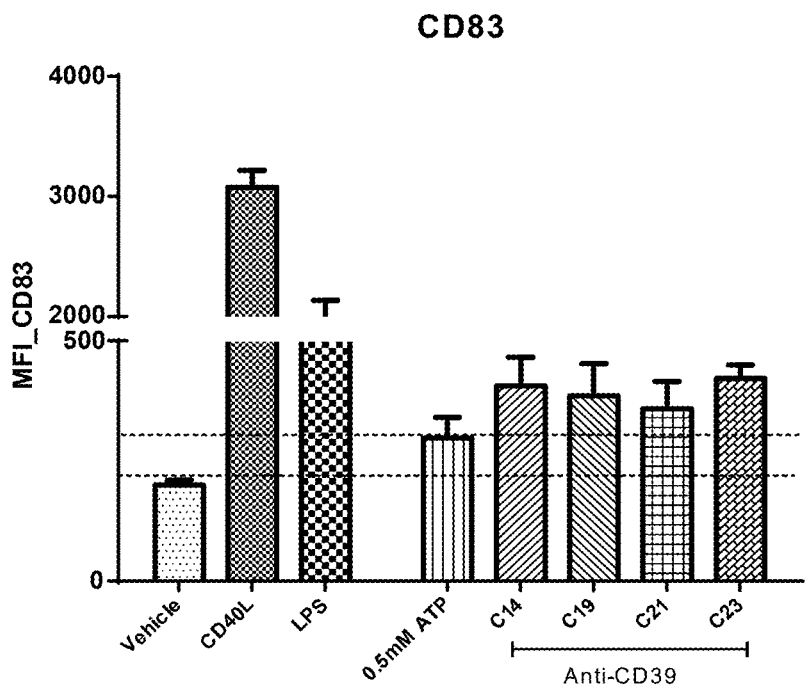
Figure 4:
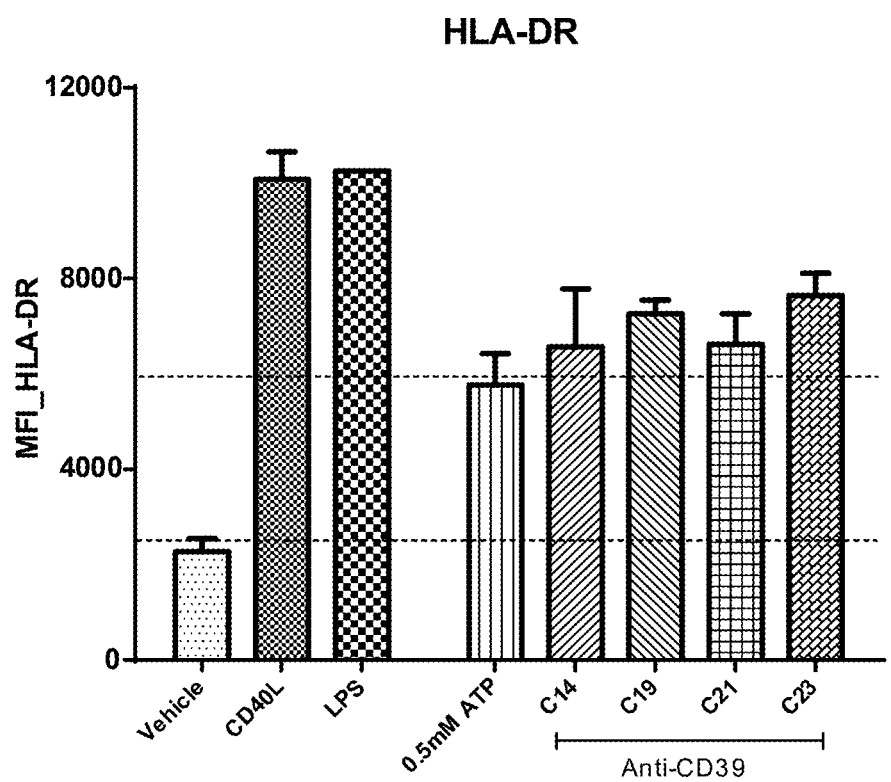

FIG. 3 showed the level of CD39 on DC surface by FACS. FIGS. 4A to 4C showed the CD86 (FIG. 4A), CD83 (FIG. 4B) and HLA-DR (FIG. 4C) expression, respectively, after the antibody treatment. The ATP induced DC maturation was shown by an increased expression of CD86, CD83, and HLA-DR, as compared with vehicle treatment. All 4 anti-CD39 antibodies c14, c19, c21 and c23 showed significant effect on enhancing ATP induced DC maturation.

The chimeric antibodies were also tested in vivo for anti-tumor activity. NOD-SCID mice were subcutaneously inoculated in the right rear flank region with tumor cells ($10\times10^6$) in 0.1 ml of PBS mixed with matrigel (1:1) for tumor development. The mice were randomized into groups when the mean tumor size reaches approximately 80 $mm^3$. The treatment was initiated on the same day of randomization at 30 mg/kg, twice dosing every week. Tumor volumes were measured twice per week after randomization in two dimensions using a caliper, and the volume was expressed in $mm^3$ using the formula: $V=(L\times W\times W)/2$, where V is tumor volume, L is tumor length (the longest tumor dimension) and W is tumor width (the longest tumor dimension perpendicular to L). Dosing as well as tumor and body weight measurements were conducted in a Laminar Flow Cabinet. Data were analyzed using two-way ANOVA by Graphpad prism.

Figure 5:
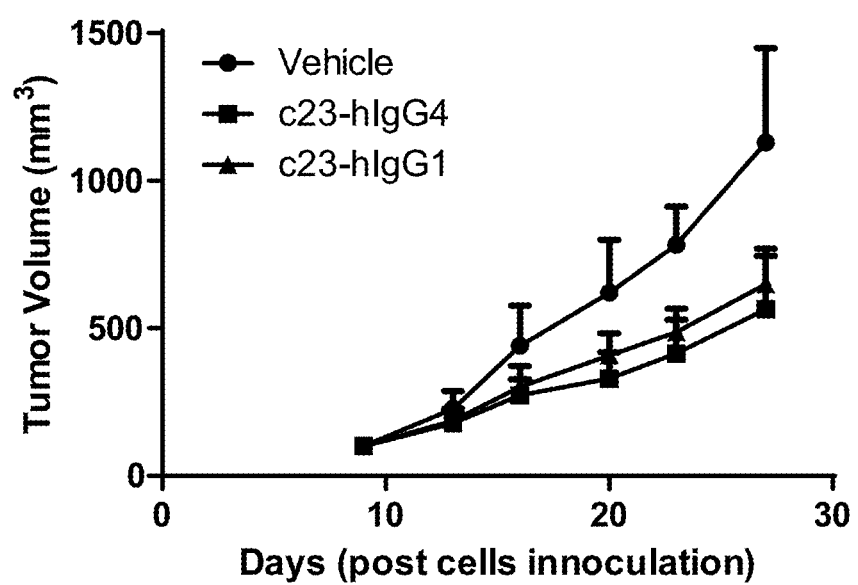
FIG. 5 shows tumor growth after treatment with anti-CD39 chimeric antibodies c23-hIgG4 and c23-hIgG1 in mice inoculated with MOLP-8 cells (human multiple myeloma cell line).

The tumor growth results of the chimeric anti-CD39 antibody c23 were shown in FIG. 5. Both the human IgG1 isotype and IgG4 isotype of c23 were obtained and tested.

Both c23-hIgG4 and c23-hIgG1 chimeric antibodies demonstrated anti-tumor efficacy compared with vehicle group, and there were no significant difference identified between c23-hIgG4 and c23-hIgG1.

Example 5. Antibody Humanization and Affinity Maturation 5.1. Humanization

Chimeric antibodies c23 and c14 were selected as the clones for humanization. Antibody sequences were aligned with human germline sequences to identify best fit model. Best matched human germline sequences were selected as the templates for humanization based on homology to the original mouse antibody sequences. The CDRs from the mouse antibody sequences were then grafted onto the templates, together with the residues to maintain the upper and central core structures of the antibodies. The optimized mutations were introduced to the framework regions to generate variants of humanized heavy chain variable regions and variants of humanized light chain variable regions, which were mixed and matched to provide multiple humanized antibody clones. After grafting and mutation, the humanized antibodies retained similar binding affinity on human CD39 expressing cells. The humanized antibodies were further evaluated by CD39 ATPase inhibition assay and in vitro immune cell activation assay. In vivo study were also conducted for some of the humanized antibodies.

A total of 31 humanized antibody clones were obtained for c23, mixing and matching 7 variants of humanized c23 heavy chain variable regions (i.e. hu23.VH_1, hu23.VH_2, hu23.VH_3, hu23.VH_4, hu23.VH_5, hu23.VH_6, and hu23.VH_7) and 7 variants of humanized c23 light chain variable regions (i.e. hu23.VL_1, hu23.VL_2, hu23.VL_3, hu23.VL_4, hu23.VL_5, hu23.VL_6, and hu23.VL_7). The 31 humanized antibody clones were designated as hu23.H1L1, hu23.H1L2, and so on, as shown in Table 9 above and Tables 13, 14 and 15 below, where the prefix "hu" indicates "humanized", and the suffix "H1L1", for example, denotes the serial number of the c23 humanized antibody clone, having the hu23.VH_1 variant and the hu23.VL_1 variant variable region.

TABLE 13

Heavy and light chain variable regions of humanized antibodies for c23.

| | hu23.VL_1 (SEQ ID NO: 61) | hu23.VL_2 (SEQ ID NO: 63) | hu23.VL_3 (SEQ ID NO: 65) | hu23.VL_4 (SEQ ID NO: 67) |
|---|---|---|---|---|
| hu23.VH_1 (SEQ ID NO: 60) | hu23.H1L1 (SEQ ID NOs: 60/61) | hu23.H1L2 (SEQ ID NOs: 60/63) | hu23.H1L3 (SEQ ID NOs: 60/65) | hu23.H1L4 (SEQ ID NOs: 60/67) |
| hu23.VH_2 (SEQ ID NO: 62) | hu23.H2L1 (SEQ ID NOs: 62/61) | hu23.H2L2 (SEQ ID NOs: 62/63) | hu23.H2L3 (SEQ ID NOs: 62/65) | hu23.H2L4 (SEQ ID NOs: 62/67) |
| hu23.VH_3 (SEQ ID NO: 64) | hu23.H3L1 (SEQ ID NOs: 64/61) | hu23.H3L2 (SEQ ID NOs: 64/63) | hu23.H3L3 (SEQ ID NOs: 64/65) | hu23.H3L4 (SEQ ID NOs: 64/67) |
| hu23.VH_4 (SEQ ID NO: 66) | hu23.H4L1 (SEQ ID NOs: 66/61) | hu23.H4L2 (SEQ ID NOs: 66/63) | hu23.H4L3 (SEQ ID NOs: 66/65) | hu23.H4L4 (SEQ ID NOs: 66/67) |

TABLE 14

Heavy and light chain variable regions of humanized antibodies for c23.

| | hu23.VL_1 (SEQ ID NO: 61) | hu23.VL_5 (SEQ ID NO: 143) | hu23.VL_6 (SEQ ID NO: 144) | hu23.VL_7 (SEQ ID NO: 145) |
|---|---|---|---|---|
| hu23.VH_1 (SEQ ID NO: 60) | hu23.H1L1 (SEQ ID NOs: 60/61) | hu23.H1L5 (SEQ ID NOs: 60/143) | hu23.H1L6 (SEQ ID NOs: 60/144) | hu23.H1L7 (SEQ ID NOs: 60/145) |
| hu23.VH_5 (SEQ ID NO: 140) | hu23.H5L1 (SEQ ID NOs: 140/61) | hu23.H5L5 (SEQ ID NOs: 140/143) | hu23.H5L6 (SEQ ID NOs: 140/144) | hu23.H5L7 (SEQ ID NOs: 140/145) |
| hu23.VH_6 (SEQ ID NO: 141) | hu23.H6L1 (SEQ ID NOs: 141/61) | hu23.H6L5 (SEQ ID NOs: 141/143) | hu23.H6L6 (SEQ ID NOs: 141/144) | hu23.H6L7 (SEQ ID NOs: 141/145) |
| hu23.VH_7 (SEQ ID NO: 142) | hu23.H7L1 (SEQ ID NOs: 142/61) | hu23.H7L5 (SEQ ID NOs: 142/143) | hu23.H7L6 (SEQ ID NOs: 142/144) | hu23.H7L7 (SEQ ID NOs: 142/145) |

TABLE 15

Heavy and light chain variable regions of humanized antibodies for c23.

| | hu23.VL_201 (SEQ ID NO: 111) | hu23.VL_203 (SEQ ID NO: 112) | hu23.VL_211 (SEQ ID NO: 63) |
|---|---|---|---|
| hu23.VH_201 (SEQ ID NO: 146) | hu23.201 (SEQ ID NOs: 146/111) | hu23.203 (SEQ ID NOs: 146/112) | — |
| hu23.VH_207 (SEQ ID NO: 147) | hu23.207 (SEQ ID NOs: 147/111) | — | — |
| hu23.VH_211 (SEQ ID NO: 39) | — | — | hu23.211 (SEQ ID NOs: 39/63) |

Similarly, a total of 16 humanized antibodies were obtained for c14, mixing and matching 4 variants of humanized c14 heavy chain variable regions (i.e. hu14.VH_1, hu14.VH_2, hu14 VH_3 and hu14.VH_4) and 4 variants of humanized c14 light chain variable regions (i.e. hu14.VL_1, hu14.VL_2, hu14.VL_3 and hu14.VL_4). The 16 humanized antibody clones were designated as hu14.H1L1, hu14.H1L2, and so on, as shown in below Table 16, by the same token.

TABLE 16

Heavy and light chain variable regions of 16 humanized antibodies for c14

|  | hu14.VL_1 (SEQ ID NO: 69) | hu14.VL_2 (SEQ ID NO: 71) | hu14.VL_3 (SEQ ID NO: 73) | hu14.VL_4 (SEQ ID NO: 75) |
|---|---|---|---|---|
| hu14.VH_1 (SEQ ID NO: 68) | hu14.H1L1 (SEQ ID NOs: 68/69) | hu14.H1L2 (SEQ ID NOs: 68/71) | hu14.H1L3 (SEQ ID NOs: 68/73) | hu14.H1L4 (SEQ ID NOs: 68/75) |
| hu14.VH_2 (SEQ ID NO: 70) | hu14.H2L1 (SEQ ID NOs: 70/69) | hu14.H2L2 (SEQ ID NOs: 70/71) | hu14.H2L3 (SEQ ID NOs: 70/73) | hu14.H2L4 (SEQ ID NOs: 70/75) |
| hu14.VH_3 (SEQ ID NO: 72) | hu14.H3L1 (SEQ ID NOs: 72/69) | hu14.H3L2 (SEQ ID NOs: 72/71) | hu14.H3L3 (SEQ ID NOs: 72/73) | hu14.H3L4 (SEQ ID NOs: 72/75) |
| hu14.VH_4 (SEQ ID NO: 74) | hu14.H4L1 (SEQ ID NOs: 74/69) | hu14.H4L2 (SEQ ID NOs: 74/71) | hu14.H4L3 (SEQ ID NOs: 74/73) | hu14.H4L4 (SEQ ID NOs: 74/75) |

Several humanized antibodies clones for c23 were also obtained by yeast display. Briefly, mouse heavy and light chain sequences were aligned with in-house database of human antibody sequences. The templates with highest homology, IGHV1-3*01 and IGKV3-11*01, were selected for heavy and light chain CDR grafting, respectively. Back mutations were identified by a high-throughput method using yeast display. Specifically, positions that contributes to CDR conformations (Vernier zone residues) were identified and a library of back mutations was created by incorporating both template and mouse residues in each position during DNA synthesis. Final candidates were identified by sequencing of top binders to human CD39 protein. Humanized antibodies for c23 obtained via yeast display are designated as hu23.201 (having a VH/VL of SEQ ID NOs:146/111), hu23.203 (having a VH/VL of SEQ ID NOs:146/112), hu23.207 (having a VH/VL of SEQ ID NOs:147/111), and hu23.211 (having a VH/VL of SEQ ID NOs:39/63).

The humanized antibodies in Tables 13, 14, 15 and 16 were recombinantly produced followed by testing for binding affinity, and were shown to be able to retain specific binding human CD39. Those having relatively higher affinity were further evaluated in functional assays including CD39 blocking assay and in vitro immune cell activation assay.

In particular, humanized antibodies hu23.H5L5, hu23.201, hu14.H1L1 and reference antibodies I394 and T895 were characterized for binding affinity against human CD39 using Biacore (GE). Briefly the antibodies to be tested were captured to CM5 chip (GE) using Human Antibody Capture Kit (GE). The antigen of 6xHis tagged human CD39 was serially diluted for multiple doses and injected at 30 µl/min for 180 s. Buffer flow was maintained for dissociation of 400 s. 3 M MgCl₂ was used for chip regeneration. The association and dissociation curves were fit with 1:1 binding model, and the Ka/Kd/$K_D$ values for each antibody were calculated. The affinity data of the tested antibodies are summarized in Table 17 below.

TABLE 17

Binding affinity of antibodies to human CD39 as measured by Biacore assay.

| Antibody | ka (1/Ms) | kd (1/s) | $K_D$ (M) |
|---|---|---|---|
| hu23.H5L5 | 8.22E+04 | 1.60E−03 | 1.95E−08 |
| hu23.201 | 6.75E+04 | 1.62E−03 | 2.40E−08 |

TABLE 17-continued

Binding affinity of antibodies to human CD39 as measured by Biacore assay.

| Antibody | ka (1/Ms) | kd (1/s) | $K_D$ (M) |
|---|---|---|---|
| hu14.H1L1 | 9.03E+05 | 4.55E−03 | 5.03E−09 |
| I394 | 2.03E+05 | 1.26E−03 | 6.21E−09 |
| T895 | 1.33E+05 | 1.39E−01 | 1.04E−06 |

In addition, humanized antibodies hu23.H5L5 and hu14.H1L2, as well as reference antibodies I394, T895, and 9-8B were characterized for binding affinity against human CD39 using Octet assay (Creative Biolabs) according to manufacturer's manual. Briefly, the antibodies were coupled on sensors and then the sensors were dipped into CD39 gradients (start at 200 nM, with 2-fold dilution and totally 8 doses). Their binding responses were measured in real-time and results were fit globally. The affinity data of the tested antibodies are summarized in Table 18 below.

TABLE 18

Binding affinity of antibodies to human CD39 as measured by Octet assay

| Antibody | $K_D$ (M) | kon (1/Ms) | kdis (1/s) |
|---|---|---|---|
| hu23.H5L5 | 6.87E−10 | 1.36E+05 | 9.36E−05 |
| hu14.H1L2 | 8.39E−10 | 3.89E+05 | 3.26E−04 |
| I394 | 4.54E−10 | 2.56E+05 | 1.16E−04 |
| T895 | 6.62E−09 | 6.71E+05 | 4.44E−03 |
| 9-8B | 2.02E−08 | 1.20E+05 | 2.43E−03 |

In addition, one NG motif (N55G56) which liable to deamidation was identified in HCDR2 of the humanized antibody clones for c23 antibody (e.g. hu23.H5L5). To remove the deamidation site, different mutations were introduced to N55 or G56, and it was found that N55 and G56 can be each mutated to a variety of residues, yet still retained the specific binding to human CD39. For example, it was found that when N55 was single point replaced by G, S or Q, the antibody binding affinity retained and there was no negative impact on its binding to human CD39. Similarly, when G56 was replaced by A or D, the mutant antibody also retained its specific binding and binding affinity to human CD39. Other mutations were also expected to work as well.

5.2. Binding Specificity Detection

Figure 6:
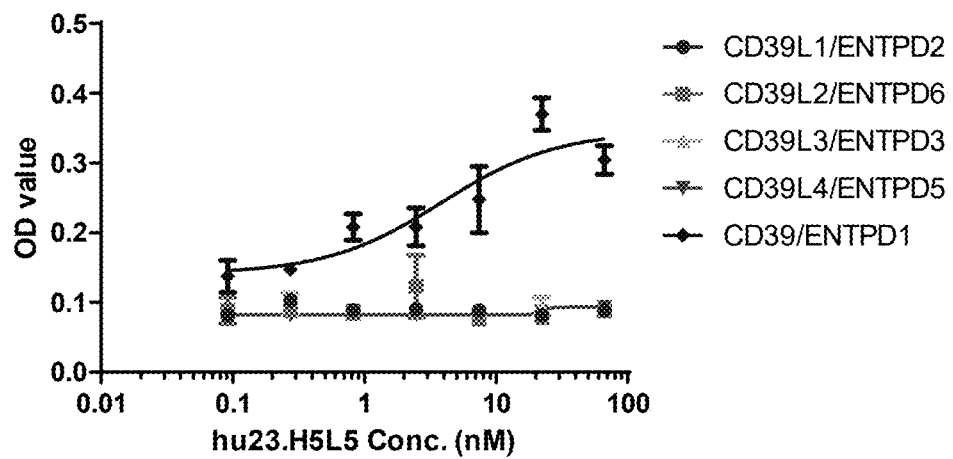
FIG. 6A shows the binding property of humanized antibody hu23.H5L5 to ENTPD1 (i.e. CD39), ENTPD2 (i.e. CD39L1), ENTPD3 (i.e. CD39L3), ENTPD5 (i.e. CD39L4) and ENTPD6 (i.e. CD39L2) proteins, respectively.
FIG. 6B shows the binding of negative control hIgG4 with ENTPD1 (i.e. CD39), ENTPD2 (i.e. CD39L1), ENTPD3 (i.e.
Figure 6:
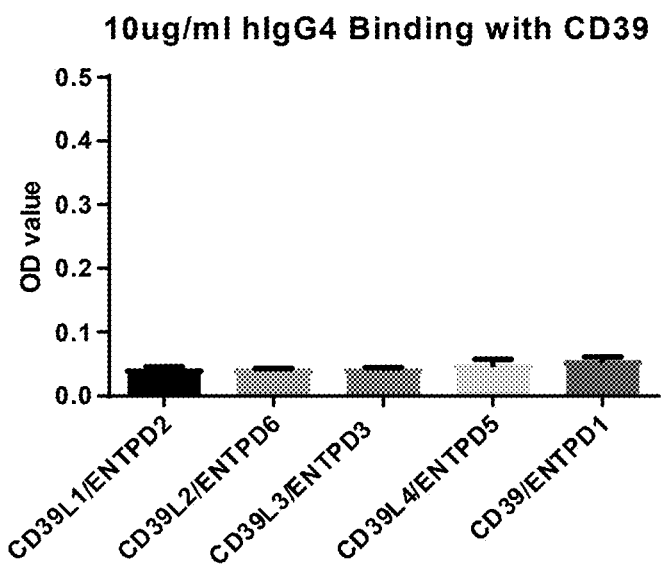

Binding specificity of the purified humanized antibody hu23.H5L5 against ENTPDase family members was detected by ELISA assay. Briefly, ENTPD1 (i.e. CD39) and ENTPD 2/3/5/6 proteins were coated on 96-well ELISA plates at 4° C. overnight, next day the ELISA plates were washed and blocked using blocking buffer (1% BSA in PBS with 0.05% Tween20) 200 μL/well for 2 hours. Then hu23.H5L5 gradients were duplicated into the wells and stained with anti-hIgG-HRP. After plate washing, the plates were developed with TMB substrate and stopped by 2N HCl. The OD450 were recorded using plate reader and platted by Graphpad Prism. The binding specificity property of hu23.H5L5 is shown in FIG. 6. It can be seen from FIG. 6A that the humanized antibody hu23.H5L5 specifically binds to human CD39, but does not bind to any of the ENTPD 2/3/5/6 proteins. FIG. 6B shows the negative control hIgG4 does not bind to any of ENTPD 1/2/3/5/6 proteins.

5.3. Humanized Antibody Characterization

The binding affinity of the humanized antibodies for c23 was determined by FACS, using similar methods as described in Example 3.2. The c23 humanized antibody clones showing good binding affinity are listed in below Table 19 and Table 20, and also shown in FIGS. 7A, 7B and FIG. 8. $EC_{50}$ is the concentration of the indicated antibodies to reach 50% of the signal in this assay.

TABLE 19

Binding activity of c23 humanized antibodies to MOLP8 cells.

| | Antibody | | | | |
|---|---|---|---|---|---|
| | hu23.H1L1 | hu23.H1L2 | hu23.H1L3 | hu23.H1L4 | hu23.H2L1 |
| $EC_{50}(nM)$ | ~77.07 | 1.158 | 2.775 | 1.498 | 65.91 |
| | Antibody | | | | |
| | hu23.H2L2 | hu23.H2L3 | hu23.H2L4 | c23 | |
| $EC_{50}(nM)$ | 0.979 | 2.033 | 1.46 | 1.035 | |
| | Antibody | | | | |
| | hu23.H3L1 | hu23.H3L2 | hu23.H3L3 | hu23.H3L4 | hu23.H4L1 |
| $EC_{50}(nM)$ | ~15.40 | 1.341 | 3.29 | 1.612 | ND |
| | Antibody | | | | |
| | hu23.H4L2 | hu23.H4L3 | hu23.H4L4 | isotype | |
| $EC_{50}(nM)$ | 1.151 | 1.868 | 1.014 | ND | |
| | Antibody | | | | |
| | hu23.H1L1 | hu23.H1L5 | hu23.H1L6 | hu23.H1L7 | hu23.H5L1 |
| $EC_{50}(nM)$ | ~78.25 | ND | ND | ND | 0.262 |
| | Antibody | | | | |
| | hu23.H5L5 | hu23.H5L6 | hu23.H5L7 | c23 | |
| $EC_{50}(nM)$ | 0.177 | 0.2021 | 0.179 | 0.3973 | |
| | Antibody | | | | |
| | hu23.H6L1 | hu23.H6L5 | hu23.H6L6 | hu23.H6L7 | hu23.H7L1 |
| $EC_{50}(nM)$ | 0.2459 | 0.593 | 0.237 | 0.122 | 0.366 |
| | Antibody | | | | |
| | hu23.H7L5 | hu23.H7L6 | hu23.H7L7 | isotype | |
| $EC_{50}(nM)$ | 0.25 | 0.271 | 0.25 | ND | |

ND: not detectable under conditions of this experiment.

TABLE 20

Binding activity of c23 humanized antibodies to MOLP8.

| | Antibody | | | | | |
|---|---|---|---|---|---|---|
| | hu23.201 | hu23.203 | hu23.207 | hu23.211 | c23 | hIgG4 |
| $EC_{50}$ (nM) | 1.289 | 0.429 | 2.246 | 1.557 | 1.279 | ND |

ND: not detectable under conditions of this experiment.

The selected humanized antibodies for c23 were tested on SK-IVEL-28 cells for ATPase inhibition assay (as described in Example 3.3). FIGS. 9A and 9B show the inhibition plot of indicated antibodies, and as summarized in Table 21. Hu23.H5L5 and hu23.201 were selected for further validation.

TABLE 21

ATPase inhibition activity of c23 humanized antibodies on SK-MEL-28 cells.

| | Antibody | | | | | | |
|---|---|---|---|---|---|---|---|
| | hu23.H7L1 | hu23.H7L5 | hu23.H7L6 | hu23.H1L2 | hu23.H1L4 | hu23.H2L2 | c23 |
| $IC_{50}$ (nM) | 0.147 | 0.144 | 0.121 | 0.964 | 0.59 | 0.767 | 0.158 |

| | Antibody | | | | | | |
|---|---|---|---|---|---|---|---|
| | hu23.H4L4 | hu23.H5L5 | hu23.H5L6 | hu23.201 | hu23.203 | hu23.211 | c23 |
| $IC_{50}$ (nM) | 0.487 | 0.122 | 0.13 | 0.264 | 0.32 | 0.386 | 0.2092 |

The binding affinity of the humanized antibodies for c14 was determined by FACS using MOLP-8 cells expressing human CD39, using similar methods as described in Example 3.2.

Humanized antibody clones of c14 showing good binding affinity were shown in FIGS. 10A, 10B and 10C. $EC_{50}$ was summarized in Table 22.

TABLE 22

Binding activity of c14 humanized antibodies to MOLP8 cells.

| | Antibody | | | | | | |
|---|---|---|---|---|---|---|---|
| | hu14.H1L1 | hu14.H2L2 | hu14.H3L1 | hu14.H3L3 | hu14.H3L4 | hu14.H4L4 | c14 |
| $EC_{50}$ (nM) | 7.212 | 6.908 | 5.952 | 6.088 | 6.046 | 5.459 | 17.52 |

5.4. Epitope Binning

The selected humanized antibodies were tested for competitive binding (methods as described in Example 3.5). The epitope binning results of humanized antibodies hu23.H5L5 and hu14.H1L1 with reference antibodies were shown in FIG. 19A.

Based on the competition results (as shown in FIG. 19A), 2 humanized anti-CD39 antibodies hu23.H5L5 and hu14.H1L1 could be grouped into 2 different epitope groups (see FIG. 19B). Specifically, anti-CD39 antibody hu23.H5L5 competed for highly similar epitopes with reference antibodies I394, T895 and 9-8B, and was grouped into epitope group I. Besides partially competing with T895, hu14.H1L1, c34 and c35 did not compete with any other antibody as tested, and were grouped into epitope group II.

5.5. Optimized Humanized Antibody Characterization 5.5.1 CD39 Blockade by hu23.H5L5 Improved Human T Cell Proliferation in the Presence of Extracellular ATP (eATP).

Human PBMC stimulated with anti-CD3 antibody and anti-CD28 antibody was incubated with 25 nM humanized anti-CD39 antibody hu23.H5L5 and vehicle respectively in the presence of ATP. Cell culture supernatants were harvested for detection of IL-2 and IFN-γ secretion, respectively. Proliferation of CD4+ T and CD8+ T cells was analyzed on day 5 in FACS by Cell Trace Violet dye dilution.

As shown in FIGS. 11A to 11D, hu23.H5L5 significantly enhanced both CD4+ and CD8+ T cell proliferation and activated their IL-2 and IFN-γ production at the concentration of 25 nM. As shown in FIGS. 11A, 11B and 11D, hu23.H5L5 showed significantly higher activity than I394 in enhancing T cell activation in PBMC.

Human CD8+ T cells were also isolated from healthy donor PBMC, then labeled with cell proliferation dye, activated with anti-CD3 antibody and anti-CD28 antibody, and treated with humanized anti-CD39 antibody hu23.H5L5 or the reference antibody I394 with different doses for a total treatment time of five days, 200 M of ATP was added to cells on day three after the start of CD39 blockade treatment. Proliferation % of CD8+ T cells, % CD25+ cells and % living cells were analyzed on day 5 using flow cytometry.

As shown in FIGS. 23A to 23C, hu23.H5L5 significantly reversed human CD8+ T cell proliferation which was inhibited by eATP.

Binding affinity of the humanized antibodies hu23.H5L5 and hu14.H1L1 were tested on different cells by FACS following the similar method as described in Example 3.2.

FIGS. 12A to 12E show binding affinity of antibodies hu23.H5L5 and hu14.H1L1 against SK-MEL-5 (FIG. 12A), SK-MEL-28 (FIG. 12B), MOLP-8 (FIG. 12C), CHOK1-cynoCD39 (FIG. 12D) and CHOK1-mCD39 (FIG. 12E), respectively. Reference antibodies T895 and I394 were tested in parallel as control antibodies. As shown in FIG. 12 and summarized in Table 23, both antibodies hu23.H5L5 and hu14.H1L1 bound to human and cynomolgus CD39 expressing cells in a dose-dependent manner and with similar affinity by $EC_{50}$ at a sub-nanomolar or nanomolar level. Neither of them recognized mouse CD39 in the FACS study. Maximum signal (mean fluorescence intensity, MFI) differed between cells for each antibody may result from their different expression level.

TABLE 23

Antibody affinity measured by FACS by $EC_{50}$ (nM).

| Cells | hu23.H5L5 | hu14.H1L1 | T895 | I394 |
|---|---|---|---|---|
| SK-MEL-5 | 0.69 | 7.88 | 0.21 | 0.49 |
| SK-MEL-28 | 0.99 | 29.14 | 0.36 | 0.94 |

TABLE 23-continued

Antibody affinity measured by FACS by EC$_{50}$ (nM).

| Cells | hu23.H5L5 | hu14.H1L1 | T895 | I394 |
|---|---|---|---|---|
| MOLP-8 | 0.14 | 0.35 | 0.11 | 0.11 |
| CHO-K1/cynoCD39 | 3.375 | ND | 4.192 | 2.708 |
| CHO-K1/mCD39 | ND | ND | ND | ND |

ND: not detectable under conditions of this experiment.

Figure 13:
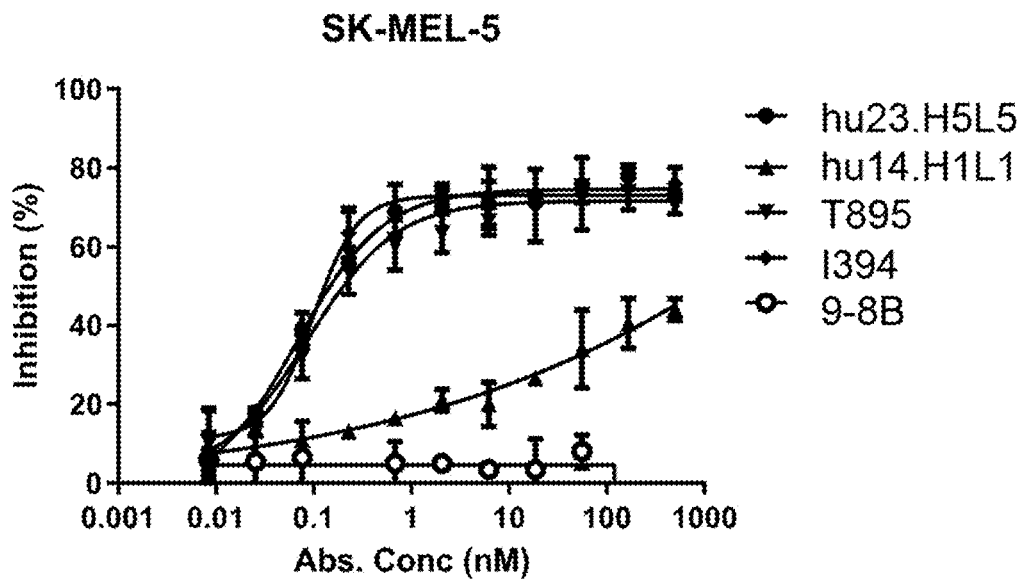
Figure 13:
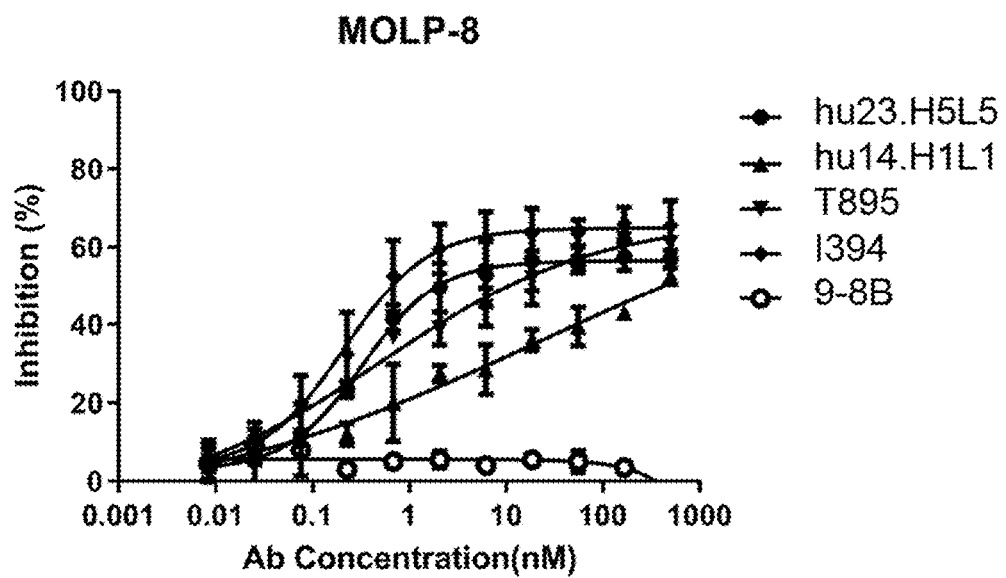

FIG. 13 shows that hu23.H5L5 blocked CD39 ATPase activity on SK-MEL-5 (FIG. 13A) or MOLP-8 (FIG. 13B) cells, similar to the reference antibodies T895 and I394 (method as described in Example 3.3). Results were summarized in Table 24.

hu23.H5L5 showed 70 pM enzymatic blocking IC$_{50}$ on SK-MEL-5 cell and 330 pM on MOLP-8 cell which were similar or slightly better than the reference antibodies T895 and I394. However, hu14.H1L1 could not reach a saturated blocking on both cells and 9-8B identified as a non-blocker in this assay.

TABLE 24

ATPase activity inhibition (IC$_{50}$) of humanized antibodies (nM)

| IC$_{50}$ (nM) | hu23.H5L5 | hu14.H1L1 | T895 | I394 | 9-8B |
|---|---|---|---|---|---|
| SK-MEL-5 | 0.07 | NA | 0.09 | 0.10 | ND |
| MOLP-8 | 0.33 | 26.51 | 0.51 | 0.21 | ND |

NA: not available
ND: not detectable under conditions of this experiment 5.5.2 CD39 Blockade by hu23.H5L5 Enhanced ATP-Mediated Monocytes Activation.

The humanized antibody hu23.H5L5 was also tested in ATP-mediated monocyte activation assay. ATP-mediated pro-inflammatory activity has an important role in regulating the function of multiple immune cell types, including monocyte. To evaluate whether CD39 blockade could enhance ATP-mediated monocytes activation, human monocytes were purified from human healthy blood, and then incubated in the presence of ATP with anti-CD39 antibodies at various concentrations ranging from 0.2 nM to 100 nM. Hu23.H5L5 was shown to be effective in inducing monocyte activation at 0.2 nM, i.e., the lowest concentration tested. Monocyte activation was assessed by analyzing CD80 (FIG. 14A), CD86 (FIG. 14B) and CD40 (FIG. 14C) expression by FACS assay (the concentration of hu23.H5L5 is 50 nM). Reference anti-CD39 antibodies I394 and T895 were used as control, hIgG4 was used as an isotype control.

Figure 14:
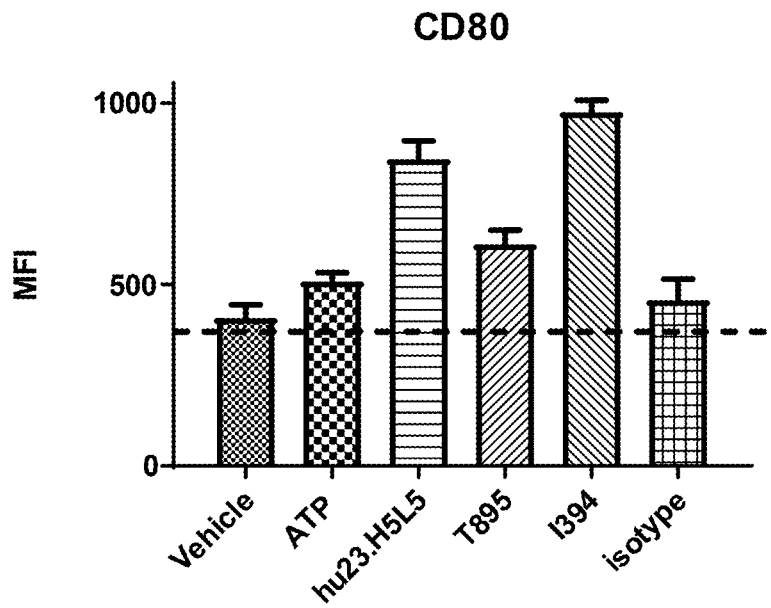
Figure 14:
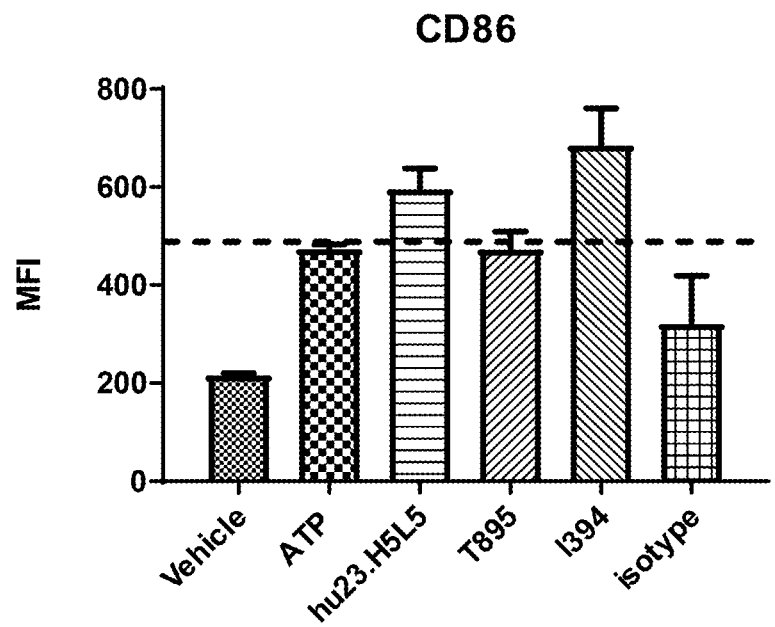
Figure 14:
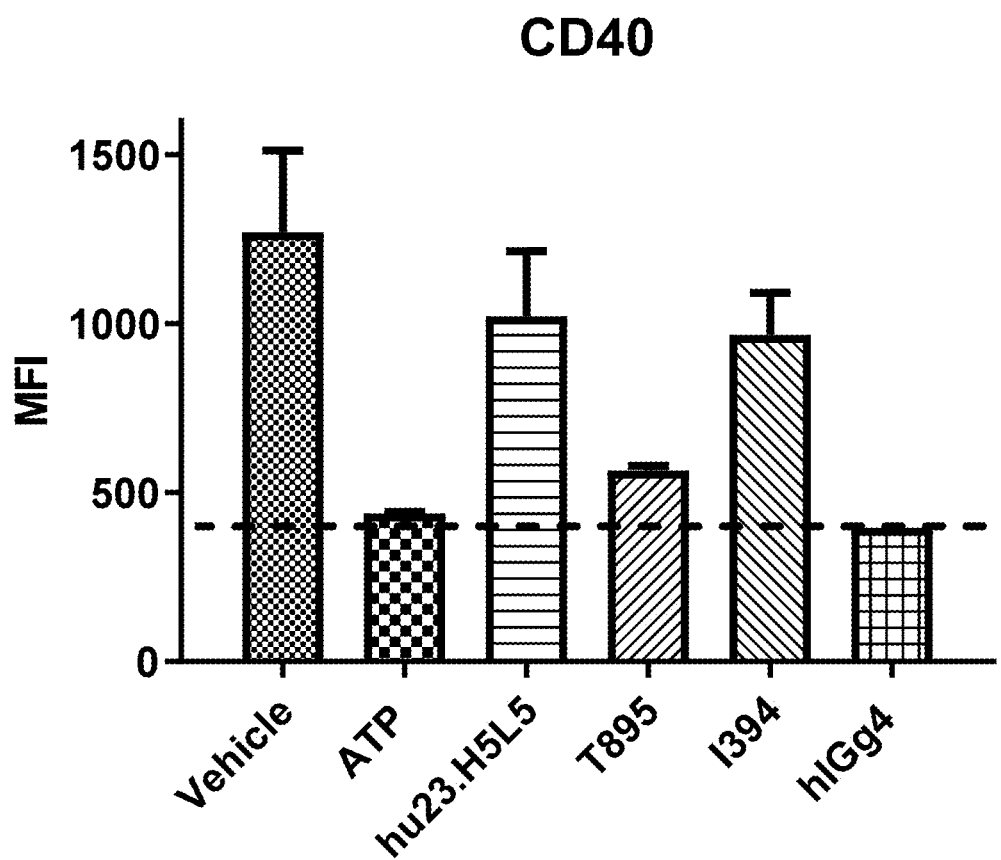

Results are shown in FIG. 14. Stimulation of ATP alone demonstrated upregulated expression of CD80 and CD86, indicating monocytes activation. Anti-CD39 humanized antibody hu23.H5L5 further enhanced the ATP-mediated monocytes activation, as evidenced by the upregulation of CD80, CD86, and CD40, at a level comparable to that of the reference antibody I394. Reference antibody T895 didn't show significant effect on ATP induced activated monocytes.

5.5.3 CD39 Blockade by hu23.H5L5 Enhanced ATP-Mediated DC Activation.

The selected humanized antibody hu23.H5L5 was also tested in ATP-mediated DC activation assay (following similar methods described in Example 4.2). Briefly, DC maturation were evaluated by analyzing CD83 expression by FACS assay. ATP induced DC maturation by showing an increased expression of CD83 (FIG. 15A). Hu23.H5L5 increased CD83 expression in a dose-dependent manner, starting from a level as low as 0.2 nM, and significantly increased CD83 expression at an antibody level of 0.6 nM. This is more potent than any of the reference antibodies T895 and I394.

To further assess the consequential effect of ATP-mediated DC activation on T cells activation, ATP-activated DC were washed and then incubated with allogenic T cells for a mixed lymphocytes reaction (MLR). T cells proliferation (FIG. 15B) and IFN-γ production from activated T cells were analyzed (FIG. 15C).

In comparison with the reference antibodies I394 and T895, anti-CD39 antibody hu23.H5L5 showed dose-dependent and significant effect on enhancing ATP induced DC maturation, reference I394 showed similar but a slightly weaker activity, while the effect of T895 was very mild. Consistently, as shown in FIGS. 15B and 15C, the enhanced ATP-mediated MoDC maturation by anti-CD39 blocking antibody hu23.H5L5 resulted in the higher T cells proliferation and IFN-γ production in the MLR assay.

5.5.4 CD39 Blockade by hu23.H5L5 Promoted Human Macrophage IL1β Release Induced by LPS Stimulation.

Human CD14$^+$ T cells were isolated from human healthy PBMC, the enriched CD14$^+$ monocytes were then seeded at the density of 2×10$^6$ per well in a 6-well plate and cultured with 100 ng/mL human GM-CSF for 6 days to generate M1-like macrophage. In vitro differentiated macrophage were treated with hu23.H5L5 or reference antibody I394 in increasing doses for 1 h and, subsequently, stimulated with 10 ng/mL LPS for 3 hours before addition of 800 μM ATP for 2 hours. IL-1β in cell culture supernatants was quantified by ELISA.

Results are shown in FIG. 20. Asterisks indicate significant differences between the respective conditions. As shown in FIG. 20, hu23.H5L5 significantly promoted human macrophage IL1β release induced by LPS stimulation, and hu23.H5L5 showed significantly higher activity than reference antibody I394 in promoting human macrophage IL1β release induced by LPS stimulation.

5.6. In Vivo Study

The effect of humanized antibodies hu23.H5L5 and hu14.H1L1 were determined on MOLP-8 xenograft mice according to methods described in Example 4.2.

Results are shown in FIG. 16, all of the anti-CD39 antibodies inhibited tumor growth compared with vehicle group. The efficacy observed for I394 was slightly weaker than the other antibodies including hu23.H5L5 and hu14.H1L1.

The anti-tumor efficacy of humanized antibody hu23.H5L5 was also tested in vivo in PBMC adoption animal model (NCG mice, inoculated with MOLP-8 cells, 5M/mouse) by testing a range of different dosages (0.03 mg/kg, 0.3 mg/kg, 3 mg/kg, 10 mg/kg, 30 mg/kg, i.p., BIW×6 doses), according to the methods described in Example 4.2.

Results are shown in FIG. 21. As shown by FIG. 21, the humanized antibody hu23.H5L5 potently inhibits tumor growth at all tested dosages.

We also determined whether the anti-tumor efficacy of the anti-CD39 antibodies were dependent on NK cells or macrophage cells. The NK depleting treatment of anti-asialo-GM1 was initiated on day 7 at 20 μl/mouse intraperitoneally, once every 5 days. The macrophage depleting treatment of clodronate liposome was also initiated on day 7 and day 9 at 200 μl/mouse intravenously, once per week. Blood samples analysis data demonstrated mononuclear phagocytic cells or NK were significantly removed by the reagent.

In the models where NK (FIG. 17) or macrophage (FIG. 18) cells were depleted, the tumor growth inhibition effect of hu23.H5L5 was abolished, suggesting that the anti-tumor effects of the anti-CD39 antibody was dependent on NK cells and macrophages.

Specifically, as shown in FIG. 17, anti-asialo-GM1 slightly enhanced tumor growth at late stage compared with vehicle. And compared with hu23.H5L5 treated group, its combination with anti-asialo-GM1 completely abolished hu23.H5L5 tumor growth inhibition efficacy. As shown in FIG. 18, clodronate liposome had no effect on tumor growth compared with vehicle. However, clodronate liposome treatment completely abolished hu23.H5L5's tumor growth inhibition efficacy.

Example 6. Epitope Mapping

To define the epitope of anti-CD39 antibodies, CD39 mutants were designed and defined by substitutions of amino acids exposed at the molecular surface over the surface of human CD39. Mutants were cloned into an expression vector which fused a C-terminal EGFP sequence and transfected in HEK-293F cells, as shown in Table 25 below. The targeted amino acid mutations are shown using numbering of UniProtKB-P49961 (ENTP1_HUMAN), which is the wild-type amino acid sequence of human CD39, and shown as SEQ ID NO: 162 herein. For example, V77G means that valine at position 77 of SEQ ID NO: 162 is replaced by glycine.

TABLE 25

Human CD39 Mutants

| Mutants ID | Substitutions |
|---|---|
| KW27-1 | V77G, H79Q, Q444K, G445D |
| KW27-2 | V81S, E82A, R111A, V115A |
| KW27-3 | E110A, R113T, E114A |
| KW27-4 | R118A, S119A, Q120K, Q122H, E123A |
| KW27-5 | D150A, E153S, R154A, S157K, N158A, L278F |
| KW27-6 | Q96A, N99A, E143A, R147E |
| KW27-7 | K188R, 190-206(SQKTRWFSIVPYETNNQ) substituted by KTPGGS |
| KW27-8 | A273S, N275A, I277S, R279A |
| KW27-9 | S294A, K298G, K303A, E306A, T308K, Q312A |
| KW27-10 | K288E, K289A, V290A, E315R |
| KW27-11 | Q354A, D3565, E435A, H436Q |
| KW27-12 | H428A, T430A, A431D, D432A |
| KW27-13 | N371K, L372K, E375A, K376G, V377S |
| KW27-14 | K388N, Q392K, P393S, E396A |
| KW27-15 | A402P, G403A, K405A, E406A |
| KW27-16 | K5A, E100A, D107A |
| KW27-17 | Q323A, Q324A, Q327A, E331K |
| KW27-18 | N334A, S336A, Y337G, N346A |

TABLE 25-continued

Human CD39 Mutants

| Mutants ID | Substitutions |
|---|---|
| KW27-19 | Q228A, I230S, D234A, Q238A |
| KW27-20 | R138A, M139A, E142K |
| KW27 | SEQ ID NO: 162 (wild-type human CD39) MEDTKESNVK TFCSKNILAI LGFSSIIAVI ALLAVGLTQN KALPENVKYG IVLDAGSSHT SLYIYKWPAE KENDTGVVHQ VEECRVKGPG ISKFVQKVNE IGIYLTDCME RAREVIPRSQ HQETPVYLGA TAGMRLLRME SEELADRVLD VVERSLSNYP FDFQGARIIT GQEEGAYGWI TINYLLGKFS QKTRWFSIVP YETNNQETFG ALDLGGASTQ VTFVPQNQTI ESPDNALQFR LYGKDYNVYT HSFLCYGKDQ ALWQKLAKDI QVASNEILRD PCFHPGYKKV VNVSDLYKTP CTKRFEMTLP FQQFEIQGIG NYQQCHQSIL ELFNTSYCPY SQCAFNGIFL PPLQGDFGAF SAFYFVMKFL NLTSEKVSQE KVTEMMKKFC AQPWEEIKTS YAGVKEKYLS EYCFSGTYIL SLLLQGYHFT ADSWEHIHFI GKIQGSDAGW TLGYMLNLTN MIPAEQPLST PLSHSTYVFL MVLFSLVLFT VAIIGLLIFH KPSYFWKDMV |

Briefly, the human CD39 mutants were generated by gene synthesis and then cloned into an expression vector pCMV3-GFPSpark. The vectors containing the validated mutated sequences were prepared and transfected into HEK293F cells. Three days post transfection, the cells were collected to testing EGFP for transgene expression. A range of dosages of antibodies (start from 100 nM, 3-folds dilution, 11 points) were tested on the 20 generated mutants and stained by AlexFluor647 labelled anti-hIgG by FACS. Antibody binding was descripted as relative binding which is derived from AlexFluor647 intensity divided by GFP intensity. The results were shown in FIG. 22.

As shown in FIG. 22, the humanized antibody hu23.H5L5 lost binding to mutant KW27-6 and KW27-20, but not to the other mutants. Mutant KW27-6 contains amino acid substitutions at residues Q96, N99, E143 and R147, indicating that one or more, or all of the residues of the mutant are important to the core epitope of hu23.H5L5; MutantKW27-20 contains amino acid substitutions at residue R138, M139 and E142, indicating that one or more, or all of the residues of the mutant are also important to the core epitope of hu23.H5L5.

As shown in FIG. 22, the chimeric antibody c34 lost binding to mutant KW27-16, but not to any other mutants. Mutant KW27-16 contains amino acid substitutions at residues K5, E100 and D107, indicating that one or more, or all of the residues of the mutant are important to the core epitope of c34.

As shown in FIG. 22, the chimeric antibody c35 lost binding to mutant KW27-2, but not to any other mutants. Mutant KW27-2 contains amino acid substitutions at residues V81, E82, R111 and V115, indicating that one or more, or all of the residues of the mutant are important to the core epitope of c35.

As shown in FIG. 22, the reference antibody T895 lost binding to mutant KW27-20, but not to any other mutants. Mutant KW27-20 contains amino acid substitutions at residue R138, M139 and E142 indicating that one or more, or all of the residues of the mutant are important to the core epitope of T895.

As shown in FIG. 22, the reference antibody I394 lost binding to mutant KW27-6 and KW27-20, but not to the other mutants. Mutant KW27-6 contains amino acid substitutions at residues Q96, N99, E143 and R147, indicating that one or more, or all of the residues of the mutant are important to the core epitope of I394; Mutant KW27-20 contains amino acid substitutions at residues R138, M139 and E142, indicating that one or more, or all of the residues of the mutant are also important to the core epitope of I394.

As shown in FIG. 22, the reference antibody 9-8B lost binding to mutant KW27-6, but not to any other mutants. Mutant KW27-6 contains amino acid substitutions at residues Q96, N99, E143 and R147, indicating that one or more, or all of the residues of the mutant are important to the core epitope of 9-8B.

What is claimed is:

1. An antibody or an antigen-binding fragment thereof capable of specifically binding to human CD39, comprising a heavy chain variable region comprising HCDR1, HCDR2 and HCDR3 and a light chain variable region comprising LCDR1, LCDR2 and LCDR3, wherein
   a) the HCDR1 comprises the amino acid sequence of DTFLH (SEQ ID NO: 4); and
   b) the HCDR2 comprises the amino acid sequence of $X_{58}IDPAX_{59}X_{60}NIKYDPKFQG$ (SEQ ID NO: 151); and
   c) the HCDR3 comprises the amino acid sequence of SPYYYGSGYRIFDV (SEQ ID NO: 16); and
   d) the LCDR1 comprises the amino acid sequence of SAFSSVNYMH (SEQ ID NO: 22); and
   e) the LCDR2 comprises the amino acid sequence of TTSNLAS (SEQ ID NO: 28); and
   f) the LCDR3 comprises the amino acid sequence of QQRSTYPFT (SEQ ID NO: 34);
   wherein $X_{58}$ is R or K, $X_{59}$ is N, G, S or Q, $X_{60}$ is G, A or D.

2. The antibody or an antigen-binding fragment thereof of claim 1, wherein:
   a) the HCDR1 comprises the sequence of SEQ ID NO: 4, the HCDR2 comprises the sequence of SEQ ID NO: 10, the HCDR3 comprises the sequence of SEQ ID NO: 16; the LCDR1 comprises the sequence of SEQ ID NO: 22, the LCDR2 comprises the sequence of SEQ ID NO: 28, and the LCDR3 comprises the sequence of SEQ ID NO: 34; or
   b) the HCDR1 comprises the sequence of SEQ ID NO: 4, the HCDR2 comprises a sequence selected from the group consisting of SEQ ID NOs: 134, 135, 136, 137, 138, and 139, the HCDR3 comprises the sequence of SEQ ID NO: 16; the LCDR1 comprises the sequence of SEQ ID NO: 22, the LCDR2 comprises the sequence of SEQ ID NO: 28, and the LCDR3 comprises the sequence of SEQ ID NO: 34.

3. The antibody or an antigen-binding fragment thereof of claim 1, further comprising one or more of heavy chain HFR1, HFR2, HFR3 and HFR4, and/or one or more of light chain LFR1, LFR2, LFR3 and LFR4, wherein:
   a) the HFR1 comprises the sequence of $X_{19}VQLVX_{20}SGX_{21}X_{22}X_{23}X_{24}KPGX_{25}SX_{26}X_{27}X_{28}SCX_{29}ASGX_{30}X_{31}X_{32}X_{33}$ (SEQ ID NO: 76) or a homologous sequence of at least 80% sequence identity thereof,
   b) the HFR2 comprises the sequence of $WVX_{34}QX_{35}PGX_{36}X_{37}LEWX_{38}X_{39}$ (SEQ ID NO: 77) or a homologous sequence of at least 80% sequence identity thereof,
   c) the HFR3 sequence comprises the sequence of $X_{40}X_{41}TX_{42}X_{43}X_{44}DX_{45}SX_{46}X_{47}TX_{48}YX_{49}X_{50}X_{51}X_{52}SLX_{53}X_{54}EDTAVYYCX_{55}X_{56}$ (SEQ ID NO: 78) or a homologous sequence of at least 80% sequence identity thereof,
   d) the HFR4 comprises the sequence of $WGQGTX_{57}VTVSS$ (SEQ ID NO: 126) or a homologous sequence of at least 80% sequence identity thereof,
   e) the LFR1 comprises the sequence of $X_3IVX_4TQSPATLX_5X_6SPGERX_7TX_8X_9C$ (SEQ ID NO: 80) or a homologous sequence of at least 80% sequence identity thereof,
   f) the LFR2 comprises the sequence of $WYQQKPGQX_{10}PX_{11}LLIY$ (SEQ ID NO: 81) or a homologous sequence of at least 80% sequence identity thereof,
   g) the LFR3 comprises the sequence of $GX_{12}PX_{13}RFSGSGSGTX_{14}X_{15}TLTISSX_{16}EPEDFAVYX_{17}C$ (SEQ ID NO: 82) or a homologous sequence of at least 80% sequence identity thereof, and
   h) the LFR4 comprises the sequence of $FGX_{18}GTKLEIK$ (SEQ ID NO: 152) or a homologous sequence of at least 80% sequence identity thereof,
   wherein $X_3$ is E or Q; $X_4$ is L or M; $X_5$ is S or T; $X_6$ is L, V or A; $X_7$ is A or V; $X_8$ is L or I; $X_9$ is S or T; $X_{10}$ is A or S; $X_{11}$ is R or K; $X_{12}$ is I or V; $X_{13}$ is A or T; $X_{14}$ is D or S; $X_{15}$ is F or Y; $X_{16}$ is L, M or V; $X_{17}$ is Y or F; $X_{18}$ is G or Q; $X_{19}$ is Q or E; $X_{20}$ is E or Q; $X_{21}$ is G or A; $X_{22}$ is G or E; $X_{23}$ is L or V; $X_{24}$ is V or K; $X_{25}$ is G or A; $X_{26}$ is L, M or V; $X_{27}$ is R or K; $X_{28}$ is V or L; $X_{29}$ is A or K; $X_{30}$ is F or Y; $X_{31}$ is N or T; $X_{32}$ is F or L; $X_{33}$ is S or K; $X_{34}$ is R or K; $X_{35}$ is A or S; $X_{36}$ is K or Q; $X_{37}$ is R or G; $X_{38}$ is M, I or V; $X_{39}$ is G or A; $X_{40}$ is R or K; $X_{41}$ is V, A or F; $X_{42}$ is I or L; $X_{43}$ is S or T; $X_{44}$ is R or A; $X_{45}$ is D or T; $X_{46}$ is K, A or S; $X_{47}$ is S or N; $X_{48}$ is L, V or A; $X_{49}$ is M or L; $X_{50}$ is Q or E; $X_{51}$ is M or L; $X_{52}$ is S, I or N; $X_{53}$ is R or K; $X_{54}$ is S or T; $X_{55}$ is A or T; $X_{56}$ is R, N or T; and $X_{57}$ is T or L.

4. The antibody or an antigen-binding fragment thereof of claim 1, comprising a heavy chain variable region comprising a sequence selected from the group consisting of SEQ ID NOs: 47, 60, 62, 64, 66, 68, 70, 72, 74, 140, 141, 142, 146, 147, 39, and a homologous sequence thereof having at least 80% sequence identity yet retaining specific binding affinity to human CD39, and
   a light chain variable region comprising a sequence selected from the group consisting of SEQ ID NOs: 56, 61, 63, 65, 67, 69, 71, 73, 75, 143, 144, 145, 111, 112, 63, and a homologous sequence thereof having at least 80% sequence identity yet retaining specific binding affinity to human CD39.

5. The antibody or an antigen-binding fragment thereof of claim 1, comprising:
   a) a heavy chain variable region comprising the sequence of SEQ ID NO: 47 and a light chain variable region comprising the sequence of SEQ ID NO: 56; or
   b) a heavy chain variable region comprising the sequence of SEQ ID NO: 60 and a light chain variable region comprising the sequence of SEQ ID NO: 63, or c) a heavy chain variable region comprising the sequence of SEQ ID NO: 62 and a light chain variable region comprising the sequence of SEQ ID NO: 63, or
d) a heavy chain variable region comprising the sequence of SEQ ID NO: 64 and a light chain variable region comprising the sequence of SEQ ID NO: 63, or
e) a heavy chain variable region comprising the sequence of SEQ ID NO: 66 and a light chain variable region comprising the sequence of SEQ ID NO: 63, or
f) a heavy chain variable region comprising the sequence of SEQ ID NO: 60 and a light chain variable region comprising the sequence of SEQ ID NO: 65, or
g) a heavy chain variable region comprising the sequence of SEQ ID NO: 62 and a light chain variable region comprising the sequence of SEQ ID NO: 65, or
h) a heavy chain variable region comprising the sequence of SEQ ID NO: 64 and a light chain variable region comprising the sequence of SEQ ID NO: 65, or
i) a heavy chain variable region comprising the sequence of SEQ ID NO: 66 and a light chain variable region comprising the sequence of SEQ ID NO: 65, or
j) a heavy chain variable region comprising the sequence of SEQ ID NO: 60 and a light chain variable region comprising the sequence of SEQ ID NO: 67, or
k) a heavy chain variable region comprising the sequence of SEQ ID NO: 62 and a light chain variable region comprising the sequence of SEQ ID NO: 67, or
l) a heavy chain variable region comprising the sequence of SEQ ID NO: 64 and a light chain variable region comprising the sequence of SEQ ID NO: 67, or
m) a heavy chain variable region comprising the sequence of SEQ ID NO: 66 and a light chain variable region comprising the sequence of SEQ ID NO: 67, or
n) a heavy chain variable region comprising the sequence of SEQ ID NO: 140 and a light chain variable region comprising the sequence of SEQ ID NO: 61, or
o) a heavy chain variable region comprising the sequence of SEQ ID NO: 141 and a light chain variable region comprising the sequence of SEQ ID NO: 61, or
p) a heavy chain variable region comprising the sequence of SEQ ID NO: 142 and a light chain variable region comprising the sequence of SEQ ID NO: 61, or
q) a heavy chain variable region comprising the sequence of SEQ ID NO: 140 and a light chain variable region comprising the sequence of SEQ ID NO: 143, or
r) a heavy chain variable region comprising the sequence of SEQ ID NO: 141 and a light chain variable region comprising the sequence of SEQ ID NO: 143, or
s) a heavy chain variable region comprising the sequence of SEQ ID NO: 142 and a light chain variable region comprising the sequence of SEQ ID NO: 143, or
t) a heavy chain variable region comprising the sequence of SEQ ID NO: 140 and a light chain variable region comprising the sequence of SEQ ID NO: 144, or
u) a heavy chain variable region comprising the sequence of SEQ ID NO: 141 and a light chain variable region comprising the sequence of SEQ ID NO: 144, or
v) a heavy chain variable region comprising the sequence of SEQ ID NO: 142 and a light chain variable region comprising the sequence of SEQ ID NO: 144, or
w) a heavy chain variable region comprising the sequence of SEQ ID NO: 140 and a light chain variable region comprising the sequence of SEQ ID NO: 145, or
x) a heavy chain variable region comprising the sequence of SEQ ID NO: 141 and a light chain variable region comprising the sequence of SEQ ID NO: 145, or
y) a heavy chain variable region comprising the sequence of SEQ ID NO: 142 and a light chain variable region comprising the sequence of SEQ ID NO: 145, or
z) a heavy chain variable region comprising the sequence of SEQ ID NO: 146 and a light chain variable region comprising the sequence of SEQ ID NO: 111, or
aa) a heavy chain variable region comprising the sequence of SEQ ID NO: 146 and a light chain variable region comprising the sequence of SEQ ID NO: 112, or
bb) a heavy chain variable region comprising the sequence of SEQ ID NO: 147 and a light chain variable region comprising the sequence of SEQ ID NO: 111, or
cc) a heavy chain variable region comprising the sequence of SEQ ID NO: 39 and a light chain variable region comprising the sequence of SEQ ID NO: 63, or
dd) a heavy chain variable region comprising the sequence of SEQ ID NO: 60 and a light chain variable region comprising the sequence of SEQ ID NO: 61, or
ee) a heavy chain variable region comprising the sequence of SEQ ID NO: 62 and a light chain variable region comprising the sequence of SEQ ID NO: 61, or
ff) a heavy chain variable region comprising the sequence of SEQ ID NO: 64 and a light chain variable region comprising the sequence of SEQ ID NO: 61, or
gg) a heavy chain variable region comprising the sequence of SEQ ID NO: 66 and a light chain variable region comprising the sequence of SEQ ID NO: 61, or
hh) a heavy chain variable region comprising the sequence of SEQ ID NO: 60 and a light chain variable region comprising the sequence of SEQ ID NO: 143, or
ii) a heavy chain variable region comprising the sequence of SEQ ID NO: 60 and a light chain variable region comprising the sequence of SEQ ID NO: 144, or
jj) a heavy chain variable region comprising the sequence of SEQ ID NO: 60 and a light chain variable region comprising the sequence of SEQ ID NO: 145.

6. The antibody or an antigen-binding fragment thereof of claim 1, further comprising one or more amino acid residue substitutions or modifications yet retains specific binding affinity to human CD39, wherein the one or more amino acid residue substitutions or modifications is within one or more of the non-CDR sequences of the heavy chain variable region or light chain variable region.

7. The antibody or an antigen-binding fragment thereof of claim 1, further comprising an Fc region.

8. The antibody or an antigen-binding fragment thereof of claim 1, which is humanized.

9. The antibody or an antigen-binding fragment thereof of claim 1, which is a monoclonal antibody, a bispecific antibody, a multi-specific antibody, a recombinant antibody, a chimeric antibody, a labeled antibody, a bivalent antibody, an anti-idiotypic antibody or a fusion protein.

10. The antibody or an antigen-binding fragment thereof of claim 1, which is a diabody, a Fab, a Fab', a F(ab')$_2$, a Fd, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a multispecific antibody, a camelized single domain antibody, a nanobody, a domain antibody, or a bivalent domain antibody.

11. The antibody or an antigen-binding fragment thereof of claim 1, which specifically binds to an epitope of CD39, wherein the epitope comprises one or more residues selected from the group consisting of Q96, N99, E143, R147, R138, M139, E142, K5, E100, D107, V81, E82, R111, and V115.

12. The antibody or an antigen-binding fragment thereof of claim 1, which is linked to one or more conjugate moieties.

13. A composition comprising the antibody or an antigen-binding fragment thereof of claim 1, and one or more pharmaceutically acceptable carriers.

14. An isolated polynucleotide encoding the antibody or an antigen-binding fragment thereof of claim 1.

15. A vector comprising the isolated polynucleotide of claim 14.

16. A host cell comprising the vector of claim 15.

17. A kit comprising the antibody or an antigen-binding fragment thereof of claim 1 and/or a pharmaceutical composition comprising the antibody or antigen-binding fragment thereof and one or more pharmaceutically acceptable carriers, and a second therapeutic agent.

18. A method of expressing the antibody or antigen-binding fragment thereof of claim 1, comprising culturing the host cell comprising a vector comprising an isolated polynucleotide encoding the antibody or antigen-binding fragment thereof under the condition at which the vector is expressed.

19. A method of modulating CD39 activity in a CD39-positive cell, comprising exposing the CD39-positive cell to the antibody or antigen-binding fragment thereof of claim 1 and/or a pharmaceutical composition comprising the antibody or antigen-binding fragment thereof and one or more pharmaceutically acceptable carriers.

20. A method of detecting the presence or amount of CD39 in a sample, comprising contacting the sample with the antibody or an antigen-binding fragment thereof of claim 1 and/or a pharmaceutical composition comprising the antibody or antigen-binding fragment thereof and one or more pharmaceutically acceptable carriers, and determining the presence or the amount of CD39 in the sample.

21. A kit comprising the antibody or an antigen-binding fragment thereof of claim 1 and/or a pharmaceutical composition comprising the antibody or antigen-binding fragment thereof and one or more pharmaceutically acceptable carriers, useful in detecting CD39.

22. The antibody or an antigen-binding fragment thereof of claim 1, further comprising an Fc region of human immunoglobulin (Ig).

23. The antibody or an antigen-binding fragment thereof of claim 1, further comprising an Fc region derived from human IgG1, IgG2, IgG3, IgG4, IgA1, IgA2 or IgM.

24. The antibody or an antigen-binding fragment thereof of claim 1, further comprising an Fc region derived from human IgG1 comprising a L234A and L235A mutation.

* * * * *